(12) United States Patent
Shalitin et al.

(10) Patent No.: US 12,258,559 B2
(45) Date of Patent: Mar. 25, 2025

(54) METHODS FOR IMPROVING TRAITS IN PLANTS

(71) Applicant: PLANTARCBIO LTD., Raanana (IL)

(72) Inventors: Dror Shalitin, Raanana (IL); Noam Grimberg, Raanana (IL); Arava Shatil Cohen, Raanana (IL)

(73) Assignee: PLANTARC BIO, LTD., Raanana (IL)

( * ) Notice: Subject to any disclaimer, the term of this patent is extended or adjusted under 35 U.S.C. 154(b) by 0 days.

(21) Appl. No.: 18/407,953

(22) Filed: Jan. 9, 2024

(65) Prior Publication Data

US 2024/0209351 A1 Jun. 27, 2024

Related U.S. Application Data

(63) Continuation of application No. 17/388,310, filed on Jul. 29, 2021, now Pat. No. 11,905,512, which is a continuation of application No. 16/496,445, filed as application No. PCT/IL2018/050349 on Mar. 27, 2018, now Pat. No. 11,111,491.

(60) Provisional application No. 62/644,600, filed on Mar. 19, 2018, provisional application No. 62/477,517, filed on Mar. 28, 2017.

(51) Int. Cl.
    *C12N 15/82* (2006.01)
    *C12N 15/10* (2006.01)

(52) U.S. Cl.
    CPC ..... *C12N 15/1075* (2013.01); *C12N 15/8273* (2013.01)

(58) Field of Classification Search
    None
    See application file for complete search history.

(56) References Cited

U.S. PATENT DOCUMENTS

| | | | |
|---|---|---|---|
| 6,030,779 A | 2/2000 | Short | |
| 6,368,798 B1 | 4/2002 | Short | |
| 6,972,183 B1 | 12/2005 | Lafferty et al. | |
| 2002/0150949 A1 | 10/2002 | Short et al. | |
| 2010/0012051 A1 | 1/2010 | Born | |
| 2011/0088126 A1 | 4/2011 | Chang et al. | |
| 2011/0252501 A1* | 10/2011 | Abad | C12N 15/8271 800/320.2 |
| 2012/0131696 A1 | 5/2012 | Sharon et al. | |
| 2014/0053298 A1 | 2/2014 | Sanz Molinero et al. | |
| 2015/0376640 A1 | 12/2015 | Shoresh et al. | |

FOREIGN PATENT DOCUMENTS

| | | |
|---|---|---|
| CN | 1314782 A | 9/2001 |
| CN | 103382476 A | 11/2013 |
| EP | 1025262 | 8/2000 |
| WO | 2008027591 | 3/2008 |
| WO | 2016095124 | 6/2016 |

OTHER PUBLICATIONS

Uniprot A0A017SJD1_ASPRC, 2014 (https://www.uniprot.org/uniprotkb/A0A017SJD1/entry) (Year: 2014).*
Gabor et al (2004) Quantifying the acccessibility of the metagenome by random expression cloning techniques, Environ Microbiol 6, 879-886.
Culligan et al (2014) Metagenomics and novel gene discovery: promise and potential for novel therapeutics, Virulence 5, 399-412.
Venter et al (2004) Environmental genome shotgun sequencing of the Sargasso Sea, Science, 304, 66-74.
Farooq et al (2009) Plant drought stress: effects, mechanisms and management, Agron. Sustain. Dev. 29, 185-212.
Zhao et al (2016) Ubiquitin-specific protease 24 negatively regulates abscisic acid signalling in *Arabidopsis thaliana*, Plant, Cell and Environment, 39:427-440.
Nonami H. (1998) Plant water relations and control of cell elongation at low water potentials, J. Plant Res. 111, 373-382.
Parida et al (2005) Salt tolerance and salinity effects on plants: a review, Ecotoxicology and Environmental Safety, 60(3), 324-349.
Carillo et al (2011) Salinity stress and salt tolerance, abiotic stress in plants—mechanisms and adaptations. In: Arun Shanker, editor Tech, DOI: 10.5772/22331.
Yang T-T et al (1996) Optimized codon usage and chromophore mutations provide enhanced sensitivity with the green fluorescent protein. Nucleic Acids Res 24:4592-4593.
Hema et al (2014) Stable Expression of mtlD Gene Imparts Multiple Stress Tolerance in Finger Millet. PLoS One 9(6): e99110.
Karaba et al (2007) Improvement of water use efficiency in rice by expression of HARDY, an *Arabidopsis* drought and salt tolerance gene, Proc Natl Acad Sci USA, 104:5270-5275.
Cao et al (1997) The *Arabidopsis* NPR1 gene that controls systemic acquired resistance encodes a novel protein containing ankyrin repeats, Cell 88(1), 57-63.
Gaj et al (2013) ZFN, TALEN and CRISPR/Cas-based methods for genome engineering, Trends in Biotechnology, 31 (7), 397-405.
Lever et al (2015) A modular method for the extraction of DNA and RNA, and the separation of DN pools from diverse environmental sample types, Frontiers in Microbiology, 6, 476.
Wujuan et al (2001) Determination of nucleic acids with crystal violet by a resonance light-scattering technique, Analyst, 126(4), 513-517.

(Continued)

*Primary Examiner* — Matthew R Keogh
(74) *Attorney, Agent, or Firm* — Booth Udall Fuller, PLC; Scott H. Blackman; Rodney J. Fuller

(57) ABSTRACT

The present invention discloses a method for screening for and identifying a desirable plant improving trait, said method comprises steps of: (a) obtaining genetic material from a sampling of a predefined source and (b) constructing an expression library from said genetic material. The aforementioned method further comprises steps of: (c) producing plants transformed with said expression library at a transformation efficiency of at least 0.05%-30%, representing at least $10^2$-$10^{10}$ trangenes; (d) screening for transformed plants expressing said desirable trait; and (e) identifying said transgene of said transformed plants expressing said desirable trait.

5 Claims, 13 Drawing Sheets

Specification includes a Sequence Listing.

(56) References Cited

OTHER PUBLICATIONS

Jayakannan et al (2015) The NPR1-dependent salicylic acid signalling pathway is pivotal for enhanced salt and oxidative stress tolerance in Arabidopsis, Journal of Experimental Botany, 66(7), 1865-1875.

Christoph Weiste et al (2007) In planta ORFeome analysis by large-scale over-expression of Gateway—compatible cDNA clones: screening of ERF transcription factors involved in abiotic stress defense: Functional analysis of the *Arabidopsis* transcription factor ORFeome, The Plant Journal, vol. 52, No. 2 pp. 382-390.

Wan-Song et al (2017) Construction of a Plant Transformation-ready Expression cDNA Library for Thellungiella halophila Using Recombination Cloning, Journal of Integrative Plant Biology, pp. 1313-1319.

Im et al (2009) Expression of Pyrococcus furiosus Superoxide Reductase in *Arabidopsis* Enhances Heat Tolerance, Plant Physiology, vol. 151:893-904.

Janbon et al (2014) (Genbank AFR94946), Analysis of the Genome and Transcriptome of *Cryptococcus neoformans* var. *grubii* Reveals Complex RNA Expression and Microevolution Leading to Virulence Attenuation, PLoS Genet. 10(4) E1004261.

NCBI Accession No. XP-009268808, 60S ribosomal protein L17 [Wallemia icthyophaga EXF-994].

Grandaubert et al (2015) RNA-seq-Based Gene Annotation and Comparative Genomics of Four Fungal Grass Pathogens in the Genus *Zymoseptoria* Identify Novel Orphan Genes and Species-Specific Invasions of Transposable Elements, G3 Genes | Genomes | Genetics, 5:1323-1333.

\* cited by examiner

SEQUENCE LISTING

```
Sequence total quantity: 333
SEQ ID NO: 1            moltype = DNA  length = 1019
FEATURE                 Location/Qualifiers
source                  1..1019
                        mol_type = genomic DNA
                        organism = unidentified
SEQUENCE: 1
ggactttctc attttcagaa ttattttcta tactctgaca agagcaagca ataccaaaca  60
tcttccacat cgaagcttta accattttgc ccttaacatt tgaacaagac gaaatggcct 120
tcttcccaca ctacaccact aatctgtcgc ctctgctcta cttgttggac gacgactatg 180
ctgtctaccg ctcaacttgt ccaaagtcca actaccacca caagcaacac cacagccgcc 240
gtcagccttc gccagttcgt tactttagtc cgaattttga tatgcgagag gggaatgact 300
cctactacct tgacggagag ctccctggtg tcaaccagaa tgatgtcgat attgaattct 360
ctgaccctca gacactggtg atcaagggtc gagtggagcg gaattacaac aatctcgacg 420
gcatgaacga ggaaaaccag caagatgaag aacaattctc tgaaactctc tctagcaagt 480
cgtaccaacc cactgtcgag gacgaggacg aggcgaacca ttcaccaccc gtggcgacac 540
caacctactc tgagaagtct gttactgaga aaactcagaa gcctgcgtac aaataccgaa 600
attctgaacg tgctattggc gaattccacc gagccttcaa tctccctaca agagtcgatc 660
aagatgcggt cagggctaca ttgaggaatg gaatcctctc gggtgagctc ccgaaggagc 720
cggcaccgaa gatgaagaag attcggattg aatagaggat ttcgaataaa atttttgatt 780
tgatgagtag ttggtgttta ttgttatgtc taattatatg gggctatgtc atgattggga 840
aatgggacac cgcatttgtt tccttttcc  ccatttcttc agacgccatc tatattacat 900
gtatgttgca tgaactatgg ttttttgctag gagcggttgc ttctgctctg cattttcatg 960
aactattttc ttttttattaa attaataact agcatatcaa ttaatgatct gtcatatgg  1019

SEQ ID NO: 2            moltype = DNA  length = 712
FEATURE                 Location/Qualifiers
source                  1..712
                        mol_type = genomic DNA
                        organism = unidentified
SEQUENCE: 2
gatcatcaat caattaatca atctactcta ctttccaaaa cataactacc aaataaccag  60
aatgcagctc ctcagcaccc tcaccccct  tgccctccta gtcaccgtcg cttccgccac 120
cggcaaagcc gtcaataatg ccgttggcaa cgccgtcgtc acaaaccact gtaaagaccc 180
aatctatctc tggtccgtcg gctcctccgt ctcccgaaa  cacaccatcc cctccggctc 240
caactatacc gagcccttcc gccacgacga cgcatctcgc ggcatccgcg tgaagatcac 300
ccgtaacgac aacgggctgt atgacgggag tgcgcagtta gtttactcct acgctttgga 360
tggggaacag gtgtggtatg attttgtcga gtgtgtttggg gatgcgtttg cagggagggc 420
tgttgctgtg aagccggaga atgaggggtg tgggagtatt tgttggccta agggtaccac 480
gcctggtgga agccaggtta aggtctgtga tgcggagggg gatgttggat tggttgtttg 540
tgcgaagggg tgttaggggg tctgagtgaa ggttggtggt ggtaatgagc aattgggtat 600
gagagggaa  aggatatgtt aatcgtttat gttatttact tgatcaaaat atttgtattg 660
acgtcggttg ttttgttatt gttgtttaa  atgcaaatgt atatgaactt tc          712

SEQ ID NO: 3            moltype = DNA  length = 580
FEATURE                 Location/Qualifiers
source                  1..580
                        mol_type = genomic DNA
                        organism = unidentified
SEQUENCE: 3
ggttcgtcaa cgcgacgatc cgcggggtc  caagctagga cgtggcagtt gtgacacaac  60
aagagcatgc tatggcaaat gccattcgcg agctcgccac taccctgtga actgtggcct 120
tactcctata cccgccagag tctgacttat tcctgtcact ggaatctggc ttactgctgg 180
tgctggagtc tggtcccagt attttagtat agtacaattg ctagctgaag ccataaggcg 240
tggattgttg gggtggcgca gggctgaagc caaatgcag  cggtgttgct gctggttgag 300
caccgggcat agcgccagaa agtgcacccg cgaacattcc ctggtattgc atgaacggct 360
gtccaggaat cgcgccaggc attggcaagg cgttgttgcg ctttgcctcc gctgccagga 420
gcctctctgc ttccgtaccg tgtctttcgc ccttaccgtc cttcttgaat gcataatcaa 480
ccgtcagagg cttgttcatc aagtactggc cattcatagc cgtgattgcc tggtccgagc 540
tgtcaaagtc gttgtactgg atgaatccat atcctttcaa                        580

SEQ ID NO: 4            moltype = DNA  length = 580
FEATURE                 Location/Qualifiers
source                  1..580
                        mol_type = genomic DNA
```

```
                        organism = unidentified
SEQUENCE: 4
ttgaaaggat atggattcat ccagtacaac gactttgaca gctcggacca ggcaatcacg    60
gctatgaatg gccagtactt gatgaacaag cctctgacgg ttgattatgc attcaagaag   120
gacggtaagg gcgaaagaca cggtacggaa gcagagaggc tgctggcagc ggaggcaaag   180
cgcaacaacg ccttgccaat gcctggcgcg attcctggac agccgttcat gcaataccag   240
ggaatgttcg cgggtgcact ttctggcgct atgcccggtg ctcaaccagc agcaacaccg   300
ctgccatttg gcttcagccc tgcgccaccc aacaatcca cgccttatgg cttcagctag    360
caattgtact atactaaaat actgggacca gactccagca ccagcagtaa gccagattcc   420
agtgacagga ataagtcaga ctctggcggg tataggagta aggccacagt tcacagggta   480
gtggcgagct cgcgaatggc atttgccata gcatgctctt gttgtgtcac aactgccacg   540
tcctagcttg gaccccgcg gatcgtcgcg ttgacgaacc                          580

SEQ ID NO: 5             moltype = DNA  length = 781
FEATURE                  Location/Qualifiers
source                   1..781
                         mol_type = genomic DNA
                         organism = unidentified
SEQUENCE: 5
gaaaaaaact ttagaataca gtttaatcaa tcttcacagc tacaaggcta tatcatttga    60
tatagcatat caaagtggct ttgatttctg taaatttata tctaataata atagtgttta   120
tatccgctaa atacatattt ctatcctatc tatatatcac cgacagacca ttttgaaac    180
tgctgttgac actattattc atatgttcgg atttaatttt aatacgacaa aattgttaaa   240
aacaattctc gttgtttgtt atttgcaggc aacagtgtta gctgatcctt atacaagagt   300
atcttgggaa gcgtatatga atcatgtcaa tggatccgac gactatcgta ctcaagggga   360
tgataccaga gctacacgct ttccagagac taaacctcca aaacaaggaa aagatttcct   420
gtggtcgagt aaaccagtcc ccagttcaga tctatttctg gagttcttta tgtatgaggg   480
agaaccagat gaattcagca ggacgactga atcgtatcaa tcacttccga gcaacgcgtt   540
aactgctagg caaaatgccc ttacttgtca ggacatagag tcatgttcgt atcctccaca   600
ggtgaacaac tttcaagctt tattcgacga cctggggcca tcaacttgta atctcataaa   660
agacgaaact cgtgactgga tattgcagca gtggcccggg ttagctgtag gagccgttat   720
atcgtttgcg gtagccgttg cgggaagctc ctgtgatata ttatattaat cagcttttggc   780
a                                                                   781

SEQ ID NO: 6             moltype = DNA  length = 661
FEATURE                  Location/Qualifiers
source                   1..661
                         mol_type = genomic DNA
                         organism = unidentified
SEQUENCE: 6
ggtcgagcta ctttcaaggt caagcaagat ggtccgttac gcacacaatg ctgagaaccc    60
agagaagacc gccaaggctc gtggtcagca cttgcgtacg cacttcaaga acacccgtga   120
agtcgctgct gctctgaccg gcttgaagct ttcaaaggct tacaagtacc tcggcgatgt   180
ccaagagcac aaggatgtca tcccattccg tcgcttcaac ggtggtgttg gcagagccgc   240
tcaggctaag aaccacggta cgacccaagg tcgttggcca gtcaagtcga ttggcttctt   300
gctcagactt ttgaagaacg ctgaggcaa cgctgacgcc aagtcactcg acacggaaga    360
cctcttgatc aagcacattg ttgtccaaca agctccaaaa acccgtcgtc gtacttaccg   420
tgctcacggt cgtatcaacc cttaccaagg acacccatgc cacattgaga tcactctggc   480
tgtcccagac gagcaagtcg ctcgcaacaa ggacgttgag gtgaaccaac caagaagat    540
ccaaggcaac aagcgtcaag tcgctgctca acgtcgcttg acctctgcat aaactggcta   600
ctcggttgtg taccactcta tacaaattat tcagtaaaat gctatccatc ttggcttcga   660
a                                                                   661

SEQ ID NO: 7             moltype = DNA  length = 713
FEATURE                  Location/Qualifiers
source                   1..713
                         mol_type = genomic DNA
                         organism = unidentified
SEQUENCE: 7
agccacaacc acatcaatcc tccaccactt tcagctttcg acttcatcaa acaactcctt    60
ctaccactac tacctcaaca accttcatca aaatgactgg acgcggcaag ggcggcaagg   120
gtctcggaaa gggcggcgcc aagcgtcacc gcaagatctt gcgcgacaac atccagggca   180
tcaccaagcc cgcacatccgc cgtctggcgc gtcgtgcgcg tgtcaagcgt atctccgcca   240
tgatctacga ggagaccgc ggtgtcctca agaccttcct caggggtacg atccgcgacg    300
ccgtcaccta caccgagcac gccaagcgca agaccgtcac ctccctcgac gtcgtctacg   360
ccctcaagag gcaaggccgc accctctacg gtttcggtgg ttaagcagct cgtctttctc   420
tcttcgactg ctttgctttc ttcaaacaca ataacaatca cgacaacaac aacttcatca   480
gatatccacc cacaatgcga gagttgggct tgcgggtatg gcgcgaatgg gcaatgggct   540
atccggggttt tttcatttt ggggttttt tctcttttcc tgttcgatg ctgcgaggtg     600
agcacactgg gctgcggctc atgaggcttt gagtgtagaa taggctcaac atcatcaaag   660
aagcattcca cgagacgtgg cgctttcttc atcaaccaaa tgaatattgc agc          713

SEQ ID NO: 8             moltype = DNA  length = 1021
FEATURE                  Location/Qualifiers
source                   1..1021
                         mol_type = genomic DNA
                         organism = unidentified
SEQUENCE: 8
ggacttgcga ccacacacat ctttatacct caaaatgtcg ctcgatgtcg gagatgtaga    60
```

```
cgcctggatc gacacgctat cgcagtgcaa gcagctatct gaatctgacg tgaagctcct    120
ctgcgacaag gccagagaaa ttcttataga ggagtccaac gtacagccag tcagatgccc    180
cgtcaccgtc tgcggcgata ttcacggtca attccacgac ttgattgagc tctttagaat    240
aggcggcaac tccccatcca ccaattacct cttcatgggc gattacgtag acaggggta    300
ctactcggtc gaaactgtca ccctcctcgt cgccttgaag ctccgctaca gggaaagaat    360
caccatcttg cgcggtaacc acgagtcgag acagatcacc caggtctacg gtttctacga    420
cgagtgcttg agaaagtatg gaaacgccaa cgtctggaag ttcttcaccg atctctttga    480
ctacctccca ctgacggcgc ttattgacaa tcaaatcttc tgtcttcacg gtggtttgtc    540
tccttccatc gacacgctcg accacatccg tctatccaag cgtatccaag aggtgcctca    600
cgaaggtcct atgtgcgatc tcctctggtc cgatccagac gaccgctgcg gctgggcat    660
atcccctcgt ggtgccggtt acaccttcgg tcaggacatt tcagaggctt tcaaccactc    720
aaacggcttg acgctcgtag cccgtgctca ccaacttgtc atggaaggtt acaactggtc    780
ccaggacagg aatgtcgtca ctctcttctc tgcgccaaat tactgctaca gatgcggtaa    840
ccaagctgcg atcatggaga ttgacgagaa tctcaagtac actttcctcc aattcgatcc    900
agcaccaaga gctggcgaac cgatggtgtc tcgaagagtt ccggactact tcttataggc    960
tcttactcac tgtatttatg tttgcactgg gtattgttta cttgtacaat gtgtaactac   1020
g                                                                    1021

SEQ ID NO: 9           moltype = DNA  length = 715
FEATURE                Location/Qualifiers
source                 1..715
                       mol_type = genomic DNA
                       organism = unidentified
SEQUENCE: 9
ggagccacaa ccacatcaat cctccaccac tttcagcttt cgacttcatc aaacaactcc     60
ttctaccact actacctcaa caaccttcat caaaatgact gacgcggca agggcggcaa    120
gggtctcgga aagggcggcg ccaagcgtca ccgcaagatc ttgcgcgaca catccaggg    180
catcaccaag cccgccatcc gccgtctggc gcgtcgtggc ggtgtcaagc gtatctccgc    240
catgatctac gaggagaccc gcggtgtcct caagaccttc ctcagggtg tcatccgcga    300
cgccgtcacc tacaccgagc acgccaagcg caagaccgtc acctccctcg acgtcgtcta    360
cgccctcaag aggcaaggcc gcaccctcta cggtttcggt ggttaagcag ctcgctcttc    420
tctcttcgac tgctttgctt tcttcaaaca caataacaat cacgacaaca caacttcat    480
cagatatcca cccacaatgc gagagttggg cttgcgggta tggcgcgaat gggcaatggg    540
ctatccgggt tttttcattt ttggggtttt tttctctttt cctgtttcga tgctgcgagg    600
tgagcacact gggctgcggc tcatgaggct ttgagtgtag aataggctca acatcatcaa    660
agaagcattc cacgagacgt ggcgctttct tcatcaacca aatgaatatt gcagc         715

SEQ ID NO: 10          moltype = DNA  length = 503
FEATURE                Location/Qualifiers
source                 1..503
                       mol_type = genomic DNA
                       organism = unidentified
SEQUENCE: 10
aatcacccaa atgttctcta aactcatcgc catcgcctct cttgccctcg ctgccaacgc     60
tgcagtcatc gacccaagtg accacactgt ccaatacgaa gctgcaccag gaaaggttgt    120
gactgagcac tacgaggttc tcagccacgc cgaagcatcg cgcataatcg aagccaatcc    180
acacatcagc gactatcgct acagatgcaa ctaccaatgc aacgatagca gcggcaacta    240
catgagaaac ctgcagcagg gagttccaaa ccaagcatgc atcttctcta gctgctacga    300
ctgtgactgg aaattccaaa actgtagcta ctgtcgcttg tcgactggcc acaactaccg    360
tgatatcggt ggactcgaga gctggtgcta caacaacggc ggtactacag tgacgcacaa    420
ctgtgggtat actgatggcg accaatgcta agagcggcct tgtaaagtaa aacttgtact    480
ctgaatttgc ctttatcttt ccc                                             503

SEQ ID NO: 11          moltype = DNA  length = 580
FEATURE                Location/Qualifiers
source                 1..580
                       mol_type = genomic DNA
                       organism = unidentified
SEQUENCE: 11
atcatctcaa acccaattat cttgaacacc tagtttctca agaacatcct caaaatgcac     60
ttcaaatctc tctttattgc tggcgccctc ttcatggtcg gtgccagtgc cgttgattgt    120
gccactcctg agattcactg cgagactagt gatggcagcc cctggtacga cgatgccgtc    180
caagccactg aatactggaa agaaatccag gacgccggca agacagctg cggtgatgct    240
ggttgcgcac agccccatgg ctctggatgc cacagcgacg tggtgactta tgtaccgcgt    300
gagatcgttc tctgccagga tgactcgtcc tcttcaactc cccaatgtgc cgactgccgg    360
tgtgtctaca gctacctgaa gcctcttctc gaccaatgca agggtgccaa caacaagatt    420
ggtggatatg ctcatgttga catgggaggc aactacatca actatgaatt tgttaagaaa    480
tgagcggatc tcacgtgtgt gagaccatca tatagggttt tgaagtctgt ttcctttgta    540
tttaacgtcg aaagacaatt atgagccagg tttatactcc                          580

SEQ ID NO: 12          moltype = DNA  length = 607
FEATURE                Location/Qualifiers
source                 1..607
                       mol_type = genomic DNA
                       organism = unidentified
SEQUENCE: 12
cgcgccgggg gaaattggac catgatagac gacctcacca ctggctcaga ggacagcttc     60
tccaacagct ggatatcgtg gttcttatct accaaaggga cgagtactt ctgtgaggtg    120
gatgaggagt acatactgga cagattcaac ctcactggcc tcaacaacga cgtgcagaac    180
```

```
tactcgcagg cgctggagct catcacagac agcctcgacg acgaggacct cgatgatgag    240
cagagagacg ctatcgagaa cagtgccagg tatctctatg gcttgatcca cgccagatac    300
atcattacct cccgcggact ggcaaagatg ctcttcttgg tgtacccgca gcagctgccg    360
tcaaagacga cgaactcagt gccgagcacg aagccggcaa cttcagcaga cgcagcggtc    420
ggggtggaca ggtacctgcc caagatattc gggttcccgg tgcacgagat gtccaagcac    480
gcgaggtggc aggaggcgca gagggatctg cagatttcga ggctgcagca aagtgcgagt    540
gacccgtcgt acgtgtagag cgttcaaaca tgtattacta ttggtataat aatttaactt    600
tactgcc                                                              607

SEQ ID NO: 13           moltype = DNA   length = 1406
FEATURE                 Location/Qualifiers
source                  1..1406
                        mol_type = genomic DNA
                        organism = unidentified
SEQUENCE: 13
aagttacccg gcttattagt cctagattcc gagatgtcgc tcactcccga acaaaccgaa     60
atcatcaagg ccaccgtgcc tgtcgttaaa gaacatggca agaccatcac caccgttttc    120
tacaagaaca tgctcgaagc gcatcctgag ctgaacgcca ttttcaacac taccaatcag    180
gtcaatggtc accagcccaa cgcactcgcc ggagccctct cgcctacgc ctccaacatt     240
gacaaccttg gcgccttggg ccctgccgtc gaactcatct gcaacaagca tgcttcgctg    300
tatatccaac ctgagcacta cggcatcgtc ggcaagttcc ttctcgaagc gatgggacag    360
gttttggggtg acgccttgac tccgcagatc ctcgacgtc gggcagctgc ctactggcag    420
ctcgccaacc tctttattgg tcgcgaaagt gctatctaca agcagagtga gggatggaca    480
cagtggcgcg agttccgggt tgcacagaag gtccctgagt ccgcggagat cacatcgttc    540
tacctcaagc ctgtcgacga aagcctttg ccccgcttcc gccccggaca gtacatttcc     600
gtccaagtgc acgttcctca gcttgaatgc cccaagctc ccaatactc cctcagcgac      660
aagccccgcg acgattacta ccgcatcagc gtgaagaagg agacgggtct caacacagca    720
aagccggagg ccaaggtcaa cccggggttac gtctcgaata ttctgcacga aacgtcaac    780
gagggcgacg tgatcaaggt gtcgcaccct tgcggcgatt tcttcttgac cgagcaggaa    840
ccgtcgcacc ctgtcgtcct catcgcagcc ggtgtggtc agccagccact tacctcgatg    900
ctcaacacat tggactccac ccccgcggac tctcagcgca agattcactt catccacggt    960
gcgcgcacca cttccgtccg cgctttcaag gaccagatta agtctcgcgc tgagcgactc   1020
ccgaatctcc aggccacctt cttcaccagc tccccgtcgg cagatgaaaa gcaaggcgtc   1080
gactatgacg tccagggccg tatcgatgtg tccaagatgg atgccagcaa ggatctttc    1140
ctcgacaatg cgcagaccga gttctacatt tgtggtccca cttccttcat gaatgatac    1200
gcgaacagct tgaaagctcg gggggctacc tcggagcgta tccacatgga attgttcggc   1260
actggcggcg tgcctgttta gatgatggct cagttagccg tgattgggtt ttatttcttt   1320
acgacgatat gactcaggtt tctaagttag tatacataat catgataat tcttatatag    1380
atatatcaat aatacatctc ctctcg                                         1406

SEQ ID NO: 14           moltype = DNA   length = 750
FEATURE                 Location/Qualifiers
source                  1..750
                        mol_type = genomic DNA
                        organism = unidentified
SEQUENCE: 14
gggtctcttc catttgaatt tttcaaccca cagcatggcc ttcatgaatc tcccatggcc     60
cactgaatgc ctgcatgccg ctctcaagaa cggatcctta cctttctggg gatttgtaat    120
ctatcgaacg acctacaccg ctcagtcaga tgccgcctgg ccgcagatta cgagctctat    180
tgcctcctat atgaaagcct tactctacca cgagtataac gacaagaaaa aagatggaga    240
tgagcgtaca gtcacgacg aaatctgggc aaggcatcag ttgacgatta tggatgatag     300
acaattcaac ggagcgtctg tgttttgatat ccaacttcac ttcgaaaagt gggttgaggc    360
gcagggaaag cgagatgaat ctactatgta tcgcatgtgt atggtcattg atgatgaatc    420
aatccagacg ttattggagg cgccaccggg ggaaaatagg aaactcggac gacgtatagg    480
gggccctgta cgcttttgtca aagtcgtgga ggctttccc tgactagaca gccttgacga    540
attccaggga tggatgaaat gtgagatcaa cgcgttatgc ccgctgtgga agatgatgct    600
tgacggagat gaaatgagga tgtcatatga tgagatgaag gggaatggaa agcaggtcta    660
tggcgcaatt taatcggttt ttcttcatgt tatcctgatg gaaaaatgg cagaacatat      720
gtctgtacat gcagaaaata aggtgattgg                                     750

SEQ ID NO: 15           moltype = DNA   length = 811
FEATURE                 Location/Qualifiers
source                  1..811
                        mol_type = genomic DNA
                        organism = unidentified
SEQUENCE: 15
gacaccacct cttttcgac aaccacaccc cgtttcgcag gaagtccatt tccagcagtc      60
aaaatggccc gtcgtcccgc gagatgttac cgctactgca agaacaagcc ttaccctaag    120
tcccggttca accgtggtgt tcccgacccc aagatcgactt tcttcgactt gggtcgtaag    180
aaggcttccg tggacgactt cccctgtgc gtccacatgg tctccaacga atacgaacag    240
cttttcctccg aagctctcga agctgcccgt atctgtgcca acaagtacct cgtcaagatc    300
gccggtaagg aaggttttcca cctgcgtgtc cgcgccacc cctccacgt cgtccgtatc    360
aacaagatgt tgtcgtgcgc tggtgccgat cgtctccaga ccggtatgcg tggtgccttc    420
ggtaagccca acggtgttgt cgccccgtg aacatcgac agatcctcct gtccatccgc    480
acccgtgact ccaaccgcgc cgccgccgtt gaggccatgc gccgctccac ctacaagttc    540
cctggtcgcc aaaagatcat tatctccaag aactggggct tcacccccgt ccgtcgtgag    600
gagtacgtca agctccgcca ggagggcaag ctcaagcagg acggtgccta cgtccagttc    660
ctgcgtggcc acggtttggt cgaggagaac atgaagcgct cccccaggc ctacgagggc    720
gttgctcagt agattgggat gaattaggtg gttttatgtg ctggtcgtat ttatcgtttt    780
```

```
tactagggcc aaatgagaac aaaaaaaggc t                                    811

SEQ ID NO: 16          moltype = DNA  length = 923
FEATURE                Location/Qualifiers
source                 1..923
                       mol_type = genomic DNA
                       organism = unidentified
SEQUENCE: 16
gtctttagtt ggccattgaa cactgacaga tttgcattgc ttatatttgc atctacctca      60
catctactca actcctcctc tccgtttgtc atgtccttct accagtctcg tccagacact     120
atcaagggtc ctgatccttt gaccgacaat tggacttatg atagtgccat tgatctcttc     180
tcttggaatc ccatgatgcc cgatcctttt acctttgacc tgcccgacga tcttatgaaa     240
tttgaatcta aggatatgtc tgctggcatg gtcgctcctt cggacattag tggttttgcc     300
attggtaacc atttgggcga ggatgctgcc tcgatatcg atcccgagag tgatgaccac      360
ccatggtccc cctccgctca tgctgccttc ccggagctct ctcccatcac atcgacagag     420
caagtccatc aagaaactgc tcgatactca actaccccg atgccacctc acctcaagaa      480
caaccctcct caccaccaac acgatctact cgccgccgat catccgctga cggtcccgtt     540
cgcaacgctg ccaaacgagc agcccacaac gtcattgaaa agcgctacag aacaaacatg     600
aatgccaaat tcgtggcact cgagaaagca atgaatggcg taatggcgt gcaaacatca      660
tcaagaggcg gagggtccgc gtcgcttaag aaatccgaaa tcctctctaa tgctattgcc     720
tacatgcatg gactgcaaga ggaaaatcgc tatttacaaa aggagcttgc tatcgttaaa     780
cagaatcttg taccggcagg gatatggcga ggggctccta gttgtaaacg ggagacgagt     840
tatcgttaac ttgttgattt ccctgtggtt gtttagattt tttttacgat gttacgtgta     900
taataatact ctcccctcgg gtc                                             923

SEQ ID NO: 17          moltype = DNA  length = 1046
FEATURE                Location/Qualifiers
source                 1..1046
                       mol_type = genomic DNA
                       organism = unidentified
SEQUENCE: 17
ggacaagccc atcttcaatt cgagacagtc gccatgggtc gcgttatccg caaccagagg      60
aagggccgtg gctccatttt cacggctcac acccgtctga acaaggctcc cgcccagttc     120
cgtaccctcg acttcgctga gcgtcacgga tacacccgtg gtgttgtcaa ggagatcatc     180
cacgatgccg gccgtggtgc tcccctcgcc aaggtcagt tccgccacct ctacaagttc      240
aagatggtga ccgagacctt catcgccaac gagggcatgt acaccggtca gttcatctac     300
gccggtaaga acgctcagct caccgtcggc aacgttctgc ccctcgcctc catgcccgag     360
ggtaccgtca tctccaacgt tgaggagaag tccggtgacc gtggtgcgct tggccgtacc     420
tccggtaact acgttaccgt cattggccac aaccccgag acggcaagac ccgtgtcaag      480
cttccctccg gtgccaaaaa ggtcatcaag aacaccgccc gtggtatggt tggtatcgtc     540
gccggtggtg gtcgtaccga caagcccctg ctcaaggctt cccgcgccaa gcacaagttc     600
gccgtcaagc gcaactcttg gcccaagact cgtggtgttg ccatgaaccc cgttgatcac     660
cctcacggtg gtggtaacca ccagcatatc ggtaaggcct ctaccatctc cgctacggcc     720
gcccagggtc aaaaggccgg tctcattgct gcccggagaa ccggtctgct ccgtggtacc     780
cagaagacca aggattaagc gtgatattac gtggagtttt ctttgtgacg ggttgaaaat     840
ggacttctgc tatgagacat atgtacttag gcgagtgcgg ataagcgtcc catgcgccct     900
tagcgaatta aggttgtggt caccatcctt ttcttttat taaatcaaaa aagggtgatg     960
gaatggggtc cgaggctggc ctcaagtcaa ggcagaacgg aaaagtcaaa aatgcccctt    1020
ggggttttgg aaatgataca cctttg                                         1046

SEQ ID NO: 18          moltype = DNA  length = 780
FEATURE                Location/Qualifiers
source                 1..780
                       mol_type = genomic DNA
                       organism = unidentified
SEQUENCE: 18
ggcgcagagg cctattactc cccagtatca tcgctaatag gcatgtccac gggtctaagg      60
ttcagcactt tgccagctgc ttccaatcca cagtcgtcgt cattgatacc cagccctagt     120
gctcccatat caacttttcc atatacttta acactcacgc taactcccct gacgggatcc     180
ctctcaacct catactcatt acgcgcctct cccaatctgt catttagctc tcggttcggt     240
ttcaatgttt acagttggga aagcgagatg gtagcgggat ttgaactatg gcgacaatcg     300
aaaaagccca agttggccgc gggaagcgat ggcgacgatc ttgaatgggc ccgcaggaag     360
gtccgtgtct gggatcctc agcttttccc ctggcaccc ctgaacctga atcccacaa       420
ccaaaccatg aagatgagtc tcaagagtca gtacttaagc ccagagtcga ccaatcctga     480
aatgttcgtc ttctctggga aggtcgggtg aaggagcttt tggtcagcgc tggtgtcggg     540
ctcggcccga gttcctctc accatcgtca tatgcaaatc ccccgggtac agccggggct     600
caaggcagcg gtggggctc accggcctca tactggaggg gcgtgggggg tttcggtatc     660
atattcttca tgagggattt cttcggatct atgtacttga atgagcactg tctagatgta     720
tatagtttat cagatttttat gagacaatag acaccatgaa tctgcgttat tgcgagacgg    780

SEQ ID NO: 19          moltype = DNA  length = 896
FEATURE                Location/Qualifiers
source                 1..896
                       mol_type = genomic DNA
                       organism = unidentified
SEQUENCE: 19
ggccctggcg tgctttctgg cttttcaacct cccgacctcc ctctaattac tcaattgaa      60
ctcgatttag acgtggtgct gccacctccc gcctgccgca caatgtttct tcgcaccgtt     120
tctcgcgctg tccctcgcag caccgcggcc atccgtgctc caccgactgc ctctgtgaac     180
```

```
gccctgcaga cccgcgctgc ctcggaccat gctatcccca accctaccct cgcaacatt     240
gagaagcgct gggaggtcat gccccctcag gagcaggccg agctctggat gcagctccgt   300
gaccgcatga aggttgactg gcaccagatg accctgcagg agaagaaggc cgcttactac   360
attgccttcg cgcccacgg ccccccgcgcc cagcccccca agggtgaggg catgcgcgtg   420
ttcgccaagg tgctccagct cactgccgcc tccgttgctg tcttctacgc catccacgcc   480
ttcgccggca agcagcccgc caccatgtcc aaggagtggc aggaggcctc caacgaatat   540
gccctgaaag agaagatcaa ccccatccac ggcatcagca agagggtta cgaaggcaag   600
ggcttcgtcc agagccccccc tgccgagaag tcataggtgt accagttgcc cgaccgggaa   660
tgagttgata tctacgccgg acggacggcg gcacccatcg cacgatctat atgtcgatct   720
tattacaagc tactctttcc atagccatgt tcgacatgtc tttgtgtcgg aggatgggcc   780
tccgcccgtg cgcgcggccg tcgattgttc cattctatct tttttggcaa gcattggaaa   840
atgcgtgtat cccgtactgt gctataatca atgtatctct tttgtagcca tagagc        896

SEQ ID NO: 20            moltype = DNA   length = 641
FEATURE                  Location/Qualifiers
source                   1..641
                         mol_type = genomic DNA
                         organism = unidentified
SEQUENCE: 20
gtggcgcgcc gggggggcat ctacctcgac ggcaacaacg acctggtcac tatgaagggt    60
aactacatct accacaccag cggccgctct cctaaggttc agggtaacac cttgctgcac   120
gctgtcaaca actactggca cgacaactcc ggccacgcct tcgagatcgg tgagggtggt   180
tacgttctgg ccgagggtaa cgtcttccag gatgttacta cccccgttga ggaccccgtt   240
gacgccagc tcttcacttc ccctgacccc agcaccaacg ctcagtgtct gtcatacctt    300
ggccgggcct gcgaaatcaa cggcttcggt aactctggta ccttcaacca ggctgacact   360
agcctgctgt ctaaatttaa gggtcagaac attgcttctg ctgatgctta ctctaaggtt   420
gcctcgagcg ttgccagcaa cgccggtcag ggacaccgt aaaatggaaa gaggaggttc   480
agagcttaat ttgctcatgt cggacgacat agccctagcg gcttgctggt gaatttggca   540
taatagcgtt tctcttctca tacctacttt attactccgt ttggatcctt attaggtaaa   600
tattagccca ttgtatggtt caattcgatt gactttgagg c                        641

SEQ ID NO: 21            moltype = DNA   length = 591
FEATURE                  Location/Qualifiers
source                   1..591
                         mol_type = genomic DNA
                         organism = unidentified
SEQUENCE: 21
gtggcgcgcc gggattctca tcatcagata aaatcaagat taatcttact ggacatcaca    60
acgatccaac acaaagttcc ttcatacttc aaacaaatct ctacaattga atcaaaatgc   120
catccaaaac cgaagcagcc cgtctacaaa acgacttcgg cgcagactac tgggttagaa   180
ataccccaaga acgccgccac tcaaccgctg gccgcggact attcgccggt ctccaggatg   240
tcaagcacta taacgtcgac catggctggg ccgtcgcaa gtctagcgat aaccccggac   300
tccttgcttc tttcttcagt cgattcaccg ggggatcaa tcatccgcg tcggaataga   360
attccttttc ttaatgtgcg atattgggag gagtgtgatt tgaattggga ataagggaaa   420
agagtgcttg gaatatttga gtctcagact taactcgagt caagtttcat ttatgagtat   480
actgaggttt ttgtgttagt agcttggagt ttgggtggtt tattagtatt acctattgca   540
ttaccatgtt tatacatcgt gaatcatcga atgaatacca tgtcttcaat t             591

SEQ ID NO: 22            moltype = DNA   length = 639
FEATURE                  Location/Qualifiers
source                   1..639
                         mol_type = genomic DNA
                         organism = unidentified
SEQUENCE: 22
gtggtatcaa cgcagagtga cgagcccacc atccccggag gcgccgctgt caccatccac    60
tcccgtaacg agaagaaggc ccgtaaggcc attggcaagc tcggtctcaa gcacgtcccc   120
ggcatcaccc gtgttactct ccgccgtcct aagaacatcc ttttcgttgt taaccagccc   180
gatgtctaca agtcgccttc cagcaacacc tggatcatct tcggtgaggc caagatcgag   240
gacctgaact ccaggcccca ggcttccgct gctcagcagc ttgccgccgc cgaggctgcc   300
gccggaggtg agcacgctgg tcacgaccac gagcagcgaa tcctcggcaa gggcaaggcc   360
cccgagaccg agggcaagaa ggaagaagag gaggacgacg cgaggaggt tgacgaggcc   420
ggcctcgagg ccaaggacat cgaccttgtc atggcccagg ccaacgtctc ccgcaagaag   480
gccgtcaagg ccctccggga acgacaat gatatcgtga actcgatcat ggctctcagc    540
atatgatttg gctgcctgcc ggcaggatga atgagtgagc tttgggcgcg aggtcacgtt   600
gatatccctg ttctgggccc tctcccttaa gtgtatagc                            639

SEQ ID NO: 23            moltype = DNA   length = 832
FEATURE                  Location/Qualifiers
source                   1..832
                         mol_type = genomic DNA
                         organism = unidentified
SEQUENCE: 23
gctcccaacg tcaacacccc ctccgccttc ccctcgacg ttactcctgc ccgtccgatt     60
acaacaagga gaatgttcct tcagcgtacg gtatctaccc tcgcgaggcg caccccgtg   120
cggggccttg ctgccgcgcg cccgtttttc tcgtccgtta gccgattcaa caagtacgag   180
gttaaggagg ccaagctccg ttctcttgac gagatccaaa ctgaagaaga cctcatcccc   240
cctggtgcta agcccggtac cgtccctagc gatatcgaac acgccactgg tctcgagcgt   300
ctcgaactgc tcggtaaaat gcagggaatt gacatcttcg acttgaggcc tctggatgct   360
tcccgcaagg gaaccctcga aaaccccatt gttgtcaacg gtgctggtga cgagcagtac   420
```

```
gctggttgca ctggttaccc cgtcgactct caccaggtta actggttgac tgtctctcgt    480
gagcgcccca tcgagcgctg caacgaatgc ggtaacgttg tcaagctgaa ctatgtcgga    540
cctgaggagg accctcacgc tcacgaccac ggccacggcc accacctgc ccccgaggag     600
cccaagacct tcgccgacta cgtcaagccc gagtactggt accggtaaat accccagcag    660
tacgacgcga gagttttcaa aaaagagaat aagaaacaag caaagggacg gatcaagacg    720
ggctagtgcg ggaatgtcaa acgcaacata tttaagcatt gggtctacta tatacgggtt    780
cattcgtcca ttgattcctc ggtctagtgt tttcttgaac gtctttagct gg            832

SEQ ID NO: 24          moltype = DNA   length = 832
FEATURE                Location/Qualifiers
source                 1..832
                       mol_type = genomic DNA
                       organism = unidentified
SEQUENCE: 24
ccagctaaag acgttcaaga aaacactaga ccgaggaatc aatggacgaa tgaacccgta    60
tatagtagac ccaatgctta aatatgttgc gtttgacatt cccgcactag cccgtcttga    120
tccgtccctt tgcttgtttc ttattctctt ttttgaaaac tctcgcgtcg tactgctggg    180
gtatttaccg gtaccagtac tcgggcttga cgtagtcggc gaaggtcttg ggctcctcga    240
gggcagggtg gtggccgtgg ccgtggtcgt gagcgtgagg gtcctcctca ggtccgacat    300
agttcagctt gacaacgtta ccgcattcgt tgcagcgctc gatggggcgc tcacgagaga    360
cagtcaacca gttaacctgg tgagagtcga cggggtaacc agtgcaacca gcgtactgct    420
cgtcaccagc accgttgaca acaatggggt tttcgagggt tcccttgcgg gaagcatcca    480
gaggcctcaa gtcgaagatg tcaattccct gcattttacc gacgagttcg agacgctcga    540
gaccagtggc gtgttcgata tcgctaggga cggtaccggg cttagcacca gggggatga    600
ggtcttcttc agtttggatc tcgtcaagag aacggagctt ggcctcctta acctcgtact    660
tgttgaatcg gctaacggac gaagaaaacg ggcgcgcggc gcaaggccc cgcacggggg   720
tgcgcctcgc gagggtagat accgtacgct gaaggaacat tctccttgtt gtaatcggac   780
gggcaggagt aacggtcgag gggaaggcgg aggggggtgtt gacgttggga gc          832

SEQ ID NO: 25          moltype = DNA   length = 1263
FEATURE                Location/Qualifiers
source                 1..1263
                       mol_type = genomic DNA
                       organism = unidentified
SEQUENCE: 25
acccaaaccc tgcgaagcaa aacgcgttac tcgatttggt catttcctcc aaagcatcat    60
tcctctttgg gcactgcctg tttcgtccat taatcaactg tgcttgaatc tctaactatc    120
ttttgatata ccctctttat ctctctcccc tttaatcttt ttctctctt ctctcttttc    180
cttttctttt cggttactca ctatcatggc cgacatccat cgcgtcggtg aggagaaccc    240
ttctcctacc caggatgagc tgcagcaggc cgcggccggt aacggcgctc ctgataaccg    300
cactcccaag cgtcgcatga gtgacgatga agaggacgag gagaagcagg gtcgcgagcg    360
cagaaagatt gagatcaagt tcattcagga taagtcgcgt cgccacatca ccttctccaa    420
gcggaaggcg ggtatcatga agaaggcata cgaattgctc gtcctcacag gcacccaggt    480
gctgttgctg gtcgtgtccg agaccggcct ggtctatacc tttaccaccc ctaagctcca    540
accattggtc accaaggcgg agggcaagaa cctgattcag gcttgcctca acgccccga    600
ccctaccacc agcgagaatg gcgtcgatgc ccccgaggtc ccagcggaga ccccgagga    660
tgtcaaccac gccaacgtca acgctgccgc agcccacatc accaacatcc ctcgtcccac    720
cggaatgcat cccggctaca tgaccaacga caacagcag cagatggcct actaccaaaa   780
ccacctccag cagcaacagc aggccggtgg gcagtaccct ggcatgtctg tcggtggtcg    840
catgcctacg cagcaccagc ctaccgcata atcttattta ctcttatcta cgctcccacg    900
cacctcctct ttctgatttc cctgcatatg gtcttgtttt tagtagctga ggagtccaga    960
gttcagttgt ttttgccttc tttccgcatc tacccttttat tttcccctct ttcgttatta   1020
tctctctccc ctgacatttg atacccgaca atccgttgt tcaatccatc gtcgcatgaa    1080
aacgggtcct ataaatataa tgcatccccc tgtttacttt cgactgcgaa cgagagcatg   1140
caaatctgaa gaacagcatg gtcaattgtc tcagtaacct cgttaaggcg ccgatgagtt    1200
tggcgtttac atactctgct ttggaacgtg tgatgccttt ttaccgttca atgaaagcga   1260
ctc                                                                 1263

SEQ ID NO: 26          moltype = DNA   length = 1066
FEATURE                Location/Qualifiers
source                 1..1066
                       mol_type = genomic DNA
                       organism = unidentified
SEQUENCE: 26
aggctttgat ggcctcttca aaggggaaca ttgttcactc gaccagagtt gagtagagcc    60
aagaccattc cataatctcc aggggcatat cgccatgccg tcttgtcaag acgatctcct    120
tctcacacat attgatgata ggtaccgtta gattggactc ggttgaaccg agtccaattt    180
ggaactacga ctcctcccgg gcctgatttt gcaacgagga ttccactccc gtacactaca    240
gaactatatc gacaccgtcg ctgagattca atgtattctt tcattcgact ggcttcttcc    300
tccgggtgag acgagctgat atttgggaga aatattggac atcccagata atctcgcgca    360
aagtctagtt tggtctggtt gatatcggaa atgatcactt gtttggctcc aaacgctgtg    420
gccgtcgctc cacagaacag accgatagtc cccgacgctt gtaccaggac agtatgaccg    480
ggagtgatac ctgccacccg agctccatga attgcaacac tcaacggctc gaccaaaaca    540
gtttcttcaa gtgagaaatt tcgggaatc ggatacacca aatcctcggg tgcgcggaat    600
agatgggtca gagtcccatg gttattgggg ggaggatccg cggcaaagct catctcggaa    660
aaaatatcat atctccctgc tttacattgt ttacatcgtc gacgagagaa actagctcga    720
tggcaaagcg gtcgccagga atcactttg tcactgccgg tccaattgag tgcacgatac    780
ctgatgcctc atgacccatg accagtggtt gctcgtcaga gaccattcga agtacccgc    840
cgtgtttcca gaaatgggcc tatggaattg gaaattagca aaagagaccc tggtgaaagg    900
```

```
aagagggatt tgtggggact catatcgctc ccatacacac ccacatacgc gatgcgaact    960
aatatatcat agggatcact gagggtaggg acatcgcggt actcaagtcg agctttccca   1020
ggcccgtaga gtaggcagga caaattattc tgaaattatg atcaac                 1066

SEQ ID NO: 27           moltype = DNA   length = 1066
FEATURE                 Location/Qualifiers
source                  1..1066
                        mol_type = genomic DNA
                        organism = unidentified
SEQUENCE: 27
gttgatcata atttcagaat aatttgtcct gcctactcta cgggcctggg aaagctcgac     60
ttgagtaccg cgatgtccct accctcagtg atccctatga tatattagtt cgcatcgcgt    120
atgtgggtgt gtatgggagc gatatgagtc cccacaaatc cctcttcctt tcaccagggt    180
ctcttttgct aatttccaat tccataggcc catttctgga aacacggcgg ggtacttcga    240
atggtctctg acgagcaacc actggtcatg ggtcatgagg catcaggtat cgtgcactca    300
attggaccgg cagtgacaaa agtgattcct ggcgaccgct ttgccatcga gctagtttct    360
ctcgtcgacg atgtaaacaa tgtaaagcag ggagatatga tattttttcca gagatgagct    420
ttgccgcgga tcctccccc aataaccatg ggactcctac ccatctattc cgcgcaccg    480
aggatttggt gtatccgatt cccgaaaatt tctcacttga agaaactgtt ttggtcgagc    540
cgttgagtgt tgcaattcat ggagctcggg tggcaggtat cactcccggt catactgtcc    600
tggtacaagc gtcgggact atcggtctgt tctgtgcagc gacggccaca gcgtttggag    660
ccaaacaagt gatcatttcc gatatcaacc agaccaaact agctttgcgg cgagattatc    720
tgggatgtcc aatatttctc ccaaatatca gctcgtctca cccggaggaa gaagccagtc    780
gaatgaaaga atacattgaa tctcagcgac ggtgtcgata tagttctgta gtgtacggga    840
gtggaatcct cgttgcaaaa tcaggcccgg gaggagtcgt agttccaaat tggactcggt    900
tcaaccgaag ccaatctaac ggtacctatc atcaatatgt gtgagaagga gatcgtcttg    960
acaagacggc atggcgatat gcccctggag attatgaat ggtcttggct ctactcaact   1020
ctggtcgagt gaacaatgtt cccctttgaa gaggccatca aagcct                 1066

SEQ ID NO: 28           moltype = DNA   length = 564
FEATURE                 Location/Qualifiers
source                  1..564
                        mol_type = genomic DNA
                        organism = unidentified
SEQUENCE: 28
agactcaacg ataattcaat acccagttgc aacactattt gttttctaaa catatcctca     60
agaccaattc taccttaatc tccccaacac aactcaattg aaaacataca ccatgcctcg    120
cggagccgaa tacgccaacg gtcctctcca gagcgacaat gccatcgaag ctggcgaaaa    180
taaggccacc ggaacctccg gtaacaccgg cctcaaccgc gtcaacaagg tcgccgaatt    240
ccccgaaggc gccagaggaa ccggtaccgc tgctaacccg ctcagtggcc agggtagcgc    300
cggccatcag gatggaaagg gtggccatga cccgaagacc cttggagaga caagggact    360
gggtactcaa tgatcttatg attcagaaga catgagttat ttgcatgagc tgggctcgct    420
gcgattctgt gggattctgt gatttgtaat atgatttgca tgggtcaggt cagacttaat    480
taagcatgcg ctattgtttc cgttatgctt atgatatgga tgggtccatg gttggagttg    540
ataatctaat atggaattga agtg                                          564

SEQ ID NO: 29           moltype = DNA   length = 39
FEATURE                 Location/Qualifiers
source                  1..39
                        mol_type = genomic DNA
                        organism = unidentified
SEQUENCE: 29
attccatcta aagctaaata ttggcctgag accgatagc                           39

SEQ ID NO: 30           moltype = DNA   length = 577
FEATURE                 Location/Qualifiers
source                  1..577
                        mol_type = genomic DNA
                        organism = unidentified
SEQUENCE: 30
gagactatga cgacgatcac agagttcccg ccattctaca cgcagcagcc gaatgcgagc     60
gcgctgacgc agcagctggg gctgtggcag aagcatatac tgagcacgtg caagcagcgg    120
cggcagttca agctgagcgt gagtgatgat atctgggcca acgagaggat aaagcgagct    180
gcttctcgtg aatttatttc tgtgattatc tcctcgctgg tgacagaagg gctagcgagc    240
tatacagacg ccaccaagga ggctgtgtgg gtgtactcag gggagtctatc tgattgggcg    300
caggcggcgt acgcgtacgc ggaaagcaca gcgcagctga acacgccgtt gacgtactat    360
gagctagtac aaggggagta cagccatcta tctgagctgc atgagatgcc agtagagctg    420
ctcaagcttg ctgtgtcgct gctggtgaag cagaacaaag cggtgataat caaaacgagt    480
caaggggaag gtgtcaaatt cgtctagtat agaataactt aggttacatt ggaatctggt    540
aatcaattcc cttgtcattc agcttctgct gctttcc                            577

SEQ ID NO: 31           moltype = DNA   length = 606
FEATURE                 Location/Qualifiers
source                  1..606
                        mol_type = genomic DNA
                        organism = unidentified
SEQUENCE: 31
gggaacaaac tctcattcta actaaatact ttttactctc tgctcccta tcgcattctt      60
tttaggacat tcagaaggtg atcgcttgac caaatgtcta tcccaaaagc ggcagctcat    120
```

```
accgacaagg cgcctcagcc tttcaaggac ctctattcgc aagcagttat tgctggtggc    180
gtggtctatt gctctggaat tgttgccatt gaccctgaaa ccggtagcct gattgaagga    240
gatgtcaagg ctcatacgga acgaatttta caaagccttt ctagtactct acaggccgcc    300
ggtaccagtc ttgatcgagc tgtaaagatc aatgtttacc tagcaaacat ggaagacttc    360
acatccatga actcagttta cgaaaagtat tttgtggatg gagtgaaacc ctgcagaacc    420
tgtgtggctg ttaagtctct acctttggc actgatgttg agatggaatg cattgcagta    480
ctgtaaatgt ttagttttat gcgcaactga gaaagacgga aggatcatcc tattactttt    540
tcgaatgtgc tctttggatt tctctgttgg atacacaaca atgccacaca ttgggtacaa    600
ccagat                                                                606
```

| SEQ ID NO: 32 | moltype = DNA   length = 411 |
|---|---|
| FEATURE | Location/Qualifiers |
| source | 1..411 |
| | mol_type = genomic DNA |
| | organism = unidentified |

SEQUENCE: 32

```
ggaaccaatt acatccatca accaaaccaa caaaatgctg agatctcaat tcggtgtaat    60
ttcaaacgca gcaaagacag ccgcattcct caagcctgtt caaaccagat tgtacgctag    120
tggcgctctc tcgaagggcg acatccaaac tcgcatttt gatgtcctca agtcgtttga    180
taaggtgaag gctgataacc tcactgaatc ggcttctttc accaacgacc tcggcttgga    240
tagcttggac gccgttgaag tcgttatggc cattgaggag gagtttgcca tcgaaattcc    300
agacgctgaa gctgacgcaa tccaaaacgt gaaccaggct atcgaataca tcgccaaaac    360
ccctgaagca cactaaacac gctaaataat tttatcaatt catttcaaac g            411
```

| SEQ ID NO: 33 | moltype = DNA   length = 619 |
|---|---|
| FEATURE | Location/Qualifiers |
| source | 1..619 |
| | mol_type = genomic DNA |
| | organism = unidentified |

SEQUENCE: 33

```
gtggtatcaa cgcagagtgg cgcgccggga acgaagaaag tttcttcgac ctacctatca    60
aagatatgta aggagcaaca taaatcaata ttcttttatc tgattgacct tcactctagt    120
gcctcgctac gatcagttac aaccttgccc gcgcgaatgg aacgtatacg actttccgaa    180
caggccgcga cgatttgcaa ccaaattcgt gaaatgatac cagagactgc cactttgccc    240
aatcaacctg gcaaggatca agctgaactc atgcatgaag atgaaaacgg gaataagata    300
tacggcggga aacttttaac ggagagagct gctcgactga aagagcacat gaagattgac    360
caagtgagtg ccagatttat ctcacagtac tttactaatg gcattcagga ctggacagag    420
cgcttggtat attggacaaa gccgacgaaa ctattgaacc aacggaaaca aggatatatc    480
ataccgttat ctaaagacat cgttctacaa cctgggggac ctttagaagc aaataacggc    540
tttcgggtca caaacgagcg gattctgagt tcaggagctg cccttttcat tatgcgccaa    600
tgatattatt ttgaaaccc                                                619
```

| SEQ ID NO: 34 | moltype = DNA   length = 1647 |
|---|---|
| FEATURE | Location/Qualifiers |
| source | 1..1647 |
| | mol_type = genomic DNA |
| | organism = unidentified |

SEQUENCE: 34

```
accgctaccg tcatcactac aaatgctggc tcgcagctta cagcaaatca gacgctcaag    60
caggctgagc ttacaattgc gcgcctacgc cagcagtcca gaccgcagcg caagcttctc    120
taagctctca gagcaagatc tcccatcact cgcctccatc ttctcatccc ccgacacctt    180
cctcctcacc acgctcggcg acaagccaac agccaccagc gacgatctcg agccattcaa    240
cgtcgactgg atgggcaagt acaagggcca ctcttcccata attgtgaaac caagacgac    300
gcaagaagtc agcaaggtgc tgcagtggtg caacgagcgc aacgtagctg ttgttccaca    360
aggtggcaac accggtctcg ttggtggatc cgtgccttg cacgacgagg tcgtcttatc    420
tctctcctca atgaacagca tcagacactt cgaccctctt tccggttacg tttctgtcga    480
ttccggtatc gtgctcgaaa atttggataa ctacctcgca caacaaggac acattgtccc    540
tctcgatctg ggtgctaaag ctcctgtca gattggtggc aacgtcgcaa ccaacgctgg    600
tggtctgcgc atgttgagat acggtagttt gcacggcaac gtgctcggtc tcgaagtcgt    660
tctgccagat ggtagagtaa tcaatggtat gaagggactc aagaaggaca cactggtag    720
cgatctcaag cagctcttca tcggctcgga gggtgttctc ggtgttatca ctggtgtcac    780
tctcgccaca cccgtcagac catccgcaac taacgtcgct gtcttcgctt tgcctgacta    840
tgagtcagtg cagactgcct tctcatcagc tagacgcgat ctcggtgaga tcttgtcggc    900
gtttgagttc ttcgatgctg cctcatacaa gctcgtcgac agccatgaac acgcagctga    960
gcgcaaaacc ttcgaagatg gggaagacgc accatttttc tgcttggtcg agacgtctgg    1020
ctcgaacaaa gaccacacg atgagaaact gggtgctttc ctagagcagc tcatggagtc    1080
aggtatcgtc aatgacggtg tattggcaca agacgagacg caaattggcc agctgtgtc    1140
gctgcgtgag ggcattccag aagctgcagg caaagctggt cgcgtgtaca agtacgactt    1200
gagtttacca gtcgagaaga tgtactcgct ggtgccaaga gtcggccaaa agcttgctga    1260
gaagggtctg cttgccgctg agtcagaggg tggtaatgga gatgggccag tcaagacagt    1320
cttcggattt ggtcaccttg gcgatggcaa cctgcacatc aacattgttg ccgatgctta    1380
cagaaaggag gtggaggaag tcgtcgagcc atacattac gagttggtag ccaagtacaa    1440
tggatctatc tcagcagagc atggtctcgg tctgatgaag gcaccttatg tcgcatacag    1500
tcaagacgcg ccatcgcttg acctcatgcg cactctcaag aagacactcg atccaaaggg    1560
cattctcaac ccatacaagt gcgtcaccgc ggaatagatt ggagttatag atttacgtta    1620
tatgcatgcg atcctgttac attatcc                                        1647
```

| SEQ ID NO: 35 | moltype = DNA   length = 669 |
|---|---|
| FEATURE | Location/Qualifiers |

```
source                  1..669
                        mol_type = genomic DNA
                        organism = unidentified
SEQUENCE: 35
gtcatcaact tcattcagca aaatggctct ctattacggc atcgtatttg gtatcttaac    60
atttgagatt attctctttt tcttattctt gttgcctatc ccaactcgtt ggcaaaaacc   120
agtgttccgt tggttagcta cctcacctac cattgcacat gctcaatata tcatgaaaat   180
tgtatttgta ttcatctttg tgctcttcct tgattccgtc aacactctcc gcgctttcta   240
cgaagtagtg aacactgaag atgagaatgg tggtattcca gctgccggta actctgattt   300
cagagctcaa gttggtcaag ctgcaaagaa gttttatgct caaagaaatt tgtatctcac   360
tggattcacc attctgttat tactcatttt gaacaagatc aagaacatgg ctatggacta   420
tattagattg gaagatcaat tcattgagct tgaaggatcc gtttccaaag atcccgccat   480
cagaaaggca agcaaagaaa tcgacactac tcccatcgaa gaccatgtta caagactcga   540
gcctgttgaa caagaacagg aaaacaaaaa ggatatctaa ttcacacctg taactaatat   600
gtaaacatct ccctcgctaa aagcgcaata aactaaaatc agcatcattg cgtatctctt   660
tcttctcac                                                           669

SEQ ID NO: 36           moltype = DNA  length = 873
FEATURE                 Location/Qualifiers
source                  1..873
                        mol_type = genomic DNA
                        organism = unidentified
SEQUENCE: 36
gtggcgcgcc gggaggcgcc taacggtcat gaattgcctc ctcgcggtta tgatcccgga    60
gaaaacactt accaagcacc acctgatgaa cgtagtcaag tagatgttgc gattgaccct   120
aaatccaacc gtcttcagct gttgaagcct ttccagaagt gggacggcaa ggacatcacc   180
aatgttccta tcttgattaa ggtgcaaggc aaatgcacta cagatcatat ttccatggcc   240
ggcccttggc tcaagtatcg tggtcatttg gacaatatca gtaacaattt cctcattggc   300
gccaagagta gcgaaggcaa agtcaacagc atcaagaatg cttttactgg tgaatacaag   360
ggtgtccaga aacagctcgt gattacaaga aggaaggtc tcgttgggtc gtggtaggtg   420
atgagaacta tggcgaaggc tcctctcgtg agcatgccgc tctagaacct cgattcctca   480
atggagctgc catcattacc aaatcatttg ctcgtatcca tgaaaccaat ctcaaaaagc   540
aaggaatgct tcctttaacc tttgctgatc ccaaggacta tgacaaggtg gacgcctcag   600
ataaagttga tattcttggc ttgactgatt tccaagaagg aaagccattg acccttcgt   660
tgcacaaaaa agatggatca actgtcgatg ttcctttgaa ccatacattc aacggtcagc   720
aaattgaatg gttcaagcat ggatctgcct tgaaccttat gaaggaaaat actgccaaga   780
acggaagctt gtaggtgcac cgttacgtta tcttcacaag catttgtatg tcaaataaac   840
tcgattagtt acttgcactt ttgttaagtt tat                                873

SEQ ID NO: 37           moltype = DNA  length = 874
FEATURE                 Location/Qualifiers
source                  1..874
                        mol_type = genomic DNA
                        organism = unidentified
SEQUENCE: 37
gtggcgcgcc gggaggcgcc taacggtcat gaattgcctc ctcgcggtta tgatcccgga    60
gaaaacactt accaagcacc acctgatgaa cgtagtcaag tagatgttgc gattgaccct   120
aaatccaacc gtcttcagct gttgaagcct ttccagaagt gggacggcaa ggacatcacc   180
aatgttccta tcttgattaa ggtgcaaggc aaatgcacta cagatcatat ttccatggcc   240
ggcccttggc tcaagtatcg tggtcatttg gacaatatca gtaacaattt cctcattggc   300
gccaagagta gcgaaggcaa agtcaacagc atcaagaatg cttttactgg tgaatacaag   360
ggtgtcccag aaacagctcg tgattacaag aaggaaggtg ttcgttgggt cgtggtaggt   420
gatgagaact atgcgaaggc tcctctcgt gagcatgccg ctctagaacc tcgattcctc   480
aatggagctg ccatcattac caaatcattt gctcgtatcc atgaaaccaa tctcaaaaag   540
caaggaatgc ttcctttaac ctttgctgat cccaaggact atgacaaggt ggacgcctca   600
gataaagttg atattcttgg cttgactgat ttccaagaag gaaagccatt gacccttcgc   660
ttgcacaaaa aagatggatc aactgtcgat gttcctttga accatacatt caacggtcag   720
caaattgaat ggttcaagca tggatctgcc ttgaacctta tgaaggaaaa tactgccaag   780
aacggaagct tgtaggtgca ccgttacgtt atcttcacaa gcatttgtat gtcaaataaa   840
ctcgattagt tacttgcact tttgttaagt ttat                               874

SEQ ID NO: 38           moltype = DNA  length = 718
FEATURE                 Location/Qualifiers
source                  1..718
                        mol_type = genomic DNA
                        organism = unidentified
SEQUENCE: 38
ggcgcgccct tgacacagga gcacgggttt cccgtgcgcg tcatcgttcc aggcgtggcg    60
ggcgcgaggg ccgtgaagtg gttggatcac atcacagtgc agcgggaaat gagcagcaat   120
cattatatgc atttcgacta caaggtccta ccaccagaag cggtcgatgc ggaaagggca   180
cgcaccttct ggcataaagt cccgccggtg atcgacatgc cagcgaattc tgccatcacg   240
tcgccacgaa atgaagacac ggtggaagtg gatgcagagg gatttatcac ggtggatggg   300
tacgctttgc cgggggagga agatgggccg gtgaaaagag tcgaggtctc cattgacaag   360
gagagatggg tcgacgcgga actgttaca catcccatgg aaagcaagtg gacttggaaa   420
atctggaagg ccaaagtgca ggtcgagccg ggcgagcgaa gatgtctcta cagcagaacc   480
actgatgaag cgggcaactc gcagccgcag cgttctcagt ggaacctgag aggcgtatgt   540
tacaacggct atgagaagt gaggaatttg aaggtggtga aaggataggc caatcgttc    600
attccatcat ccatcaagat gtgtctgtat gtgtatgaag gctgaagcg accacgggac   660
cccagggtgg tcactaaaca gtactcaaac ggactgtttg gttcgtttga cactttcg   718
```

| SEQ ID NO: 39 | moltype = DNA length = 160 |
|---|---|
| FEATURE | Location/Qualifiers |
| source | 1..160 |
| | mol_type = genomic DNA |
| | organism = unidentified |

SEQUENCE: 39

```
aatcaagttc gactgtcaaa atgccagcca acacgatgtc tgccactctc agatccctcc   60
acgttcccgg gaaaccagtc atcttcgcca atgtctggga caccgtctcc gccaaatcaa  120
tcgcacctct ggattcatgc aaagctctag caacggccag                        160
```

| SEQ ID NO: 40 | moltype = DNA length = 1274 |
|---|---|
| FEATURE | Location/Qualifiers |
| source | 1..1274 |
| | mol_type = genomic DNA |
| | organism = unidentified |

SEQUENCE: 40

```
gccttgccca tgctactcat caaccctcct cgcaacctca tcggccaaag tcagtctggt    60
accggcaaga cggctgcatt caccctcaac atgctctcac gagtcgaccc aaacatcatg   120
accctcagg ctatctgttt ggcaccgtcg cgagagcttg ctcgacagat tcaggaagta    180
gtcgacaaga ttggccagtt cacccagatc aagagtttcc tcgctgttcc gggctcttgg   240
tcgcgtaatg tcaagatcga caagcacatt cttgtcgta cgcctggtac actcgtcgac    300
atgctttcgc gaggaggcag gatcttcgac ccgaagcaga ttagagtctt tgtgctggat   360
gaagcggacg aaatgatcgc tttgcaaggt ctggggacc agacgaagcg catcaagagg    420
atgctgccgc tggggtcca gaacgtcctg ttctccgcta cttcccga caacgtccga      480
gactttgcag gcgacttcgc acccgaggcg aaccagatct tcctgaagaa agaggagatc   540
actgtcgacg ccatcaagca gctctacctc gagtgtgatg gagaggagca gaagtacaac   600
gcccttctg ccttgtacga catcatgtcg atcggtcaga gtatcgtatt ctgcaagcga    660
aaagacacgg ccgaccgaat tgcggcgaga ctgacggatg agggtcactc tgtcgcttct   720
ctacacggtg acaaacagac tcgagaccgt gatgacatcc ttgacgcttt ccgagatgtc   780
aaaaccaagg ttctgatcac caccaacgtc gttgctcgag gtatcgatat ccagcaagtg   840
aacatggtgg tcaactatga cgttcccgat ctccggtccag agggagattg gaagcctgat   900
atcgagacct atatccatcg aataggtcga accggtcgat ttggtcgaaa aggttgttcg   960
gtcatctttg cccatgatca gaggtcgatg caggatgttc agttcatcgc cgatacgctc  1020
ggcaagaaaa tgagcagaat caacgctacc aggcagactg atctcgatca gctcgaagcg  1080
gctttgaaag ccgccatcaa gggcaatcaa ccgaaagagt gaagagtggc accgaattcg  1140
aagagacggg cgctggaaga tatcctgaag caacagggag gagctcccct tatagcatga  1200
tcattgacga taaccatcta gggcctgaag tacattatga tagatagcag acatcaatgc  1260
aacgtcgcgt cgcc                                                    1274
```

| SEQ ID NO: 41 | moltype = DNA length = 919 |
|---|---|
| FEATURE | Location/Qualifiers |
| source | 1..919 |
| | mol_type = genomic DNA |
| | organism = unidentified |

SEQUENCE: 41

```
cacctccaac ctctttctag tttaccttca aaacacatcg gtgtaaggtc ttgcccaaca    60
tggctacctt ctcgacccgc atcaacctcg tccccacctc ccgaacgctc gctagcggcg   120
ttccattcgc acccaggatc gcccttgttc atcctcccgc gtctcacggt cacggaacga   180
gcggtcccag gagtgatgtc ccacccaggt gggctggtgt ccaggtggaa ttcgcctcga   240
actcgagggt caatgtactc cccaccggca acttccagca acgattcatg tccaccacgc   300
cagcccgcaa gatcgaggct caaccccacg tccgaggtgt tcccgattgg tcggcatatc   360
agtcttcggg caagggcgag aacacccgat cccttcgta cttcatggtc ggatctctcg    420
gtgtcctcgc tgcttcaggt gccaagtcga ccgtcagcga cattctgagc aacatggccg   480
cttcggctga tgttttggct ttggccaaga tcgaagttga gatgggtgct atccctgagg   540
gcaagaacct gatcgtcaag tggcgaggaa agcccgtctt cattcgacac cgaacggaag   600
atgagattaa cgaggcacgc gcagtcgaca tcaagtcttt gcgtgatccg agagcgacg    660
aggataggac ccaaaggga gagtggcttg tcatgctggg tgtctgcact cacttgggtt    720
gtgttcccat tggcgaggct ggtgattacg gaggatggtt ctgcccctgt cacggatctc   780
actacgatat ctctggccga atccgacgag gtcccgcccc tctcaacttg gaggttcccg   840
agtacgcttt caacgacgac gaggagaagc ttgtcattgg ttaggtgtag atggacatat   900
gcagtctatg gccatagcg                                                919
```

| SEQ ID NO: 42 | moltype = DNA length = 1459 |
|---|---|
| FEATURE | Location/Qualifiers |
| source | 1..1459 |
| | mol_type = genomic DNA |
| | organism = unidentified |

SEQUENCE: 42

```
ggggagcatc accatagtga cagggactgt agctcggtca agcgcgtatt cgcacttggg    60
cgcctggacg ttactctggc cgtggagtgc gggagtgtca ggacgatgtc ccttcgtgac   120
ctcgcttgct acactctcac gctcaagcca tctaccgaga ataccctcct gaccgagctc   180
acggctttgg agggaccgag tgaggagcca cgattcgcaa gagtgcggga aaggtggaa    240
ggagaggtct attcgtctgc catatacgat gcgttgacgg gacccaagct ggcctcggtg   300
ggtttcgctt ccgaaaagca gaagaacagg aggctacagc tacacaaccc ggatgagagt   360
gtgcctttg acaatactag caagctaggt ttcgaatgga cattcatctt cgaaggcaac   420
aagtacaggt ggacgagaga gctatacgga aaagattata tctgctcact agaccggaaa   480
cccgatccaa gggtggagat ctgcctagct cgagacgcag attcgaaagc gcctggacga   540
ctgcagatcc tacactacaa catcgaacga ttcccgaacg agatcaagga tttgagggga   600
```

```
ctggaaacgc tactcattgc taccctcatg tgcttcgtcg acgcggccga agatcggtcc    660
aattccggtc cgacccgcac ttcgcccttg cctgctaagc cggttgccaa tgctgcagca    720
ggtcaaagcg gcaccagcgc aagtggatct tctgataccc gagcgaaagt tgcgccggtg    780
acagtgccaa taatcactgc agaggacttt gaggatgatt gtgacccgaa tgagatactg    840
gtaggaacgg agactgatgt gggcgagcac attgcacgac ctatagcgct tttggaggac    900
ccgaccatgc tgttcattgt cattcgaacg cgaactgcgg ccgcgagctc aagagcgtta    960
gaagtctcct taggggttac aaggttccgg caccgtgagg gcatgagcga gctgcatcaa    1020
tacgtggtag aggaagatcc ggtccggaag ccgaaaccca ttatgcctgc tcagggcctc    1080
aagttgatca acctggatga tcgaccagcg gcacaatcac ccaccaaacc ggaatggtct    1140
gccccaccta acatcgctgt ttacctatca tcgatcgagt tgccagatct cacgcccaag    1200
cccaagcctg tccaggggca cacacggccg ccaactcaag cacctcatgc tcggcctccg    1260
ccgccttctc aactaccaca aaagccgcag ccgcggccac gcccgcctcc atccgatggt    1320
tcaggtagta gtcagactac actcgcttca acgcgaccgc cccaggacga cgggaaggat    1380
tcgagaaagt ctagctttgg aagactcttt ggcaggtagt acgatacact tagcagggca    1440
tatgcaggtg tatcgacgg                                                 1459

SEQ ID NO: 43          moltype = DNA  length = 623
FEATURE                Location/Qualifiers
source                 1..623
                       mol_type = genomic DNA
                       organism = unidentified
SEQUENCE: 43
ggcgacgaca acaagaaaac aatacctcac ctgaacatat tcaataatgg cgtcccaatt    60
gatgcccctg gagctgatcg atcgttgcat cggatcaaga atgcgtgtga tcatgaaagg    120
cgacaaagag ttcagcggca cacttctcgg attcgacgac ttcgtcaata tggtgctcga    180
ggatgtcacc gagtacgact acaccggcgc aacgaccaag cttcccaaga tccttctgaa    240
cggcaacaac atctgcatgc tcatcccagg tggcatgccc gagggcgagt catgaatcac    300
ggacatatga tatcccttct tacgtctctt gaaatggcaa agcgagtctg atttaagaac    360
cacacgtgtc atgagaaggc agactatacc gctgtccagt ccaagctgct tgaacaataa    420
ttatcccgac ggagccacga aaacgtgaca agcggaagct cgcattcgca aagcgccggc    480
gcaataaaac gccttgttca gctcgccgac tttgtgcatg catgcagctc gccacacccc    540
gcagatatca ggctgccttc ttgttatcag gtatgcgtgt ttatactcag gcttatttca    600
gctatgcaaa acctatatca tcc                                            623

SEQ ID NO: 44          moltype = DNA  length = 489
FEATURE                Location/Qualifiers
source                 1..489
                       mol_type = genomic DNA
                       organism = unidentified
SEQUENCE: 44
gcaaaggagt tgtcgcctga cgtcaagcct gagccgacat ggtcttgtgg cgaggttgtc    60
aatgtcgtcg atgagcacgg caatgtcatc aaaccgtcag acctctgggt caagatgggg    120
atgcagcagc aggacaatgt ggacaaccta ttgatcgacg acctgtgtga tcagatgagg    180
gccaaggcca aatgcacaga gaacggcgct caattgaatg tcgacgacct gaaccacatg    240
atgtcgtatg acaagtcata taagcagaaa agggtagacg acctcaaaga caagtacggc    300
tggggagcag tctttggccc gaaatgagcc gcctccgcgg gggcaaggtg gacggacgat    360
ggtagacatg aatatgagag caaacagaca tagggtctga gtccagtagt gtgctttgtac    420
caccactgta aatatttgta cgatagccct acaccactta caattgatca tgtaactgtg    480
tgaaccgtg                                                            489

SEQ ID NO: 45          moltype = DNA  length = 480
FEATURE                Location/Qualifiers
source                 1..480
                       mol_type = genomic DNA
                       organism = unidentified
SEQUENCE: 45
gggagcctga cccgccgtgc ttggttcatc caatccacct cgccaccac tggtgatggt      60
ctctacgagg gtctggagtg gctcgccgac actctccgga aaacgaaccg cgattaaacg    120
cgtataatac gaaattgtga tggggaggat tgtgtacgta gcagagcaag agaaatacca    180
cgggaaatct gcaaatgatg gaatgatgat tatggcggga gtttcttcca atgttcttct    240
gcgaggccaa atatcccggc gatgaaaaag aattccctca ccggcatggc atggccatcc    300
tcaggagcaa ggtgtttgtg tttggctcgc cagggctcta tttctcttcg ctatgctatt    360
agcctcatttt gttctttttct ctctggcgcc acgtcaaaat tgctggttta tctccttttg    420
attgcatgtt cagtatcggt atgatctcag tataccagca cttgggttga gcattcttct    480

SEQ ID NO: 46          moltype = DNA  length = 1139
FEATURE                Location/Qualifiers
source                 1..1139
                       mol_type = genomic DNA
                       organism = unidentified
SEQUENCE: 46
acctcacttt gtgcgaatta tcctcctaca gcatcagctc tcttcagaaa gaggctaaat     60
ctatagaccg tccggaacag gttgtcaaca cgcgcgataa gagaagaagg gaatctactg    120
gtagacaaca gatcgatcgc tcttcagcaa acgcaagatg gagaaccttc ttcgtcagat    180
gcaaggggga ggtggtagga tgggtgcacg gccaggccct ggaggcgaaa ctatcctcgc    240
cgacaacggt gaaacagtcc atatttcatc tcttgctcta ttgaagatgc tcaagcatgg    300
acgagcgggt gtgcctatgg aagtcatggg tctcatgctt ggcgaatttg ttgatgacta    360
cactatctcc tgtgtcgacg tttttgcaat gcctcaatcc ggtacgacag tgacggtcga    420
atcagtggat cacgtctttc aaaccaagat gttggatatg ttaaaacaga cgggccgacc    480
```

```
cgagatggtc gtcggttggt accactcgca ccccggtttt ggttgttggc tgtccagtgt    540
cgatgtcaac actcagcagt ctttcgaaca gctacatccg cgagcagtag ccgttgtcat    600
cgaccctatc cagtctgttc gtggtaaagt cgtcatcgac gctttccgat ccatcaaccc    660
tcaatcactt gtcgctggac aagagtcgag gcaaacaacg agtaacattg gtcatctgaa    720
caaaccgtcc attcaggctc tcatacacgg tctgaatcag cattactaca gtctggccat    780
cgattacagg aaaacagaag gggagcaggg tatgttgttg aacctgcaca agcggggatg    840
gacagagggt ttgaagatgc gtgatcactc agagatgaag gagggtaatg agaaggcaat    900
caaggaaatg ctctctcttg cctcggccta cacgaaatct gttcaggaag acgacaat     960
gacggccgaa cagcttaaaa cccgtcacgt aggaaagctt gatccaaaac gtcatttggg   1020
cgaggcggct gagaaagcga tgggtgatca agtgacgcag agtcgtggcca tgggtgtcct   1080
ggctgagctg tagacgtaga agagggaaga aaggaaacga catgcattgt acatatcgc    1139

SEQ ID NO: 47         moltype = DNA  length = 674
FEATURE               Location/Qualifiers
source                1..674
                      mol_type = genomic DNA
                      organism = unidentified
SEQUENCE: 47
ggacacaccg gtgacgtctt gagcgtctcg ttctcggccg acaaccgaca aatcgtttct     60
gcttcccgag accgaactac caagctctgg aacactctcg gagagtgcaa gttcaacatt    120
gttgacgatg gtcactcgga gtgggtctct tgcgttcgat tctctcctaa ccccgtcatt    180
cccgtcatcg tctctgctgg tttgggacaag gtcgtcaagg tctgggaatt gtccaagtgc   240
aagctcaaga ccaaccacca cggtcacact ggttacatca acaccctcgc cgtttcgccc    300
gacggatcgc tcgccgcatc cggtggaaag tatggcatca ccatgctttg ggatttgaac    360
gatggcaaac acctctactc tctagaggct ggagacattg tcaactcgct cgtcttctct    420
cctaaccgat actggctctg tgccgccact gcttcgtcaa tcaagatctt agacttggag    480
tccaagtcaa tcgttgacga cctcaagcca gacttctccg ccgagtaccc tgacaaggct    540
caaaagccac aatgtacttc cctcgcctgg tctgccgatg tcagaccct ctttgccggt     600
ttctccgaca acctcgtccg agtctgggtt gtcactgctt agagtcgtga ggattgtatg    660
catggataac gtgg                                                     674

SEQ ID NO: 48         moltype = DNA  length = 674
FEATURE               Location/Qualifiers
source                1..674
                      mol_type = genomic DNA
                      organism = unidentified
SEQUENCE: 48
ccacgttatc catgcataca atcctcacga ctctaagcag tgacaaccca gactcggacg     60
aggttgtcgg agaaaccggc aaagagggtc tgaccatcga cagaccaggc gagggaagta    120
cattgtggct tttgagcctt gtcagggtac tcggcggaga agtctggctt gaggtcgtca    180
acgattgact tggactccaa gtctaagatc ttgattgacg aagcagtggc ggcacagagc    240
cagtatcggt taggagagaa gacgagcgag ttgacaatgt ctccagcctc tagagagtag    300
aggtgtttgc catcgttcaa atcccaaagc atggtgatgc catactttcc accggatgcg    360
gcgagcgatc cgtcgggcga aacggcgagg gtgttgatgt aaccagtgtg accgtggtgg    420
ttggtcttga gcttgcactt ggacaattcc cagaccttga cgaccttgtc ccaaccagca    480
gagacgatga cgggaatgac ggggttagga gagaatcgaa cgcaagagac ccactccgag    540
tgaccatcgt caacaatgtt gaacttgcac tctccgagag tgttccagag cttggtagtt    600
cggtctcggg aagcagaaac gatttgtcgg ttgtcggccg agaacgagac gctcaagacg    660
tcaccggtgt gtcc                                                     674

SEQ ID NO: 49         moltype = DNA  length = 480
FEATURE               Location/Qualifiers
source                1..480
                      mol_type = genomic DNA
                      organism = unidentified
SEQUENCE: 49
gggagcctga cccgccgtgc ttggttcatc caatccacct gcgccaccac tggtgatggt     60
ctctacgagg gtctggagtg gctcgccgac actctccgga aaacgaaccg cgattaaacg    120
cgtataatac gaaattgtga tggggaggat tgtgtacgta gcagagcaag agaaatacca    180
cgggaaatct gcaaatgatg gaatgatgat tatggcggga gtttcttcca atgttcttct    240
gcgaggccaa atatcccggc gatgaaaaag aattccctca ccggcatggc atggccatcc    300
tcaggagcaa ggtgtttgtg tttggctcgc cagggctcta tttctcttcg ctatgctatt    360
agcctcattt gttcttttct ctctggcgcc acgtcaaaat tgctggttta tctccttttg    420
attgcatgtt cagtatcggt atgatctcag tataccagca cttgggttga gcattcttct    480

SEQ ID NO: 50         moltype = DNA  length = 1170
FEATURE               Location/Qualifiers
source                1..1170
                      mol_type = genomic DNA
                      organism = unidentified
SEQUENCE: 50
aaagttgatc gaccacattg ggtctgagaa aaacccaatg cttttttgta cagcagtgag     60
gaatattggt caatggccga aaggctgaac cagtaacttg gaagaatgaa attgtatttg    120
tataaataca atagtggtta aaccacataa aattctaaat agattatata taatgacaaa    180
atctatttat aagtcttgac caaactacgt gccagcagtc gcggtaatac gtagaaggct    240
agtgttagtt atctttattg ggtttaaagg gtaagtagac ggtaaattaa actctaaaag    300
agtacttatt tactagagtt atatgagaga aggaagaatt cctggagtag agataaaatt    360
ttttgatacc aggaggactg tcaacggcga aggcgtcctt ctatgtaata actgacgttg    420
agagacgaag gcttgggtag caaacaggat tagataccct aatagtccaa gcagacaatg    480
```

-continued

```
atgaatgtca tacattagat agattttaat gtataaacga aagtgtaagc attccacctc    540
aagagtacta tggcaacata taaactgaaa tcattagacc gtttctgaaa ccagtagtga    600
agtatgttat ttaattcgat gatccgcgaa aaaccttacc acagcttgta tagcagttat    660
gaaaaattgt tacaagcgct gcatggctgt ctttagttaa tgtcgtgaga tttggttaac    720
tcctctaatt aacgaaaacc ctcactttat ttatatatat aaagtggttc gctattacat    780
tggttgataa tagggattaa gacaagtcat tatggcctaa atgctgtggg ctatagacgt    840
gccacatacg cctttacaaa gggatgcgat attgtgaaat ggagctaacc cccaaaaaag    900
gaaatactat ggatagtagt ctgtaactcg actgcttgaa taaggaatta ctagtaatcg    960
tgaatcacca tcgtcacggt gaattatttc tcagttaggt actaaccact cgtcaggcgc   1020
tgaaagaaga agatgcagta agtttgatgt tttctgttgt tgattataca taaagttgtt   1080
gtataactac gcagaaaagt tttcgtatgc aaaactttga ttggtgttaa gtcgaaataa   1140
ggttcgtgta atggaaattg cacggggagc                                    1170

SEQ ID NO: 51           moltype = DNA   length = 1231
FEATURE                 Location/Qualifiers
source                  1..1231
                        mol_type = genomic DNA
                        organism = unidentified
SEQUENCE: 51
ggacgatatg acttcaagca gcctcagcga attcgagacg cttctgtcac ggccacgcca     60
gaatggaacc tgcttgaaga gatcgagttt ggccgattgg gcaagctcaa cctttccgtc    120
gaagagcccg aagacctcga atcgcacggt accctccagg gttacgacaa gacgtttgac    180
cgcatcaaca ctcgtaccga aagacctctc gagatcattg atcgagcatg gtacaatcaa    240
accacttctg acgatccgt tattgctcag ctcgctcaaa cgcagtctgc ccaaatcttc     300
gcgacagatg ccattcttgc ggttctgatg tgcaccactc gttccgtaaa ctcgtgggat    360
atcattctcg agcgacgagg taaccagctt ttcctcgaca aacgagattc tggtccattc    420
gactacgtca ctgttcacga aaacgccgcc gacccacctg ccgactctga cgatcccaac    480
aacgtaaact cggcttcttc cctttcgctc gaggccacct acattacccg aaatttctcg    540
tctcaagtca ttgatgccaa gtccaagcca tattcgccta gccccaatcc gttctattcg    600
gaggacgagc catcacccgt cgcttcctgc ttgtacaagt accgaaagtt cgacctgtct    660
gttggcgagg aagataccct ggacctcatt gtacgaaccg aagtcgacgc ctatcaaggc    720
aagaaggact ctctcgtcac tgtcaaggca ttgaacgagt ttgatcctcg agcttcaggt    780
ggtgccaaag ccctagactg gcgaaagtac ctcgacactc aaaagggtgc cattgtcgcc    840
tcggaaatga agaacaactc ggctaaactc gctcgatggg ctatccagtc tgtcttggcc    900
ggtgccgaag tcatgaagat gggatacatc tcgcgagctt cgcccaggga tacaactcat    960
cacgtcattg tcggtgtgca aaattacaag ccaaaagact tgccgctcca atgaatgtg   1020
tccctcaaca acgttggggg tatcgtccga acgattccg atcttgtcct caagcagcca   1080
gagggcaagt atgtcctcgt caaggaccca aatgcaggca tcattcgtct ctacagtgtg   1140
ccagagaatg ctttcgaggc agaggaggag gaggagcaat agtcgaaaag tctagacagg   1200
ccgtgtcgga catgcatcat atacttcaag g                                  1231

SEQ ID NO: 52           moltype = DNA   length = 788
FEATURE                 Location/Qualifiers
source                  1..788
                        mol_type = genomic DNA
                        organism = unidentified
SEQUENCE: 52
gagcgctcaa ggtccttggc cccagaagcc gatcaaggtg tcgcgactca gtgtcacgaa     60
gtcagatcgt caggtagcta cgacacgttc gagatcggcc atcaccaacc tgacagcgat    120
acctcggag tagctgactt gcgcacttcc agtcgtatgg acacctgcga cgcgcatctt    180
ctacgcggga tcaaaagctg ccctcttttc agctaccgcg aagacgaggt gtccgaaact    240
gtacaattgc ctacaggcga atggacgacg atcagagata tcactccgag tgcaccaaag    300
atcggctttg aagtgcgcga ctcgctctcc gcgttcccga cagccaagcc tgtcgaagcg    360
aagcacgagt ccgcctccag catatccaat gatttaccct ctcagccatc ctcaaggccg    420
ctgattgagt gtccgacact ggtcgcgat tcacgcacaa cgacggggtc caactctgtg     480
cgcagtttcg acgccagac cgaacgcctg agcggcttga gcgacgtgca ccacagatac     540
atgcaggaca agccgtcaca gcgttctgat tcctggaccg acgtcaaatc ctccgctccg    600
tcctcccagt cgatggcagt ccccaacaaa gcggcttacc tggctccgat cccagctggc    660
ccaaatgaca gtaagacttc gagttccggt cgcgccccgt cagacgccgc gaccgaacac    720
gagtgttcgc tacaataagt cagacttgct gttggaacgt ttcctacctc atgcatacct    780
ggcatgct                                                             788

SEQ ID NO: 53           moltype = DNA   length = 706
FEATURE                 Location/Qualifiers
source                  1..706
                        mol_type = genomic DNA
                        organism = unidentified
SEQUENCE: 53
accctccaaa ctccaagctc ttttcaaccc tttcctacct tacacaacaa cttcaacaac     60
aactatggca cccaagtcca ctgacaagcc cgcatccacc gctggcaagg ccccctctgc    120
tggaggcaag gctcctgcct ccaagactgt cggtgctaag aagaccgcag caagaagtc     180
tgctaagtct actggcgagg gcggcgagaa gaagaagcgt gtcaagtcca aaaggagac     240
ctactctacc tacatctaca aggtcctcaa gcaggtccac cctgacactg gtatctccaa    300
caaggccatg cttatcctca actctttcgt gaacgacatt ttcgagcgta ttgccggtga    360
agcctccaag ctcgctactt acaacaagaa gtctaccatc tcctcccgcg agatccagac    420
tgctgtccgc ctgatcctcc ccggtgaact gtccaagcac gctatttctg agggcaccaa    480
gggtgtcacc aagtactcca gctccaagta aacttgtctt ttgcttggct gagagtcttt    540
cccctttcct tcttcattgt ccctaccctc ctgttcttcc cctctccctc acattcatca    600
tgttgtctat taggcgagct gcctgcagac ttgctcgctg tcaaggctga agcagtcgcg    660
```

```
tagttagtgt aatggagcca caaatgtaat tctagagcac atgcag          706
```

SEQ ID NO: 54          moltype = DNA   length = 1203
FEATURE                Location/Qualifiers
source                 1..1203
                       mol_type = genomic DNA
                       organism = unidentified
SEQUENCE: 54
```
gatgtcaagc gattcaccaa ggatctgctg ttcaactcgg agggcaacct aaccttcaag   60
ccccacttgt ggaacgacat ccgtcacacc ctcctcccca cctttatccg acagatcgga  120
tacgttccca tcccacgagc cgagttctcc tcgcctgaca ttgaccttgt catcgagaat  180
ctggtcctgt ccggacccaa cctcttcccc aacgtcgtct cgctcgagag ccacaactcg  240
ttcaagttct cgccttacca gcagctcaac aagggtatgg acacgcatca ccacaagttc  300
aggctgggta tgagccagat ccaggccgat atccgacgat tccgattctc gttccgacga  360
aagactggat ggcccaagct caaggaccac ggtctcgccg atgtcatcct tgccggtaag  420
ggtatgtcga tcgacgtcga gctcgagtct gtcgagggac gacgagactc tgttgtgcga  480
gtcaaccacg tccacaccac catcgacacc ctcaccttct ccatccgaga ctccaagcac  540
gacttgctct acaagttcgt caagtcggtg gccacgggtg cgatcaagaa ggcaatccag  600
gccgccgtcg acaatgccat ccgtacggct gtcggtcacc tcgacgacca gctcgtccga  660
gtccgaaaca ccgtcgatga cgccaagaag tctgacgaga ccacccgaac gcaagccctc  720
aaggacttgt actcgaagaa ggcggacacg gcacagaaga agcaggccga gtccaaggag  780
cagcctggta ctttccgaat cgtcgccaac cgagactgtc ttctcaaccc cgacatgggc  840
ggtggcaagg gcgccatgac caacaagatg tggaagaccg aggaccttgc acactctggc  900
aaggaatggc actctcccgc tttcgacttg ctcgactcca agcacccagc acgtaccggt  960
cagacccacc ccgaggccaa ggagggtgct ggacacggaa acagcttgag ctcaaaggct 1020
cagcccggca ccaacgcggc cgaccagctc aaggctactc acggtcagtc tgaggctgag 1080
gccatcgctg gtcagaagcg acagcaatag gtggaagaga gggagccgcg tattgagaag 1140
taggaaggac tagctgtata cccccttata cttttgtgtc tatagtaatg aatgcgtgaa 1200
acc                                                              1203
```

SEQ ID NO: 55          moltype = DNA   length = 962
FEATURE                Location/Qualifiers
source                 1..962
                       mol_type = genomic DNA
                       organism = unidentified
SEQUENCE: 55
```
ggaccttcca tccatcagcg tatcgcatat cagcttcctg acaaagtaag aggtaataac   60
aagacaccac actctttcag cacgtacctc ataccggacc gccatgtaca catccgccgt  120
gacactgctc tcttttggtct tgctcctggc gacttccgtt attgcacaag aacaagctgg  180
tcggcctggc actcagcgag gcggcgtctt ctttgggtgt tatgccgatc gacctacagg  240
caatgccaac cagcccatca ctcgagtcgc caactccgac acattctttg aatgcatgga  300
gaattgtgct gcgataacgt ctccttcgtt gctgggatac tatcaaccct cctccggtca  360
atgcttctgc ggcaacctt tatttaaccc tcaagtcaa ttgaacggta acggttgtca  420
aggtagtgat tggtcctttg gccggacttc gaccaccttc aggaggttcg gtgacgcttg  480
tcgacccttc ggtggtgtcg gattttctgc gaatcaatac actacagtca ctggtcccgt  540
agcttgtcat gttcaatgcg catcaaacag attcgcctat gtctggtccg atactggaag  600
caactcatgg caatgtgctt gcagcaacaa tgtccgtgct caggaggact tccagtacac  660
ttgtcaaggt ggcggtgtat ttgtgtttga acattcagta caagctcagg cttcttcgct  720
taacaggaag cggacggtgg aggaacaatg ggctgttccg aaagacgccc tctgtccatt  780
cggaatgtca gcgtgcaagg tatcaggtgt cgataatgct tacgaggtat gcttctttc   840
agaccgctag gcccctggtt ccctggccac gaggtttgaa acacgccatt gacctgtagt  900
gcctcgatac ctcagccgag ctagaatcgt gcggtggttg tctgcatggt caattgttct  960
ga                                                                 962
```

SEQ ID NO: 56          moltype = DNA   length = 909
FEATURE                Location/Qualifiers
source                 1..909
                       mol_type = genomic DNA
                       organism = unidentified
SEQUENCE: 56
```
gggggaggaa cggtcgttag caatgctttg ctggagaatg ccaagctctg caagacccag   60
ggcaaggaga gctctcttcg agtcatcgtg tgtggccgaa ataggttgga gaatgggtct  120
gcacctcatt gggccgaggc gtttgctacg catggcaaat tggtggaagt gaggatgccg  180
caaaacggca ttcgcatgga gggcatcaaa gctatccgcg ggactggc caagtgtccg  240
acattggaag tgcttgattt gcaggacaac acgctacca agacaggaac acggagtatt  300
gtccgacacc tctcaacttg gcctaaactt cgaatactca atctctcgga ctgtcttttg  360
ggttcggtcg gcggtatcgc tcttgcaacc gcattgtcca ctggctcgaa caagcacctc  420
gaacagctca aactgcaata tggcgagttt gacaagagga cggttgagat actgtcgacg  480
gcaattagcc agcatttgcc aaaattgacg acactcgaac tgaatggaaa ccgtttcgat  540
gccgaagacg aatgcgttga gaccctgaag aaggcacttg agctacatgg gaacgaggat  600
gctttgacg aacttgacga tatggaggag gtggacgagg acgaagagga tgatgatgac  660
gaggacgagg aggacgaaga cgaggacaag gacactagcg ccgacgatgg gatcgatgca  720
ggagctgctg gagaagacgc tctaccacca gtcacgaaga aggacgagga cgtacttgcg  780
gatctcctgt ccaaggtcca cgttcagcct agctgagtcc aagcgctttc cggtcggcaa  840
gtagatagac tagacacgcat aataccttga ccctcatgat gccacccgca tgtacacatt  900
tgttctccg                                                          909
```

SEQ ID NO: 57          moltype = DNA   length = 909
FEATURE                Location/Qualifiers

| source | 1..909 |
| | mol_type = genomic DNA |
| | organism = unidentified |

SEQUENCE: 57

```
cggagaacaa atgtgtacat gcgggtggca tcatgagggt caaggtatta tgctgtctag    60
tctatctact tgccgaccgg aaagcgcttg gactcagcta ggctgaacgt ggaccttgga   120
caggagatcc gcaagtacgt cctcgtcctt cttcgtgact ggtggtagag cgtcttctcc   180
agcagctcct gcatcgatcc catcgtcggc gctagtgtcc ttgtcctcgt cttcgtcctc   240
ctcgtcctcg tcatcatcat cctcttcgtc ctcgtccacc tcctccatat cgtcaagtcc   300
gtccaaagca tcctcgttcc catgtagctc aagtgccttc ttcagggtct caacgcattc   360
gtcttcggca tcgaaacggt ttccattcag ttcgagtgtc gtcaattttg gcaaatgctg   420
gctaattgcc gtcgacagta tctcaaccgt cctcttgtca aactgccat attgcagttt    480
gagctgttcg aggtgcttgt tcgagccagt ggacaatgcg gttgcaagag cgataccgcc   540
gaccgaaccc aaaagacagt ccgagagatt gagtattcga agtttaggcc aagttgagag   600
gtgtcggaca atactccgtg ttcctgtctt ggtagccgtg ttgtcctgca aatcaagcac   660
ttccaatgtc ggacacttgg ccagtccgtc ggcgatagct ttgatgccct ccatgcgaat   720
gccgttttgc ggcatcctca cttccaccaa tttgccatgc gtagcaaacg cctcggccca   780
atgaggtgca gacccattct ccaacctatt tcggccacac acgatgactc gaagagagct   840
ctccttgccc tgggtcttgc agagcttggc attctccagc aaagcattgc taacgaccgt   900
tcctccccc                                                          909
```

| SEQ ID NO: 58 | moltype = DNA length = 596 |
| FEATURE | Location/Qualifiers |
| source | 1..596 |
| | mol_type = genomic DNA |
| | organism = unidentified |

SEQUENCE: 58

```
ggatggtgaa gcttagtaac agtcttgtcc gtcgtcttaa atggcaacac gttcgcagtc    60
tcggcgtggt ggcgctgact gcccaattgc gaggaccaca acctcagagc gccgaggacg   120
aagattctga agcagctggc aagaagctca aactggctgg cgaccaagct acatctgcgg   180
tcattcccaa gtccgcagac aagcccgata cttttccctct actcgacaca ctacctgcta   240
ctatggctgc tggcaccagg tctatgacta ggcccttgca tgtcggtgat ctgaggttgg   300
ctgatctgcg taaaatcatg caggcagctg gccacacggc tgagttccga ggtgagggaa   360
cactactcat tgacaagtcc gtcgctgtca gaaaatcagg acagggcag attgaaatcg    420
aggcatctgc tcaagcagct gcaaaccaag ctactcctgg ccgaggtgcg agtagcttcc   480
tcgctgtcaa aagaaagata tacgagggtc tcgctgttgt cacaggaagt taaatgaccg   540
tgtaccctat attcaatttt tgtataattt acgcaatacc aacgatattc tctcgt       596
```

| SEQ ID NO: 59 | moltype = DNA length = 418 |
| FEATURE | Location/Qualifiers |
| source | 1..418 |
| | mol_type = genomic DNA |
| | organism = unidentified |

SEQUENCE: 59

```
gaaaatgaaa attgatgtgg agaagctgaa taaagatatc agccttttcc cgcaggtgca    60
tccgattacg gaagatatga aaatcacgca caaaggtgtt tcgcgccttg taatgctgga   120
caggtattca tttaaagaca ctgaaaaaat tacgctatct gaaggcgatt ttgtagtgct   180
gacgatcaag gaagatccaa aatttcctgc aagagggcta ggctacatta agaaattga    240
ttgggaaaat aaaaaggcaa aggttcaggt cgaagaagag tttcgtcata ctcttgaaaa   300
gcctgaagaa cgggagacgg gaatcatcgt tcgctcttta gatgtcatcg aaaaaccgct   360
tgaaatttt tatgaacaaa ttgccaaaag aaatgcaaca ggtcttgctg ctgttgaa      418
```

| SEQ ID NO: 60 | moltype = DNA length = 988 |
| FEATURE | Location/Qualifiers |
| source | 1..988 |
| | mol_type = genomic DNA |
| | organism = unidentified |

SEQUENCE: 60

```
ggggatgcaa cggtgactca actgcgcgaa atcatggacg acccagctgg ctatttcttg    60
ccaaatctca aacatggcgc cgataacatg ttctacgtcg gtccacgcgg acttgcacaa   120
gagctcgagg agcttttac cttcccaagc acaatcctca gaaagcgcca ggataccagt    180
cagcatgacg aaaggcaggc aaagaagcg cgcacgcaag aggacgaagc ggctggtgac     240
gcgttggagg agcccgagac tgggcgacgc gacagtgtgc ttccgactga acgggccgct   300
tttggtctcg agggtgatga ctcgggcttt tccttgacg accagacgat gggagacgac   360
atgctgccta tggacgacat gggagccatg gacaccggag tggaccagcg acgcatgcga   420
acaccatcag tcgcaccgtc ggtcaccgaa tcgatcgcac gtcagattca gaatgaccga   480
agcgctggca cacaccccact ggctatattc gagaaggagg caaggacga cacgcagtcg   540
caatcgcagg ctacgcccaa caaatcggtg gcctccgagt ctatcagcaa gacttcttct   600
ggccaatcaa agaatctggg catggccgta ggtttgttgc gaaggggat tgaggcgatc    660
gaggaggaag acaagatggt cgggtttgat cacttggcag acaaggcgtc caagcgagca   720
gcgtctgcat tcttcttcga gctgttggtg cttggtacca aacatgcggt caagcttgaa   780
caagctcagg ctttcggcga catccacata cgcggcaaag acaagctgtt tgcagaggtt   840
gttgcataga caaacttgaa gagccacgat cttacgcgca acgagggag atctaatgac   900
catcttgatg tcgactttaa tgtttatttgg tacttgtaca tgagctgcta agagggtctt   960
gaatgagatg atgcatcgct tcatgagg                                     988
```

| SEQ ID NO: 61 | moltype = DNA length = 614 |
| FEATURE | Location/Qualifiers |
| source | 1..614 |

```
                        mol_type = genomic DNA
                        organism = unidentified
SEQUENCE: 61
gcagaccgtc tcttttaaat ctcctccttg acacccgtct cctttgcaca tttactacac    60
tccacatatc tccataacaa ccttatatct ttacacaatg ggtgaccacg ccactaccaa   120
cgacccctcc aacgccacct tcgaggagaa gggcaagggc aaggacgtcc aggatcaaat   180
cgcggaggac tccagcgacg aggagagtga ccaggagcct gagatggttg acgaggaaga   240
ggatgacaac aacctcgagc ccatctccca agacaacatc atctcaggtg gtcgccgtac   300
acgcggcaag atcatcgatt atgccgccga agccgagaaa aacaaggatg agatggagga   360
ctctgaggat gacgaggatt accaaggcgc taatgacgac gaggatgacc agatgcgcga   420
ctaagcgcat ggtcttgatg acggatctca attaacatag gactttggag gattggcgct   480
atggtttctg aaggaggttc tctcgtgcgc ctttgtggtt agcatctcac ctatgaaatg   540
tcatggcctg agcctggcaa tggacatgac tatgaataaa tgaaatgaag cctgcttctg   600
tctttgtgta acag                                                    614

SEQ ID NO: 62           moltype = DNA   length = 418
FEATURE                 Location/Qualifiers
source                  1..418
                        mol_type = genomic DNA
                        organism = unidentified
SEQUENCE: 62
gaacttaagt atttttaaagc agttgcacta tacaacctga gccggtactt ggatgcacgg    60
aaagcaatca atgacctcat tcagagctac ccggacttcc ggcaagctga ggccctcaag   120
tcagccattg atgacaaggt ggtgcgcgat gggctgattg gcgtgagtgt ggcaggagca   180
gtggtggctg cgtcgtggg cttggctgtg gctcttgcac gtggcaacag aggatgatgc   240
tacaggaggc agcaggttgt tggacagttc agtgcaccgt gccaatgctt caacggtctg   300
gcacaggagg cagcaggttg tgaccctgca caagcttggg ccatgattct acagacacac   360
cttatggcaa tcaaatgtgt gtttgcatgt gcgttgaaga gtgtaaatgt gctcttcc     418

SEQ ID NO: 63           moltype = DNA   length = 94
FEATURE                 Location/Qualifiers
source                  1..94
                        mol_type = genomic DNA
                        organism = unidentified
SEQUENCE: 63
tatcccgagt agcatgggac acgtggaatc ccgtgtgaat cagcgaggac cacctcgtaa    60
ggctaaatac tcctgggtga ccgatagcga aaaa                               94

SEQ ID NO: 64           moltype = DNA   length = 371
FEATURE                 Location/Qualifiers
source                  1..371
                        mol_type = genomic DNA
                        organism = unidentified
SEQUENCE: 64
cacgatttaa ataccegggg gacgttttgg attcgacagg gatagatcga gcttaagctg    60
cgagccggag ggatcgtctc cgtcatcaac gtcgcctaaa gataactggc aaacaaaaca   120
actacgcttt agctgcttaa tgctaaaggc tcctttcttc catcgcccat gtggaggaaa   180
aggggttcaa cttaagtggg ctacgcccga ttccgccgtc tgaggaagag ggaagagacg   240
aatcagacta gctgtccgga tgcctgccga caggctaagg aacagtgaaa tgttaaatat   300
gtcggatacg ctcgtagatg cttaagtggc gatatctctg gacgtgggtt cgattcccac   360
cgtctccacc a                                                       371

SEQ ID NO: 65           moltype = DNA   length = 681
FEATURE                 Location/Qualifiers
source                  1..681
                        mol_type = genomic DNA
                        organism = unidentified
SEQUENCE: 65
gccatcagca ccgcaaagct acctcatcaa ccattgaaag cacgcaaata actcccaaa    60
gttaatgccc gtacgaccct acctggaaga aatggccgac atgcccgtgc ccctgttcgc   120
gtacgacgca ccgccaccc tggccgacca ccctcacgcc cgcgagcacc aacacacgac   180
cttcatgcaa taccttgcgc gcaagcagcc ggacccaaag aactacccca actacccctga   240
cgtggacatc cgcgacgcca tcaatcacta cctgatcgag ctcgaatgcc cggggatcaa   300
agacgcagcc gacatccact gccagtggac gagctccgga caccctgaccg tcaccggcga   360
catcgcccgt cctgaggaaa gccagatcga agcgcagatc gagagcaggc ccgtctacct   420
ggttctggga gagagacgca ttggctctt ccgtcgcaac tttaccttcc ctgtggaggt   480
cgagcaggaa aatatgactg ccaagttgga ggccggattg ttgaagattg tcttgcccaa   540
gcacaagcac catactccga agggaacagg aaaggtcgac attgatgtca ttgagtgaac   600
gtcttttggg tctgcgatta tatgcgagga gttcttagat tgccggagtg ggtacctgta   660
tgggaattat gtatctgcaa c                                            681

SEQ ID NO: 66           moltype = DNA   length = 681
FEATURE                 Location/Qualifiers
source                  1..681
                        mol_type = genomic DNA
                        organism = unidentified
SEQUENCE: 66
gttgcagata catcattccc atacaggtac ccactccggc aatctaagaa ctcctcgcat    60
ataatcgcag acccaaaaga cgttcactca atgcatcaa tgtcgacctt tcctgttccc   120
```

```
ttcggagtat ggtgcttgtg cttgggcaag acaatcttca acaatccggc ctccaacttg    180
gcagtcatat tttcctgctc gacctccaca gggaaggtaa agttgcgacg gaaagagcca    240
atgcgtctct ctcccagaac caggtagacg ggcctgctct cgatctgcgc ttcgatctgg    300
ctttcctcag gacgggcgat gtcgccggtg acggtcaggt gccgcgagct cgtccactgg    360
cagtggatgt cggctgcgtc tttgatcccc gggcattcga gctcgatcag gtagtgattg    420
atggcgtcgc ggatgtccac gtcagggtag ttggggtagt tctttgggtc cggctgcttg    480
cgcgcaaggt attgcatgaa ggtcgtgtgt tggtgctcgc gggcgtgagg gtggtcggcc    540
agggtgggcg gtgcgtcgta cgcgaacagg ggcacgggca tgtcggccat tcttccagg    600
tagggtcgta cgggcattaa ctttgggag ttatttgcgt gctttcaatg gttgatgagg    660
tagctttgcg gtgctgatgg c                                              681

SEQ ID NO: 67          moltype = DNA   length = 50
FEATURE                Location/Qualifiers
source                 1..50
                       mol_type = genomic DNA
                       organism = unidentified
SEQUENCE: 67
gggatgatat gcatcatata gatcttgaga aatcaaggta agtatacaaa                50

SEQ ID NO: 68          moltype = DNA   length = 558
FEATURE                Location/Qualifiers
source                 1..558
                       mol_type = genomic DNA
                       organism = unidentified
SEQUENCE: 68
gggaaaaaaa ctttagaata cagtttaatc aatcttcaca gctacaaggc tatatcattt     60
gatatagcat atcaaagtgg ctttgatttc tgtaaattta tatctaataa taatagtgtt    120
tatatcagct aaatacatat ttctatccta tctatatatc accgacagac catatttgaa    180
actgctgttg acactattat tcatatgttc ggatttaatt ttaatacgac aaaattgtta    240
aaaacaattc tcgttgtttg ttatttgcag gcaacagtgt tagctgatcc ttatacaaga    300
gtatcttggg aagcgtatat gaatcatgtc aatggatccg acgactatcg tactcaaggg    360
gatgatacca gagctacacg ctttccagag actaaacctc caaaacaagg aaaagatttc    420
ctgtggtcga gtaaaccagt ccccagttca gatctatttc tggagttctt tatgtatgag    480
ggagaaccag atgaattcag caggacgact gaatcgtatc aatcacttcc gagcaacgcg    540
ttaactgcta ggcaaaaa                                                  558

SEQ ID NO: 69          moltype = DNA   length = 1164
FEATURE                Location/Qualifiers
source                 1..1164
                       mol_type = genomic DNA
                       organism = unidentified
SEQUENCE: 69
ggacacatca cacaacaaca atgtctccaa caccaacatc accacacaac aagctctcgc     60
tccccgcaag agcttcttcc cacgactcga cagacggcat ccgtaagcga gtatgcaagg    120
cttgcgacag gtgtcgattg aagaagagca aatgcgacgg atcaagtcca tgctctcgat    180
gcaaagcaga caacgccatc tgcgtgttcg gagagcgcaa acgatcacat gataaacact    240
atcccaaagg ctatgtcgag atgctcgaac aacagcaggc tcagctcgtc tcaggcctca    300
aagaaatgta ccacagactc cagaaagcct ccgcctggga tggccctgtg ttggacgaaa    360
gcaccggaca gcctctcact cacgacatcc tgtcagcatt agacctcctc gaaccaaagc    420
atgacgacag caacgagcca gaagtcttcg aagagaactg cgaaaagctg caatcaaaat    480
tgctcgcaga cggcgcgggc tttgcccacc gacgaggatc gatcagttcg gattctgaac    540
acagccatca cgatcgaccc aaaacatcct cacgccacga cacgcccgtg caacccaaac    600
cgtcgatctt caaggagaac ctgagcttcg ccagcgcggc ctcatcacca ctcacgcaaa    660
gccccatccc tcgatcgaaa cccttgaacg tcatgccata ccaaacgctg caaccgtcgt    720
caagaccatc cccactccag atgccctcag catacaaccc ccgcaacta tacgcacccg    780
aatgggcaca agcactggca gacatgagcg gcgatcccaa ctaccgcaa agattctcca    840
tgcagcagca acaacaaaac gacttcgaca acctgctctg ggatccctca gcgcaagcgc    900
ccatggaatc gcccttcagc caaccagcct tcttcaacca ggcgcaactg atcggcagcg    960
gcaacgtctt tgggctgtct gacatcaacg atctgggccc caaccccgcg gatgcgggga   1020
tggactttga cttcagcaag ttcgtgcagc agaccgaagt catgacatga acatgattct   1080
tgccttctgt caatacgcgc gagaattttg cttcagagtt ccagtccgtg taattcttgt   1140
gtatttatta cgatacgaac acgc                                          1164

SEQ ID NO: 70          moltype = DNA   length = 923
FEATURE                Location/Qualifiers
source                 1..923
                       mol_type = genomic DNA
                       organism = unidentified
SEQUENCE: 70
agagctcttc gtactccaca ccaccatctt ccatccgacc acactttcat cccaaatcca     60
tcaacaaccc atctcaactc catctccacca cctcaccatc atcacaatgt cttccttccg    120
cgtcgccgcc cccaagatgg cctccatggc cgctcagtcc tccgtgaagg tcgcccgccc    180
ggccttccag gctgctcagc tccagaagtt caccgcgcc tactccgcgg tccccaagaa    240
caccgtcttc aacaccatga agcgcaccca gatgatggcc cgcaggcct cccccatccc    300
caagcgtgcc tactcctctg agatggccaa cgccctcgtc caggtctccc agaacatcgg    360
tatgggttcc gccgccatcg gtcttgccgg tgctggtgtc ggtatcggtc tcgtcttcgc    420
cgccctcatc caggccgtcg cccgcaaccc ctccctccgt ggccagcttt tctcttacgc    480
cattcttggt ttcgctttcg tcgaggcat cggtctcttc gacctcatgg ttgccatgat    540
ggccaagttc ttgtaaaaaat gtgcattcca ttacctaccg agatggagat ggatgcgaag    600
```

```
gcgattgggg acggagacag tgcgttgctg cagcagcatt agtaccggtg ttggtcgtgt   660
accagtagtc tgatggagac ggatagatgg atagaaagct ggtgaatggg ggctacgaag   720
aaaacgtacc tctcgatcca tttgtaccca tactcatgaa gtatatccgt cttctttcct   780
tctatcattc gcgcgcactt ccttgctggt ggcttttttgg ggttgcgctc tcaccgaaaa   840
gcaacgtcac tcttgtatat aacttattcg accacggcca tatcttggtt tggctgggga   900
aataacaatg tctcatttgt acc                                            923

SEQ ID NO: 71         moltype = DNA  length = 923
FEATURE               Location/Qualifiers
source                1..923
                      mol_type = genomic DNA
                      organism = unidentified
SEQUENCE: 71
ggtacaaatg agacattgtt atttccccag ccaaaccaag atatggccgt ggtcgaataa    60
gttatataca agagtgacgt tgcttttcgg tgagagcgca accccaaaaa gccaccagca   120
aggaagtgcg cgcgaatgat agaaggaaag aagacggata tacttcatga gtatgggtac   180
aaatggatcg agaggtacgt tttcttcgta gcccccattc accagctttc tatccatcta   240
tccgtctcca tcagactact ggtacacgac caacaccggt actaatgctg ctgcagcaac   300
gcactgtctc cgtccccaat cgccttcgca tccatctcca tctcggtagg taatggaatg   360
cacatttttta caagaacttg gccatcatgg caaccatgag gtcgaagaga ccgatggcct   420
cgacgaaagc gaaaccaaga atggcgtaag agaaaagctg gccacggagg gaggggttgc   480
gggcgacggc ctgatgagg gcggcgaaga cgagaccgat accgacacca gcaccggcaa   540
gaccgatggc ggcggaaccc ataccgatgt tctgggagac ctggacgagg gcgttggcca   600
tctcagagga gtaggcacgc ttggcgatgg gggaggcctg gcgggccatc atctgggtgc   660
gcttcatggt gttgaagacg tgttcttgg gaccgcgga gtaggcgcgg gtgaacttct    720
ggagctgagc agcctggaag gccggccggg cgaccttcac gggagactga cgaagccatc   780
aggccatctt gggggcggcg acgcggaagg aagacattgt gatgatgtg aggtggtgag   840
atggagttga gatggttgt tgatggattt gggatgaaag tgtggtcgga tggaagatgg   900
tggtgtggag tacgaagagc tct                                            923

SEQ ID NO: 72         moltype = DNA  length = 1368
FEATURE               Location/Qualifiers
source                1..1368
                      mol_type = genomic DNA
                      organism = unidentified
SEQUENCE: 72
ggaggattct cggtcaagtt caggaccgca gaaggaaatt gggactttgt ggccaacaac    60
accccgtct tcttcctccg agacccggcc aagttcccc acttcatcca caccagaag    120
cgagatcccg ccacccactt gtctggtgac gatgactcga ccatgttctg ggactacctg   180
tcgcagaacc ccgagtcgat ccaccaagtc atgatcctca tgggtgatcg aggtatcccc   240
aagggctggc gattcatgca tggctactac ggccacaccc tcaagattgt caatgacaag   300
ggcgaatggg tctacgccca gttccacctc atctctgatc agggcaccca gaacttcacg   360
ggtgacggca ctgctcagca atccaacgat tacggacaga aggatctgta cgaagccatc   420
gagaagggag acttccctc gtggacgatg aagttcaga tcatgaccga gaagcaagcc   480
gaggaggcat gggagcaaaa gaggatcaac gtctttgatt tgacccacgt ctggcctcat   540
ggtgattacc cacttcgaac agtcggtaaa ttcaccctta acgagaatgc caagaactac   600
ttcgccgagg tggaacaagt cgcattcaac ccgtctcaca tgattcccgg tgtcgagccg   660
tccaacgacc cagtgttgca gtcgcgactg ttctcttacc ccgatgctca ccgacaccga   720
atcggagcca actatcagca actgcccgtt aaccagaatg tgtgcccctt cgccttgggc   780
aacttccagc gagacggcca gatggcattc tacaatcaag gtagtcgacc caactacctt   840
tcttcgattg agccaatctc attcaaggag agggcgttag atctcaacaa ggtccacggc   900
aaattcgtcg gagaagccgt cgccttcttg tctgaaatca ggccagagga cttcaatgcc   960
ccaagggcac tgtggcagaa agtctttagc gaggaaagca agcagcgatt cgtcgacacc  1020
gtctctggtc acatgtcgac agtccgagac aaagccatca ccgctcgaat gatgactatc  1080
ttccgagaag tttcgcctga tcttggtgat cgacttgaga aggccactgg tgtcaagggc  1140
gaatccacca ttgccgggat gaagttcaac ggaacgcaca atgggtttga caaggccaac  1200
aagatcccgg ctaatgggat gaagaaggggt ggagaagtca tctttgacaa tggtgcacct  1260
gctactgctg ccaggtaaat gagcggtcag gcgtacttga tatatgttgt tacgatatgt  1320
cggtctcgta gtcatgtagc caggataaat gaagcggatg tggcagtg                1368

SEQ ID NO: 73         moltype = DNA  length = 1368
FEATURE               Location/Qualifiers
source                1..1368
                      mol_type = genomic DNA
                      organism = unidentified
SEQUENCE: 73
cactgccaca tccgcttcat ttatcctggc tacatgacta cgagaccgac atatcgtaac    60
aacatatatc aagtacgcct gaccgctcat ttacctggca gcagtagcag gtgcaccatt   120
gtcaaagatg acttctccac ccttcttcat cccattagcc gggatcttgt tggccttgtt   180
aaacccattg tgccgttccgt tgaacttcat cccggcaatg gtggattcgc ccttgacacc   240
agtggccttc tcaagtcgat caccaagatc aggcgaaact tctcggaaga tagtcatcat   300
tcgagcggtc atggctttgt ctcggactgt cgacatgtga ccagagacgg tgtcgacgaa   360
tcgctgcttg ctttcctcgc taaagacttt ctgccacagt gcccttgggg cattgaagtc   420
ctctggtaca atttcagaca agaaggcgac ggctctccg acgaatttgc cgtggacctt   480
gttgagatca tacgccctct ccttgaatga gattggctca atcgaagaaa ggtagttggg   540
tcgactacct tgattgtaga atgccatctg gcgtctcgc tggaagttgc ccaaggcgaa   600
ggggcacaca ttctggttaa cgggcagttg ctgatagttg gctccgattc ggtgtcggtg   660
agcatcgggg taagagaaca gtcgcgactg caacactggg tcgttggacg gctcgacacc   720
gggaatcatg tgagacgggt tgaatgcgac ttgttccacc tcggcgaagt agttcttggc   780
```

```
attctcgtta agggtgaatt taccgactgt tcgaagtggg taatcaccat gaggccagac   840
gtgggtcaaa tcaaagacgt tgatcctctt ttgctcccat gcctcctcgg cttgcttctc   900
ggtcatgatc tgaaccttca tcgtccacga ggggaagtct cccttctcga tggcttcgta   960
cagatccttc tgtccgtaat cgttggattg ctgagcagcc tcgtcacccg tgaagttctg  1020
ggtgccctga tcagagatga ggtggaactg ggcgtagacc cattcgccct tgtcattgac  1080
aatcttgagg gtgtggccgt agtagccatg catgaatcgc cagcccttgg ggatacctcc  1140
atcacccatg aggatcatga cttggtggat cgactcgggg ttctgcgaca ggtagtccca  1200
gaacatggtc gagtcatcgt caccagacaa gtgggtggcg ggatctcgct tctgggtgtg  1260
gatgaagtgg ggaacttggg ccgggtctcg gaggaagaag acggggtgt tgttggccac  1320
aaagtcccaa tttccttctg cggtcctgaa cttgaccgag aatcctcc              1368

SEQ ID NO: 74           moltype = DNA   length = 1377
FEATURE                 Location/Qualifiers
source                  1..1377
                        mol_type = genomic DNA
                        organism = unidentified
SEQUENCE: 74
ggacaccatt gacgcagagg tgctcgacag tttgggtgtc acccaagaga acttccagtt    60
tgcccttggc gtcagcaacc cctctgccct tcgcgaggtc gcagtggtcg aggttcccaa   120
cgtcagatgg gaggacattg gtggtctcga ggaggtcaag agggagctca tcgagagcgt   180
gcaataccc gtcgaccacc ccgagaagtt cctcaagttt ggcatgtccc catcaaaggg   240
tgtgctttc tacggtcccc ctggtactgg taagactctt ctggccaagg ctgtcgccaa   300
cgagtgcgcg gccaaccttta tttccgtcaa gggtcccgag cttctctcca tgtggttcgg   360
tgagtctgag agcaacattc gtgacatctt cgacaaggct cgtgctgccg cgccttgcgt   420
tgtcttcctc gacgagctgg actccatcgc caagtctcgt ggcggttctc agggcgatgc   480
tggcgtgct tccgaccgtg tggtcaacca gcttctcact gagatggacg gtatgaccag   540
caagaagaac gttttcgtca tcggtgccaa caacaggcct gagcagctcg acaacgctct   600
ctgccgtcct ggtcgtctcg acactctcgt ctacgttccc ctgcctgacc aggagggccg   660
tgagagcatt ctcaaggccc agctccgcaa gactcctatc gccgacgaca tcgacctttc   720
ctacatggcc tccaagactc acggttttctc tggtgccgat cttggcttca tcacccagcg   780
tgccgtcaag ctggccatca gcagtctat tgacctggcc atccagaacc aaaaggctag   840
agaggccgag ggtgacaccg ccatggacga ggacatcgag gaggacgacc ccgtgcccga   900
gctgaccaag gctcactttg aggaggctat gagcatggct cgtcgctccg tcaccgcacac   960
cgagatcagg cgctacgagg cttccgccca gagcatgaag agctccggtg gcggcagcgc  1020
tttcttccgc ttccctgaga gcggtgccga tggcaacgca gccgagcagc agcaaaatgg  1080
tgctggcgag gaggacctct acgactaaat tggtttcacg aacctcacga cctaatcctt  1140
tgctgttatc ggagtaatat tccagatgga gagagcaatc atgcattcag gcgcgtctat  1200
ggactgaagg ggaagatgga tagagtgttc cagtagccct ttctcttttt tttctgggaa  1260
ctcttgctgt ttggctggtc gcctcttatc gagtgtggtt gtgctagagt aggcagttca  1320
gagtttccct gttatgttat gcctttccgg gcagtatgga aataatttcc ttgcaaa     1377

SEQ ID NO: 75           moltype = DNA   length = 1377
FEATURE                 Location/Qualifiers
source                  1..1377
                        mol_type = genomic DNA
                        organism = unidentified
SEQUENCE: 75
tttgcaagga aattattctc atactgcccg gaaaggcata acataacagg gaaactctga    60
actgcctact ctagcacaac cacactcgat aagaggcgac cagccaaaca gcaagagttc   120
ccagaaaaaa agagaaaagg gctactgaa cactctatcc atcttcccct tcagtccata   180
gacgcgcctg aatgcatgat tgctctctcc atctggaata ttactccgat aacagcaaag   240
gattaggtcg tgaggttcgt gaaaccaatt tagtcgtaga ggtcctcctc gccagcacca   300
ttttgctgct gctcggctgc gttgccatcg gcaccgctct cagggaagcg gaagaaagcg   360
ctgccgccac cggagctctt catgctctgg gcgaaagcct cgtagcgcct gatctcggtg   420
tcggtgacgg agcgacgagc catgctcata gcctcctcaa agtgagcctt ggtcagctcg   480
ggcacgggt cgtcctcctc gatgtcctcg tccatggcgg tgtcaccctc ggcctctcta   540
gcctttggt tctggatggc caggtcaata gactgcttga tggccagctt gacggcacgc   600
tgggtgatga agccaagatc ggcaccagag aaaccgtgag tcttggaggc catgtaggaa   660
aggtcgatgt cgtcggcgat aggagtcttg cggagctggg ccttgagaat gctctccagg   720
ccctcctggt caggcagggg aacgtagacg agagtgtcga gacgaccagg acggcagagg   780
gcgttgtcga gctgctcagg cctgttggtg gcaccgatga cgaaaacgtt cttcttgctg   840
gtcataccgt ccatctcagt gagaagctgg ttgaccacac ggtcggaagc accgccagca   900
tcgccctgag aaccgccacg agacttggcg atggagtcca gctcgtcgag gaagacaacg   960
caaggcgcgg cagcacgagc cttgtcgaag atgtcacgga tgttgctctc agactcaccg  1020
aaccacatga gagaagctc gggacccttg acggaaataa agttggccgc gcactcgttg  1080
gcgacagcct tggccagaag agtcttacca gtaccagggg gaccgtagaa aagcacaccc  1140
tttgatgggg acatgccaaa cttgaggaac ttctcggggt ggtcgacggg gtattgcacg  1200
ctctcgatga gctccctctt gacctcctcg agaccaccaa tgtcctccca tctgacgttg  1260
ggaacctcga ccactgcgac ctcgcgaagg cagagggt tgctgacgcc aagggcaaac  1320
tggaagttct cttgggtgac acccaaactg tcgagcacct ctgcgtcaat ggtgtcc     1377

SEQ ID NO: 76           moltype = DNA   length = 699
FEATURE                 Location/Qualifiers
source                  1..699
                        mol_type = genomic DNA
                        organism = unidentified
SEQUENCE: 76
gaaggtgacg acgagcagac tttgcgcccc acgacgatac taacgtaacg acccagcaca    60
cattaatcca caatgggtca ctccgccggt ctcaggaagg gcactcgcta tgcctttctct   120
```

```
cgcgacttca agaagagggg catgatcccc ctctccacct acccttaagca gtacaaggtc   180
ggcgacatcg tccacgtcgt ctgcaacggt gccgtccaga agggcatgcc ccacaaggac   240
ttccacggca agactggtgt cgtctacaac gtgaccaagt ccgccgtcgg cgtcatcctg   300
tacaagcagg ttggcaaccg ttacatcgag aagcgcgtca acctccgcat cgagcacgtc   360
cgcctctccc gctcgcgtga ggagttcatc gtccgcgtca agaccaacgc tgagaagaag   420
cgcaaggcca aggaggaggg caccaccgtc ttcctcaagc gccaggccga caagcccgc    480
gaggcccgca ccatcagcgc caaggacaac aagcccgaga gcatcgctcc tatcgcctac   540
gacacccaca tttaagcgtg cttgtttcga aagggagggc gtacgggctg gtatgatggc   600
gaggctagga ggttggtatc ggcggatcgg attccaccgg atgggaaata cctgccggat   660
gagccagcta gcttcgcaag gtgcatgaat tctagcgcc                          699

SEQ ID NO: 77         moltype = DNA   length = 1664
FEATURE               Location/Qualifiers
source                1..1664
                      mol_type = genomic DNA
                      organism = unidentified
SEQUENCE: 77
ggggacatgg gcatcggtgg tcttgatacg gagttctcgg ctatcttccg acgagcattt    60
gccagtcgta ttttcccgcc gggactggtc gagaaattag gtatccagca cgtcaagggt   120
atcttactgt ttggcccgcc aggaacagga aaaaccttga tggcacggca gatcggaacg   180
atgctcaacg ccagagagcc taaggtggtc aacggtcccg aaatcctcaa caagttcgtc   240
ggtcagagtg aggagaatat cagaaagctg tttgccgatc ctgagaaaga gcaaaaggaa   300
aaggggatg aaagtggctt gcacatcatc atcttcgatg agctggacgc tatctgtaaa    360
cagcgaggat ctacaaacag cggtaccggc gttggagact cggttgtcaa tcagctgtta   420
tcgaagatga acgtgtagat caactgaac aatgtcttga tcatcggtat gactaatcga    480
atggacatga tcgacgaagc gctcctccga cctggacgtc tggaagtcca cattgagatc   540
tcgttgcctg acgaagctgg ccgattccga atcctcaaca ttcataccaa caagatgagg   600
acgaatggtg tcatggacag cgatgtggat ctgggcgaac tagcggccct gacgaagaac   660
ttctcggggtc ccgagattgg tggtctggtc aaatcagcga ccagtttcgc tttcaaccgt   720
cacgtcaagg ttggctccgt cgccgcgttt gatgatatcg acaatatgaa gatctcacga   780
gccgacttcc tccacgccct agacgaggtt acacctgcgt ttggtgtctc cgaagaagag   840
ctgcaacagg tcgtgcagaa cggtatcatt cactactcgc aacacgtcaa tgacacacta   900
aacgatggaa gtctgcttgt ggagcaagtg cgaaaatccg accgcacccc gcttgtctcg   960
gccctccttc acggtccatc tggcgcgggc aagacggctt tggcagccac gatcgccatg  1020
gcatccgagt tcccctttcat caagctcatc tcgcctgaaa caatggttgg gtttttctgag 1080
ccgcagaaga ttgctcaact caacaaggtt ttcacagaca gctacaagag tccgatgagc  1140
atcatcgttg tcgacagtct cgagagattg ctggactgga acccgatcgg acccaggttc  1200
tcgaatggtg tgcttcaggc tttggttgtc ctctttggca aacgtccgcc caagggtcgg  1260
cgtcttctca ttctggccac cacgtcaaat cgcaacatcc tcacggatat ggacgtcctt  1320
tcggcttttcg acactgatat ccccattaac cccatctcat cgatcgatgc agtggtgcac  1380
gttctagatg aggtcaagtt attcccgaac tcgaaggaaa agcagagagc aacacagatg  1440
cttcgcgagg cgagactggg cgaaggtggt cgaccagact tgttggtcgg agtgaaaaag  1500
ctgttgagta tggcagagat ggcccggcag gatccgaatc ccacgatgaa gatcgtgacg  1560
agcattctca gggaggcgag ttaggatgtg tgaagcgtga tcatgataga gtgtagtcca   1620
aacaatgtac tagtgcaaca gaagctatgc agatgaataa cgtt                    1664

SEQ ID NO: 78         moltype = DNA   length = 1368
FEATURE               Location/Qualifiers
source                1..1368
                      mol_type = genomic DNA
                      organism = unidentified
SEQUENCE: 78
ggaggattct cggtcaagtt caggaccgca gaaggaaatt gggactttgt ggccaacaac    60
accccgtct tcttcctccg agacccggcc aagttccccc acttcatcca cacccagaag   120
cgagatcccg ccaccacttt gtctggtgac gatgactcga ccatgttctg ggactacctg   180
tcgcagaacc ccgagtcgat ccaccaagtc atgatcctca tgggtgatcg aggtatcccc   240
aagggctggc gattcatgca tggctactac ggccacaccc tcaagattgt caatgacaag   300
ggcgaatggg tctacgccca gttccacctc atctctgatc agggcaccca gaacttcacg   360
ggtgacgagg ctgctcagca atccaacgat tacggacaga aggatctgta cgaagccatc   420
gagaagggag acttcccctc gtggacgatg aaggttcaga tcatgacga gaagcaagcc    480
gaggaggcat gggagcaaaa gaggatcaac gtctttgatt tgacccacgt ctggcctcat   540
ggtgattacc cacttcgaac agtcggtaaa ttcaccctta acgagaatgc caagaactac   600
ttcgccgagg tggaacaagt cgcattcaac ccgtctcaca tgattcccgg tgtcgagccg   660
tccaacgacc cagtgttgca gtcgcgactg ttctcttacc ccgatgctca ccgacacgga   720
atcggagcca actatcagca actgcccgtt aaccagaatg tgtgcccctt cgccttgggc   780
aacttccagc gagacggcca gatggcattc tacaatcaag gtagtcgacc caactacctt   840
tcttcgattc agccaatctc attcaaggag agggcgtatg atctcaacaa ggtccacggc   900
aaattcgtcg gagaagccgt cgccttcttg tctgaaatca ggcagagga cttcaatgcc   960
ccaaggcgca tgtggcagaa agtctttagc gaggaaagca gcagcgatt cgtcgacacg   1020
gtctctggtc acatgtcgac agtccgagac aaagccatca ccgctcgaat gatgactatc  1080
ttccgagaag tttcgcctga tctttggtgat cgacttgaga aggccactgg tgtcaagggc  1140
gaatccacca ttgccgggat gaagttcaac ggaacgcaca atgggtttga caaggccaac  1200
aagatcccgg ctaatgggat gaagaagggt ggagaagtca tctttgacaa tggtgcacct  1260
gctactgctg ccaggtaaat aagcggtcag gcgtacttga tatatgttgt tacgatatgt  1320
cggtctcgta gtcatgtagc caggataaat gaagcggatg tggcagtg              1368

SEQ ID NO: 79         moltype = DNA   length = 1280
FEATURE               Location/Qualifiers
source                1..1280
```

```
                        mol_type = genomic DNA
                        organism = unidentified
SEQUENCE: 79
gagcacatac acacaccacc gcaatcatgc ctccccgcca accagcaaca cggctctttg    60
ccctaccgcc tcgcttcctc tgcccttcgc tgcccaccac gcaaacgcgc accatccgct   120
ccatcgacaa acccgcccca aaacccagcc gattcaatgc ctcactcaat ctccccgtgc   180
tgggctcctc gtccaccgcc gccttcgcgc gcaaagagca ctcgctcccc ctgcgcaccg   240
gcgcgctcgc catcaaaaag ggcatgacgg cactcttcga cccggtcaca gcgaagcgca   300
cgccctgcac cgtcctgcaa ctcgacagat gccaggtggt cagccacaag cgacgcgaca   360
tccacggcta ctgggcggtg caagtgggcg cgggcgccaa agaagcgagg aacgtcacgc   420
ggccggagag gggccacttc gccgcctaca acgtgccctt gagcaggcac ctggccgagt   480
tcagagtcaa gaacgccgag ggcctgcccc ccgttggctc ggctattacc gccgacctgt   540
tcatcgaggg ccagttcatc gatgccaaag ccgaccgcag aggcatgggt ttcgagggtg   600
gtatgaagcg ctggaacttc ggcggacagc ccgcgtcgca cggtaactcg ctcgcgcaca   660
gattgatggg ttcgtccggt ggtggacagg gcagcggtag cagagtcttg cccggcaaga   720
agatgccggg tcgcatgggt ggcgagcagg cgaccgttgc gaacctgagg gtcatgcagg   780
tggacaagga gaacggtatc gtggttgtga gtggcgctgt gcctggcccg aagaactgca   840
tggtcaagct gcaggatgcg ctcaagaagc cttggcctga tgcgacttgg ccgccgtcta   900
ttgagggcgc gacggaggtt ctgagggagg ccactgagaa ggcgcctgct gcgtaagggg   960
gtcggtcgag gtcaagaaat atcgttgcaa tttgggagat gatgctgtcc gatgcctgtc  1020
gaaaagggt tcttgtgggg aggtctggag aatcatcgat gcaagcatta acatgagcgt   1080
gatctcacga gcaatcccag agaagcggtt acagctgctt ctcgaaatg tacactgctc   1140
aaagcttgcc ggagaagttg gccaaagtca tcactctcgg cacaggaata tactttgtaa  1200
ccataggaa aagaggagag ggtctcgagc caggatcaaa aataggaaat gtacattata   1260
attgcatatc gtcatcatcc                                              1280

SEQ ID NO: 80          moltype = DNA   length = 677
FEATURE                Location/Qualifiers
source                 1..677
                       mol_type = genomic DNA
                       organism = unidentified
SEQUENCE: 80
ggaatcgacg aacgacacct caatcgaaac caccactcgc cattgtgaat cttttccacct   60
gtcgcaatgg gtatctggga cgctttcacc gatattgtcg aggctgtgac gccatggagc   120
gtcgttgagg ccgaggctcc tgctgaggag ccccaggagg agaacgagtc caagaccgag   180
tccaaggacg agcccgagga ggaggaagag gatgaggaag aagaggagga tgaggatgat   240
gaggaggagc tcgtcgaccc caaggagact ctcgaggaag agtgcaagaa ctctcctcaa   300
tgtgcccccg ccaagcacca cttcgacgag tgtgttgagc gcgttcagca gcaggagagc   360
gagggtggtg ctaaggagga ctgtgtcgag gagttcttcc accttgccca ctgtgcgacc   420
gcttgcgccg ctcccaagct ttggtctcag ctcaagtaaa ctcacaacat tgggttatcg   480
gttactacga cgacgcaatg gctacatcaa cgtcgaaaag atgcctggag ccggaacgag   540
gcaatgctgc ccactacgga aggctgttcc cttgtacgaa tgctcatctg ccgggtatca   600
agtcggccag agattactct gatgtcgact ctctctgtac catacgctct tacgcctgaa   660
tagatttctt gcactttt                                                677

SEQ ID NO: 81          moltype = DNA   length = 1019
FEATURE                Location/Qualifiers
source                 1..1019
                       mol_type = genomic DNA
                       organism = unidentified
SEQUENCE: 81
gggagatact accgtgcgcc cgagatcatg ttgacatggc aaaaatacga tgtcgccgtc    60
gacatttgga gcacaggatg tatcttcgcc gagatgctcg agggaaagcc cctgttcccg   120
ggcaaggacc acgttaatca gttctcgatc atcacagaat tgctcggcac acctcctgac   180
gatgtcatcc agaccatcgc atctgagaac accctccgat tcgtccagtc gctgcccaag   240
cgtgagaagg tcccattcac tacgaaattc gccaatgccg accgctttc gcttgacttg   300
ttggagaaga tgcttgtctt cgatccacgt acccgtatct cggcatcaga agggctgtcg   360
cacgagtacc ttgcgccata ccatgacccg acggatgagc ccgtcgctgc cgaggtgttt   420
gactggagtt tcaacgatgc ggatctacca gtagacacct ggaaggtcat gatgtactcc   480
gagatcctgg acttccacaa ctttgggtgat atccagcaag accaggccgc cgaaggaccc   540
gtcactggcg acctagcccc accttccgct acgacttcgg catagacagc ttgcctttag   600
gggtttttt ctcgttttc tcttctcgtc tcattacgtt cctagtcaac atgtgtccat   660
tagcatccca aattattggt ggtagaaagg agggaaggaa ttggtgcaac atgatctctc   720
ctagaaaatc gtttctcttc atctctcgtc catgatccac gctttcccaa gctttatctc   780
ccccttcccc ttcctcacgc tcaacttct cctgtaccaa caaatcttcg ctaccgcttt   840
ctcgaccgtc gaacgaacat cacaaagaat caagaaaggt agaagaggtg tgaatagacc   900
aggaaaggca ttcttggagc gagggggag gaggaagtaa tctggaacga aagcccatca   960
cactgttttc tttgaaccta catacacgga cagagggaa tgcatgtgca tggtaatgt   1019

SEQ ID NO: 82          moltype = DNA   length = 391
FEATURE                Location/Qualifiers
source                 1..391
                       mol_type = genomic DNA
                       organism = unidentified
SEQUENCE: 82
cgctaccggt cgccgcgcg ccggggttga cctcggatca ggtagggata cccgctgaac    60
ttaagcatat caataagcgg aggaaaagaa accaaccggg attgccctag taacggcgag   120
tgaagcggca agagctcaaa tttgaaagct ggccccctcg gggtccgcat tgtaatttgc   180
agaggatgct tcgggaacgg ccccccatcta agtgccctgg aacgggccgt catagagggt   240
```

```
gagaatcccg tctgggatgg ggtggccgcg cccgtgtgaa gctccttcga cgagtcgagt    300
tgtttgggaa tgcagctcta attgggtggt aaatttcatc taaagctaaa tattggccgg    360
agaccgatag cgcacaagta gagtgatcga a                                   391

SEQ ID NO: 83            moltype = DNA   length = 391
FEATURE                  Location/Qualifiers
source                   1..391
                         mol_type = genomic DNA
                         organism = unidentified
SEQUENCE: 83
cgctaccggt cgccggcgcg ccggggttga cctcggatca ggtagggata cccgctgaac    60
ttaagcatat caataagcgg aggaaaagaa accaaccggg attgccctag taacggcgag    120
cgaagcggca agagctcaaa tttgaaagct ggccccctcg gggtccgcat tgtaatttgc    180
agaggatgct tcgggaacgg cccccatcta agtgccctga acgggccgt catagaggt     240
gagaatcccg tctgggatgg ggtggccgcg cccgtgtcaa gctccttcga cgagtcgagt    300
tgtttgggaa tgcagctcaa attgggtggt aaatttcatc taaagctaaa tattggccgg    360
agaccgatag cgcacaagta gagtgatcga a                                   391

SEQ ID NO: 84            moltype = DNA   length = 124
FEATURE                  Location/Qualifiers
source                   1..124
                         mol_type = genomic DNA
                         organism = unidentified
SEQUENCE: 84
gggtctggtg gcgatagcga gacgccaca cccgttccca tgccaaacac ggaagttaag     60
cgtctcagcg ccgaaagtag ttgggggatc tcccctgtg aggataggac gttgccaggc    120
aaaa                                                                 124

SEQ ID NO: 85            moltype = DNA   length = 717
FEATURE                  Location/Qualifiers
source                   1..717
                         mol_type = genomic DNA
                         organism = unidentified
SEQUENCE: 85
agatggagcc tgaccaagaa gagtctgaag aggaagaaga ggaagaggat gacgagatgg    60
atgaagatga ggatgagggc cagcagcagg acgccagtgg catgcagaca ccctctgggc    120
tcgccacgcc ctcaggctat gcctctacta catctacaat gctggtggc atggagacgc    180
ctgactttat ggacttgcgc aagcagcgac agacgcgcga cgagaccgct gatcaagagg    240
accagggtgc accgcgagac ctctatacgg tcgtgccgga gcgcagagcc accgcttctg    300
gcttcctcgg ttctgaccgc gcctatgact tgtccaatgc gccacagtct tccaacatgc    360
ctgtgttggg tcaagaagac tcgcgcaaga agaaaggcgg cagatctggt gcagacgacg    420
tcgacctggc cttggatcca gctgagctcg agggcatgtc tgagcaagag cttaggcaga    480
agtacgactc gcacaggcgc tcctcgtcca gtcaaggcgc gcgccgacag caggacaaag    540
aagattctc agatttcgtc gcgcaagagg tcgcaaagaa gagggcagagg gctcagcagc    600
gcggcggcag tggacgcgac cgcgaaagct ctcggagcaa ggaaaagttc aagttttaga    660
gtgtatgttt gtattgtatg aagatcagac aaaaatgcta tgggtggcgt tgctgct      717

SEQ ID NO: 86            moltype = DNA   length = 872
FEATURE                  Location/Qualifiers
source                   1..872
                         mol_type = genomic DNA
                         organism = unidentified
SEQUENCE: 86
cgtgtagcat aaaagctagaa gtaatattca cagctaactc tacagtagaa caaagttctt    60
gtttcgttct ccagatccaa gtgatagcaa ctgcttcaca aggatggaag aaccaaattg    120
ttgaaagatt cggcacctaa taggcggcac ccatgttgaa atcgtcagtc atgttgaaac    180
tccgtaaacc cgcttttggt gccctctaat ccgcaaaacc ttgaaccct atgttgaact     240
tttggtatca tcttcgtaat cgtcataaaa cagaactccc cgtgccagag gcggcaggtt    300
gagaataccg ccccttgaat taacacatta taggaagtgg aacaaaggaa aaatgagaaa    360
tgttaatgcg cacagaatta ctgagtgtac ttctggcggt agaacttagc agcctgacc     420
agagaggtca gctggccgat agtctgctca gtggtacggg tcttcagacc gcagtcaggg    480
ttgatccaga gctgctcagg cttgaggtac tggagcatct gctcgatacg ctccttgatc    540
tcatccacgg agggaacacg aggagagtgg atatcgtaga caccaggtcc aatgtgggcg    600
gggaaactct gatcaacgaa gacctggagg gcttgggcat cggactttgct gttctcgatg    660
gacaaaacat cggtatcaag ggcagcaata gcgtggaaga agtcctggaa ttcactgtag    720
cagaagtggg agtggacctg ggtgctgtcg gtgacaccag cagtagacag cttgaaagca    780
ttgacagccc acttaacata agcatcacgg gcagcgccag tacgcagagg aagaccctca    840
cgcagggcag gctcgtcgac ttggatgacc cc                                 872

SEQ ID NO: 87            moltype = DNA   length = 872
FEATURE                  Location/Qualifiers
source                   1..872
                         mol_type = genomic DNA
                         organism = unidentified
SEQUENCE: 87
ggggtcatcc aagtcgacga gcctgccctg cgtgagggtc ttcctctgcg tactggcgct    60
gcccgtgatg cttatgttaa gtgggctgtc aatgctttca agctgtctac tgctggtgtc    120
accgacagca cccaggtcca ctcccacttc tgctacagta aattccagga cttcttccac    180
gctattgctg cccttgatac cgatgttttg tccatcgaga cagcaagtc cgatgccaag    240
```

```
ctcctccagg tcttcgttga tcagagtttc cccgcccaca ttggacctgg tgtctacgat   300
atccactctc ctcgtgttcc ctccgtggat gagatcaagg agcgtatcga gcagatgctc   360
cagtacctca agcctgagca gctctggatc aaccctgact gcggtctgaa gacccgtacc   420
actgagcaga ctatcggcca gctgacctct ctggtcgagg ctgctaagtt ctaccgccag   480
aagtacactc agtaattctg tgcgcattaa catttctcat ttttcctttg ttccacttcc   540
tataatgtgt taattcaagg ggcggtattc tcaacctgcc gcctctggca cggggagttc   600
tgttttatga cgattacgaa gatgatacca aaagttcaac atagggtttc aaggttttgc   660
ggattagagg gcaccaaaag cgggtttacg gagtttcaac atgactgacg atttcaacat   720
gggtgccgcc tattaggtgc cgaatctttc aacaatttgg ttcttccatc cttgtgaagc   780
agttgctatc acttggatct ggagaacgaa acaagaactt tgttctactg tagagttagc   840
tgtgaatatt acttctagct ttatgctaca cg                                 872
```

SEQ ID NO: 88              moltype = DNA   length = 362
FEATURE                    Location/Qualifiers
source                     1..362
                           mol_type = genomic DNA
                           organism = unidentified
SEQUENCE: 88
```
gttgacctcg gatcaggtag ggatacccgc tgaacttaag catatcaata agcggaggaa    60
aagaaaccaa cagggattgc tctagtaacg gcgagtgaag cagcaatagc tcaaatttga   120
aatctggcgt cttcggcgtc cgagttgtaa tttgtagagg atgcttctgg gcagccaccg   180
acctaagttc cttggaacag gacgtcatag agggtgataa tcccgtatgc ggtcggaaag   240
gcaccctaca cgtagctcct tcgacgagtc gagttgtttg ggaatgcagc tctaaatggg   300
aggtaaattt cttctaaagc taaatattgg ccagagaccg atagcgcaca agtagagtaa   360
cc                                                                  362
```

SEQ ID NO: 89              moltype = DNA   length = 663
FEATURE                    Location/Qualifiers
source                     1..663
                           mol_type = genomic DNA
                           organism = unidentified
SEQUENCE: 89
```
gaccctcact ctctttctcc ctctcttaca tagcgagctg gtctccatcc ttgttgtttg    60
atttgatctt ctttgcattt ccctatccca gtgatgaagt tatccaattc cgctcattac   120
tcgcttttcc tcctatcctc catcctcggc ttctccagcg cgtcggccaa ctctcacctc   180
agtgatgatt ctccttgtgt ggcccgctcg ccaacaagtg ggctctatta tgatctgaat   240
gctatctcat tagcaccgcc ggaatggaag aacgggaaga aagttgatca ggaagcgcga   300
gatgaaagct ggcatgccaa ggggcatgac taccccgcga acttcacaat caatgtctgc   360
gcgccggttc ttgagaatgt aaccaatgtt gtcggggtag atgcctctcg atgggcgaat   420
gtcagtgctt tctatgagca agctgggaag atatactcaa tgggagagca agcctccgag   480
cctttcttcc gcggccgcaa gctagtactc aactacacgg acggttcgcc atgtcccggt   540
gattcgaata ctgctagcgg caatagctct attcgaacca agtccactct gatgtccttc   600
ctctgcgatc gcgcggccga attccccggg ctcgagaagc ttggatccac cggatctaga   660
taa                                                                 663
```

SEQ ID NO: 90              moltype = DNA   length = 1243
FEATURE                    Location/Qualifiers
source                     1..1243
                           mol_type = genomic DNA
                           organism = unidentified
SEQUENCE: 90
```
atgtccatcc gcaatgaatg gcttcaatga gaaaggcctc gacggggatg cctttggaga    60
gaagtccaat ctctccgggc taaagacatt tgacgctttc cccaaaacaa aaacatccta   120
cacaacccca acccgacgag gcggccaatg gaccgttctc atcctagcag tatgcacact   180
attcagcctc cacgaactcc gcacctggtg gcgcggcaca gaagcccacc acttcagcgt   240
ggaaaaaggc gtatcccacg atctccaatt aaacctcgat atggtcgttc acatgccctg   300
tgacactctc gcataaaaca ttcaagacgc ctccggagac cgcgttttag ctggcgaact   360
cctaacccgc gaagacacaa actgggacct ttggatgaag aagcgcaatt tcgaatccca   420
cggcgaacac gaataccaaa cgctcaatca tgaagcggct gatcgattaa gtgcgcagga   480
tgaagacgcg cacgtacacc atgtcctggg tgaagtcgc cgtaacccgc gccgcaagtt   540
ttctaagggt ccacgtctac gctggggcga taacaaggat tcttgtcgaa tttatgaag   600
tcttgaaggg aataaagtgc aaggggattt ccatattacg gcacgggac atggatatat    660
ggaattggcg ccgcatttgg atcacgaagt cttcaatttc tcccacatga ttacagaact   720
gtccttcgga ccacactatc catccttct aaaccctct gacaagacca tcgccgaaag   780
cgaaacccac taccagaaat tccaatactt cctttccgtc gtcccgaccc tctactcaaa   840
gggccacaat gcacttgacc tcgtgacaac aaataaagat aactccgtcc gctacggccg   900
taacacaatc ttcacaaacc aatacgcagc cacaagccag agtaccgccc tccctgaaat   960
cccacccta atcccgggaa tctttttcaa gtataatatc gagccgatct tgctacttgt   1020
cagcgaagag cggacgggat tcttggctct tgtcattcga gtcattaata ccgtttctgg   1080
ggtcttggtt acgggtggtt ggatctacca gatttctggg tggattgttg agatccttgg   1140
gaaaaggaaa cggcagtctg aggggtgttt gactgggaag cattattcgg attgatttgt   1200
ttctagtagt ttcgtctcaa tataagtttg attttccttt tcc                    1243
```

SEQ ID NO: 91              moltype = DNA   length = 1007
FEATURE                    Location/Qualifiers
source                     1..1007
                           mol_type = genomic DNA
                           organism = unidentified
SEQUENCE: 91

```
gaacggtgat agtagtagta ggctcgtcat ctatctacaa cccctctctc ctcactcccc    60
tctctcgacg ccatgttcac gcgtactctc cgaccggccg tggcggtcgc caggactcag   120
gctgtccagc agcaacaggc cggtatggcc acattgaagg aaatcgacca gcgtttgaaa   180
tccgtcaaga acattgggaa gatcaccaag tcgatgaagg tcgttgcctc gaccaagttg   240
acgcgagctg agaaggccat gcgtgaagcc aagaagtacg gtgccgccaa caacgttctg   300
ttcgagcaga ccaaggctgg tgaggaggag cccaaggagc gcaagatcct ctacctcgcc   360
atgacatccg acggtggtct gtgcggtggt atccactcca acattacgcg atacatgaag   420
aaggctgtgg ccaaggaacc cggaatgctg gctgttgtcg gtgacaagcc caaggctcag   480
ctctctcgag cgatgcccaa ggctttgacc atgtctttca acggcgtcgg caaggatgtc   540
cccactttcg tcgaggccag cgctatcgcc gatgagatta tgaaatctgc cggtgacttt   600
gacgagatcc gaatcgtctc taacaagtac ctttccgcta tcgcctacga acctcacacc   660
aacgccgtca tctccgctga ggcactccga caagccgccg gtttccagca atacgagatg   720
gaggaggatg tctccaagga cttggccgag ttcgctcttg ccaacgccat ctacactgcc   780
ctggtcgagg gacacgccgc cgagatctct gcaaggaggc aagctatgga gaacgcttcg   840
aacaacgcca acgacatgat caactctctc cagctgcagt acaaccgtgg tcgacaggct   900
gtcattacca ccgagctgat cgatatcatt accggtgcct cggctctgta agcgggtgta   960
gactagatgg acaaaacaac aaaaatggca tgcagcgaat gacattg                1007

SEQ ID NO: 92           moltype = DNA  length = 1007
FEATURE                 Location/Qualifiers
source                  1..1007
                        mol_type = genomic DNA
                        organism = unidentified
SEQUENCE: 92
caatgtcatt cgctgcatgc cattttgtt gttttgtcca tctagtctac acccgcttac    60
agagccgagg caccggtaat gatatcgatc agctcggtgg taatgacagc ctgtcgacca   120
cggttgtact gcagctggag agagttgatc atgtcgttgg cgttgttgga agcgttctcc   180
atagcttgcc tccttgcaga gatctcggcg gcgtgtccct cgaccagggc agtgtagatg   240
gcgttggcaa gagcgaactc ggccaagtcc ttggagacat cctcctccat ctcgtattgc   300
tggaaaccgg cggcttgtcg gagtgcctca gcggagatgg ccggcgttggt gtgaggttcg   360
taggcgatag cggaaaggta cttgttagag acgattcgga tctcgtcaaa gtcaccggca   420
gatttcataa tctcatcggc gatagcgctg gcctcgacga aagtggggac atccttgccg   480
acgccgttga agacatggt caaagccttg ggcatcgctc gagagagctg agccttgggc   540
ttgtcaccga caacagccag cattccgggt tcctggcca cagccttctt catgtatcgc   600
gtaatgttgg agtggatacc accgcacaga ccaccgtcgg atgtcatggc gaggtagag   660
atcttgcgct ccttgggctc ctcctcacca gccttggtct gctcgaacag aacgttgttg   720
gcggcaccgt acttcttggc ttcacgcatg gccttctcag ctcgcgtcaa cttggtcgag   780
gcaacgacct tcatcgactt ggtgatcttc ccaatgttct tgacggattt caaacgctgg   840
tcgatttcct tcaatgtggc cataccggcc tgttgctgct ggacagcctg agtcctggcg   900
accgccacgg ccggtcggag agtacgcgtg aacatggcgt cgagagaggg gagtgaggag   960
agaggggttg tagatagatg acgagcctac tactactatc accgttc                1007

SEQ ID NO: 93           moltype = DNA  length = 1139
FEATURE                 Location/Qualifiers
source                  1..1139
                        mol_type = genomic DNA
                        organism = unidentified
SEQUENCE: 93
acctcacttt gtgcgaatta tcctcctaca gcatcagctc tcttcagaaa gaggctaaat    60
ctatagaccg tccggaacag gttgtcaaca cgcgcgataa gagaagaagg gaatctactg   120
gtagacaaca gatcgatcgc tcttcagcaa acgcaagatg gagaaccttc ttcgtcagat   180
gcaagggga ggtggtagga tgggtgcacg gccaggccct ggaggcgaaa ctatcctcgc   240
cgacaacggt gaaacagtcc atatttcatc tcttgctcta ttgaagatgc tcaagcatgg   300
acgagcgggt gtgcctatgg aagtcatggg tctcatgctt ggcgaatttg ttgatgacta   360
cactatctcc tgtgtcgacg tttttgcaat gcctcaatcc ggtacgacag tgacggtcga   420
atcagtggat cacgtctttc aaaccaagat gttggatatg ttaaaacaga cgggccgacc   480
cgagatggtc gtcggttggt accactgcga ccccggtttt ggtgttggc tgtccagtgt   540
cgatgtcaac actcagcagt ctttcgaaca gctacatccg cgagcagtag ccgttgtcat   600
cgaccctatc cagtctgttc gtgtaaagt cgtcatcgac gcttttccgat ccatcaaccc   660
tcaatcactt gtcgctggac aagagtcgag gcaaacaacg agtaacattg gtcatctgaa   720
caaaccgtcc attcaggctc tcatacacg tctgaatagg cattactaca gtctggccat   780
cgattacagg aaaacagaag gggagcaggg tatgttgttg aacctgcaca agcggggatg   840
gacagagggt ttgaagatgc gtgatcactc agagatgaag gagggtaatg agaaggcaat   900
caaggaaatg ctctctcttg cctcggccta cacgaaaatt gttcaggaag agacgaaat   960
gacggccgaa cagcttaaaa cccgtcacgt aggaaagctt gatccaaaac gtcatttggg  1020
cgaggcggct gagaaagcga tgggtgatca agtgacgcag agtctggcca tgggtgtcct  1080
ggctgagctg tagacgtaga agagggaaga aggaaacga catgcattgt acatatcgc    1139

SEQ ID NO: 94           moltype = DNA  length = 526
FEATURE                 Location/Qualifiers
source                  1..526
                        mol_type = genomic DNA
                        organism = unidentified
SEQUENCE: 94
aacccacccc gccattctca attcttcgtc cgtgttcttc tcgagaagct acacttcgca    60
aaaatgggtg ccattccgga atatgatccc gaggagcccc tcgagaccaa gcccttcaag   120
ttcgtgactc ctggttacga cgctcgtttc ccccagcaga accagaccaa gcactgctgg   180
caaaactacg tcgactacta caagtgtgtc gaggccaagg tgaagacttc cgcccctgc   240
aagcagttct accacgcttt ccgctccctc tgccccaagg cctggactga ccgctgggac   300
```

```
acccagcgcg agggtggtaa cttccctgct atccttaaca aatagataac caatggctgc   360
tttgtgttgg tgaattgggt tatagcagat tctgtattga caaactttcc aatgtactct   420
acctggtcat gcgggatac atttcttttc tgtttggatg taattttccc actctgatga    480
agaaagtgtg tctataaact cgctgttttg aaactaaacg tcttcc                  526

SEQ ID NO: 95            moltype = DNA   length = 839
FEATURE                  Location/Qualifiers
source                   1..839
                         mol_type = genomic DNA
                         organism = unidentified
SEQUENCE: 95
gggccattgc tcgaggagct cgatgtcgag gcgtacgcca agaagtaccg ttacctgaga   60
ttcatgtgcc aggagacgct ggaccatctc gcctttctca aggacaaagt gaaggatgtc   120
gaagggttct gggcatccac cttgttgaag caccgcgatc tcagggggcta catcacttca  180
cgatccgaca aggacgcatt gaagtacttg actcacattg agctcgttca ggatcccaag   240
gatccccgtc cgttcgctct caaattctac ttcaaggaga acccatactt ctccgacttg   300
gtcttggaga agaagtacga tatgtccgag ggttccgaac ccgcacctgc cgatggtagc   360
attacggagg gaatgcgcaa tttcaaagaa gacgagctgg tcaccaaggc taccacgatc   420
aactggaagt cggacgacaa gaatctagtc gccaagcagc ccagatccaa aattcccgac   480
aatgacgacg atgaagattt cgacggggac gtcggatcgt tcttcaacta ctttacagat   540
gacacagata ttttccagat tggggccctc ctgcagtcgg agctactgcc tgatgccatc   600
gactactttg ttggccgagg cgagcaggtg gactctgaag gaggaagct agacgagctg    660
gaagaggatg atgaagacga cgatgaggat gatgagggca gtatcgacct cgaagacgag   720
gaggagcagc cgagtaaaaa gaagcccaag agggcctaag aaacatttga tccgtcaaca   780
tgtacggacg aggtaatcgt gttcgaatgt taatgatcat gcatatgcta gtaaattcg    839

SEQ ID NO: 96            moltype = DNA   length = 804
FEATURE                  Location/Qualifiers
source                   1..804
                         mol_type = genomic DNA
                         organism = unidentified
SEQUENCE: 96
ggatctttcc tcacccctca acacactcac acaccattcg gacgcgctat gcacaatgcc   60
ttgacggttt cgaggctcaa cgacaagttc caagagccgc tcgttgttct tgtggagctt   120
ttgcgtgctc gtgttctgca cgaccgcaac ttctcgaaca gacaattctc aggtggtcct   180
tcattcggga cagacaatca gaagagaagc atgcttttga tcttccgtac tctgtccatt   240
attccgctcc aattcaaggc cgagcactgg tcaggaccat gtcaagagag gctgcttgtc    300
ttcaactcat tccacaagac actgtcaaga tccctgagaa cgctggtcga atcaatcact   360
atgaacgcct tcctcaagaa caatgcgaga agagcacgtg acgactatct tgacattgca   420
cttttcactac cattccaaaa cgataccaac actggattcg gtatcttctt taagatttac   480
ttggatgcat tgactacatt tgcagaaggc aacatcactg aagagaacaa agacagcgag   540
tctgtgaaag aggccaagca gtcagcaatg gagatcctag tgacgccat accgaacgtg    600
aaggacccag aggccgagct tttgcgggt ttcagattct ggatgctgt gctcgtgtgc    660
gtccgtacac tcaaagcaga cagggcaatc gatctcaagc tagctgagtc tttcgaggcg   720
gcaaacagct acccttaatat gatgagacca aattgatacg gcgttttgta gcaatcttga  780
gctttatgca atctacttct gtcg                                          804

SEQ ID NO: 97            moltype = DNA   length = 848
FEATURE                  Location/Qualifiers
source                   1..848
                         mol_type = genomic DNA
                         organism = unidentified
SEQUENCE: 97
ggatctttcc tcacccctca acacactcac acaccattcg gacgcgctat gcacaatgcc   60
ttgacggttt cgaggctcaa cgacaagttc caagagccgc tcgttgttct tgtggagctt   120
ttgcgtgctc gtgttctgca cgaccgcaac ttctcgaaca gacaattctc aggtggtcct   180
tcattcggga cagacaatca gaagagaagc atgcttttga tcttccgtac tctgtccatt   240
attccgctcc aattcaaggc cgagcactgg tcaggaccat gtcaagaga gctgcttgtc    300
ttcaactcat tccacaagac actgtcaaga tccctgagaa cgctggtcga atcaatcact   360
atgaacgcct tcctcaagaa caatgcgaga agagcacgtg acgactatct tgacattgca   420
cttttcactac cattccaaaa cgataccaac actggattcg gtatcttctt taaggttggt   480
ggccttgcag gagtctgaca tagcgctgac gcagacagat ttacttggat gcattgacta   540
catttgcaga aggcaacatc actgaagaga acaaagacag cgagtctgtg aaagaggcca   600
agcagtcagc aatggagatc ctaggtacg ccataccgaa cgtgaaggac ccagaggcca    660
agcttttgcg gggtttcaga ttctgggatg ctgtgctcgt gtgcgtccgt acactcaaag   720
cagacagggc aatcgatctc aagctagctg agtctttcga ggcggcaaac agctacctta   780
atatgatgag accaaattga tacggcgttt tgtagcaatc ttgagctttt gcaatctac    840
ttctgtcg                                                            848

SEQ ID NO: 98            moltype = DNA   length = 628
FEATURE                  Location/Qualifiers
source                   1..628
                         mol_type = genomic DNA
                         organism = unidentified
SEQUENCE: 98
ggggcatcta cctcgacggc aacaacgacc tggtcactat gaagggtaac tacatctacc   60
acaccagcgg ccgctctcct aaggttcagg taacaccttt gctgcacgct gtcaacaact   120
actggcacga caactccggc cacgccttcg agatcggtga gggtggttac gttctggccg   180
agggtaacgt cttccaggat gttactaccc ccgttgagga ccccgttgac ggccagctcc   240
```

```
tcacttcccc tgaccccagc accaacgctc agtgctcgtc ataccttggc cgggcctgcg  300
aaatcaacgg cttcggtaac tctggtacct tcaaccaggc tgacactagc ctgctgtcta  360
aatttaaggg tcagaacatt gcttctgctg atgcttactc taaggttgcc tcgagcgttg  420
ccagcaacgc cggtcaggga cacctgtaaa atggaaagag gaggttcaga gcttaatttg  480
ctcatgtcgg acgacatagc cctagcggct tgctggtgaa tttggcataa tagcgtttct  540
cttctcatac ctactttatt actccgtttg gatccttatt aggtaaatat tagcccattg  600
tatggttcaa ttcgattgac tttgaggc                                     628

SEQ ID NO: 99              moltype = DNA   length = 804
FEATURE                    Location/Qualifiers
source                     1..804
                           mol_type = genomic DNA
                           organism = unidentified
SEQUENCE: 99
agttggaaat ctgatcaatt actctccatc ttctcgttct actatctaat cctctcttcc  60
ttccaaaaca tatcatcatg tctgctcaac ctctccgcat tgtcatggcc tgtgacgagg  120
ctggtgttcc ttacaaggat gccatcaagg ccgttctcga aagagcccc ctcgtcgcct  180
ccgtctctga cgtcggtgtc aacgatgcct ccgataagac cgcctacccc caccccgcg  240
tcgagggtgc tcaacagatc aaggccggta aggctgaccg tggcctcttc atctgcggta  300
ctggtctagg tgtcgctatc gccgccaaca aggttccgg tattcgtgcc gttactgccc  360
acgaccctt ctccgtcgag cgttccattc tgagcaacga tgctcaggtc ctctgcatgg  420
gtcaacgtgt cattggcgtc gaacttgcga agaagctgc ctcgattgg ctcaactacc  480
gtttcgatcc taagagtgcc tctgccgcga aggtccaggc tatctccgac tacgagacca  540
agttcgctgg ctcttcttaa atgcattatc ttgcatgaat gacggtcttc gtacatactt  600
tgccacatat gggttctaat tgcactgcgt ctgcagtctc gatatgaaac cattggattg  660
cgatggatgt cccttttcca tttgcaactt tttatatact ttcttttcta ccaagcgctt  720
catgatacca cgattcgatt accgagttct gctgtttgct tggtcggta gatctagata  780
cacaatgcag tatattcgag tttc                                         804

SEQ ID NO: 100             moltype = DNA   length = 782
FEATURE                    Location/Qualifiers
source                     1..782
                           mol_type = genomic DNA
                           organism = unidentified
SEQUENCE: 100
acttctcctt ttctgttagc tttgactcta ctatcctgct cctcctctaa atccgtggaa  60
tccaattttt tcacaataac ttcgctacca taatgtccgt cactaccact tcctccgccg  120
ccgcagcctc ctgcactccc tcttggcaga ttcctgtcga cgatgttgcc tgtgccggtc  180
agatcagcgg taatatcacc aaggttttcg atacctgctg taagggaaac agccctgtca  240
agtacaacga cgactgcaac atctactgtc ttgcccaagg acaaaccaag caagagttga  300
ccgactgttt gaccgagaag agcggaaaca ccagatctt ctgtggtcat ggcaagcaga  360
atgccactgc tacagctgaa gccaccacca ccaaggagac tggcacatcg accggcactt  420
caacctcttc cactggcact tctaccgaga ccaacgctgc cgtgctcaac caacccatct  480
ccaagaccgg tcttggactc gtcgccatgc tcttctgctc tgccctcgtt ggtgttgtcg  540
cctaagttat gactccaaaa cgaacacatt actgcggtat ggatacggca attatgacaa  600
ccagaggacc gcagggacgg agaatggtaa ttgatgaacc cggaaaagat acgtggtgca  660
tggacataaa tgtttgattt actcttactg tctgcttcaa ctttccgaga ggaatattgt  720
ttcttctgta ccaatagcga tagcattaac agcatcttaa ttctaatttt gcatatcact  780
tc                                                                 782

SEQ ID NO: 101             moltype = DNA   length = 693
FEATURE                    Location/Qualifiers
source                     1..693
                           mol_type = genomic DNA
                           organism = unidentified
SEQUENCE: 101
gccggggtcg atcgaggtgt catcaccaag gacgagaagg acagcagtat caatagacta  60
ctcgtcactg gttacggtct ggccgaggtc atgggtacag atggtgtgaa cggcatcaag  120
acgcgaacca atcacgtcat ggagacgtgc gaggttctgg gcatcgaagc cgctcgacag  180
accatctaca acgagattca gcataccatg acatgccacg gaatgtcaat cgatcctcga  240
cacgttatgc tgctcggaga cgtcatgact tacaagggcg aggtgctcgg tatcactcga  300
ttcggtgtgc aaaagatgaa ggactcggtt ctcatgttgg ccagtttcga gaagaccact  360
gatcatctgt tcgatgcctc gctgttttcg aaaaaggatg aaatcaagg cgtctccgag  420
tgtatcatta tgggcacacc cgcgccaggt tgtggcacct ctgctgtcca  480
cctgcccctc tcctcccacg caaaaagcct ttgctgtttg aaacagcgtt caaagctggt  540
caggatcgat tgagctatca cgaaaacaat ggcggcatgg aggtggacat gtgaacccgg  600
tccctcatac atcttcttct gattgtctgt accatacata catcgcattg cttcttttca  660
catacgacac gacatgcatc tgacatctac gac                               693

SEQ ID NO: 102             moltype = DNA   length = 776
FEATURE                    Location/Qualifiers
source                     1..776
                           mol_type = genomic DNA
                           organism = unidentified
SEQUENCE: 102
gcaggatcag gaggagcata ttccttctct ctgaccacct tctcgccttc tggaaagctt  60
gtccagatcg aacatgcatt ggcagcagta gcggtggaa caacatcact gggtatcaaa  120
gctaccaacg gtgttgtcct tgcgactgag aagaagtcac cgtcactcct gctcgatacg  180
tctgttctcg aaaaggtagc tcctatatgt cccaacattg gttcgtcta ctcgggtatg  240
```

```
ggacccgatt tccgagtcct ggtcgccaaa gctaggaaga tcgcccaagc gtactataaa    300
gtgtatggcg agtacccacc tacaaaggtt ctagtgcagg aggtggcggg cgtgatgcaa    360
aaggctacgc aatctggtgg tgtgcgacca tatggtatct ccctcttgat cgctggttgg    420
gattcgcacc gaggtcagag cctgtaccaa gtggatccgt caggtagcta ctgggcgtgt    480
aaggcaagcg cgatcggcaa gaacatggtc aacggaaaga cattccttga gaagcgatac    540
aatgacgacc tgtcactcga agatgccatt cacacggccc ttctcacgct gaaagaaggt    600
ttcgagggac agatgactga gaacacgatc gagatcggtg tagtgacggt accgacggcc    660
gagcagatgc aggagaagcc aggagagagg ctacctccca cgttcaggaa gttgacggag    720
caggaagtga gggactatct cgccttgtag acgatgcaga cagaacatga ccatcc       776
```

SEQ ID NO: 103         moltype = DNA   length = 1191
FEATURE                Location/Qualifiers
source                 1..1191
                       mol_type = genomic DNA
                       organism = unidentified
SEQUENCE: 103

```
aagtctacga ctcctccagc caatttactt tgatccaaaa tgttgaccag cgccttttct     60
acatctgctt ccaagatgct cggcaagaga gcagtctcgt cttccagcga cttgaacgga    120
aaggttgccg tcctcggtgc tgctggcggt attggccagc ccctctcctt gctggtcaag    180
cagaaccctg ctgtctccag cctctccctt tacgatgttc gcggctcccc tggtgttgct    240
gctgacatta gccacatcaa caccectgct gtcaccgagg gcttcctccc cgacaacgat    300
ggcctcaagc aagccctcga gggtgctaag gtggtcctca ttcctgctgg tgttcctcgc    360
aagcccggca tgaccgtgaa cgacctttc aacaccaacg cttccatcgt caagatgctt    420
gctgaggctt ctgccaagta ctgccccaag gctatgatgc tcatcattgc caaccccgtc    480
aactccaccg tgccgatcgt cgctgagacc ttcaagcgtg ctggtgtcta cgaccctgcc    540
cgtctcttcg gtgtcaccac cctcgacgtt gtccgctctt ccactttcgt tctctggcct    600
accggtgcca agccctccga caccggtggt caggtcatcg tgggtcactc tggcgccacc    660
atcgtgcccc tgctctccca gatccctcag ggcgacaaga ttgtcaaggc tggcggcag    720
cagtacgctg acctcgtcaa gcgcatccag tttggcggtg acgaagtcgt caaggccaag    780
gacggcactg gctccgctac cctctccatg gcttacgccg ctgccgtctt caacgacgct    840
ctcctcaagg ctatggacgg ccaaaaggt ctcgttcaac ccgcttacgt cgagagcccc    900
cacttcgcca aggagggtgc taagtacttc gcctccaacg tcgagctcgg ccccaacggt    960
gttgagaaga tcctcgacat cggcaacatg tcctctgagg agcaggagct ccttaaggag   1020
tgccttcccc agctcgccaa gaacattgct gctggtgaga agttcgtcgc tgacaactag   1080
aggatatccc acgacgttgc tccctataat aatgagagca agcgagaaca agagaaataa   1140
agacatagca aattgaatag ggcttccaac tgcaccaaaa agcagtgatg c            1191
```

SEQ ID NO: 104         moltype = DNA   length = 1191
FEATURE                Location/Qualifiers
source                 1..1191
                       mol_type = genomic DNA
                       organism = unidentified
SEQUENCE: 104

```
gcatcactgc ttttggtgc agttggaagc cctattcaat ttgctatgtc tttatttctc     60
ttgttctcgc ttgctctcat tattataggg agcaacgtcg tgggatatcc tctagttgtc    120
agcgacgaac ttctcaccag cagcaatgtt cttggcgagc tggggaaggc actccttaag    180
gagctcctgc tcctcagagg acatgttgcc gatgtcgaag atcttctcaa caccgttggg    240
gccgagctcg acgttggagg cgaagtactt agcaccctcc ttggcgaagt gggggctctc    300
gacgtaagcg ggttgaacga gacccttttg gccgtccata gccttgagga gagcgtcgtt    360
gaagacggca gcggcgtaag ccatggagag ggtagcggag ccagtgccgt ccttggcctt    420
gacgacttcg tcaccgccaa actgatgcg cttgacgagg tcagcgtact gctggccgcc    480
agccttgaca atcttgtcgc cctgagggat ctgggagagc aggggcacga tggtggcgcc    540
agagtgacca ccgatgacct ggaccacggt gtcggagggc ttggcaccgg tgatgccaga    600
gacgaaagtg gaagagcgga caacgtcgag ggtggtgaca ccgaagagac gggcagggtc    660
gtagacacca gcacgcttga aggtctcagc gacgatcggc acggtggagt tgacggggtt    720
ggcaatgatg agcatcatag ccttggggca gtacttggca gaagcctcag caagcatctt    780
gacgatggaa gcgttggtgt tgaaaaggtc gtcacgggtc atgccgggct tgcgaggaac    840
accagcagga atgaggacca cctcagcacc ctcgagggct tgcttgaggc catcgttgtc    900
ggggaggaag ccctcggtga cagcaggggt gttgatgtgg ctaatgtcag cagcaacacc    960
aggggagccg cgaacatcgt aaagggagag gctgagaca gcagggttct gcttgaccag   1020
caaggagagg ggctggccaa taccgccagc agcaccgagg acggcaacct ttccgttcaa   1080
ggcgctggaa gacgagactg ctctcttgcc gagcatcttg gaagcagatg tagaaaaggc   1140
gctggtcaac attttggatc aaagtaaatt ggctggagga gtcgtagact t            1191
```

SEQ ID NO: 105         moltype = DNA   length = 1505
FEATURE                Location/Qualifiers
source                 1..1505
                       mol_type = genomic DNA
                       organism = unidentified
SEQUENCE: 105

```
gggcaagcg tgctgcttcc ggcactgcat ttcgacgagc gggagcaacg acctggacgt      60
acgtcttcga ctgcaagtct gctgcagcgt cacgatcgca atgaacccttt atcgctcaac    120
tcgcactcgc cgacatctgt ggaccacact cccactactg cgcatttcac tggtgctgaa    180
gagttgctcg cctccgacgt cggaccgacc gcgacagctg ggctaccgg tgatgcggaa    240
cttgagagca agctcaagct gcttgaagag gtcaaacgtg cacggaatc ggtacatagc    300
tcgctcgaga ggatcagagc cggcacgcct acccgtgcta tcagccaggg aatgcccagc    360
ccgacaccct ctggtgcccc tggttacgct agaactccgt cgtctgtcgg cctgtcggac    420
gacgtgcgct cgagacgagg ctcaacgacc agctccaagg ttcttgacgc tatcgacaag    480
cctcgagtcg ctacccaatc cgaatgggac gagtacgttc gcaaccggca tgtcatctca    540
```

-continued

```
cctccaccca ctcagtttgc cgtattgccc acatctgctg cgatggtcga tcgtggtacc   600
agtcgacaca gccagtatgc ccttgtttcc gacggcgttg ccaaagcgct tgacaggcgg   660
gagcgaacta tttcaatgat ggagccgcaa gttgccgagg actggggacc aagagagacg   720
ctcgacagca ctccggctca tgtctcgatg ggccgtcgag ccatgtcatt ccatgagata   780
cctctggcat cgcctgtcgc tgcctctcga cctcaggacc gctcctccta ctctgccgga   840
ccacgtcagg tcatagggtc agctgctggc cacacgcagc gacccgggtat cagtcaatcg   900
agatcagccc acggccggac tatgacatac gacgagctga cggagagaca tcgtcagcgc   960
ttgtcggcat gcaagcgcc agtcagcgcc aaaatcaggg agccgatgga catcgcgtcc  1020
gccaaagcca gctgggacaa gcaaaagcgg gtcgagcggg acgaaatgaa gaggcgagaa  1080
gccgagaagc tcgctcaggc tcacgcaaga gagcgacgag aggcccgctgt cgacaagaag  1140
gaagttctca agtcgaccga cgaatggagg cgaagcgtcc acggcggtct cgacggtttc  1200
gccgttccgc acctaccggc ccacgctcga ggttccacgc agcctggtgg atccggcgcc  1260
aagcgatctt cactctctca aaggcccagc aactactcg ccaactaggc ataatcgaat  1320
cgcggacagt catctgtaca tagaaccgta cctgtattac caaccctgca cttccgctca  1380
cacctgttgc ctatacctcg tctaccaacg ctcattccaa tatcatagct acattcattt  1440
gcaaggacac tatcacaccg cagtcatgac tccgtatgga tattcaatgc ataccctcttc 1500
cagag                                                              1505

SEQ ID NO: 106          moltype = DNA   length = 1391
FEATURE                 Location/Qualifiers
source                  1..1391
                        mol_type = genomic DNA
                        organism = unidentified
SEQUENCE: 106
aacctcggcc gagaggacaa gattatcaag aatgggatct cctgcgcctc accaccgcca    60
tcaatcctca cttgaaggag tcattgactt ttctactgat agagggcatc cattgaatcc   120
ctatcaacgc gacaaggccg agagcgtttt tactggcatt atcaaccgct tcgaggactc   180
gtcgaccgta gagaaaccat acaaccgtgc caagctggtt cgcctgacgt atgagtatgc   240
tcgctcggaa gattctcgat gcaatttctt gcaagcattc ttcggatcag taaacgttac   300
gatggatgac tctattgatt tcgacgatga agcggtagga gagggattc gtcgagcct    360
gaattccttc gcagatttct tggtggagaa cttcttcctt ccactcaagg cttccgccaa   420
caggacgccc ccagcccccc agcccaagtt ccgagcagac gtcctgctgt ggggtctgtg   480
gaaagagtgg cctcgctcag acgcgactgc ctcatccgcg atcgacatcg ttgcgtaatc   540
tctcgcaact tcgacatgaa agaagctgag cgacgtcttg acgatagcgg atatgaccat   600
gcctcggacg atgaaggaca tttactgaaa gatcaggage atgggtcatt cgcggaacta   660
gaagttgcgc atatacttcc tcactcattg atgactacga cagcgaactc cgagctgaac   720
aagtccaaag aaacggcatt gacaatactt aatatgttcg acagtggcat tgtccatcta   780
atcgacggtc cagacattga tcgccctcga aatgctctta ccttaagcat tgacctccat   840
cgacagtttg gcaacttcaa ggttttttttt gagcctatgc ctgagccca taccaccgg   900
attgattcaa ccctccgcca gccatttaga aacccgattt tccctgtaac ccgtgcactc   960
tacctcaccc ctgagcgaac tattgatccc cgtccggtc gacttcttgc cgttcatcgc  1020
gcaatttgcc acattttaca tctcagtgct gctgggaatt acatcgacag catacttcgc  1080
gacatggatg acgggactgt acaagccaac ggctcgactcc gcctggctag catagttcgt  1140
ctgaaactgg ggggttggtg ggatggcact gttgttggat agtcaaccac ttcgaccctc  1200
tccatacacc acaacggcaa ctcgagctga tgcatcaccg atctacctac gccattcgcg  1260
tggaggattg tcgcatatca ccactaggtt cgtgcgactg gatatgaaac gcggcccgta  1320
cttttgggtc gtgtatccgg tttcacatcc agcttgtcgc atcaaggatt ccaatcctaa  1380
cgacatgagc c                                                       1391

SEQ ID NO: 107          moltype = DNA   length = 665
FEATURE                 Location/Qualifiers
source                  1..665
                        mol_type = genomic DNA
                        organism = unidentified
SEQUENCE: 107
ggacgaccga ataccgtca aaatggtcaa catcccgaag acgcgcagga cctactgcaa     60
gggcaaggaa tgcaagaagc acacccagca caaggtcacc cagtacaagg ctggcaaggc   120
ctccctcttc gcgcagggta agcgtcgtta cgaccgtaag cagtccggtt acggtggtca   180
gaccaagccc gtcttccaca agaaggccaa gaccaccaac aagtcgtcc tcagattaga   240
atgcacttcg tgcaagacca aggcgcagct cgctctcaag cgctgcaagc acttcgagct   300
tggtggtgac aagaagacca agggtgccgc tcttgtcttc tagatgggtg cataacggtt   360
atggcgctag gatgatgat ggagcggtct gtgcatgtag cctccttgag tacatgatcc    420
tcgagggctc ggaatcaaag cttcgtttct cctacgatcg tcccactcgc aaagacatgt   480
ctcgtcatat catggcttgc gcacaacatt cttcgagggt catcagaga tgcccgaccc   540
tgccgctacg ctgcgtggga tgtgactcca gcacaaccgc cttccagtat catctcttcg   600
cgtgcagaag tgaggacgat tttacgacag tccatataac aaatcggaaa tgccaacaag   660
atcaa                                                               665

SEQ ID NO: 108          moltype = DNA   length = 1327
FEATURE                 Location/Qualifiers
source                  1..1327
                        mol_type = genomic DNA
                        organism = unidentified
SEQUENCE: 108
ggcccctctt gaactttgga cttttttagca tctattttct ctacttctct ctccctcctc    60
ctatctacct tctctatcat ctccttcagc tccctacaac atgaagctca cctttaagga   120
cctgaagcag gagaagttcg taatcgaggt cgagccctcc gagactgttc gcgaagtcaa   180
gcaaaaaatt gctcaagaaa aaggcgaata tgaggcggaa cgaatgaaag ttatctactc   240
gggcaagatc cttcaggatg acaagaccgt cgaatcatac aacatccagg agaaggattt   300
```

```
cctagtctgt ctgccttcaa agggtcctaa gcccgctgcc tcgtcgtctg cctcccaggc    360
acccgccact ccggccccta gagctcctgt tgctactcct gctgctcctg ccccgctgc    420
tcctgcacct gctagttcta cgcctgctgt ccctgcgact ccctcgcctg ctggcgccca    480
gaccggtccc tctttcggtg acccatctgc attgaccatg ggttctgcgg ctgagggtgc    540
cgtcactcag atggaagcaa tgggatttgc cagaagcgat attgaccggg acatgcgggc    600
tgcattcttc aatcctgacc gcgctgtcga ttacctcttg aacggtattc cgccgatgt    660
tcaacaggaa caacagcagc ggcaacaaga gcaacaagcg gaccgtgctg cagaacaagc    720
tcctgtgccc agcgctgagg atgctgctgc tgccgccgct ctgggtggcg atgagggttt    780
taacatgttc gaggctgccg ctcaggctgg tgatggtcgt ggtggtggtg ctcggtctgt    840
aggtagcgag gcccttgcga acctggactt tctccgcagt aaccccatt tccagcaact    900
gagacagttg gtccagcagc agccgcacat gctcgaaccc atcctgcaac aggttgctgc    960
cggaaaccca cagatttccc agatcattgg ccaaaactct gaacagtttc tccaactgct   1020
aagtgaggag ggtgatgagg aagatgcggc cctgcctcct ggtacacaag ctatctccgt   1080
tacagaggag gagcgggacg ccattgagcg gttgtgccgt ctgggtttcc cccgggattc   1140
cgtcatccag gcctacttcg cctgcgacaa gaacgaagaa ctcgcagcaa acttcctctt   1200
cgaccagccg gacgatgatg aggagtaaat ctgatccacg atgctgtggt tcacttcttt   1260
actccatgtc ttatccccttt cccctttgc ttctttacgt tctgatgaat accaagcatg   1320
cctgttg                                                              1327

SEQ ID NO: 109         moltype = DNA   length = 1326
FEATURE                Location/Qualifiers
source                 1..1326
                       mol_type = genomic DNA
                       organism = unidentified
SEQUENCE: 109
ggcccctctt gaactttgga cttttttagca tctattttct ctacttctct ctccctcctc    60
ctatctacct tctctatcat ctccttcagc tccctacaac atgaagctca cctttaagga   120
cctgaagcag gagaagttcg taatcgaggt cgagccctcc gagactgttc gcgaagtcaa   180
gcaaaaattg ctcaagaaaa aggcgaatat gaggcggaac gaatgaaagt tatctactcg   240
ggcaagatcc ttcaggatga caagaccgtc gaatcataca acatccagga gaaggatttc   300
ctagtctgtc tgcccttcaaa gggtcctaag cccgctgcct cgtcgtctgc ctcccaggca   360
cccgccactc cggccctag agctcctgtt gctactcctg ctgctcctgc cccgctgct    420
cctgcacctg ctagttctac gcctgctgtc cctgcgactc cctcgcctgc tggcgcccag   480
accggtccct ctttcggtga cccatctgca ttgaccatgg gttctgcggc tgagggtgcc   540
gtcactcaga tggaagcaat gggatttgcc agaagcgata ttgaccggga catgcgggct   600
gcattcttca atcctgaccg cgctgtcgat tacctcttga acggtattcc gccgatgtt   660
caacaggaac aacagcagcg gcaacaagag caacaagcgg accgtgctgc agaacaagct   720
cctgtgccca gcgctgagga tgctgctgct gccgccgctc tgggtggcga tgagggtttt   780
aacatgttcg aggctgccgc tcaggctggt gatggtcgtg gtggtggtgc tcggtctgga   840
ggtagcgagg cccttgcgaa cctggacttt ctccgcagta acccccattt ccagcaactg   900
agacagttgg tccagcagca gccgcacatg ctcgaaccca tcctgcaaca ggttgctgcc   960
ggaaaccca gatttcccca gatcattggc caaaactctg aacagtttct ccaactgcta  1020
agtgaggagg gtgatgagga agatgcggcc ctgcctcctg gtacacaagc tatctccgtt  1080
acagaggagg agcgggacgc cattgagcgg ttgtgccgtc tgggttttccc ccgggattcc  1140
gtcatccagg cctacttcgc ctgcgacaag aacgaagaac tcgcagcaaa cttcctcttc  1200
gaccagccgg acgatgatga ggagtaaatc tgatccacga tgctgtggtt cacttctta  1260
ctccatgtct tatccccttc ccctttgct tctttacgtt ctgatgaata ccaagcatgc  1320
ctgttg                                                              1326

SEQ ID NO: 110         moltype = DNA   length = 1162
FEATURE                Location/Qualifiers
source                 1..1162
                       mol_type = genomic DNA
                       organism = unidentified
SEQUENCE: 110
gcgccggggg acatggagac tgccgacgcc aagaacaggg ctatgcgagc cgctggcttc    60
atcgttcccg acaccttcga agacctgccc gaggtcctca agaccaccta cactggtctg   120
gttcaaaagg gtgtcatcgt tcccaaggcc gagatcgacc cacccaacat ccccatggac   180
taccagtggg cttccaagtt gggtcttatc cgaaagcccg ccgccttcat ctcgaccatc   240
tcggacgagc gaggtcagga gttgatgtac gccggtatgc gaatctccga cgttttcaag   300
gaggagatcg gtatcggtgg tgtcatctcc ctcctgtggt tcaagcgacg attgccacct   360
ttcgcctgca aattcatcga gatggttctg caattgactg ccgaccacgg acccgccgtt   420
tcgggtgcca tgaacaccat catcaccgct cgagcaggca aggacctgat ctcgtccctg   480
gccgctggtc tcttgaccat cggtgaccga ttcggtggcg ctctcgatgg tgccgccgcc   540
gagttctctc gaggtctcaa ctctggtgct accccacgag aatttgtcga ctcgatgcga   600
aaggccaacc gattgattcc cggtatcgga cacaagatca agtcaaagac caaccccgat   660
ctccgagtcg ttctcgttgt cgattacgtc aagaagcact cccgtctcca agacgctc    720
gactttgcct tggccgtcga ggacgtcacg acgcaaaagt ccaacacgtc catcttgaac   780
gttgatggtg ctattgccgc ttccttctgt gatttgctta gcggttgcgg tgcttttcact   840
gaggatgagg ctgccgatta cctcaagaac ggtactctta acggtctttt cgttcttggt   900
cgatcgatcg gtttcatcgg tcactacctc gaccaaaggc tcctcaagca gcctctctac   960
gacaccccg ccgacgacat tttcatcaac atgaagagc gagttgtctt ccagcctggg  1020
tccaactaag aggcgaccgc gactacgggt ctcggccaat ttctcccttg ggtttcctcc  1080
ttcaattaaa actactgtac ataccaccca catcattat ctcttcttc atgactatag  1140
acgcatgcac gggatcgctc gg                                            1162

SEQ ID NO: 111         moltype = DNA   length = 965
FEATURE                Location/Qualifiers
source                 1..965
```

```
                           mol_type = genomic DNA
                           organism = unidentified
SEQUENCE: 111
ggggcataca aggagggcaa gttcaccagc gaaagcatcc aaaagtcaaa gctcagattc    60
caggacatcc tcgttgagct gcccctcagg gttcacaact cccaccttct caccagcttc   120
ctgcaccagg tcccgcaggc gccgccggca agaaccccc tcgacttccc ttcatccctt    180
gcagagcttt cgcgcgactc cgatgtcagc tccaacccct tcgcacccaa ccttgacacc   240
ctggacctca gcatcgaccc cttccagtac tggcagcgcg ccctcggccg cgagcagcag   300
aagatcaccg catggcaaca gaagcgcaag gctgagaatg ctgcacgcgc cgcgagcaag   360
cagccgcccc ttgacgagaa tgagtggcag aagctgttca agctgcccac ggagcccagc   420
aggctcgagg ctctgcttgt cggcaggcag gtcgagcagt acgccgcca ggtcgacgga    480
ttctccgcca ccgtttccgc caagatgttt ggcgtcaggg gcaacctcct ccctaacgag   540
atcgagtaga ggacgaatat tacgagacg ggaccggcgt ttatgcatag cgaggcgttc    600
tcggctgggt ggggtagagt acatgcggca tggctacaaa aaaaaggatg atgtggttcc   660
gccatcgacg agttcagggc aacgctgcat agaatcccaa aagaagaaag gattttaacg   720
tttttgaatt tggaacttct tcgcattgga cgattgcttt cttgacgact ccgtcagttg   780
cgcgcttttt ccatggccca taccctcttt atctctaatg agggtgcgcc accgcagacc   840
caccagctac tcgaagaaaa gtcgctattt tttatttgga gttattagcg agtacaaacg   900
gaggcatgtc tagaggctga ggagtgtggt agtaagatta tagatgtctt tatgctcgat   960
atgag                                                               965

SEQ ID NO: 112        moltype = DNA   length = 965
FEATURE               Location/Qualifiers
source                1..965
                      mol_type = genomic DNA
                      organism = unidentified
SEQUENCE: 112
ctcatatcga gcataaagac atctataatc ttactaccac actcctcagc ctctagacat    60
gcctccgttt gtactcgcta ataactccaa ataaaaata gcgacttttc ttcgagtagc    120
tggtgggtct gcggtggcgc accctcatta gagataaaga gggtatgagc catggaaaaa   180
gcgcgcaact gacggagtcg tcaagaaagc aatcgtccaa tgcgaagaag ttccaaattc   240
aaaaacgtta aaatcctttc ttcttttggg attcatgca gcgttgccct gaactcgtcg    300
atggcggaac cacatcatcc tttttttgt agccatgccg catgtactct accccaccca    360
gccgagaacg cctcgctatg cataaacgcc ggtcccgtct ccgtaatatt cgtcctctac   420
tcgatctcgt tagggaggag gttgccctg acgccaaaca tcttggcgga aacggtggcg    480
gagaatccgt cgacctggcg ggcgtactg tcgacctgcc tgccgacaag cagagcctcg    540
agcctgctgg gctccgtggg cagcttgaac agcttctgcc actcattctc gtcaggggc    600
ggctgcttgc tcgcggcgcg tgcagcattc tcagccttgc gcttcgtgttg ccatgcggtg   660
atcttctgct gctcgcggcc gagggcgcgc tgccagtact ggaagggtc gatgctgagg    720
tccagggtgt caaggttggg tgcgaagggg ttggagctga catcggagtc gcgcgaaagc   780
tctgcaaggg atgaagggaa gtcgaggggg ttctttgccg gcggcgcctg cgggacctgg   840
tgcaggaagc tggtgagaag gtgggagttg tgaaccctga ggggcagctc aacgaggatg   900
tcctggaatc tgagctttga cttttggatg ctttcgctgg tgaacttgcc ctccttgtat   960
gcccc                                                               965

SEQ ID NO: 113        moltype = DNA   length = 1160
FEATURE               Location/Qualifiers
source                1..1160
                      mol_type = genomic DNA
                      organism = unidentified
SEQUENCE: 113
gacttcggcg aaggcgatga gcaactcttt cataaggcac cttccttcga ctcttcgtgc    60
gtttcgttca tctactgcat tctctcttac acgttcattc tcttccacca tggcatccaa   120
cgggacatcc acaaatggcg ttcagcatga cgctcgcaag gtcttcttct tcgacatcga   180
caactgtctt tacccgaaat cgtatcaaat acacgacaag atggccgtgc tgatcgacaa   240
ctactttcaa aaccatctgt cgctgtccca agaagatgcg accactcttc atcagcggta   300
ctataaggac tacggcctcg ccatcgaggg gcttgttcgc caccacaaag tcgacccact   360
tgagtacaac gagaaggtcg acgatgcgtt gcctctggat gatatcatca aacccgatcc   420
gaaacttcga aaattgctgc aagacataga caccgacaag gtgaagctgt ggctattcac   480
caacgcctac gtgaaccacg ccaaaagggt gactcgcctg cttggtgtag acgatttgtt   540
cgaaggcatg acttttgcg actacgccgc ggaacgcctc ctctgcaagc ccacgacgga   600
gatgtacaac aaggctatgc aagaggcaa cgccaccgat atcgatcagt gctactttgt   660
tgatgattca gcgctgaatg cggctgctgc tatgaaatac ggttggaaaa ctgcgcatct   720
ggtcgagcct accgcgaagc ctccgcccca gcccgtccca caaccagc tcagcaacct    780
tgaagagctg cgcaaggtct tccctgaagt atttaagact tcatgatggc atggaaattt   840
taacgaagac acgagtgtat tttacgaaa ctactcagga ttcccttgcc ttgtaagatg    900
cgaccatcgc tactgggttg ggattggaga tggtgcccag caacgctttt gcgacactat   960
caggtctaag gactctattg taaaacccgg gtcgatttgc atatggttaa ttcgaatctt   1020
ccatgaacac agcatttcgt gaaccaaaga gcacacacgt cgaagtgttg ggatgtcttt   1080
gagcagccag cttggatttc ttgagaggtc ggaagcaatt ctataggata gacagcataa   1140
atgcaataaa gccactattg                                              1160

SEQ ID NO: 114        moltype = DNA   length = 982
FEATURE               Location/Qualifiers
source                1..982
                      mol_type = genomic DNA
                      organism = unidentified
SEQUENCE: 114
atacaagact taccatcaac acaatggctc gcatctttat cactggcagc accgacggcc    60
```

```
tcggtcttct ttctgcgaag cttctctcgg aacaaggcca cagcgtcttc ctccatgccc    120
gcaatgccga acgagcatcc caggccaaag cagcagtgcc caaagcccaa ggtgtcatca    180
tcggcgatct ttcaaacgtc tcagacgtga agcagctcgc cgccgatgcc aacaagctg    240
gaccttttga cgccgttgtt cacaatgctg gcctcggact caccaccaat ggccagaaga    300
ctgctgaggg cgtagcccag attttttgccg ttaacagcat ggcaccttac attctgaccg    360
ctctcatgga caagccgaag aggctcttgt acgtcagctc cggactgcac ttcggtggc    420
acccagcct cgaggacgtc acttgggcca caagggagtt ccgaccatcg gatgcataca    480
acgtacaaa gatgcaaaac gtcatgctct cgaaagcagt cgccaaacgc tggcctgatg    540
tgcagagcgg ctctcttgac ccaggctggg tgaagactaa gctcggcggg tcgccgcgc    600
ctggcaccac cgacgctcca gcagagatga ttgctgagta cgctgccggc aaatcttgcg    660
caggcgatca aacaggtgcc tacttgactc cgcgtggcgt ggaagagcc catgatgcga    720
ctaagctggc cgagaagcag gatcgtctga tgcagattta caaggaggta tcgggtgttt    780
cgttcccca gtaaacacag cttcatggct ttgcctcgcg gagacctcac attttcaatt    840
agatctccct gccgattgca gcagaccagt actcactagg ctgtgcaggg ggcatgttga    900
tcaagaacga gccataacga catgccatgt caacggacaa tgagtgggcg aagtaacaca    960
tgaaattcat tatctaagcg cc    982

SEQ ID NO: 115         moltype = DNA    length = 982
FEATURE                Location/Qualifiers
source                 1..982
                       mol_type = genomic DNA
                       organism = unidentified
SEQUENCE: 115
ggcgcttaga taatgaattt catgtgttac ttcgcccact cattgtccgt tgacatggca    60
tgtcgttatg gctcgttctt gatcaacatg cccctgcac agcctagtga gtactggtct    120
gctgcaatcg gcagggagat ctaattgaaa atgtgagtc tccgcgagc aaagccatga    180
agctgtgttt actggggaa cgaaacaccc gataccttcct tgtaaatctg catcagacga    240
tcctgcttct cggccagctt agtcgcatca tgcggctctt ccacgccacg cggagtcaag    300
taggcacctg tttgatcgcc tgcgcaagat ttgccggcag cgtactcagc aatcatctct    360
gctggagcgt cggtggtgcc aggcgcggcc gacccgccga gcttagtctt cacccagcct    420
gggtcaagag agccgctctg cacatcaggc cagcgtttgg cgactgcttt cgagagcatg    480
acgtttttgca tctttgtatc gttgtatgca tccgatggtc ggaactccct tgtgcccaa    540
gtgacgtcct cgaggctggg gtcgccaccg aagtgcagtc cggagctgac gtacaagagc    600
ctcttcggct tgtccatgag agcggtcaga atgtaaggtg ccatgctgtt aacggcaaaa    660
atctgggcta cgccctcagc agtcttctgg ccattggtg tgagtccgag gccagcattg    720
tgaacaacgg cgtcaaaagg tccagccttg ttggcatcgg cggcgagctg cttcacgtct    780
gagacgtttc aaagatcgcc gatgatgaca ccttgggctt tgggcactgc tgctttggcc    840
tgggatgctc gttcggcatt gcgggcatgg aggaagacgc tgtggccttg ttccgagaga    900
agcttcgcag aaagaagacc gaggccgtcg gtgctgccag tgataaagat gcgagccatt    960
gtgttgatgg taagtcttgt at    982

SEQ ID NO: 116         moltype = DNA    length = 821
FEATURE                Location/Qualifiers
source                 1..821
                       mol_type = genomic DNA
                       organism = unidentified
SEQUENCE: 116
agcgactccg acaacaacga ccaccgggac gactctatatc cttcacaatg gccattggac    60
aatcctcgca gcagcaggcc gacggccaga atgtcgtcac ccagggcaac tctgacaagg    120
ccgccaaccc catgcgcgag ctgcgcatcc agaagctcgt cctcaacatc tccgtcggcg    180
agtctggtga cagacttact cgtgccgcca aggtgctcga gcagctgagc ggtcagaccc    240
ccgtctacag caaggcccgc tacaccgtcc gtaccttcgg tatccgccgt aacgagaaga    300
tctccgtcca cgttaccgtc cgtgcgcca aggccgagga tcctcgag cgtggcctca    360
aggtcaagga gtacgagctc cgcaagcgca acttctctgc caccggtaat ttcggtttcg    420
gtatctccga gcacatcgac ctgggtatca agtacgaccc tgcgatcggt atctacgcca    480
tggacttcta cgtcgtcatg tcccgtcccg gtgagcgtgt cgcccgcgc cgtcgcgcga    540
agacccgcgt tggtgcttct cacaaggtca acgctcccga ggtcatcaag tggtacaaga    600
accgcttcga gggcatcgtc aggtaaaag cttgaaaggt ggtctgggat gatgaaaaat    660
tcaacttgtg gttttggcaa cggcgcaaaa gagcgaggct attttccgt agcttgagga    720
tatatccggc ctatcggagc tttactttta cgcttgagca agatcgcaaa aatggaggcc    780
tcgtatacca agcgagcgtg ccgcataacc attgatcgct c    821

SEQ ID NO: 117         moltype = DNA    length = 674
FEATURE                Location/Qualifiers
source                 1..674
                       mol_type = genomic DNA
                       organism = unidentified
SEQUENCE: 117
ggacacaccg gtgacgtctt gagcgtctcg ttctcggccg acaaccgaca aatcgtttct    60
gcttcccgag accgaactat caagctctgg aacactctcg gagagtgcaa gttcaacatt    120
gttgacgatg gtcactcgga gtgggtctct tgcgttcgat tctctcctaa ccccgtcatt    180
cccgtcatcg tctctgctgg ttgggacaag gtcgtcaagg tctgggaatt gtccaagtgc    240
aagctcaaga ccaaccacca cggtcacact ggttacatca cacccctcgc cgtttcgccc    300
gacggatcgc tcgccgcatc cggtggaaag gatggcatca ccatgctttg ggatttgaac    360
gatggcaaac acctctactc tctagaggct ggagacattg tcaactcgct cgtcttctct    420
cctaaccgat actggctctg tgccgccact gcttcgtcaa tcaagatctt cgacttggag    480
tccaagtcaa tcgttgacga cctcaagcca gacttctccg ccgagtactc tgacaaggct    540
caaaagccac aatgtacttc cctcgcctgg tctgccgatg tcagaccct ctttgccggt    600
ttctccgaca acctcgtccg agtctgggtt gtcactgctt agagtcgtga ggattgtatg    660
```

```
catggataac gtgg                                                           674

SEQ ID NO: 118           moltype = DNA   length = 1183
FEATURE                  Location/Qualifiers
source                   1..1183
                         mol_type = genomic DNA
                         organism = unidentified
SEQUENCE: 118
gaagtaccgt tttctgtgca gttttttta aacccagaac ttgcaattga gatcacgcgt           60
cgcaatggca ccctctaccc agaagcaatg gaccgttaaa aacgggagc aggactttga          120
cggcctcgtt tacggcgacg cgccagttcc gactgcgggg gactcggaag tcgttgtcaa         180
gctccatggt gcctcgctca actaccgtga cctgattatc cccaagggaa agtacccctt         240
cccgctctcg ttcccggtcg tccccggctc tgacggtgcc ggtgaagtcg tcgaggtcgg         300
atccaaggtc aagcaattca agaagggcga caaggttgtt accctcttca accagctcca        360
tcagtacggc cccgttgacg ctgctgcggc atcgtcgggc ctcggtggtg cggttgacgg         420
aaccctgcgc cagtacggtg tcttcaatga aacggcgtc gtcagggccc cgaccaacct         480
gaacttcctt gagtcgagca cactaacctg tgcgggacta acaagctgga atgcgctgta        540
tgggctgaag ccgcttcttc ctggccagac cgtcctggtg caggcgcactg gcgtgtgag        600
tatctttgct ttgcagttcg caaaagcagc gggcgcaact gtgatcgcaa caacctcatc         660
cgaagagaaa ggcaagcgcc ttaaggacct cggtgccgat cacgtcatta actacaagac        720
ccaaaccaac tggggcgaga tcgcgcgcgg tttgacgcgc gacaacatcg gggttgacca         780
catcattgag gttggaggcg ccggcaccct ggagcagagc ttcaagtgca tcaagttcga        840
gggagtcatt agtattattg gcttcttggg cggaatgaac cccagcacca tacccaatgt        900
tctgcagacc ctgagcaaca tctgcactgt gcgcggtgtg tatgttggca gcaaggcgct        960
gatgaacgac atgatcaacg ccatcgaggc gaacaatatc caccctgttg tggatggaac       1020
tgtgttcacc cttgagaaga cacgagaggc ctatgtagtc gtgtgggcgc agaagcactt       1080
cggaaagctg accatccaga tcgcttaatc acttgatgaa tataatgagg gatatatgcg       1140
actaggaatt atgcgctaat gaatataata accatgcaat tag                          1183

SEQ ID NO: 119           moltype = DNA   length = 1563
FEATURE                  Location/Qualifiers
source                   1..1563
                         mol_type = genomic DNA
                         organism = unidentified
SEQUENCE: 119
ggggccatgc tcgagcagca gtaccagatg cgaaaggagc agcaagtgca atttacacct          60
atggcatcgc cgtccagcac tccttaccac atgcatcaag atttcactgt tccgggcgac        120
tttttctccc ccctcacatc gcctgcgctc acgctcaga atcagccaca atcgcgacag         180
caattcacgg ctcatcaaca gggctactac acgaatccca gcaccgctgc gagctcggcg        240
gctccgagtc caatcgacgc gaacggagat gtggaaatgg gtggcgacgg tgttgcgctg        300
ccagagtcag cgagccaacc gaagaagcct tcccgaagga agcctgcgac accgaggact        360
ttcgccatga acaaggtcaa gcaaagtccc atacaaaaac cgcaaaaaag gaagtctgtg        420
gcgttggcac acaaggatgc agatgctgtg gtgcaggacg cccaacggtc tggccatatc        480
gcgcccaaat ccgcaggtct ccaaatgccg cctccgtttg agagctcgga aaacgacagt        540
gtttcgccgg aagcgctgaa cgacctgcct atgggccccc cgcctagacc tggatcggtt        600
tcgcagtcgc ccgccatcgc tcctcagaat cagagcgttt ctggaccggc cgcgactccc        660
aaatctctcc tttctatgaa gggcgctcaa gatatgaatg cacctgccag tactggtatt        720
tctggccaaa tgggacaggc atccttagaa gatctcgaac ttcccgaagc tgccgaaaat        780
ccaggatcga ctgcgacaca ctcgcaagtc ttgaactcgc aagagccgac acctcgcctc        840
atgccctccc gtaaaacgcc aaaactcggc cctcttagca cgccttcatc gggcaagcct        900
acttctgctt ccaacagtcc cgctcatgcg ttgtctccta gacagcgag taccccctgc        960
ggtctgctga aggacaagaa ggacaacaaa ggcggacgtg caaccagcaa gaagcgtggt       1020
agtgtcagta ccaccaattc agcaatggtc tctccggcac tccgaccgaa ggtcagcccg       1080
agtatcaagc ctctgctacc cgaaggcacc agcctcaact ccccgaccca tgccctcctc       1140
ctcgcctcca aatccaatta ccagaaccct ctggaagga accacctcc cggcatctcc        1200
tacccggact ccctctcaac cggcctcacc agcaaacgca cctcgcacaa agtcgccgag       1260
caaggccgcc gcaaccgcat caacgacgcc ctcaaagaaa tgcaagccct catcccgcc        1320
tcgtccggcg cccgcgccga agagctcatg accgccgacg ccggcgacga cgacagccag       1380
gaaaccaagg agaaggaccg cgacgccgct gtcaagagca atagctccaa agccgcgacc       1440
gtcgagagtg cgaatcggta tattcgcgtg ttgaaggaga gcgacgcggc gcagaaggat       1500
gcgatcgcgc ggccgaattc cccgggctcg agaagcttgg atccaccgga tctagataac       1560
tga                                                                     1563

SEQ ID NO: 120           moltype = DNA   length = 939
FEATURE                  Location/Qualifiers
source                   1..939
                         mol_type = genomic DNA
                         organism = unidentified
SEQUENCE: 120
gacgacacaa tgagaaacat cctcctagta ttggcgtctg cagcgcttgc tgttgtggca         60
caaaagccag atctcgacgt gaaaggcacg tttggagacg cgaacccctt ctccaaggtc        120
gtcaacggcc aaagcaacaa gctctacctc acgctggaca ccacagccc tgagtctctg        180
gtggtcaagt ctatcagcgg gtcatggtct gagaagacgt ccgcttcatc cggtcaagag        240
aagttcctta gaactctac cacccaagag aagtcacctc tcccatcc tccaagtcc           300
gagggcgcat tccagcctcc tacagtcttg acctaccagt tctggagcga attcaagcct        360
agagagttgc tcttgaccgt tttgggttga ctatgttgat gctaccggtc actcgtacag        420
agaaacagcc tacgaaggcc aagtgactgt cgttgaggcc ccgggatctt tctttgaccc        480
cgccttgctc tttgcctacg ccatggtgct ggctctcgtc ggcggcgccg gctaccttgc        540
ctacaacatc tactttccac ctgccgcaa gcccagaaga agcgccaaca ccgcacctac        600
```

```
agatgctcct gctgctccgg ctgaccctga cgaatggatt cctgtccacc acaagagggc    660
caaaaagacg tctggcggcg gggccaccag tggtgaagag agcgaagcca ctgaaggcta    720
tgcaagcgag aagtctgcca gtggagccaa aagagaggc aaaggtggca gaaaataaat    780
actgacatgt gcctcgagct gcagacgacg ctcgtcaaaa gtgtagcaag ttgaagaagc    840
ccagcacgaa gtccccagct tgactgctgc cgtttggctt aatggcacag aaagcgagtg    900
tacgtcgtac acggcttata gtctcgaatg caacaaagg                           939

SEQ ID NO: 121         moltype = DNA   length = 896
FEATURE                Location/Qualifiers
source                 1..896
                       mol_type = genomic DNA
                       organism = unidentified
SEQUENCE: 121
gccaaccacg acattgatcc ctttcacgac ttgctttcgc catgtcagat aacaacgatg     60
gaaatcacgg gggaggcgta ggcgcgtctt actactatgg cggcatcgcg attgcgctgt    120
gtcttgtgat tgtgttgacg cttgtatcaa gaatattata tcgacgacgt gtaaggaaca    180
gactcctgcg agccaacaga caagagcgca ttactttgcg agaccgggga gaagcgccag    240
gcctgccaac ctatcgggag tctcgcaatc agccctcatt accgacgatac acggccgagg    300
cagactacgc acctccaccc ggcccgcctc cttccaacag cccggacaac gaaggccacc    360
acttccactt ccatttcccc tctttacatg tgcctcaggc actgcacttg cggcctaggc    420
aggcagacga tcctgctgac cagatcccca ccgtgccccc tccgtcctac gagccgccca    480
agtatgagcc gcccagtgga gcgcctccag agcagcaaca agccctgtg gctagcggga    540
gtagcgagca tcatcaccag cagtctgctt gggcgaaca taccgcggcg gcaacagccg    600
ctgccacaac tccggcagag cacagtggcg agtcgacaga gcttaggagt gcgtcgcctt    660
ctcagccaca atctcaatcc caacctcaag caccagcaca accacaagag caggattacg    720
gctacgacga tgccgacttt atccatcctg aagagcgaca caggatcgag gctgtgagga    780
gcaatgatcc gcagacatga ttcaaacatg tgttgtaaag tgtactacta tgaactcgtt    840
gaccagtata atcgaagcgt atataacggc acaaatgcaa agctgccatc atcccg        896

SEQ ID NO: 122         moltype = DNA   length = 697
FEATURE                Location/Qualifiers
source                 1..697
                       mol_type = genomic DNA
                       organism = unidentified
SEQUENCE: 122
cattacggcc gggaagcttt cagaagctaa tcgagttctt cctatccctt tcaactttac     60
acaccatgtc tagaattggc gatccaacga acaaccctgc tacccagcaa ctgtactctg    120
ataggcccctt gcatctccct ggccccggcc tcaagccatc caggcagctc actatcagct    180
cggctgttgc gttccgcgag gattcgggcc aaacacgctt caacctcatc agctctgacc    240
accgcgaggt gttgcacatt agtattcgtg caagggacaa cgttctcgtg ctcaaccaca    300
aggcccccga tggcgattgg ggcaaagaag agcgacatga tctcaaaccc cttttcgata    360
ccccactgct gccttacatc accgtaatgg caacgaagaa cagctatatc cttttctgttc    420
ctggtaaacg ggagatcatc ttcaataaga gaaagggt catgaaggcct gctgtgagga    480
ttgagtatga ctatgatgag atgtctgcgt tctccgaccc ctgctacatt acagtcccat    540
cttcatctta aagctttcct agttggcttg gagttggcgg atatggtcac attggttttt    600
tcacacggca aacggtaaag aattacggct tctctctcct gtcatgttca gcggacgatg    660
tatgatgtag tgttctgttc aattgatctg gttgttg                             697

SEQ ID NO: 123         moltype = DNA   length = 329
FEATURE                Location/Qualifiers
source                 1..329
                       mol_type = genomic DNA
                       organism = unidentified
SEQUENCE: 123
ggaacgacca cgagcagttt ttaaaatgcc acaagaaatc aaggacatca agaacttact     60
cgaaatcgct cgtcgtaagg acgctcgttc cgcccgcatc aagaagacca agaccgttgg    120
tgctaagggc gagccagctc aacttaccaa gttcaagatt cgttgctctc gctacctcta    180
cactctcgtc gtctctgacg gtgagaaggc agagaagctt aagcaatcac tcccaccaac    240
cctcaacgtc gaggagattg gtaaggtttc aaagaagtag attagtgatg taatttgctg    300
ccttgattga ttgtccttgt tggtatttt                                      329

SEQ ID NO: 124         moltype = DNA   length = 747
FEATURE                Location/Qualifiers
source                 1..747
                       mol_type = genomic DNA
                       organism = unidentified
SEQUENCE: 124
gtacacataa ctcttcattc ctcatcatgt ctcacacttt ctacgatggc accatcgtgg     60
tgcttcaagg cattcttgaa actttttctc atatccttca caaagccgaa gaaagcccaa    120
actctagcgc ttttcccgca gctcgtctgc acgaggacat gtatccattg accgaccaaa    180
ttcgcctagc aactcaattt tctgagtata ttctggctaa agtgaccggc cgcgagccaa    240
ggaagttcga aggcaatcca ttgaccttcg ctgaattcta tgagcgtatc gataccatgc    300
tgaagtcact caaagaagca gataaggatg tcgtcaatgc aaatgccgac aaggaggagc    360
ttactcaagt tggacctacc gcaaaaattg aattgagtag tgctatatac gcccatccga    420
tagccttgcc caacatttac ttccatctca acattgctta cggcattttg cggaaggagg    480
gcgtgcctct tggcaagctt gactattttg cgggcttttt cccaccgagc atggctcaag    540
gcaagtaaag aagtgatgtt ggttatgttt ccggatggaa agggtgctga tctatgagaa    600
tgagttccga gtagaccatg atggtctaga gtgtggcttg agctttcatt tgccaaattc    660
ttgtggaaag atagcaatga cggaacaagc gatttgtatg tacatttaat gaagtctatc    720
```

```
tatagaatta atctccgatc tatcgcg                                        747

SEQ ID NO: 125             moltype = DNA   length = 693
FEATURE                    Location/Qualifiers
source                     1..693
                           mol_type = genomic DNA
                           organism = unidentified
SEQUENCE: 125
aagctcttca aagctaatta tcgagttctc ctatctcttg cacttataca caccatgtct    60
agaattggcg attttgcgaa caacaaccag gctacccagc agctgttctc tgatagaccc   120
atgcagctcc ctggcccgg ccttaagccg tccaggcagc tcacggtcag ctcagctatg    180
gcgttccgct gggactctgg ccaaacccgc ttcaacctca tcagctctga ccgtcgtgaa   240
gtgctgcaca tcagcatccg cgcaaaagac gacgtccttg tgcttaacac taaggctcct   300
gatggcaatt ggggcaagga agagcgacac gagctcaaac cccttttcga caccccgatg   360
ctgccttata tcaccgtaac ggcgactaag actagctata tcctgtccgt tcctggtaat   420
caggagatca tcttcaataa gaggaaaggg ttcatggagc tgctgtcaa gattgagtat    480
gactatgacg agaaccctgc gttctctgat ccgtgctacg tcacagttcc gcatttatct   540
taaggtctta ttggcttgga gttggcggat agtcacaccg ttttttttca cacggcaaaa   600
ggcaaagtat tacggctttt ctctcctgtc ctgtttagcg gatgtacgat gtatgttgta   660
gtagtgttct ggaatttgtg ttcaagttgt tgg                                693

SEQ ID NO: 126             moltype = DNA   length = 1030
FEATURE                    Location/Qualifiers
source                     1..1030
                           mol_type = genomic DNA
                           organism = unidentified
SEQUENCE: 126
gagcgacttc atcaaaaatg tcagagcaac ttcactacaa gggttcattg gccggccacg    60
gcaactgggg tactgccatc gctacctctg cagagaaccc agacatgatc ctcactgctt   120
cccgtgacaa gtctgtcatc gtctggcaac tcacccgtga cgacgctcag tacggttacc   180
caaagagaat cctcaagggc cacaaccact tcgtctctga cgtctccatc tcatacgacg   240
gtcaattcgc tttgtcctcc tcatgggaca agaccctccg tctctgggac ctcaacactg   300
gtcttaccac cagacgtttc gttggccacg aagcagacgt tctctccgtc tccttctccg   360
ccgacaacag acaaatcgtc tctggctccc gcgaccgcac catcaagctc tggaacaccc   420
ttggtgaatg caagttcgac atcaaggatg aaggccactc cgaatgggtt tcatgcgttc   480
gtttctctcc aaacccaatg aacccagtca tcgtctcagc tggttgggac aaggttgtca   540
aggtttggga actctcaaac tgcaagctca agaccaacca ctacggtcac actggctaca   600
tcaacaccgt ctctgtctcc ccagacggat cccttgctgc ctccggcggt aaggacggca   660
tcaccatgct ttgggacctc aacgagggca agcacctctc ctccctcgag gctggtgaca   720
ttgtcaacgc actccgtctc tcaccaaacc gttactggtt gtgcgctgct actgcctcat   780
gcatcaagat cttcgacctc gagtccaagt ccatgtcga cgagctcaag ccagactttg   840
tcgacgtcgg caagaactcc cgcgagccag aagctgtctc cctctcctgg tccgctgatg   900
gtcaaaccct cttcgctggt ttcaccgaca acgccgtccg tgtctggacc gtcgcataaa   960
actaagctgt atctaataga cagggtattg ggttttgtaa cactattgcg aggaactcat   1020
gattttaccg                                                         1030

SEQ ID NO: 127             moltype = DNA   length = 668
FEATURE                    Location/Qualifiers
source                     1..668
                           mol_type = genomic DNA
                           organism = unidentified
SEQUENCE: 127
ggggaaggtg gtggtatcca cggaaccacc ttcaactcca tcatgaagtg tgatgttgac    60
gtccgtaagg atctctatgg caacattgtc atgtctggtg gtactactat gtaccctggt   120
attgccgacc gtatgcagaa ggaaatcacc gctcttgctc cttcgtcgat gaaggtcaag   180
atcattgctc ctcctgagcg taaatactct gtgtggattg gtggttccat cctggcttct   240
ctgtccacct tccagcagat gtggatctcg aagcaggagt acgacgagag cggcccttcg   300
atcgtccacc gcaagtgctt ctaagcttaa gcgcatggtt gatttgcttg tttgtacttc   360
ttttctggcg tatcaaaagg caggacagtg tggcatgcgg accttttctg acctgatgac   420
gagagggatc gcctaagaaa aaggaacttt attttagttg tggaataga acggtttatt    480
tgacgctagt tctcgtccag agcatcctcg agacgatagt ctgggttcgt cttaagcgat   540
ggatggtggt gattctcttc gtattgttcc tgtacctgta ctacatattg cctacaccat   600
gtcctgttca tttcttctct gtttgcgttg cgttagacct tataaattta aatgtcgtat   660
tgctcccc                                                           668

SEQ ID NO: 128             moltype = DNA   length = 668
FEATURE                    Location/Qualifiers
source                     1..668
                           mol_type = genomic DNA
                           organism = unidentified
SEQUENCE: 128
ggggagcaat acgacattta aatttataag gtctaacgca acgcaaacag agaagaaatg    60
aacaggacat ggtgtaggca atatgtagta caggtacagg aacaatcga agagaatcac    120
caccatccat cgcttaagac gaacccagac tatcgtctct aggatgctct ggacgagaac   180
tagcgtcaaa taaccgtctc ctattccaca actaaaataa agttcctttt tcttaggcga   240
tccctctcgt catcaggtca gaaaaggtcc gcatgccaca ctgtcctgcc ttttgatacg   300
ccagaaaaga agtacaaaca agcaaatcaa ccatgcgctt aagcttagaa gcacttgcgg   360
tggacgatcg aagggccgct ctcgtcgtac tcctgcttcg agatccacat ctgctggaag   420
gtggacagag aagccaggat ggaaccacca atccacacag agtatttacg ctcaggagga   480
```

```
gcaatgatct tgaccttcat cgacgaagga gcaagagcgg tgatttcctt ctgcatacgg    540
tcggcaatac cagggtacat agtagtacca ccagacatga caatgttgcc atagagatcc    600
ttacggacgt caacatcaca cttcatgatg gagttgaagg tggttccgtg gataccacca    660
ccttcccc                                                              668

SEQ ID NO: 129          moltype = DNA    length = 1018
FEATURE                 Location/Qualifiers
source                  1..1018
                        mol_type = genomic DNA
                        organism = unidentified
SEQUENCE: 129
gactttctca tttcagaatt attttctata ctctgacaag agcaagcaat accaaacatc    60
ttccacatcg aagctttaac catttttgccc ttaacatttg aacaagacga aatggccttc   120
ttcccacact acaccactaa tctgtcgcct ctgctctact tgttggacga cgactatgct   180
gtctaccgct caacttgtcc aaagtccaac taccaccaca agcaacacca cagccgccgt   240
cagccttcgc cagttcgtta ctttagtccg aattttgata tgcagagggg gaatgactcc   300
tactaccttg acggagagct ccctggtgtc aaccagaatg atgtcgatat tgaattctct   360
gaccctcaga cactggtgat caagggtcga gtggagcgga attacaacaa tctcgacggc   420
atgaacgagg aaaaccagca agatgaagaa caattctctg aaactctctc tagcaagtcg   480
taccaaccca ctgtcgagga cgaggacgag gcgaaccatt caccaccegt ggcgacacca   540
acctactctg agaagtctgt tactgagaaa actcagaagc ctgcgtacaa ataccgaaat   600
tctgaacgtg ctattggcga attccaccga gccttcaatc tccctacaag agtcgatcaa   660
gatgcggtca gggctacatt gaggaatgga atcctctcgc tggagctccc gaaggagccg   720
gcaccgaaga tgaagaagat tcggattgaa tagaggattt cgaataaaat tttgatttg    780
atgagtagtt ggtgttatt gttatgtcta attatatggg gctatgtcat gattgggaaa    840
tgggacaccg cattttgtttc cttttcccc atttcttcag agccatcta tattgcatgt   900
atgttgcatg aactatggtt tttgctagga gcggttgctt ctgctttgca ttttcatgaa   960
ctatttctct tttattaaat taataactag catatcaatt aatgatctgt catatggc    1018

SEQ ID NO: 130          moltype = DNA    length = 686
FEATURE                 Location/Qualifiers
source                  1..686
                        mol_type = genomic DNA
                        organism = unidentified
SEQUENCE: 130
aagctttcag aagctaatcg agttcttcct atcccttca actttacaca ccatgtctag     60
aattggcgat ccaacgaaca accctgctac ccagcaactg tactctgata ggcccttgca   120
tctccctggc cccggcctca agccatccag gcagctcact atcagctcgg ctgttgcgtt   180
ccgcgaggat tcgggccaaa cacgcttcaa cctcatcgac tctgaccacc gcgaggtgtt   240
gcacattagt attcgtgcaa gggacaacgt tctcgtgctc aacaccaagg cccccgatgg   300
cgattggggc aaagaagagc gacatgatct caaaccccctt ttcgatacc cactgctgcc   360
ttacatcacc gtaatggcaa cgaagaacag ctatatcctt tctgttcctg gtaaacggga   420
gatcatcttc aataagagga aagggttcat ggagcctgct gtgaggattg agtatgacta   480
tgatgagatg tctgcgttct ccgacccctg ctacattaca gtcccatctt catcttaaag   540
cttttcctagt tggcttggag ttggcggata tggtcacatt ggtttttttca cacggcaaac   600
ggtaaagaat tacggcttct ctctcctgtc atgttcagcg gacgatgtat gatgtagtgt   660
tctgttcaat tgatctggtt gttgac                                         686

SEQ ID NO: 131          moltype = DNA    length = 698
FEATURE                 Location/Qualifiers
source                  1..698
                        mol_type = genomic DNA
                        organism = unidentified
SEQUENCE: 131
gggcatataa ccacaggtca ttcgcatccg tcgcagaact tcttacatct gagctttcct     60
gtccgttaga tataggcaaa atgaaggcct actggtacga taaccaaccg ggcgaccagc   120
gcttgcctca cgactccggc cgccccgtca ccgagtccta cctcgagtcc atcggcgtct   180
tctaccgcca ctgcccaaca attgaccttg tcgactccct ggccgccgag cgcggctaca   240
agaaccgcga cgaggtctgc gtctcgccgc agactatggg cgatgtctac gaggagaagg   300
tgaagacgtt ctttagtgaa catttgcacg aggacgagga gattcggtac attcgagatg   360
gggaggggta ctttgatgtg cgtgggcagg aggatgagtg ggtacggatt cggttgagta   420
aggatgatct gatcattctt ccggctggga tctaccatcg gtttacgaca gatgataaga   480
actacgtcaa ggctatgcgt ctcttccagg aggagcccaa gtggacgccc ttgaaccgtg   540
gccctgaggt tgatgtcaac cctcaccgga agacatacc tgaaaccgtc cccagccctg   600
ctgtggctgc gaactaagtg agcatcgaat gctcttgttg aacaatctat ttgcacatct   660
ttagcctttta tacacctcaa tgcatcaatg gatttagg                           698

SEQ ID NO: 132          moltype = DNA    length = 884
FEATURE                 Location/Qualifiers
source                  1..884
                        mol_type = genomic DNA
                        organism = unidentified
SEQUENCE: 132
gtggctgccg gctacacccc cgaggccctc gagatcctct ccaagaagaa gggcggcaag     60
tacctcgtcc tcgagatgga cgagacctac aaccccccg ccgaggagac acgtactctc   120
tacggtgtcc agctcaccca ggcccgcaac gatgctgtca tctcccccca gaagaccttc   180
aataccatca ttaccccccaa gaacaccgag tccctcccccg agtccgccct ccgcgacctc   240
accgtcgcca ccctcgccct gaaatacaca cagtccaact ccgtctgcta cgcgctcaac   300
ggacaggtcg tcggcctcgg tgccggccag caaagtcgta tccactgcac tcgtcttgcc   360
```

```
ggcgacaaga ccgacaactg gtggatgcgc ttccacgagc gcgtgctcaa catcaagtgg   420
aagcagggca ccaagcgtgc tgacaagagc aacgccatcg acctgctctg ctcgggccag   480
acgccccgca atgacgctga gaaggtcgag tacgagcgtg tgttcgcgga ggttcctgct   540
ccgttcaccc aggaggagcg tgatgcttgg ctctcgcagt tgaccaacgt tgctatttct   600
tcggatgctt tcgtatgtct ctcccctctg ttagagcatt ctaagttcta agatcatgct   660
aattggtgaa atagttcccc ttcatcgaca acgtcttccg agccgccgc tccggcgtca    720
agtacatcgc tgcacccagc ggttcgcaga acgacggccc tgtcttcgag actgccgaga   780
agcttggtat ctcgttcgtt gagcagggta ctcgtctgtt ccaccactaa cttgcttttc   840
cggtggcgtg gtattatggt ataaaaagaa aaagggtttg gggg                    884

SEQ ID NO: 133          moltype = DNA   length = 822
FEATURE                 Location/Qualifiers
source                  1..822
                        mol_type = genomic DNA
                        organism = unidentified
SEQUENCE: 133
gtggctgccg gctacacccc cgaggccctc gagatcctct ccaagaagaa gggcggcaag   60
tacctcgtcc tcgagatgga cgagacctac aaccccccg ccgaggagac acgtactctc    120
tacggtgtcc agctcaccca ggcccgcaac gatgctgtca tctcccccca gaagaccttc   180
aataccatca ttaccccaa gaacaccgag tccctcccg agtccgccct ccgcgacctc     240
accgtcgcca ccctcgccct gaaatacaca cagtccaact ccgtctgcta cgcgctcaac   300
ggacaggtcg tcggcctcgg tgccggccag caaagtcgta tccactgcac tcgtcttgcc   360
ggcgacaaga ccgacaactg gtggatgcgc ttccacgagc gcgtgctcaa catcaagtgg   420
aagcagggca ccaagcgtgc tgacaagagc aacgccatcg acctgctctg ctcgggccag   480
acgccccgca atgacgctga gaaggtcgag tacgagcgtg tgttcgcgga ggttcctgct   540
ccgttcaccc aggaggagcg tgatgcttgg ctctcgcagt tgaccaacgt tgctatttct   600
tcggatgctt tcttcccctt catcgacaac gtcttccgag ccgccgctc cggcgtcaag    660
tacatcgctg cacccagcgg ttcgcagaac gacggccctg tcttcgagac tgccgagaag   720
cttggtatct cgttcgttga gcagggtact cgtctgttcc accactaact tgcttttccg   780
gtggcgtggt attatggtat aaaaagaaaa agggtttggg gg                      822

SEQ ID NO: 134          moltype = DNA   length = 996
FEATURE                 Location/Qualifiers
source                  1..996
                        mol_type = genomic DNA
                        organism = unidentified
SEQUENCE: 134
tgaagcagtg gtatcaacgc aagcagtggt atcaacgcag aatgtgcgat cgctctagaa   60
tcggtcccaa gggttgggaa gcagtggtat caacgcaagc agtggtatca acgcaagcag   120
tggtatcaac gcaagcagtg gtatcaacgc aagcagtggt atcaacgcaa gcagtggtat   180
caacgcagag tgcgcagccc ggtgctatct ctgctcctgt ggcagctggt aaggacgttg   240
agctgcagtg gaccgaatgg ccggaaaagtc atcatggccc tgtcattact tacctggcca   300
actgcaacgg tgactgctct gaggtcgaca aatcctctct ggagtttttc aagatcgatc   360
agaagggtct catcgatgac agcaatgtcc ctggcacatg gctaccgac aaactaatct    420
ccaacaacaa cagctacacc gtcaccatcc ccagcgacat tgctgccggt aactacgtcc   480
tccgccatga aatcattgct ctgcactccg ctggcaacga ggatggtgcc cagaactacc   540
ccagtgtct caacctcaag gttactggtg gtggcaacge ttctccctca ggtactcttg    600
gtaccaagct ctacaacgag gacgactcgg gtatccttgt cagtatctac cagcagcttg   660
actcctacga catccccggc cctgctctgt actggcgc ttcctcgtcc tccaactctg     720
gttcttcttc cagcgttgct tcggccactg ctttctgccac ttctgccgct gcttcctctc   780
cctcgtcctc tcaggcttcc ggtacccccg cttcccagct caaggctcag accgctcagt   840
ctactcctag cgcttcgtcc ggtgccactt ccggcagtg tccgactac ttcagctctc      900
tgagcgctga ggagttcctc aacgttatca gcgagactct gtcttggttg gtcactgaca   960
agattccacg ctcgtgacttg tcgaccgcat aaatgg                             996

SEQ ID NO: 135          moltype = DNA   length = 823
FEATURE                 Location/Qualifiers
source                  1..823
                        mol_type = genomic DNA
                        organism = unidentified
SEQUENCE: 135
gtggtatcaa cgcagagtgc gcagcccggt gctatctctg ctcctgtggc agctggtaag   60
gacgttgagc tgcagtggac cgaatggccg gaaagtcatc atggccctgt cattacttac   120
ctggccaact gcaacggtga ctgctctgag gtcgacaaat cctctctgga gttttcaag    180
atcgatcaga agggtctcat cgatgacagc aatgtccctg gcacatgggc taccgacaaa   240
ctaatctcca acaacaacag ctacaccgtc accatcccca gcgacattgc tgccggtaac   300
tacgtcctcc gccatgaaat cattgctctg cactccgctg caacgagga tggtgcccag    360
aactaccccc agtgtctcaa cctcaaggtt actggtggtg gcaacgcttc tccctcaggt   420
actcttggta ccaagctcta caacgaggac gactcgggta tccttgtcag tatctaccag   480
cagcttgact cctacgacat ccccggccct gctctgtact ggcgcttc ctcgtcctcc     540
aactctggtt cttcttccag cgttgcttcg gccactgctt ctgccacttc tgccgctgct   600
tcctctcct cgtcctctca ggcttccggt accccgctt cccaggtcaa ggctcagacc     660
gctagctcta ctcctagcgc ttcgtccggt gccacttccg gcagtctgtc cgactacttc   720
agctctctga gcgctgagga gttcctcaac gttatcagcg agactctgtc ttggttggtc   780
actgacaaga ttcacgctcg tgacttgtcg accgcataaa tgg                     823

SEQ ID NO: 136          moltype = DNA   length = 1000
FEATURE                 Location/Qualifiers
source                  1..1000
```

```
                        mol_type = genomic DNA
                        organism = unidentified
SEQUENCE: 136
gacggtgaag ttggaataga ataaaatgtt gagcatgttt accagagtgg ccagaggaca    60
ggccaaggtg tttacccgca acgcatccac agcatccaac aaaccaacga atcaatcatc   120
caacaaggct gccactatcg cagcttcaat ttcaggtgtt accgccgcgt tatacgccca   180
ccaatacggc ctcattgaca gcgtcttcgc tagtggctta gaagagggtt tgcacgctcc   240
tcatttccct tggtcacaca atggctggtt ggacagcttt gacccacaact ccattagacg   300
cggttaccaa gtttaccgtg aggtgtgcag ctcgtgtcac tctttggaca gaatagcgtg   360
gagaaacctt gtcgctcgtgt cacacacttc agatgaagcc agagcgatgg ctgaagacga   420
agagtacact gatggtccaa atgaccaagg agagtctttc caaagacctg gtaaattggc   480
tgattacatg ccagctcctt atccaaatga ggaagcttcg agggccgcca atggtggtgc   540
tcttcctcct gatctttctc tcatcgttaa agcaagacac ggaggagctg attacattat   600
ggctctgctc actggttacc aggatcctcc tgctgtatt caagttcaag agggcatgaa   660
cttcaaccca tatttcccag gtggtggtat tgccatgggt agagttttgt tcgatggtct   720
ggtagaatac gacgatggca ctcctgctac tactacacaa atggctaagg atgtcgctac   780
tttcctcagc tgggctagtg agccagaaca cgacgacaga aagaagatgg gcttccaagc   840
tgtcattatc ctctcagcta tgaccgccat ctcactctac gtcaagagac tcaagtggtc   900
gcctatcaag acgaggaaac tgacttacaa cccaccaaag tgatctgaat gtagagaaaa   960
gtttgacccg tataaaaaat ttcatcctct ccttttccg                          1000

SEQ ID NO: 137         moltype = DNA  length = 544
FEATURE                Location/Qualifiers
source                 1..544
                        mol_type = genomic DNA
                        organism = unidentified
SEQUENCE: 137
ggaggtagtc cagccaaaaa gagtttgata ggcgcgatgg aggcacaaaa tctcaagact    60
ttcccaaagc aacctatctt ccaaaactca agacccgtg gtaacaagaa ggtcaccaag    120
gaccgtcgtt ggtacaagga cgtcggtctc ggtttcaaga ctcctcaaga agccatcacc   180
ggtacttaca tcgacaagaa gtgcccatgg accggtgagg tttccatcag aggccgtatc   240
ttgtccggca aggtggtctc taccaagatg acccgtacga tcgtcatcag aagagagtac   300
cttcactacg tgccaaagta caacagatac gagaagcgtc acaagaacct cccagtgcac   360
gcatcacctg cattccgtat cgagaatggt gaccaagtcg tcgttggcca atgccgtcca   420
ctttcaaaga ctgtgagatt caacgtcctc cgtgtcatca agaacaaggc tgctgctaag   480
gctttcgcaa agttctaaac ttgttattaa tgtagttggt ccattcacag aatttgaaa   540
gtcc                                                                544

SEQ ID NO: 138         moltype = DNA  length = 938
FEATURE                Location/Qualifiers
source                 1..938
                        mol_type = genomic DNA
                        organism = unidentified
SEQUENCE: 138
acgttcaatt gacttttcca ttcttttgtt cgttctgaag agtttctttt tttctttcat    60
tgtcgcctcc tttcttcgc cttccgtttg tttccgatca tcgggtgttg ccagagtata   120
tatagagttg gggctcccctt ttatctatct caccgcaagc gtcctcctga tcctctctcc   180
tgatcctcct ccttcattcc ttgactcctc ttcacgctcc tcctgaccag ccaagtctta   240
catccctctc tacaactact actcttcaaa taatcctctc ctctcggtgg gcttgaatcc   300
cttatcttcc gcctctcccc acgaaccgga ccggatcgtc ttatcgcctc cgcaccagct   360
ggcgcttact acctcatcca cctctttccc gtctcgccac cgaaaccagt ctacaatgcc   420
tcctcgcaag cccagatgct cctttaagga gtgcaaggaa caagcccagc gcattgtcgg   480
agactgcagc ttctgcagcg gtcacttctg ctccaagcat cgcatgctcg aagcccactc   540
ctgctccggt ctgaagact gcaagaagga gtcccacgcc cgcaatgctg ataagttgaa   600
cagcgagcgc acacaggtta tcaagggtgt atgacgggat cacatctaca ctactacaac   660
aatctcggcg catttcgatt gcatttactt gccatttta tccgacgttg agttagcgca   720
gtgttattta caatttcttc ttttctttat tttgcctacg atgtctcccc ctatcggtat   780
ggtggtgtct cgtttcggga gcgacatggt ttacaatgat tttggttttgg ggtggtctct   840
cggtatttgt ctattatcca cttatttcc ggggtattat gcgcatggcg ttactatatg   900
gagtttgata ttctatctcg aatcgatact tttacaac                           938

SEQ ID NO: 139         moltype = DNA  length = 687
FEATURE                Location/Qualifiers
source                 1..687
                        mol_type = genomic DNA
                        organism = unidentified
SEQUENCE: 139
aagctctccc aagctaatcg agttttact gtcacttgca tttatacata ccatgtctag     60
gaacttcggc gatttttcga ctaaccaggc tactcagcag ctgtactccg atagaccctt   120
gcatctccct ggaaatggcc ttaagccggc tagacagctc acgatcagtt cagctgtcgc   180
attccgctgg gactctgacc aaacccgctt caacctgatc agctctgacc gtcgcgaagt   240
gttgcacatc agcattcgcg caaaagacaa cgttctcgtc ctcaacacca aggcgcccga   300
tggtgactgg ggcagggaag agcgacacga gctcaagaaa cttttcgata cccctatgct   360
gccttactac accgtgacgg cgacgaagat gacctataac tcactactcg ctagtggtca   420
agaaatcatc ttcaacaaga ggaaaggatt catggaacct gctgtgaaga ttgagtgatga   480
ctatgatgag cactctgcgt tctccgaccc atgctacatt acggttccat cttcttaaag   540
gctcgtcggc ttagagttgg cggatagtca cactggtttt tcatacggca aacggcaatg   600
tattacggct tttctctcct gtcctgttca gcggtagatg tacgatgtat gttgtagtgt   660
ttcaaatttg agttcaagtt gttggcc                                       687
```

| SEQ ID NO: 140 | moltype = DNA length = 601 |
|---|---|
| FEATURE | Location/Qualifiers |
| source | 1..601 |
| | mol_type = genomic DNA |
| | organism = unidentified |

SEQUENCE: 140
```
gtctgcttgc ttcaacgagc gctgaatttc ttgttggccg gtgttgattc cccggattcc   60
ctgttatcgc ctgctgtgtt cgccttggta gcaggtgttt gaattggtcc tgcaatttcg  120
ctgattgctg gcctcgaact cccgatcgaa cgaactctcc tctcctccgt caacgcacct  180
tcacatatcg caaagcacaa tggtttccaa gattctcttc tggagtggct tcggcatcgc  240
cgtccgtctc tggcaactcg gtatcgaaat gcgtcccatt cttgccaagc agggtctctg  300
ggcctacccc gtcttcgcag gtgtcggtgg aagcttcggt tactggctcc agggtgtcga  360
ggaccgtcag ctgaagattc ttgcgcagcg ccgcgaaacg atcctcgaca agcgccggac  420
acgggacgag cgtgagggtc tgagcaacat tgagaaggag ggtactttgg ctgcgacccc  480
atgatttgtt gcgttggctg ttgtttattt tcactgcctt cggagaaaga ccggcaattg  540
cattgctggg catgtatcat accaaaacag aggaaggtta atggtcaatt gtttaatgac  600
c                                                                 601
```

| SEQ ID NO: 141 | moltype = DNA length = 601 |
|---|---|
| FEATURE | Location/Qualifiers |
| source | 1..601 |
| | mol_type = genomic DNA |
| | organism = unidentified |

SEQUENCE: 141
```
ggtcattaaa caattgacca ttaaccttcc tctgttttgg tatgatacat gcccagcaat   60
gcaattgccg gtctttctcc gaaggcagtg aaaataaaca acagccaacg caacaaatca  120
tggggtcgca gccaaagtac cctccttctc aatgttgctc agaccctcac gctcgtcccg  180
tctccggcgc ttgtcgagga tggcttcgcg gcgctgcgca agaatcttca gctgacggtc  240
ctcgacaccc tggagccagt aaccgaagct tccaccgaca cctgcgaaga cgggtaggc  300
ccagagaccc tgcttggcaa gaatgggacg catttcgata ccgagttgcc agagacggac  360
ggcgatgccg aagccactcc agaagagaat cttggaaacc attgtgcttt gcgatatgtg  420
aaggtgcgtt gacggaggag aggagagttc gttcgatcgg gagttcgagg ccagcaatca  480
gcgaaattgc aggaccaatt caaacacctg ctaccaaggc gaacacagca ggcgataaca  540
gggaatccgg ggaatcaaca ccggccaaca agaaattcag cgctcgttga agcaagcaga  600
c                                                                 601
```

| SEQ ID NO: 142 | moltype = DNA length = 380 |
|---|---|
| FEATURE | Location/Qualifiers |
| source | 1..380 |
| | mol_type = genomic DNA |
| | organism = unidentified |

SEQUENCE: 142
```
gggggcgaca tggcttcgac gccggtgaca atccctgagg tgcatgccga gagcgtaacg   60
tatctcgtaa atccaacgtt acgataaaat agtcgcaaac gacgacaact acgctcaggg  120
cgcgctggca gcgtaacaac tgctagcttc tagtccggcc cggaggtgat gtgcccattc  180
atcaccgaag ggatacgagc tcagactgat gggatcgcgg ctggctttgt cctcgcgtca  240
gccgctaaaa cttagaggaa tcgcgtcgct ggatcctgcc cgtcggagcc agaggcgcta  300
aatcaaaaga cggacctaag catgtagagc cgatgggtga gtgccggcgg acggggttc   360
aattccccc gcctccacca                                              380
```

| SEQ ID NO: 143 | moltype = DNA length = 977 |
|---|---|
| FEATURE | Location/Qualifiers |
| source | 1..977 |
| | mol_type = genomic DNA |
| | organism = unidentified |

SEQUENCE: 143
```
gggaccagaa cagcttcagc tacaatgcca ttcatcaagg aagccaagag caacagctac   60
ttctctcgct accaagtcaa gtaccgcaga cgtcgtgaag gcaagactga ctttctacga  120
cgtaagcgct tggtaacgca agctaagaac aagtacaacg caccaaagta ccgtctcgta  180
gttagattca cgaacaagga catcatctgt caaatcgtgt catcaaagct tcaaggtgac  240
gttgttctca ctcacgctcg cgcccgcgaa cttccacgtt acggcatcaa gcacggtctc  300
acgtcatggt catccgctta cgcggttggt ctcctcgtcg caagaagagc gctcaccaag  360
ctcggtcttg ctgacaagta cgagggtgac gttgaagcta ctggtgaata caacctcacc  420
gagccacttg gcgatgatga accacgtcct ttcaaggtct tccttgacgt tggtcttaag  480
cgtacctcta ctggttctag agtcttcggt gctcttaagg gcgcctcaga cggtggtctc  540
tacatccctc actctgagaa ccgtttccca ggttacgata tcgagagcaa ggaactcgac  600
gctgaaatct tgaacaagta catcttgggt ggtcacattg ctgagtacat ggaggctctt  660
gaggaggaag atgaggagag attcaaggct caattctcta cctatcttga agacggtatt  720
ggatctgagg acattgaaga aatcttctcg ggcgcacacg aggctatccg tgctgaccca  780
accttcaagc caagtgaggc tgccaagggc accgactgga gtccgagtc aaagaagcac  840
cgcgctgtca gactcaccaa gcaacaacgc gaggacgcta tccaacagcg tatcaagtac  900
taccagcaag ctggcgacct cgagtaaacg gtaattgtat cggtctacat agacaatcaa  960
tgtctgttgt tccttag                                                977
```

| SEQ ID NO: 144 | moltype = DNA length = 73 |
|---|---|
| FEATURE | Location/Qualifiers |
| source | 1..73 |
| | mol_type = genomic DNA |

```
                        organism = unidentified
SEQUENCE: 144
gattacccgc tgaacttaag catatcaata agcggaggaa agaaactaa caaggattcc   60
cctagtaacg gcg                                                     73

SEQ ID NO: 145          moltype = DNA   length = 823
FEATURE                 Location/Qualifiers
source                  1..823
                        mol_type = genomic DNA
                        organism = unidentified
SEQUENCE: 145
gggtctcttc catttgaatt tttcaaccca cagcatggcc ttcatgaatc tcccatggcc   60
cactgaatgc ctacatgccg ctctcaagaa cggatcctta cctttctggg gatttgtaat  120
ctatcgaacg acctacaccg ctcagtcaga tgccgcctgg ccgcagatta tcgagcttat  180
tgcctcctat atgaaagcct tactctacca cgagtataac gacaagaaaa agatgggaga  240
tgagcctaca gtctacgacg aaatctgggc aaggcatcag ttgacgatta tggatgatag  300
acaattcaac ggagcgtctg tgtttgatat ccaacttcac ttcgaaaagt gggttgaggc  360
gcagggaaag cgagatgaat ctactatgta tcgcatgtgt atggtcattg atgatgaatc  420
aatccagacg ttattggagg cgccaccccgg ggaaaatagg aaactcggac gacgtatagg  480
gggccctgta cgctttgtca aagtcgtgga ggctttcccc gagctagaca gccttgacga  540
attccaggga tggatgaaat gtgagatcaa cgcgttatgg ccgctgtgga agatgatgtc  600
tgacggagat gaaatgagga tgtcatatga tgagatgaag gggaatgaga agcaggtcta  660
tggcgcaatt taatcggttt ttcttcatgt tatcctgatg gaaaaaatgg cagaacatat  720
gtctgtacat gcagaaaata aggtgattgg aaaatacttg aatgctatga agttagatag  780
tagctgttct agcggccaga taaagccgcg catgtgaatt tcg                   823

SEQ ID NO: 146          moltype = DNA   length = 181
FEATURE                 Location/Qualifiers
source                  1..181
                        mol_type = genomic DNA
                        organism = unidentified
SEQUENCE: 146
gtactaacca ctcgtcaggc gctgaaagaa gaagatgcag taagtttgat gttttctgtg   60
tatgattata cataaagttg ttgtataact acgcagaaaa gttttcgtat gcaaaacttt  120
gattggtgtt aagtcgaaat aaggttcgtg taatggaaat tgcacgggga gtataaaatg  180
t                                                                 181

SEQ ID NO: 147          moltype = DNA   length = 734
FEATURE                 Location/Qualifiers
source                  1..734
                        mol_type = genomic DNA
                        organism = unidentified
SEQUENCE: 147
atgacagaga aactttacac cgagcaagtg aatgcgttcg gaaacgaatt acctcctcta   60
tcatacaaag acctggacaa actcccctta caccaaaacg tcatcaaaga aactcttcga  120
atccacaact caattcatac actcatgcgt aaagtgaaaa atcccctccc agtcccagga  180
acaagattcg ttataccaac cagtcacacc ctcctcgcgt ccccgggcgt aacaacccgc  240
gacgattcac acttccgaaa cgcaatgacc tgggatccac accgttggga aacacgaagt  300
gaggtcgaag atgatggtga cacaatcgat tatggatatg gggttgtttc aaaggggacg  360
aagagtcctt atttgccctt tggagcgggt cgacatcgat gtattgggga gaaattcgca  420
tacttgaatc ttactgttat tgttgctact cttgtgagga attttcggtt ttctgaacct  480
gatgatagag agggtgttcc tgaaacggat tattcgtcac tctttttctag acctatgcgg  540
ccggcgactc tccggtggga acgacgtggg gagtactaga ggtgggatta ttggggatt   600
gattgctttt tggaattggg atggaagagt tcttgggata tattcttgtt cttcgaggct  660
ttcccaggtg attttccaca gggcttggta ttatcgtatt taatcaatca attcactaca  720
cttttcgagc ttgc                                                   734

SEQ ID NO: 148          moltype = DNA   length = 801
FEATURE                 Location/Qualifiers
source                  1..801
                        mol_type = genomic DNA
                        organism = unidentified
SEQUENCE: 148
gacatcattg catccaatat cagatcacat tccatagcct catttactgc ccaagaaggc   60
ttatggccca ttggagagag gagtacctaa ctgcactggc agtgcgagat cagagggaga  120
aggccaatct cagtatttac gatgcctata cccgactcgc agatagcacg gccaaacttc  180
cagctacaat agatacaagt ggcagcccct caggtgataa agggccatct ggtacctacg  240
agtccgaaaa gacggcattt tctcaatcaa ggacagccaa gaagcagcag acagaagtgg  300
agccttcagt tacggagctt ctaaatacta cacgtgcaga actaccgaa gcacagcgct  360
ctcgggcaga attgcgagat cgtctagagc gagctactaa cgaagcggag aaattgcgga  420
aacagattgg caaagatggt cgacgaatac atggactgga aaatgaagtt gctcaacagc  480
aaaagcgccg caaagatgtt gaagaagagt tgagaggaaa ggctaagcta ctcaatgaat  540
tccaagacga aattgcagct ctgactctcc aggtgaacat ggccgagaga aaagctaaga  600
agcttggaga ggagaacgat gatcttgtta tcgttggat gaagagaatg ggccaggaag  660
ctgatgcaat gaatgatgcc tcaagttttt cgtgactgcc gaatcagaat agaatcaaat  720
ggcccagata ggccttcgca ttgttatgac atgatcgaat tccgaggcaa attcgcctat  780
catggtaatg aacggataaa g                                           801

SEQ ID NO: 149          moltype = AA   length = 213
```

```
FEATURE                    Location/Qualifiers
source                     1..213
                           mol_type = protein
                           organism = unidentified
SEQUENCE: 149
MAFFPHYTTN LSPLLYLLDD DYAVYRSTCP KSNYHHKQHH SRRQPSPVRY FSPNFDMREG    60
NDSYYLDGEL PGVNQNDVDI EFSDPQTLVI KGRVERNYNN LDGMNEENQQ DEEQFSETLS   120
SKSYQPTVED EDEANHSPPV ATPTYSEKSV TEKTQKPAYK YRNSERAIGE FHRAFNLPTR   180
VDQDAVRATL RNGILSLELP KEPAPKMKKI RIE                                213

SEQ ID NO: 150             moltype = AA  length = 164
FEATURE                    Location/Qualifiers
source                     1..164
                           mol_type = protein
                           organism = unidentified
SEQUENCE: 150
MQLLSTLTPL ALLVTVASAT GKAVNNAVGN AVVTNHCKDP IYLWSVGSSV SPKHTIPSGS    60
NYTEPFRHDD ASGGIALKIT RNDNGLYDGS AQLVYSYALD GEQVWYDLSS VFGDAFAGEA   120
VAVKPENEGC GSICWPKGTT PGGSQVKVCD AEGDVGLVVC AKGC                    164

SEQ ID NO: 151             moltype = AA  length = 149
FEATURE                    Location/Qualifiers
source                     1..149
                           mol_type = protein
                           organism = unidentified
SEQUENCE: 151
LLAEAIRRGL LGWRRAEAKW QRCCCWLSTG HSARKCTREH SLVLHERLSR NRARHWQGVV    60
ALCLRCQQPL CFRTVSFALT VLLECIINRQ RLVHQVLAIH SRDCLVRAVK VVVLDESISF   120
QKKKKKKKKK TGGQVLKLPE GISPHGQKF                                     149

SEQ ID NO: 152             moltype = AA  length = 119
FEATURE                    Location/Qualifiers
source                     1..119
                           mol_type = protein
                           organism = unidentified
SEQUENCE: 152
LKGYGFIQYN DFDSSDQAIT AMNGQYLMNK PLTVDYAFKK DGKGERHGTE AERLLAAEAK    60
RNNALPMPGA IPGQPFMQYQ GMFAGALSGA MPGAQPAATP LPFGFSPAPP QQSTPYGFS   119

SEQ ID NO: 153             moltype = AA  length = 188
FEATURE                    Location/Qualifiers
source                     1..188
                           mol_type = protein
                           organism = unidentified
SEQUENCE: 153
MFGFNFNTTK LLKTILVVCY LQATVLADPY TRVSWEAYMN HVNGSDDYRT QGDDTRATRF    60
PETKPPKQGK DFLWSSKPVP SSDLFLEFFM YEGEPDEFSR TTESYQSLPS NALTARQNAL   120
TCQDIESCSY PPQVNNFQAL FDDLGPSTCN LIKDETRDWI LQQWPGLAVG AVISFAVAVA   180
GSSCDILY                                                            188

SEQ ID NO: 154             moltype = AA  length = 187
FEATURE                    Location/Qualifiers
source                     1..187
                           mol_type = protein
                           organism = unidentified
SEQUENCE: 154
MVRYAHNAEN PEKTAKARGQ HLRTHFKNTR EVAAALTGLK LSKAYKYLGD VQEHKDVIPF    60
RRFNGGVGRA AQAKNHGTTQ GRWPVKSIGF LLRLLKNAEA NADAKSLDTE DLLIKHIVVQ   120
QAPKTRRRTY RAHGRINPYQ GHPCHIEITL AVPDEQVARN KDVEVNQPKK IQGNKRQVAA   180
QRRLTSA                                                             187

SEQ ID NO: 155             moltype = AA  length = 103
FEATURE                    Location/Qualifiers
source                     1..103
                           mol_type = protein
                           organism = unidentified
SEQUENCE: 155
MTGRGKGGKG LGKGGAKRHR KILRDNIQGI TKPAIRRLAR RGGVKRISAM IYEETRGVLK    60
TFLEGVIRDA VTYTEHAKRK TVTSLDVVYA LKRQGRTLYG FGG                    103

SEQ ID NO: 156             moltype = AA  length = 307
FEATURE                    Location/Qualifiers
source                     1..307
                           mol_type = protein
                           organism = unidentified
SEQUENCE: 156
MSLDVGDVDA WIDTLSQCKQ LSESDVKLLC DKAREILIEE SNVQPVRCPV TVCGDIHGQF    60
HDLIELFRIG GNSPSTNYLF MGDYVDRGYY SVETVTLLVA LKLRYRERIT ILRGNHESRQ   120
ITQVYGFYDE CLRKYGNANV WKFFTDLFDY LPLTALIDNQ IFCLHGGLSP SIDTLDHIRS   180
```

```
IDRIQEVPHE GPMCDLLWSD PDDRCGWGIS PRGAGYTFGQ DISEAFNHSN GLTLVARAHQ    240
LVMEGYNWSQ DRNVVTLFSA PNYCYRCGNQ AAIMEIDENL KYTFLQFDPA PRAGEPMVSR    300
RVPDYFL                                                              307

SEQ ID NO: 157          moltype = AA   length = 103
FEATURE                 Location/Qualifiers
source                  1..103
                        mol_type = protein
                        organism = unidentified
SEQUENCE: 157
MTGRGKGGKG LGKGGAKRHR KILRDNIQGI TKPAIRRLAR RGGVKRISAM IYEETRGVLK    60
TFLEGVIRDA VTYTEHAKRK TVTSLDVVYA LKRQGRTLYG FGG                      103

SEQ ID NO: 158          moltype = AA   length = 151
FEATURE                 Location/Qualifiers
source                  1..151
                        mol_type = protein
                        organism = unidentified
SEQUENCE: 158
GATTTSILHH FQLSTSSNNS FYHYYLNNLH QNDWTRQGRQ GSRKGRRQAS PQDLARQHPG    60
HHQARHPPSG ASWRCQAYLR HDLRGDPRCP QDLPRGCHPR RRHLHRARQA QDRHLPRRRL    120
RPQEARPHPL RFRWLSSSLF SLRLLCFLQT Q                                   151

SEQ ID NO: 159          moltype = AA   length = 146
FEATURE                 Location/Qualifiers
source                  1..146
                        mol_type = protein
                        organism = unidentified
SEQUENCE: 159
MFSKLIAIAS LALAANAAVI DPSDHTVQYE AAPGKVVTEH YEVLSHAEAS RIIEANPHIS    60
DYRYRCNYQC NDSSGNYMRN LQQGVPNQAC IFSSCYDCDW KFQNCSYCRL STGHNYRDIG    120
GLESWCYNNG GTTVTHNCGY TDGDQC                                         146

SEQ ID NO: 160          moltype = AA   length = 142
FEATURE                 Location/Qualifiers
source                  1..142
                        mol_type = protein
                        organism = unidentified
SEQUENCE: 160
MHFKSLFIAG ALFMVGASAV DCATPEIHCE TSDGSPWYDD AVQATEYWKE IQDAGKDSCG    60
DAGCAQPHGS GCHSDGGSYG TAEIVLCQDD SSSSTPQCAD CRCVYSYLKP LLDQCKGANN    120
KIGGYAHVDM GGNYINYEFV KK                                             142

SEQ ID NO: 161          moltype = AA   length = 100
FEATURE                 Location/Qualifiers
source                  1..100
                        mol_type = protein
                        organism = unidentified
SEQUENCE: 161
LLAPSSWSVP VPLIVPLLRF TARLVMAAPG TTMPSKPLNT GKKSRTPAKT AAVMLVAHSP    60
MALDATATVV AMVPPRSFSA RMTRPLQLPN VPTAGVSTAT                          100

SEQ ID NO: 162          moltype = AA   length = 185
FEATURE                 Location/Qualifiers
source                  1..185
                        mol_type = protein
                        organism = unidentified
SEQUENCE: 162
RAGGNWTMID DLTTGSEDSF SNSWISWFLS TKGNEYFCEV DEEYILDRFN LTGLNNDVQN    60
YSQALELITD SLDDEDLDDE QRDAIENSAR YLYGLIHARY IITSRGLAKM LFLVYPQQLP    120
SKTTNSVPST KPATSADAAV GVDRYLPKIF GFPVHEMSKH ARWQEAQRDL QISRLQQSAS    180
DPSYV                                                                185

SEQ ID NO: 163          moltype = AA   length = 415
FEATURE                 Location/Qualifiers
source                  1..415
                        mol_type = protein
                        organism = unidentified
SEQUENCE: 163
MSLTPEQTEI IKATVPVVKE HGKTITTVFY KNMLEAHPEL NAIFNTTNQV NGHQPNALAG    60
ALFAYASNID NLGALGPAVE LICNKHASLY IQPEHYGIVG KFLLEAMGQV LGDALTPQIL    120
DAWAAAYWQL ANLFIGRESA IYKQSEGWTQ WREFRVAQKV PESAEITSFY LKPVDEKPLP    180
RFRPGQYISV QVHVPQLECP QARQYSLSDK PRDDYYRISV KKETGLNTAK PEAKVNPGYV    240
SNILHENVNE GDVIKVSHPC GDFFLTEQEP SHPVVLIAAG VGLTPLTSML NTLDSTPADS    300
QRKIHFIHGA RTTSVRAFKD QIKSRAERLP NLQATFFTSS PSADEKQGVD YDVQGRIDVS    360
KMDASKDLFL DNAQTEFYIC GPTSFMNDIA NSLKARGATS ERIHMELFGT GGVPV         415

SEQ ID NO: 164          moltype = AA   length = 212
FEATURE                 Location/Qualifiers
```

```
source                    1..212
                          mol_type = protein
                          organism = unidentified
SEQUENCE: 164
MAFMNLPWPT ECLHAALKNG SLPFWGFVIY RTTYTAQSDA AWPQIIELIA SYMKALLYHE     60
YNDKKKDGDE PTVYDEIWAR HQLTIMDDRQ FNGASVFDIQ LHFEKWVEAQ GKRDESTMYR    120
MCMVIDDESI QTLLEAPPGE NRKLGRRIGG PVRFVKVVEA FPELDSLDEF QGWMKCEINA    180
LWPLWKMMSD GDEMRMSYDE MKGNGKQVYG AI                                  212

SEQ ID NO: 165            moltype = AA  length = 222
FEATURE                   Location/Qualifiers
source                    1..222
                          mol_type = protein
                          organism = unidentified
SEQUENCE: 165
MARRPARCYR YCKNKPYPKS RFNRGVPDPK IRIFDLGRKK ASVDDFPLCV HMVSNEYEQL     60
SSEALEAARI CANKYLVKIA GKEGFHLRVR AHPFHVVRIN KMLSCAGADR LQTGMRGAFG    120
KPNGVVARVN IGQILLSIRT RDSNRAAAVE AMRRSTYKFP GRQKIIISKN WGFTPVRREE    180
YVKLRQEGKL KQDGAYVQFL RGHGLVEENM KRFPQAYEGV AQ                       222

SEQ ID NO: 166            moltype = AA  length = 252
FEATURE                   Location/Qualifiers
source                    1..252
                          mol_type = protein
                          organism = unidentified
SEQUENCE: 166
MSFYQSRPDT IKGPDPLTDN WTYDSAIDLF SWNPMMPDPF TFDLPDDLMK FESKDMSAGM     60
VAPSDISGFA IGNHLGEDAA SISDPESDDH PWSPSAHAAF PELSPITSTE QVHQETARYS    120
TTPDATSPQE QPSSPPTRST RRRSSADGPV RNAAKRAAHN VIEKRYRTNM NAKFVALEKA    180
MNGGGNGVQTS SRGGGSASLK KSEILSNAIA YMHGLQEENR YLQKELAIVK QNLVPAGIWR    240
GAPSCKRETS YR                                                        252

SEQ ID NO: 167            moltype = AA  length = 254
FEATURE                   Location/Qualifiers
source                    1..254
                          mol_type = protein
                          organism = unidentified
SEQUENCE: 167
MGRVIRNQRK GRGSIFTAHT RLNKAPAQFR TLDFAERHGY TRGVVKEIIH DAGRGAPLAK     60
VQFRHPYKFK MVTETFIANE GMYTGQFIYA GKNAQLTVGN VLPLASMPEG TVISNVEEKS    120
GDRGALGRTS GNYVTVIGHN PEDGKTRVKL PSGAKKVIKN TARGMVGIVA GGGRTDKPLL    180
KASRAKHKFA VKRNSWPKTR GVAMNPVDHP HGGGNHQHIG KASTISRYAA QGQKAGLIAA    240
RRTGLLRGTQ KTKD                                                      254

SEQ ID NO: 168            moltype = AA  length = 249
FEATURE                   Location/Qualifiers
source                    1..249
                          mol_type = protein
                          organism = unidentified
SEQUENCE: 168
GAEAYYSPVS SLIGMSTGLR FSTLPAASNP QSSSLIPSPS APISTFPYTL TLTLTPLTGS     60
LSTSYSLRAS PNLSFSSRFG FNVYSWESEM VAGFELWRQS KKPKLAAGSD GDDLEWARRK    120
VRVWDPSAFP LAPPEPEIPQ PNHEDESQES VLKLRVDQSW NVRLLWEGRV KELLVSAGVG    180
LGPSSFSPSS YANPPGTAGA QGSGGGSPAS YWRGVGGFGI IFFMRDFFGS MYLNEHCLDV    240
YSLSDFMRQ                                                            249

SEQ ID NO: 169            moltype = AA  length = 211
FEATURE                   Location/Qualifiers
source                    1..211
                          mol_type = protein
                          organism = unidentified
SEQUENCE: 169
GPGVLSGFQP PDLPLITSIE LDLDVVLPPP ACRTMFLRTV SRAVPRSTAA IRAAPTASVN     60
ALQTRAASDH AIPNPTLANI EKRWEVMPPQ EQAELWMQLR DRMKVDWHQM TLQEKKAAYY    120
IAFGAHGPRA QPPKGEGMRV FAKVLQLTAA SVAVFYAIHA FAGKQPATMS KEWQEASNEY    180
ALKEKINPIH GISKEGYEGK GFVQSPPAEK S                                   211

SEQ ID NO: 170            moltype = AA  length = 153
FEATURE                   Location/Qualifiers
source                    1..153
                          mol_type = protein
                          organism = unidentified
SEQUENCE: 170
VARRGGIYLD GNNDLVTMKG NYIYHTSGRS PKVQGNTLLH AVNNYWHDNS GHAFEIGEGG     60
YVLAEGNVFQ DVTTPVEDPV DGQLFTSPDP STNAQCSSYL GRACEINGFG NSGTFNQADT    120
SLLSKFKGQN IASADAYSKV ASSVASNAGQ GHL                                  153

SEQ ID NO: 171            moltype = AA  length = 120
FEATURE                   Location/Qualifiers
```

```
                               source          1..120
                                               mol_type = protein
                                               organism = unidentified
SEQUENCE: 171
VRVVTFWPRV TSSRMLLPPL RTPLTASSSL PLTPAPTLSA RHTLAGPAKS TASVTLVPST   60
RLTLACCLNL RVRTLLLLML TLRLPRALPA TPVRDTCKME RGGSELNLLM SDDIALAACW  120

SEQ ID NO: 172                 moltype = AA  length = 80
FEATURE                        Location/Qualifiers
source                         1..80
                               mol_type = protein
                               organism = unidentified
SEQUENCE: 172
MPSKTEAARL QNDFGADYWV RNTQERRHST AGRGLFAGLQ DVKHYNVDHG WARRKSSDNP   60
GLLASFFSRF TGGSYHPPSE                                               80

SEQ ID NO: 173                 moltype = AA  length = 137
FEATURE                        Location/Qualifiers
source                         1..137
                               mol_type = protein
                               organism = unidentified
SEQUENCE: 173
VARRDSHHQI KSRLILLDIT TIQHKVPSYF KQISTIESKC HPKPKQPVYK TTSAQTTGLE   60
IPKNAATQPL AADYSPVSRM SSTITSTMAG PVASLAITPD SLLLSSVDSP GDHTIRPRNR  120
IPFLNVRYWE ECDLNWE                                                 137

SEQ ID NO: 174                 moltype = AA  length = 181
FEATURE                        Location/Qualifiers
source                         1..181
                               mol_type = protein
                               organism = unidentified
SEQUENCE: 174
VVSTQSDEPT IPGGAAVTIH SRNEKKARKA IGKLGLKHVP GITRVTLRRP KNILFVVNQP   60
DVYKSPSSNT WIIFGEAKIE DLNSQAQASA AQQLAAAEAA AGGEHAGHDH EHDILGKGKA  120
PETEGKKEEE EDDGEEVDEA GLEAKDIDLV MAQANVSRKK AVKALRENDN DIVNSIMALS  180
I                                                                  181

SEQ ID NO: 175                 moltype = AA  length = 191
FEATURE                        Location/Qualifiers
source                         1..191
                               mol_type = protein
                               organism = unidentified
SEQUENCE: 175
MFLQRTVSTL ARRTPVRGLA AARPFSSSVS RFNKYEVKEA KLRSLDEIQT EEDLIPPGAK   60
PGTVPSDIEH ATGLERLELV GKMQGIDIFD LRPLDASRKG TLENPIVVNG AGDEQYAGCT  120
GYPVDSHQVN WLTVSRERPI ERCNECGNVV KLNYVGPEED PHAHDHGHGH HPAPEEPKTF  180
ADYVKPEYWY R                                                       191

SEQ ID NO: 176                 moltype = AA  length = 261
FEATURE                        Location/Qualifiers
source                         1..261
                               mol_type = protein
                               organism = unidentified
SEQUENCE: 176
MNPYIVDPML KYVAFDIPAL ARLDPSLCLF LILFFENSRV VLLGYLPVPV LGLDVVGEGL   60
GLLGGRVVAV AVVVSVRVLL RSDIVQLDNV TAFVAALDGA LTRDSQPVNL VRVDGVTSAT  120
SVLLVTSTVD NNGVFEGSLA GSIQRPQVED VNSLHFTDEF ETLETSGVFD IARDGTGLST  180
RGDEVFFSLD LVKRTELGLL NLVLVESANG RRKRARGSKA PHGGAPREGR YRTLKEHSPC  240
CNRTGRSNGR GEGGGGVDVG S                                            261

SEQ ID NO: 177                 moltype = AA  length = 221
FEATURE                        Location/Qualifiers
source                         1..221
                               mol_type = protein
                               organism = unidentified
SEQUENCE: 177
MADITAVGEE NPSPTQDELQ QAAAGNGAPD NRTPKRRMSD DEEDEEKQGR ERRKIEIKFI   60
QDKSRRHITF SKRKAGIMKK AYELSVLTGT QVLLLVVSET GLVYTFTTPK LQPLVTKAEG  120
KNLIQACLNA PDPTTSENGV DAPEVPAETP EDVNHANVNA AAAQQTNIPR PTGMHPGYMT  180
NEQQQQMAYY QNHLQQQQQA GGQYPGMSVG GRMPTQHQPT A                      221

SEQ ID NO: 178                 moltype = AA  length = 176
FEATURE                        Location/Qualifiers
source                         1..176
                               mol_type = protein
                               organism = unidentified
SEQUENCE: 178
MSFAADPPPN NHGTLTHLFR APEDLVYPIP ENFSLEETVL VEPLSVAIHG ARVAGITPGH   60
TVLVQASGTI GLFCAATATA FGAKQVIISD INQTKLDFAR DYLGCPIFLP NISSSHPEEE  120
```

```
ASRMKEYIES QRRCRYSSVV YGSGILVAKS GPGGVVVPNW TRFNRVQSNG TYHQYV        176

SEQ ID NO: 179             moltype = AA  length = 86
FEATURE                    Location/Qualifiers
source                     1..86
                           mol_type = protein
                           organism = unidentified
SEQUENCE: 179
MPRGAEYANG PLQSDNAIEA GENKAHGTSG NTGLNRVNKV AEFPEGARGT GTAANPLSGQ     60
GSAGHQDGKG GHDPKTLGEN KGLGTQ                                         86

SEQ ID NO: 180             moltype = AA  length = 78
FEATURE                    Location/Qualifiers
source                     1..78
                           mol_type = protein
                           organism = unidentified
SEQUENCE: 180
MPSKLAKIRP TEPPVTPAST ASTRSPNSPK APEEPVPLLT RSVARVAPAI RMERVAMTRR     60
PLERTRDWVL NDLMIQKT                                                  78

SEQ ID NO: 181             moltype = AA  length = 166
FEATURE                    Location/Qualifiers
source                     1..166
                           mol_type = protein
                           organism = unidentified
SEQUENCE: 181
MTTITEFPPF YTQQPNASAL TQQLGLWQKH ILSTCKQRRQ FKLSVSDDIW ANERIKRAAS     60
REFISVIISS LVTEGLASYT DATKEAVWVY WRSLSDWAQA AYAYAESTAQ LNTPLTYYEL   120
VQGEYSHLSE LHEMPVELLK LAVSLLVKQN KAVIIKTSQG EGVKFV                  166

SEQ ID NO: 182             moltype = AA  length = 130
FEATURE                    Location/Qualifiers
source                     1..130
                           mol_type = protein
                           organism = unidentified
SEQUENCE: 182
MSIPKAAAHT DKAPQPFKDL YSQAVIAGGV VYCSGIVAID PETGSLIEGD VKAHTERILQ     60
SLSSTLQAAG TSLDRAVKIN VYLANMEDFT SMNSVYEKYF VDGVKPCRTC VAVKSLPFGT   120
DVEMECIAVL                                                          130

SEQ ID NO: 183             moltype = AA  length = 113
FEATURE                    Location/Qualifiers
source                     1..113
                           mol_type = protein
                           organism = unidentified
SEQUENCE: 183
MLRSQFGVIS NAAKTAAFLK PVQTRLYASG ALSKGDIQTR IFDVLKSFDK VKADNLTESA     60
SFTNDLGLDS LDAVEVVMAI EEEFAIEIPD AEADAIQNVN QAIEYIAKTP EAH          113

SEQ ID NO: 184             moltype = AA  length = 200
FEATURE                    Location/Qualifiers
source                     1..200
                           mol_type = protein
                           organism = unidentified
SEQUENCE: 184
VVSTQSGAPG TKKVSSTYLS KICKEQHKSI FFYLIDLHSS ASLRSVTTLP ARMERIRLSE     60
QAATICNQIR EMIPETATLP NQPGKDQAEL MHEDENGNKI YGGKLLTERA ARLKEHMKID   120
QVSARFISQY FTNGIQDWTE RLVYWTKPTK LLNQRKQGYI IPLSKDIVLQ PGGPLEANNG   180
FRVTNERILS SGAALFIMPQ                                               200

SEQ ID NO: 185             moltype = AA  length = 524
FEATURE                    Location/Qualifiers
source                     1..524
                           mol_type = protein
                           organism = unidentified
SEQUENCE: 185
MLARSLQQIR RSSRLSLQLR AYASSPDRSA SFSKLSEQDL PSLASIFSSP DTSLLTTLGD     60
KPTATSDDLE PFNVDWMGKY KGHSSIIVKP KTTQEVSKVL QWCNERNVAV VPQGGNTGLV   120
GGSVPLHDEV VLSLSSMNSI RHFDPLSGYV SVDSGIVLEN LDNYLAQQGH IVPLDLGAKG   180
SCQIGGNVAT NAGGLRMLRY GSLHGNVLGL EVVLPDGRVI NGMKGLKKDN TGIDLKQLFI   240
GSEGVLGVIT GVTLATPVRP SATNVAVFAL PDYESVQTAF SSARRDLGEI LSAFEFFDAA   300
SYKLVRSHGH AAERKTFEDG EDAPFFCLVE TSGSNKDHDD EKLGAFLEQL MESGIVNDGV   360
LAQDETQIGQ LWSLREGIPE AAGKAGRVYK YDLSLPVEKM YSLVPELRQK LAEKGLLAAE   420
SEGGNGDGPV KTVFGFGHLG DGNLHINIVA DAYRKEVEEV VEPIYIELVA KYNGSISAEH   480
GLGLMKAPYV AYSQDAPSLD LMRTLKKTLD PKGILNPYKC VTAE                   524

SEQ ID NO: 186             moltype = AA  length = 185
FEATURE                    Location/Qualifiers
source                     1..185
```

```
                              mol_type = protein
                              organism = unidentified
SEQUENCE: 186
MALYYGIVFG ILTFEIILFF LFLLPIPTRW QKPVFRWLAT SPTIAHAQYI MKIVFVFIFV    60
LFLDSVNTLR AFYEVVNTED ENGGIPAAGN SDFRAQVGQA AKKFYAQRNL YLTGFTILLL   120
LILNKIKNMA MDYIRLEDQF IELEGSVSKD PAIRKASKEI DTTPIEDHVT RLEPVEQEQE   180
NKKDI                                                              185

SEQ ID NO: 187            moltype = AA   length = 138
FEATURE                   Location/Qualifiers
source                    1..138
                          mol_type = protein
                          organism = unidentified
SEQUENCE: 187
VARREAPNGH ELPPRGYDPG ENTYQAPPDE RSQVDVAIDP KSNRLQLLKP FQKWDGKDIT    60
NVPILIKVQG KCTTDHISMA GPWLKYRGHL DNISNNFLIG AKSSEGKVNS IKNAFTGEYK   120
GVQKQLVITR RKVFVGSW                                                138

SEQ ID NO: 188            moltype = AA   length = 144
FEATURE                   Location/Qualifiers
source                    1..144
                          mol_type = protein
                          organism = unidentified
SEQUENCE: 188
GCPETARDYK KEGVRWVVVG DENYGEGSSR EHAALEPRFL NGAAIITKSF ARIHETNLKK    60
QGMLPLTFAD PKDYDKVDAS DKVDILGLTD FQEGKPLTLR LHKKDGSTVD VPLNHTFNGQ   120
QIEWFKHGSA LNLMKENTAK NGSL                                         144

SEQ ID NO: 189            moltype = AA   length = 264
FEATURE                   Location/Qualifiers
source                    1..264
                          mol_type = protein
                          organism = unidentified
SEQUENCE: 189
VARREAPNGH ELPPRGYDPG ENTYQAPPDE RSQVDVAIDP KSNRLQLLKP FQKWDGKDIT    60
NVPILIKVQG KCTTDHISMA GPWLKYRGHL DNISNNFLIG AKSSEGKVNS IKNAFTGEYK   120
GVPETARDYK KEGVRWVVVG DENYGEGSSR EHAALEPRFL NGAAIITKSF ARIHETNLKK   180
QGMLPLTFAD PKDYDKVDAS DKVDILGLTD FQEGKPLTLR LHKKDGSTVD VPLNHTFNGQ   240
QIEWFKHGSA LNLMKENTAK NGSL                                         264

SEQ ID NO: 190            moltype = AA   length = 195
FEATURE                   Location/Qualifiers
source                    1..195
                          mol_type = protein
                          organism = unidentified
SEQUENCE: 190
GAPLTQEHGF PVRVIVPGVA GARAVKWLDH ITVQREMSSN HYMHFDYKVL PPEAVDAERA    60
RTFWHKVPPV IDMPANSAIT SPRNEDTVEV DAEGFITVDG YALPGGEDGP VKRVEVSIDK   120
ERWVDAELFT HPMESKWTWK IWKAKVQVEP GERRCLYSRT TDEAGNSQPQ RSQWNLRGVC   180
YNGYGEVRNL KVVKG                                                   195

SEQ ID NO: 191            moltype = AA   length = 50
FEATURE                   Location/Qualifiers
source                    1..50
                          mol_type = protein
                          organism = unidentified
SEQUENCE: 191
MPANTMSATL RSLHVPGKPV IFANVWDTVS AKSIAPLDSC KALATASYAI               50

SEQ ID NO: 192            moltype = AA   length = 373
FEATURE                   Location/Qualifiers
source                    1..373
                          mol_type = protein
                          organism = unidentified
SEQUENCE: 192
ALPMLLINPP RNLIGQSQSG TGKTAAFTLN MLSRVDPNIM TPQAICLAPS RELARQIQEV    60
VDKIGQFTQI KSFLAVPGSW SRNVKIDKHI LVGTPGTLVD MLSRGGRIFD PKQIRVFVLD   120
EADEMIALQG LGDQTKRIKR MLPPGVQNVL FSATFPDNVR DFAGDFAPEA NQIFLKKEEI   180
TVDAIKQLYL ECDGEEQKYN ALSALYDIMS IGQSIVFCKR KDTADRIAAR LTDEGHSVAS   240
LHGDKQTRDR DDILDAFRDG KTKVLITTNV VARGIDIQQV NMVVNYDVPD LGPEGDWKPD   300
IETYIHRIGR TGRFGRKGCS VIFAHDQRSM QDVQFIADTL GKKMSRINAT RQTDLDQLEA   360
ALKAAIKGNQ PKE                                                     373

SEQ ID NO: 193            moltype = AA   length = 274
FEATURE                   Location/Qualifiers
source                    1..274
                          mol_type = protein
                          organism = unidentified
SEQUENCE: 193
```

```
MATFSTRINL VPTSRTLASG VPFAPRIALV HPPASHGHGT SGPRSDVPPR WAGVQGGFAS    60
NSRVNVLPTG NFQQRFMSTT PARKIEAQPH VRGVPDWSAY QSSGKGENTR SLSYFMVGSL   120
GVLAASGAKS TVSDILSNMA ASADVLALAK IEVEMGAIPE GKNLIVKWRG KPVFIRHRTE   180
DEINEARAVD IKSLRDPESD EDRTQRGEWL VMLGVCTHLG CVPIGEAGDY GGWFCPCHGS   240
HYDISGRIRR GPAPLNLEVP EYAFNDDEEK LVIG                              274

SEQ ID NO: 194           moltype = AA   length = 472
FEATURE                  Location/Qualifiers
source                   1..472
                         mol_type = protein
                         organism = unidentified
SEQUENCE: 194
GEHHHSDRDC SSVKRVFALG RLDVTLAVEC GSVRTMSLRD LACYTLTLKP STENTLLTEL    60
TALEGPSEEP RFARVREKVE GEVYSSAIYD ALTGAKLASV GFASEKQKNR RLQLHNPDES   120
VPFDNTSKLG FEWTFIFEGN KYRWTRELYG KDYICSLDRK PDPRVEICLA RDADSKAPGR   180
LQILHYNIER FPNEIKDLRG LETLLIATLM CFVDAAEDRS NSGPTRTSPL PAKPVANAAA   240
GQSGTSASGS SDTRAKVAPV TVPVITAEDF EDDCDPNEIL VGTETDVGEH IARAIALLED   300
PTMLFIVIRT RTAAASSRAL EVSLGVTRFR HREGMSELHQ YVVEEDPVRK PKPIMPAQGL   360
KLINLDDRPA AQSPTKPEWS APPNIAVYLS SIELPDLTPK PKPVQGHTRP PTQAPHARPP   420
PPSQLPQKPQ PRPRPPPSDG SGSSQTTLAS TRPPQDDGKD SRKSSFGRLF GR           472

SEQ ID NO: 195           moltype = AA   length = 82
FEATURE                  Location/Qualifiers
source                   1..82
                         mol_type = protein
                         organism = unidentified
SEQUENCE: 195
MASQLMPLEL IDRCIGSRMR VIMKGDKEFS GTLLGFDDFV NMVLEDVTEY DYTGATTKLP    60
KILLNGNNIC MLIPGGMPEG ES                                            82

SEQ ID NO: 196           moltype = AA   length = 116
FEATURE                  Location/Qualifiers
source                   1..116
                         mol_type = protein
                         organism = unidentified
SEQUENCE: 196
GDDNKKTIPH LNIFNNGVPI DAPGADRSLH RIKNACDHER RQRVQRHTSR IRRLRQYGAR    60
GCHRVRLHRR NDQASQDPSE RQQHLHAHPR WHARGRVMNH GHMISLLTSL EMAKRV       116

SEQ ID NO: 197           moltype = AA   length = 108
FEATURE                  Location/Qualifiers
source                   1..108
                         mol_type = protein
                         organism = unidentified
SEQUENCE: 197
AKELSPDVKP EPTWSCGEVV NVVDEHGNVI KPSDLWVKMG MQQQDNVDNL LIDDLCDQMR    60
AKAKCTENGA QLNVDDLNHM MSYDKSYKQK RVDDLKDKYG WGAVFGPK                108

SEQ ID NO: 198           moltype = AA   length = 38
FEATURE                  Location/Qualifiers
source                   1..38
                         mol_type = protein
                         organism = unidentified
SEQUENCE: 198
GSLTRRAWFI QSTCATTGDG LYEGLEWLAD TLRKTNRD                            38

SEQ ID NO: 199           moltype = AA   length = 311
FEATURE                  Location/Qualifiers
source                   1..311
                         mol_type = protein
                         organism = unidentified
SEQUENCE: 199
MENLLRQMQG GGGRMGARPG PGGETILADN GETVHISSLA LLKMLKHGRA GVPMEVMGLM    60
LGEFVDDYTI SCVDVFAMPQ SGTTVTVESV DHVFQTKMLD MLKQTGRPEM VVGWYHSHPG   120
FGCWLSSVDV NTQQSFEQLH PRAVAVVIDP IQSVRGKVVI DAFRSINPQS LVAGQESRQT   180
TSNIGHLNKP SIQALIHGLN RHYYSLAIDY RKTEGEQGML LNLHKRGWTE GLKMRDHSEM   240
KEGNEKAIKE MLSLASAYTK SVQEETTMTA EQLKTRHVGK LDPKRHLGEA AEKAMGDQVT   300
QSLAMGVLAE L                                                        311

SEQ ID NO: 200           moltype = AA   length = 213
FEATURE                  Location/Qualifiers
source                   1..213
                         mol_type = protein
                         organism = unidentified
SEQUENCE: 200
GHTGDVLSVS FSADNRQIVS ASRDRTTKLW NTLGECKFNI VDDGHSEWVS CVRFSPNPVI    60
PVIVSAGWDK VVKVWELSKC KLKTNHHGHT GYINTLAVSP DGSLAASGGK YGITMLWDLN   120
DGKHLYSLEA GDIVNSLVFS PNRYWLCAAT ASSIKILDLE SKSIVDDLKP DFSAEYPDKA   180
QKPQCTSLAW SADGQTLFAG FSDNLVRVWV VTA                                213
```

```
SEQ ID NO: 201           moltype = AA  length = 76
FEATURE                  Location/Qualifiers
source                   1..76
                         mol_type = protein
                         organism = unidentified
SEQUENCE: 201
MVTRSGSLAF DSLLTPSFPS SSLLVGTRSS RSGNCPSASS RPTTTVTLVT STPSPFRPTD    60
RSPHPVESMA SPCFGI                                                   76

SEQ ID NO: 202           moltype = AA  length = 99
FEATURE                  Location/Qualifiers
source                   1..99
                         mol_type = protein
                         organism = unidentified
SEQUENCE: 202
MLWDLNDGKH LYSLEAGDIV NSLVFSPNRY WLCAATASSI KILDLESKSI VDDLKPDFSA    60
EYPDKAQKPQ CTSLAWSADG QTLFAGFSDN LVRVWVVTA                           99

SEQ ID NO: 203           moltype = AA  length = 124
FEATURE                  Location/Qualifiers
source                   1..124
                         mol_type = protein
                         organism = unidentified
SEQUENCE: 203
VPAIVQIPKH GDAILSTGCG ERSVGRNGEG VDVTSVTVVV GLELALGQFP DLDDLVPTSR    60
DDDGNDGVRR ESNARDPLRV TIVNNVELAL SESVPELGSS VSGSRNDLSV VGRERDAQDV   120
TGVS                                                                124

SEQ ID NO: 204           moltype = AA  length = 38
FEATURE                  Location/Qualifiers
source                   1..38
                         mol_type = protein
                         organism = unidentified
SEQUENCE: 204
GSLTRRAWFI QSTCATTGDG LYEGLEWLAD TLRKTNRD                            38

SEQ ID NO: 205           moltype = AA  length = 393
FEATURE                  Location/Qualifiers
source                   1..393
                         mol_type = protein
                         organism = unidentified
SEQUENCE: 205
GRYDFKQPQR IRDASVTATP EWNLLEEIEF GRLGKLNLSV EEPEDLESHG TLQGYDKTFD    60
RINTRTERPL EIIDRAWYNQ TTSDDPVIAQ LAQTQSAQIF ATDAILAVLM CTTRSVNSWD   120
IILERRGNQL FLDKRDSGPF DYVTVHENAA DPPADSDDPN NVNSASSLSL EATYITRNFS   180
SQVIDAKSKP YSPSPNPFYS EDEPSPVASC LYRYRKFDLS VGEEDTLDLI VRTEVDAYQG   240
KKDSLVTVKA LNEFDPRASG GGKALDWRKY LDTQKGAIVA SEMKNNSAKL ARWAIQSVLA   300
GAEVMKMGYI SRASPRDTTH HVIVGVQNYK PKDFAAQMNV SLNNGWGIVR TIADLVLKQP   360
EGKYVLVKDP NAGIIRLYSV PENAFEAEEE EEQ                                393

SEQ ID NO: 206           moltype = AA  length = 106
FEATURE                  Location/Qualifiers
source                   1..106
                         mol_type = protein
                         organism = unidentified
SEQUENCE: 206
MTSSSLSEFE TLLSRPRQNG TCLKRSSLAD WASSTFPSKS PKTSNRTVPS KVTTRRLTAS    60
TLVPKDLSRS LIEHGTIKPL LTIPLLLSSL KRSLPKSSRQ MPFLRF                  106

SEQ ID NO: 207           moltype = AA  length = 245
FEATURE                  Location/Qualifiers
source                   1..245
                         mol_type = protein
                         organism = unidentified
SEQUENCE: 207
ERSRSLAPEA DQGVATQCHE VRSSGSYDTF EIGHHQPDSD TSGVADLRTS SRMDTCDAHL    60
LRRVKSCPLF SYREDEVSET VQLPTGEWTT IRDITPSAPK IGFEVRDSLS APPTAKPVEA   120
KHESASSISN DLPSQPSSRP LIECPTLVAD SRTTTGSNSV RSFDAQTERL SGLSDVHHRY   180
MQDKPSQRSD SWTDVKSSAP SSQSMAVPNK AAYLAPIPAG PNDSKTSSSG RAPSDAATEH   240
ECSLQ                                                               245

SEQ ID NO: 208           moltype = AA  length = 148
FEATURE                  Location/Qualifiers
source                   1..148
                         mol_type = protein
                         organism = unidentified
SEQUENCE: 208
MAPKSTDKPA STAGKAPSAG GKAPASKTVG AKKTAAKKSA KSTGEGGEKK KRVKSRKETY    60
```

```
STYIYKVLKQ VHPDTGISNK AMLILNSFVN DIFERIAGEA SKLATYNKKS TISSREIQTA    120
VRLILPGELS KHAISEGTKG VTKYSSSK                                      148

SEQ ID NO: 209          moltype = AA  length = 369
FEATURE                 Location/Qualifiers
source                  1..369
                        mol_type = protein
                        organism = unidentified
SEQUENCE: 209
DVKRFTKDLL FNSEGNLTFK PHLWNDIRHT LLPTFIRQIG YVPIPRAEFS SPDIDLVIEN    60
LVLSGPNLFP NVVSLESHNS FKFSPYQQLN KGMDTHHHKF RLGMSQIQAD IRDVRFSFRR    120
KTGWPKLKDH GLADVILAGK GMSIDVELES VEGRRDSVVR VNHVHTTIDT LTFSIRDSKH    180
DLLYKFVKSV ATGTIKKAIQ AAVDNAIRTA VGHLDDQLVQ VRNTVDDAKK SDETTRTQAL    240
KDLYSKKADT AQKKQAESKE QPGTFRIVAN RDSVLNPDMG GGKGAMTNKM WKTEDLAHSG    300
KEWHSPAFDL LDSKHPARTG QTHPEAKEGA GHGNSLSSKA QPGANAADQL KATHGQSEAE    360
AIAGQKRQQ                                                           369

SEQ ID NO: 210          moltype = AA  length = 173
FEATURE                 Location/Qualifiers
source                  1..173
                        mol_type = protein
                        organism = unidentified
SEQUENCE: 210
MSDSRSDERL DGPSSRTTVS PMSSLPVRVC RSTSSSSLSR DDETLLCEST TSTPPSTPSP    60
SPSETPSTTC STSSSSRWPR VRSRRQSRPP STMPSVRLSV TSTTSSSRSE TPSMTPRSLT    120
RPPERKPSRT CTRRRRTRHR RSRPSPRSSL VLSESSPTET LFSTPTWAVA RAP          173

SEQ ID NO: 211          moltype = AA  length = 248
FEATURE                 Location/Qualifiers
source                  1..248
                        mol_type = protein
                        organism = unidentified
SEQUENCE: 211
MYTSAVTLLS LVLLLATSVI AQEQAGRPGT QRGGVFFGCY ADRPTGNANQ PITRVANSDT    60
FFECMENCAA ITSPSLLGYY QPSSGQCFCG NLLFNPQAQL NGNGCQGSDW SFGRTSTTFR    120
RFGDACRPFG GVGFSANQYT TVTGPVACHV QCASNRFAYV WSDTGSNSWQ CACSNNVRVQ    180
EDFQYTCQGG GVFVFEHSVQ AQASSLNRKR TVEEQWAVPK DALCPFGMSA CKVSGVDNAY    240
EVCFFSDR                                                            248

SEQ ID NO: 212          moltype = AA  length = 116
FEATURE                 Location/Qualifiers
source                  1..116
                        mol_type = protein
                        organism = unidentified
SEQUENCE: 212
MFNAHQTDSP MSGPILEATH GNVLAATMSV FRRTSSTLVK VAVYLCLNIQ YKLRLLRLTG    60
SGRWRNNGLF RKTPSVHSEC QRARYQVSIM LTRYASFQTA RPLVPWPRGL KHAIDL       116

SEQ ID NO: 213          moltype = AA  length = 271
FEATURE                 Location/Qualifiers
source                  1..271
                        mol_type = protein
                        organism = unidentified
SEQUENCE: 213
GGGTVVSNAL LENAKLCKTQ GKESSLRVIV CGRNRLENGS APHWAEAFAT HGKLVEVRMP    60
QNGIRMEGIK AIADGLAKCP TLEVDLQDN TATKTGTRSI VRHLSTWPKL RILNLSDCLL     120
GSVGGIALAT ALSTGSNKHL EQLKLQYGEF DKRTVEILST AISQHLPKLT TLELNGNRFD    180
AEDECVETLK KALELHGNED ALDELDDMEE VDEDEEDDDD EDEEDEDEDK DTSADDGIDA    240
GAAGEDALPP VTKKDEDVLA DLLSKVHVQP S                                  271

SEQ ID NO: 214          moltype = AA  length = 222
FEATURE                 Location/Qualifiers
source                  1..222
                        mol_type = protein
                        organism = unidentified
SEQUENCE: 214
LDRRSASTSS SFFVTGGRAS SPAAPASIPS SALVSLSSSS SSSSSSSSSS SSSSTSSISS    60
SSSKASSFPC SSSAFFRVST HSSSASKRPP FSSSVVNFGK CWLIAVDSIS TVLLSNSPYC    120
SLSCSRCLFE PVDNAVARAI PPTEPKRQSE RLSIRSLGQV ERCRTILRVP VLVAVLSCKS    180
STSNVGHLAS PSAIALMPSM RMPFCGILTS TNLPCVANAS AQ                      222

SEQ ID NO: 215          moltype = AA  length = 176
FEATURE                 Location/Qualifiers
source                  1..176
                        mol_type = protein
                        organism = unidentified
SEQUENCE: 215
MVKLSNSLVR RLKWQHVRSL GVVALTAQLR GPQPQSAEDE DSEAAGKKLK LAGDQATSAV    60
IPKSADKPDT FPLLDTLPAT MAAGTRSMTR PLHVGDLRLA DLRKIMQAAG HTAEFRGEGT    120
```

```
LLIDKSVAVR KSGTGQIEIE ASAQAAANQA TPGRGASSFL AVKRKIYEGL AVVTGS        176

SEQ ID NO: 216          moltype = AA  length = 139
FEATURE                 Location/Qualifiers
source                  1..139
                        mol_type = protein
                        organism = unidentified
SEQUENCE: 216
KMKIDVEKLN KDISLFPQVH PITEDMKITH KGVSRLVMLD RYSFKDTEKI TLSEGDFVVL     60
TIKEDPKFPA RGLGYIKEID WENKKAKVQV EEEFRHTLEK PEERETGIIV RSLDVIEKPL    120
EIFYEQIAKR NATGLAAVE                                                 139

SEQ ID NO: 217          moltype = AA  length = 282
FEATURE                 Location/Qualifiers
source                  1..282
                        mol_type = protein
                        organism = unidentified
SEQUENCE: 217
GDATVTQLRE IMDDPAGYFL PNLKHGADNM FYVGPRGLAQ ELEELFTFPS TILRKRQDTS     60
QHDERQAKKA RTQEDEAAGD ALEEPETGRR DSVLPTERAA FGLEGDDSGF FLGDQTMGDD    120
MLPMDDMGAM DTGVDQRRMR TPSVAPSVTE SIARQIQNDR SAGTHPLAIF EKEARDDTQS    180
QSQATPNKSV ASESISKTSS GQSKNTGMAM GLLRREIEAI EEEDKMVGFD HLADKASKRA    240
ASAFFFELLV LGTKHAVKLE QAQAFGDIHI RGKDKLFAEV VA                       282

SEQ ID NO: 218          moltype = AA  length = 261
FEATURE                 Location/Qualifiers
source                  1..261
                        mol_type = protein
                        organism = unidentified
SEQUENCE: 218
MAPITCSTSV HADLHKSSRS FLPSQAQSSE SARIPVSMTK GRQRRRARKR TKRLVTRWRS     60
PRLGDATVCF RLNGPLLVSR VMTRAFSLAT RRWETTCCLW TTWEPWTPEW TSDACEHHQS    120
HRRSPNRSHV RFRMTEALAH THWLYSRRRQ GTTRSRNRRL RPTNRWPPSL SARLLLANQR    180
ILAWPWVCCE GRLRRSRRKT RWSGLITWQT RRPSEQRLHS SSSCWCLVPN MRSSLNKLRL    240
SATSTYAAKT SCLQRLLHRQ T                                              261

SEQ ID NO: 219          moltype = AA  length = 108
FEATURE                 Location/Qualifiers
source                  1..108
                        mol_type = protein
                        organism = unidentified
SEQUENCE: 219
MGDHATTNDP SNATFEEKGK GKDVQDQIAE DSSDEESDQE PEMVDEEEDD NNLEPISQDN     60
IISGGRRTRG KIIDYAAEAE KNKDEMEDSE DDEDYQGAND DEDDQMRD                 108

SEQ ID NO: 220          moltype = AA  length = 78
FEATURE                 Location/Qualifiers
source                  1..78
                        mol_type = protein
                        organism = unidentified
SEQUENCE: 220
ELKYFKAVAL YNLSRYLDAR KAINDLIQSY PDFRQAEALK SAIDDKVVRD GLIGVSVAGA     60
VVAGVVGLAV ALARGNRG                                                  78

SEQ ID NO: 221          moltype = AA  length = 27
FEATURE                 Location/Qualifiers
source                  1..27
                        mol_type = protein
                        organism = unidentified
SEQUENCE: 221
MGHVESRVNQ RGPPRKAKYS WVTDSEK                                        27

SEQ ID NO: 222          moltype = AA  length = 27
FEATURE                 Location/Qualifiers
source                  1..27
                        mol_type = protein
                        organism = unidentified
SEQUENCE: 222
MLKAPFFHRP CGGKGVQLKW ATPDSAV                                        27

SEQ ID NO: 223          moltype = AA  length = 177
FEATURE                 Location/Qualifiers
source                  1..177
                        mol_type = protein
                        organism = unidentified
SEQUENCE: 223
MPVRPYLEEM ADMPVPLFAY DAPPTLADHP HAREHQHTTF MQYLARKQPD PKNYPNYPDV     60
DIRDAINHYL IELECPGIKD AADIHCQWTS SRHLTVTGDI ARPEESQIEA QIESRPVYLV    120
LGERRIGSFR RNFTFPVEVE QENMTAKLEA GLLKIVLPKH KHHTPKGTGK VDIDVIE       177
```

```
SEQ ID NO: 224          moltype = AA   length = 163
FEATURE                 Location/Qualifiers
source                  1..163
                        mol_type = protein
                        organism = unidentified
SEQUENCE: 224
MVLVLGQDNL QQSGLQLGSH IFLLDLHREG KVATERANAS LSQNQVDGPA LDLRFDLAFL    60
RTGDVAGDGQ VPRARPLAVD VGCVFDPRAF ELDQVVIDGV ADVHVRVVGV VLWVRLLARK   120
VLHEGRVLVL AGVRVVGQGG RCVVREQGHG HVGHFFQVGS YGH                     163

SEQ ID NO: 225          moltype = AA   length = 118
FEATURE                 Location/Qualifiers
source                  1..118
                        mol_type = protein
                        organism = unidentified
SEQUENCE: 225
MFGFNFNTTK LLKTILVVCY LQATVLADPY TRVSWEAYMN HVNGSDDYRT QGDDTRATRF    60
PETKPPKQGK DFLWSSKPVP SSDLFLEFFM YEGEPDEFSR TTESYQSLPS NALTARQK     118

SEQ ID NO: 226          moltype = AA   length = 349
FEATURE                 Location/Qualifiers
source                  1..349
                        mol_type = protein
                        organism = unidentified
SEQUENCE: 226
MSPTPTSPHN KLSLPARASS HDSTDGIRKR VCKACDRCRL KKSKCDGSSP CSRCKADNAI    60
CVFGERKRSH DKHYPKGYVE MLEQQQGQLV SGLKEMYHRL QKASAWDGPV LDESTGQPLT   120
HDILSALDLL EPKHDDSNEP EVFEENCEKL QSKLLADGAG FAHRRGSISS DSEHSHHDRP   180
KTSSRHDTPV QPKPSIFKEN LSFASAASSP LTQSPIPRSK PLNVMPYQTL QPSSRPSPLQ   240
MPSAYNDPQL YAPEWAQALA DMSGDPNYRQ RFSMQQQQQN DFDNLLWDPS AQAPMESPFS   300
QPAFFNQAQL IGSGNVFGLS DINDLGPNPA DGGMDFDFSK FVQQTEVMT               349

SEQ ID NO: 227          moltype = AA   length = 149
FEATURE                 Location/Qualifiers
source                  1..149
                        mol_type = protein
                        organism = unidentified
SEQUENCE: 227
MSSFRVAAPK MASMAAQSSV KVARPAFQAA QLQKFTRAYS AVPKNTVFNT MKRTQMMARQ    60
ASPIAKRAYS SEMANALVQV SQNIGMGSAA IGLAGAGVGI GLVFAALIQA VARNPSLRGQ   120
LFSYAILGFA FVEAIGLFDL MVAMMAKFL                                     149

SEQ ID NO: 228          moltype = AA   length = 165
FEATURE                 Location/Qualifiers
source                  1..165
                        mol_type = protein
                        organism = unidentified
SEQUENCE: 228
MECTFLQELG HHGNHEVEET DGLDESETKN GVREKLATEG GVAGDGLDEG GEDETDTDTS    60
TGKTDGGGTH TDVLGDLDEG VGHLRGVGTL GDGGGLAGHH LGALHGVEDG VLGDRGVGAG   120
ELLELSSLEG RAGDLHGGLS GHGGHLGGGD AEGRHCDDGE VVRWS                   165

SEQ ID NO: 229          moltype = AA   length = 425
FEATURE                 Location/Qualifiers
source                  1..425
                        mol_type = protein
                        organism = unidentified
SEQUENCE: 229
GGFSVKFRTA EGNWDFVANN TPVFFLRDPA KFPHFIHTQK RDPATHLSGD DDSTMFWDYL    60
SQNPESIHQV MILMGDRGIP KGWRFMHGYY GHTLKIVNDK GEWVYAQPHL ISDQGTQNFT   120
GDEAAQQSND YGQKDLYEAI EKGDFPSWTM KVQIMTEKQA EEAWEQKRIN VFDLTHVWPH   180
GDYPLRTVGK FTLNENAKNY FAEVEQVAFN PSHMIPGVEP SNDPVLQSRL FSYPDAHRRP   240
IGANYQQLPV NQNVCPFALG NFQRDGQMAF YNQGSRPNYL SSIEPISFKE RAYDLNKVHG   300
KFVGEAVAFL SEIRPEDFNA PRALWQKVFS EESKQRFVDT VSGHMSTVRD KAITARMMTI   360
FREVSPDLGD RLEKATGVKG ESTIAGMKFN GTHNGFDKAN KIPANGMKKG GEVIFDNGAP   420
ATAAR                                                               425

SEQ ID NO: 230          moltype = AA   length = 239
FEATURE                 Location/Qualifiers
source                  1..239
                        mol_type = protein
                        organism = unidentified
SEQUENCE: 230
VSVSIGVREQ SRLQHWVVGR LDTGNHVRRV ECDLFHLGEV VLGILVKGEF TDCSKWVITM    60
RPDVGQIKDV DPLLLPCLLG LLLGHDLNLH RPRGEVSLLD GFVQILLSVI VGLLSSLVTR   120
EVLGALIRDE VELGVDPFAL VIDNLEGVAV VAMHESPALG DTSITHEDHD LVDRLGVLRQ   180
VVPEHGRVIV TRQVGGGISL LGVDEVGELG RVSEEEDGGV VGHKVPISFC GPELDRESS    239
```

```
SEQ ID NO: 231             moltype = AA   length = 368
FEATURE                    Location/Qualifiers
source                     1..368
                           mol_type = protein
                           organism = unidentified
SEQUENCE: 231
DTIDAEVLDS LGVTQENFQF ALGVSNPSAL REVAVVEVPN VRWEDIGGLE EVKRELIESV      60
QYPVDHPEKF LKFGMSPSKG VLFYGPPGTG KTLLAKAVAN ECAANFISVK GPELLSMWFG     120
ESESNIRDIF DKARAAAPCV VFLDELDSIA KSRGGSQGDA GGASDRVVNQ LLTEMDGMTS     180
KKNVFVIGAT NRPEQLDNAL CRPGRLDTLV YVPLPDQEGR ESILKAQLRK TPIADDIDLS     240
YMASKTHGFS GADLGFITQR AVKLAIKQSI DLAIQNQKAR EAEGDTAMDE DIEEDDPVPE     300
LTKAHFEEAM SMARRSVTDT EIRRYEAFAQ SMKSSGGGSA FFRFPESGAD GNAAEQQQNG     360
AGEEDLYD                                                              368

SEQ ID NO: 232             moltype = AA   length = 317
FEATURE                    Location/Qualifiers
source                     1..317
                           mol_type = protein
                           organism = unidentified
SEQUENCE: 232
MHDCSLHLEY YSDNSKGLGR EVRETNLVVE VLLASTILLL LGCVAIGTAL REAAESAAAT      60
GALHALGESL VAPDLGVGDG ATSHAHSLLK VSLGQLGHGV VLDVLVHGG VTLGLSSLLV     120
LDGQVNRLLD GQLDGTLGDE AKIGTRETVS LGGHVGKVDV VGDRSLAELG LENALTALLV     180
RQGNVDESVE TTRTAESVVE LLRPVGGTDD ENVLLAGHTV HLSEKLVDHT VGSTASIALR     240
TATRLGDGVQ LVEEDNARRG STSLVEDVTN VALRLTEPHG EKLGTLDGNK VGRALVGDSL     300
GQKSLTSTRG TVEKHTL                                                    317

SEQ ID NO: 233             moltype = AA   length = 166
FEATURE                    Location/Qualifiers
source                     1..166
                           mol_type = protein
                           organism = unidentified
SEQUENCE: 233
VSPKRTSSLP LASATPLPFA RSQWSRFPTS DGRTLVVSRR SRGSSSRACN TPSTTPRSSS      60
SLACPHQRVC FSTVPLVLVR LFWPRLSPTS ARPTLFPSRV PSFSPCGSVS LRATFVTSST     120
RLVLPRLALS SSTSWTPSPS LVAVLRAMLA VLPTVWSTSF SLRWTV                    166

SEQ ID NO: 234             moltype = AA   length = 160
FEATURE                    Location/Qualifiers
source                     1..160
                           mol_type = protein
                           organism = unidentified
SEQUENCE: 234
MGHSAGLRKG TRYAFSRDFK KRGMIPLSTY LKQYKVGDIV HVVCNGAVQK GMPHKDFHGK      60
TGVVYNVTKS AVGVILYKQV GNRYIEKRVN LRIEHVRLSR SREEFIVRVK TNAEKKRKAK     120
EEGTTVFLKR QADKPREART ISAKDNKPES IAPIAYDTHI                            160

SEQ ID NO: 235             moltype = AA   length = 526
FEATURE                    Location/Qualifiers
source                     1..526
                           mol_type = protein
                           organism = unidentified
SEQUENCE: 235
DMGIGGLDTE FSAIFRRAFA SRIFPPGLVE KLGIQHVKGI LLFGPPGTGK TLMARQIGTM      60
LNAREPKVVN GPEILNKFVG QSEENIRKLF ADAEKEQKEK GDESGLHIII FDELDAICKQ     120
RGSTNSGTGV GDSVVNQLLS KMDGVDQLNN VLIIGMTNRM DMIDEALLRP GRLEVHIEIS     180
LPDEAGRFQI LNIHTNKMRT NGVMDSDVDL GELAALTKNF SGAEIGGLVK SATSFAFNRH     240
VKVGSVAAFD DIDNMKISRA DFLHALDEVT PAFGVSEEEL QQVVQNGIIH YSQHVNDTLN     300
DGSLLVEQVR KSDRTPLVSA LLHGPSGAGK TALAATIAMA SEFPFIKLIS PETMVGFSEP     360
QKIAQLNKVF TDSYKSPMSI IVVDSLERLL DWNPIGPRFS NGVLQALVVL FGKRPPKGRR     420
LLILATTSNR NILTDMDVLS AFDTDIPINP ISSIDAVVHV LDEVKLFPNS KEKQRATQML     480
REARLGEGGR PDLLVGVKKL LSMAEMARQD PDPTMKIVTS ILREAS                    526

SEQ ID NO: 236             moltype = AA   length = 425
FEATURE                    Location/Qualifiers
source                     1..425
                           mol_type = protein
                           organism = unidentified
SEQUENCE: 236
GGFSVKFRTA EGNWDFVANN TPVFFLRDPA KFPHFIHTQK RDPATHLSGD DDSTMFWDYL      60
SQNPESIHQV MILMGDRGIP KGWRFMHGYY GHTLKIVNDK GEWVYAQFHL ISDQGTQNFT     120
GDEAAQQSND YGQKDLYEAI EKGDFPSWTM KVQIMTEKQA EEAWEQKRIN VFDLTHVWPH     180
GDYPLRTVGK FTLNENAKNY FAEVEQVAFN PSHMIPGVEP SNDPVLQSRL FSYPDAHRHR     240
IGANYQQLPV NQNVCPFALG NFQRDGQMAF YNQGSRPNYL SSIEPISFKE RAYDLNKVHG     300
KFVGEAVAFL SEIRPEDFNA PRALWQKVFS EESKQRFVDT VSGHMSTVRD KAITARMMTI     360
FREVSPDLGD RLEKATGVKG ESTIAGMKFN GTHNGFDKAN KIPANGMKKG GEVIFDNGAP     420
ATAAR                                                                 425

SEQ ID NO: 237             moltype = AA   length = 122
```

```
FEATURE                 Location/Qualifiers
source                  1..122
                        mol_type = protein
                        organism = unidentified
SEQUENCE: 237
MLTDTESEPT ISNCPLTRMC APSPWATSSE TARWHSTIKV VDPTTFLRLS QSHSRRGRMI    60
STRSTANSSE KPSPSCLKSG QRTSMPQGHC GRKSLARKAS SDSSTPSLVT CRQSETKPSP   120
LE                                                                 122

SEQ ID NO: 238          moltype = AA   length = 309
FEATURE                 Location/Qualifiers
source                  1..309
                        mol_type = protein
                        organism = unidentified
SEQUENCE: 238
MPPRQPATRL FALPPRFLCP SLPTTQTRTI RSIDKPAPKP SRFNASLNLP VLGSSSTAAF    60
ARKEHSLPLR TGALAIKKGM TALFDPVTAK RTPCTVLQLD RCQVVSHKRR DIHGYWAVQV   120
GAGAKEARNV TRPERGHFAA YNVPLSRHLA EFRVKNAEGL PPVGSAITAD LFIEGQFIDA   180
KADRRGMGFE GGMKRWNFGG QPASHGNSLA HRLMGSSGGG QGSGSRVLPG KKMPGRMGGE   240
QATVANLRVM QVDKENGIVV VSGAVPGPKN CMVKLQDALK KPWPDATWPP SIEGATEVLR   300
EATEKAPAA                                                          309

SEQ ID NO: 239          moltype = AA   length = 130
FEATURE                 Location/Qualifiers
source                  1..130
                        mol_type = protein
                        organism = unidentified
SEQUENCE: 239
MGIWDAFTDI VEAVTPWSVV EAEAPAEEPQ EENESKTESK DEPEEEEEDE EEEEDEDDEE    60
ELVDPKETLE EECKNSPQCA PAKHHFDECV ERVQQQESEG GAKEDCVEEF FHLAHCATAC   120
AAPKLWSQLK                                                         130

SEQ ID NO: 240          moltype = AA   length = 136
FEATURE                 Location/Qualifiers
source                  1..136
                        mol_type = protein
                        organism = unidentified
SEQUENCE: 240
MRKKRRMRMM RRSSSTPRRL SRKSARTLLN VPPPSTTSTS VLSAFSSRRA RVVLRRTVSR    60
SSSTLPTVRP LAPLPSFGLS SSKLTTLGYR LLRRRNGYIH VEKMPGAGTR QCCPLRKAVP   120
LYECSSAGYQ VGQRLL                                                  136

SEQ ID NO: 241          moltype = AA   length = 194
FEATURE                 Location/Qualifiers
source                  1..194
                        mol_type = protein
                        organism = unidentified
SEQUENCE: 241
GRYYRAPEIM LTWQKYDVAV DIWSTGCIFA EMLEGKPLFP GKDHVNQFSI ITELLGTPPD    60
DVIQTIASEN TLRFVQSLPK REKVPFTTKF ANADPLSLDL LEKMLVFDPR TRISASEGLS   120
HEYLAPYHDP TDEPVAAEVF DWSFNDADLP VDTWKVMMYS EILDFHNLGD IQQDQAAEGP   180
VTGDLAPPSA TTSA                                                    194

SEQ ID NO: 242          moltype = AA   length = 134
FEATURE                 Location/Qualifiers
source                  1..134
                        mol_type = protein
                        organism = unidentified
SEQUENCE: 242
MSPSTFGAQD VSSPRCSRES PCSRARTTLI SSRSSQNCSA HLLTMSSRPS HLRTPSDSSS    60
RCPSVRRSHS LRNSPMPTRF RLTCWRRCLS SIHVPVSRHQ KGCRTSTLRH TMTRRMSPSL   120
PRCLTGVSTM RIYQ                                                    134

SEQ ID NO: 243          moltype = AA   length = 111
FEATURE                 Location/Qualifiers
source                  1..111
                        mol_type = protein
                        organism = unidentified
SEQUENCE: 243
GYPLNLSISI SGGKETNRDC PSNGERSGKS SNLKAGPLGV RIVICRGCFG NGPHLSALER    60
AVIEGENPVW DGVAAPVSSS FDESSCLGMQ LKLGGKFHLK LNIGRRPIAH K            111

SEQ ID NO: 244          moltype = AA   length = 41
FEATURE                 Location/Qualifiers
source                  1..41
                        mol_type = protein
                        organism = unidentified
SEQUENCE: 244
GLVAIARRPH PFPCQTRKLS VSAPKVVGGS PPVRIGRCQA K                        41
```

```
SEQ ID NO: 245           moltype = AA   length = 218
FEATURE                  Location/Qualifiers
source                   1..218
                         mol_type = protein
                         organism = unidentified
SEQUENCE: 245
MEPDQEESEE EEEEEDDEMD EDEDEGQQQD ASGMQTPSGL ATPSGYASTT STMPGGMETP    60
DPMDLRKQRQ TRDETADQED QGAPRDLYTV VPERRATASG FLGSDRAYDL SNAPQSSNMP   120
VLGQEDSRKK KGGRSGADDV DLALDPAELE GMSEQELRQK YDSHRRSSSS QGAGGQQDKE   180
DFSDFVAQEV AKKRQRAQQR GGSGRDRESS RSKEKFKF                          218

SEQ ID NO: 246           moltype = AA   length = 210
FEATURE                  Location/Qualifiers
source                   1..210
                         mol_type = protein
                         organism = unidentified
SEQUENCE: 246
MTRWMKMRMR ASSRTPVACR HPLGSPRPQA MPLLHLQCLV AWRRLTLWTC ASSDRRATRP    60
LIKRTRVHRE TSIRSCPSAE PPLLASSVLT APMTCPMRHS LPTCLCWVKK TRARRKAADL   120
VQTTSTWPWI QLSSRACLSK SLGRSTTRTG APRPVKAPAD SRTKKISQIS SRKRSQRRGR   180
GLSSAAAVDA TAKALGARKS SSFRVYVCIV                                   210

SEQ ID NO: 247           moltype = AA   length = 164
FEATURE                  Location/Qualifiers
source                   1..164
                         mol_type = protein
                         organism = unidentified
SEQUENCE: 247
GVIQVDEPAL REGLPLRTGA ARDAYVKWAV NAFKLSTAGV TDSTQVHSHF CYSEFQDFFH    60
AIAALDTDVL SIENSKSDAK LLQVFVDQSF PAHIGPGVYD IHSPRVPSVD EIKERIEQML   120
QYLKPEQLWI NPDCGLKTRT TEQTIGQLTS LVEAAKFYRQ KYTQ                    164

SEQ ID NO: 248           moltype = AA   length = 125
FEATURE                  Location/Qualifiers
source                   1..125
                         mol_type = protein
                         organism = unidentified
SEQUENCE: 248
VRVFLCVLAL PVMLMLSGLS MLSSCLLLVS PTAPRSTPTS ATVNSRTSST LLLPLIPMFC    60
PSRTASPMPS SSRSSLIRVS PPTLDLVSTI STLLVFPPWM RSRSVSSRCS STSSLSSSGS   120
TLTAV                                                              125

SEQ ID NO: 249           moltype = AA   length = 171
FEATURE                  Location/Qualifiers
source                   1..171
                         mol_type = protein
                         organism = unidentified
SEQUENCE: 249
MLMRTELLSV LLAVELSSLD QRGQLADSLL SGTGLQTAVR VDPELLRLEV LEHLLDTLLD    60
LIHGGNTRRV DIVDTRSNVG GETLINEDLE ELGIGLAVLD GQNIGIKGSN SVEEVLEFTV   120
AEVGVDLGAV GDTSSRQLES IDSPLNISIT GSASTQRKTL TQGRLVDLDD P            171

SEQ ID NO: 250           moltype = AA   length = 66
FEATURE                  Location/Qualifiers
source                   1..66
                         mol_type = protein
                         organism = unidentified
SEQUENCE: 250
LKSGVFGVRV VICRGCFWAA TDLSSLEQDV IEGENPVCGR KGTLHVAPST SRVVWECSSK    60
WEVNFF                                                              66

SEQ ID NO: 251           moltype = AA   length = 189
FEATURE                  Location/Qualifiers
source                   1..189
                         mol_type = protein
                         organism = unidentified
SEQUENCE: 251
MKLSNSAHYS LFLLSSILGF SSASANSHLS DDSPCVARSP TSGLYYDLNA ISLAPPEWKN    60
GKKVDQEARD ESWHAKGHDY PANFTINVCA PVLENVTNVV GVDASRWANV SAFYEQAGKI   120
YSMGEQASEP FFRGRKLVLN YTDGSPCPGD SNTASGNSSI RTKSTLMSFL CDRAAEFPGL   180
EKLGSTGSR                                                          189

SEQ ID NO: 252           moltype = AA   length = 393
FEATURE                  Location/Qualifiers
source                   1..393
                         mol_type = protein
                         organism = unidentified
SEQUENCE: 252
```

```
MNGFNEKGLD GDAFGEKSNL SGLKTFDAFP KTKTSYTTPT RRGGQWTVLI LAVCTLFSLH    60
ELRTWWRGTE AHHFSVEKGV SHDLQLNLDM VVHMPCDTLR INIQDASGDR VLAGELLTRE   120
DTNWDLWMKK RNFESHGEHE YQTLNHEAAD RLSAQDEDAH VHHVLGEVRR NPRRKFSKGP   180
RLRWGDNKDS CRIYGSLEGN KVQGDFHITA RGHGYMELAP HLDHEVFNFS HMITELSFGP   240
HYPSLLNPLD KTIAESETHY QKFQYFLSVV PTLYSKGHNA LDLVTTNKDN SVRYGRNTIF   300
TNQYAATSQS TALPEIPTLI PGIFFKYNIE PILLLVSEER TGFLALVIRV INTVSGVLVT   360
GGWIYQISGW IVEILGKRKR QSEGVLTGKH YSD                                393

SEQ ID NO: 253          moltype = AA  length = 292
FEATURE                 Location/Qualifiers
source                  1..292
                        mol_type = protein
                        organism = unidentified
SEQUENCE: 253
MFTRTLRPAV AVARTQAVQQ QQAGMATLKE IDQRLKSVKN IGKITKSMKV VASTKLTRAE    60
KAMREAKKYG AANNVLFEQT KAGEEEPKER KILYLAMTSD GGLCGGIHSN ITRYMKKAVA   120
KEPGMLAVVG DKPKAQLSRA MPKALTMSFN GVGKDVPTFV EASAIADEIM KSAGDFDEIR   180
IVSNKYLSAI AYEPHTNAVI SAEALRQAAG FQQYEMEEDV SKDLAEFALA NAIYTALVEG   240
HAAEISARRQ AMENASNNAN DMINSLQLQY NRGRQAVITT ELIDIITGAS AL            292

SEQ ID NO: 254          moltype = AA  length = 317
FEATURE                 Location/Qualifiers
source                  1..317
                        mol_type = protein
                        organism = unidentified
SEQUENCE: 254
MSFAACHFCC FVHLVYTRLQ SRGTGNDIDQ LGGNDSLSTT VVLQLERVDH VVGVVGSVLH    60
SLPPCRDLGG VSLDQGSVDG VGKSELGQVL GDILLHLVLL ETGGLSECLS GDDGVGVRFV   120
GDSGKVLVRD DSDLVKVTGR FHNLIGDSAG LDESGDILAD AVERHGQSLG HRSRELSLGL   180
VTDNSQHSGF LGHSLLHVSR NVGVDTTAQT TVGCHGEVED LALLGLLLTS LGLLEQNVVG   240
GTVLLGFTHG LLSSRQLGRG NDLHRLGDLP NVLDGFQTLV DFLQCGHTGL LLLDSLSPGD   300
RHGRSESTRE HGVERGE                                                  317

SEQ ID NO: 255          moltype = AA  length = 311
FEATURE                 Location/Qualifiers
source                  1..311
                        mol_type = protein
                        organism = unidentified
SEQUENCE: 255
MENLLRQMQG GGGRMGARPG PGGETILADN GETVHISSLA LLKMLKHGRA GVPMEVMGLM    60
LGEFVDDYTI SCVDVFAMPQ SGTTVTVESV DHVFQTKMLD MLKQTGRPEM VVGWYHSHPG   120
FGCWLSSVDV NTQQSFEQLH PRAVAVVIDP IQSVRGKVVI DAFRSINPQS LVAGQESRQT   180
TSNIGHLNKP SIQALIHGLN RHYYSLAIDY RKTEGEQGML LNLHKRGWTE GLKMRDHSEM   240
KEGNEKAIKE MLSLASAYTK SVQEETTMTA EQLKTRHVGK LDPKRHLGEA AEKAMGDQVT   300
QSLAMGVLAE L                                                        311

SEQ ID NO: 256          moltype = AA  length = 93
FEATURE                 Location/Qualifiers
source                  1..93
                        mol_type = protein
                        organism = unidentified
SEQUENCE: 256
MGAIPEYDPE EPLETKPFKF VTAGYDARFP QQNQTKHCWQ NYVDYYKCVE AKGEDFRPCK    60
QFYHAFRSLC PKAWTDRWDT QREGGNFPAI LNK                                 93

SEQ ID NO: 257          moltype = AA  length = 252
FEATURE                 Location/Qualifiers
source                  1..252
                        mol_type = protein
                        organism = unidentified
SEQUENCE: 257
GPLLEELDVE AYAKKYRYLR FMCQETLDHL AFLKDKVKDV EGFWASTLLK HRDLRGYITS    60
RSDKDALKYL THIELVQDPK DPRPPALKFY FKENPYFSDL VLEKKYDMSE GSEPAPADGS   120
ITEGMRNFKE DELVTKATTI NWKSDDKNLV AKQPRSKIPD NDDDEDFDGD VGSFFNYFTD   180
DTDIFQIGAL LQSELLPDAI DYFVGRGEQV DSEGEELDEL EDDEDDDED DEGSIDLEDE   240
EEQPSKKKPK RA                                                       252

SEQ ID NO: 258          moltype = AA  length = 165
FEATURE                 Location/Qualifiers
source                  1..165
                        mol_type = protein
                        organism = unidentified
SEQUENCE: 258
GSFLTPQHTH TPFGRAMHNA LTVSRLNDKF QEPLVVLVEL LRARVLHDRN FSNRQFSGGP    60
SFGTDNQKRS MLLIFRTLSI IPLQFKAEHW SGPLSRELLV FNSFHKTLSR SLRTLVESIT   120
MNAFLKNNAR RARDDYLDIA LSLPFQNDTN TGFGIFFKVG GLAGV                   165

SEQ ID NO: 259          moltype = AA  length = 94
FEATURE                 Location/Qualifiers
```

| | | |
|---|---|---|
| source | 1..94 | |
| | mol_type = protein | |
| | organism = unidentified | |

SEQUENCE: 259
```
QIYLDALTTF AEGNITEENK DSESVKEAKQ SAMEILGDAI PNVKDPEAEL LRGFRFWDAV    60
LVCVRTLKAD RAIDLKLAES FEAANSYLNM MRPN                               94
```

| | | |
|---|---|---|
| SEQ ID NO: 260 | moltype = AA length = 251 | |
| FEATURE | Location/Qualifiers | |
| source | 1..251 | |
| | mol_type = protein | |
| | organism = unidentified | |

SEQUENCE: 260
```
GSFLTPQHTH TPFGRAMHNA LTVSRLNDKF QEPLVVLVEL LRARVLHDRN FSNRQFSGGP    60
SFGTDNQKRS MLLIFRTLSI IPLQFKAEHW SGPLSRELLV FNSFHKTLSR SLRTLVESIT   120
MNAFLKNNAR RARDDYLDIA LSLPFQNDTN TGFGIFFKIY LDALTTFAEG NITEENKDSE   180
SVKEAKQSAM EILGDAIPNV KDPEAELLRG FRFWDAVLVC VRTLKADRAI DLKLAESFEA   240
ANSYLNMMRP N                                                       251
```

| | | |
|---|---|---|
| SEQ ID NO: 261 | moltype = AA length = 148 | |
| FEATURE | Location/Qualifiers | |
| source | 1..148 | |
| | mol_type = protein | |
| | organism = unidentified | |

SEQUENCE: 261
```
GIYLDGNNDL VTMKGNYIYH TSGRSPKVQG NTLLHAVNNY WHDNSGHAFE IGEGGYVLAE    60
GNVFQDVTTP VEDPVDGQLL TSPDPSTNAQ CSSYLGRACE INGFGNSGTF NQADTSLLSK   120
FKGQNIASAD AYSKVASSVA SNAGQGHL                                     148
```

| | | |
|---|---|---|
| SEQ ID NO: 262 | moltype = AA length = 120 | |
| FEATURE | Location/Qualifiers | |
| source | 1..120 | |
| | mol_type = protein | |
| | organism = unidentified | |

SEQUENCE: 262
```
VRVVTFWPRV TSSRMLLPPL RTPLTASSSL PLTPAPTLSA RHTLAGPAKS TASVTLVPST    60
RLTLACCLNL RVRTLLLLML TLRLPRALPA TPVRDTCKME RGGSELNLLM SDDIALAACW   120
```

| | | |
|---|---|---|
| SEQ ID NO: 263 | moltype = AA length = 160 | |
| FEATURE | Location/Qualifiers | |
| source | 1..160 | |
| | mol_type = protein | |
| | organism = unidentified | |

SEQUENCE: 263
```
MSAQPLRIVM ACDEAGVPYK DAIKAVLEKS PLVASVSDVG VNDASDKTAY PHPAVEGAQQ    60
IKAGKADRGL FICGTGLGVA IAANKVPGIR AVTAHDPFSV ERSILSNDAQ VLCMGQRVIG   120
VELAKKLALD WLNYRFDPKS ASAAKVQAIS DYETKFAGSS                         160
```

| | | |
|---|---|---|
| SEQ ID NO: 264 | moltype = AA length = 150 | |
| FEATURE | Location/Qualifiers | |
| source | 1..150 | |
| | mol_type = protein | |
| | organism = unidentified | |

SEQUENCE: 264
```
MSVTTTSSAA AASCTPSWQI PVDDVACAGQ ISGNITKVFD TCCKGNSPVK YNDDCNIYCL    60
AQGQTKQELT DCLTEKSGNN QIFCGHGKQN ATATAEATTT KETGTSTGTS TSSTGTSTET   120
NAAVLNQPIS KTGLGLVAML FCSALVGVVA                                   150
```

| | | |
|---|---|---|
| SEQ ID NO: 265 | moltype = AA length = 197 | |
| FEATURE | Location/Qualifiers | |
| source | 1..197 | |
| | mol_type = protein | |
| | organism = unidentified | |

SEQUENCE: 265
```
AGVDRGVITK DEKDSSINRL LVTGYGLAEV MGTDGVNGIK TRTNHVMETC EVLGIEAARQ    60
TIYNEIQHTM TSHGMSIDPR HVMLLGDVMT YKGEVLGITR FGVQKMKDSV LMLASFEKTT   120
DHLFDASLFS KKDEIQGVSE CIIMGTPAPG CGTSLASIVT PAPLLPRKKP LLFETAFKAG   180
QDRLSYHENN GGMEVDM                                                 197
```

| | | |
|---|---|---|
| SEQ ID NO: 266 | moltype = AA length = 249 | |
| FEATURE | Location/Qualifiers | |
| source | 1..249 | |
| | mol_type = protein | |
| | organism = unidentified | |

SEQUENCE: 266
```
AGSGGAYSFS LTTFSPSGKL VQIEHALAAV AGGTTSLGIK ATNGVVLATE KKSPSLLLDT    60
SVLEKVAPIC PNIGFVYSGM GPDFRVLVAK ARKIAQAYYK VYGEYPPTKV LVQEVAGVMQ   120
KATQSGVRP YGISLLIAGW DSHRGQSLYQ VDPSGSYWAW KASAIGKNMV NGKTFLEKRY   180
NDDLSLEDAI HTALLTLKEG FEGQMTENTI EIGVVTPTA EQMQEKPGER LPPTFRKLTE   240
```

```
QEVRDYLAL                                                                        249

SEQ ID NO: 267           moltype = AA  length = 346
FEATURE                  Location/Qualifiers
source                   1..346
                         mol_type = protein
                         organism = unidentified
SEQUENCE: 267
MLTSAFSTSA SKMLGKRAVS SSSALNGKVA VLGAAGGIGQ PLSLLVKQNP AVSSLSLYDV    60
RGSPGVAADI SHINTPAVTE GFLPDNDGLK QALEGAEVVL IPAGVPRKPG MTRDDLFNTN   120
ASIVKMLAEA SAKYCPKAMM LIIANPVNST VPIVAETFKR AGVYDPARLF GVTTLDVVRS   180
STFVSGITGA KPSDTVVQVI GGHSGATIVP LLSQIPQGDK IVKAGGQQYA DLVKRIQFGG   240
DEVVKAKDGT GSATLSMAYA AAVFNDALLK AMDQKGLVQ PAYVESPHFA KEGAKYFASN    300
VELGPNGVEK ILDIGNMSSE EQELLKECLP QLAKNIAAGE KFVADN                  346

SEQ ID NO: 268           moltype = AA  length = 373
FEATURE                  Location/Qualifiers
source                   1..373
                         mol_type = protein
                         organism = unidentified
SEQUENCE: 268
MSLFLLFSLA LIIIGSNVVG YPLVVSDELL TSSNVLGELG KALLKELLLL RGHVADVEDL    60
LNTVGAELDV GGEVLSTLLG EVGALDVSGL NETLLAVHSL EESVVEDGSG VSHGEGSGAS   120
AVLGLDDFVT AKLDALDEVS VLLAASLDNL VALRDLGEQG HDGGARVTTD DLDHGVGGLG   180
TGDARDESGR ADNVEGGDTE ETGRVVDTST LEGLSDDRHG GVDGVGNDEH HSLGAVLGRS   240
LSKHLDDGSV GVEKVVTGHA GLARNTSRNE DHLSTLEGLL EAIVVGEEAL GDSRGVDVAN   300
VSSNTRGAAN IVKGEAGDSR VLLDQQGEGL ANTASSTEDG NLSVQGAGRR DCSLAEHLGS   360
RCRKGAGQHF GSK                                                      373

SEQ ID NO: 269           moltype = AA  length = 435
FEATURE                  Location/Qualifiers
source                   1..435
                         mol_type = protein
                         organism = unidentified
SEQUENCE: 269
GASVLLPALH FDEREQRPGR TSSTASLLQR HDRNEPLSLN SHSPTSVDHT PTTAHFTGAE    60
ELLASDVGPT ATAGLPGDAE LESKLKLLEE VKRARESVHS SLERIRAGTP TPSISQGMPS   120
PTPSGAPGYA RTPSSVGLSD DVRSRRGSTT SSKVLDAIDK PRVATQSEWD EYVRNRHVIS   180
PPPTQFAVLP TSAAMVDRGT SRHSQYALVS DGVAKALDRR ERTISMMEPQ VAEDWGPRET   240
LDSTPAHVSM GRRAMSFHEI PLASPVAASR PQDRSSYSAG PRQVIGSAAG HTQRPGISQS   300
RSAHGRTMTY DELTERHRQR LSALQAPVSA KIREPMDIAS AKASWDKQKR VERDEMKRRE   360
AEKLAQAHAR ERRGPAVDKK EVLKSTDEWR RSVHGGLDGF AVPHLPAHAR GSTQPGGSGA   420
KRSSLSQRPS NYFAN                                                    435

SEQ ID NO: 270           moltype = AA  length = 225
FEATURE                  Location/Qualifiers
source                   1..225
                         mol_type = protein
                         organism = unidentified
SEQUENCE: 270
GQACCFRHCI STSGSNDLDV RLRLQVCCSV TIAMNLYRST RTRRHLWTTL PLLRISLVLK    60
SCSPPTSDRP RQLGYPVMRS LRASSSCLKR SNVHGNRYIA RSRGSEPARL PRLSARECPA   120
RHPLVPLVTL ELRRLSACRT TCARDEAQRP APRFLTLSTS LESLPNPNGT STFATGMSSH   180
LHPLSLPYCP HLLRWSIVVP VDTASMPLFP TALPKRLTGG SELFQ                   225

SEQ ID NO: 271           moltype = AA  length = 168
FEATURE                  Location/Qualifiers
source                   1..168
                         mol_type = protein
                         organism = unidentified
SEQUENCE: 271
MGSPAPHHRH QSSLEGVIDF STGRGHPLNP YQRDKAESVF TGIINRFEDS STVEKPYNRA    60
KLVRLTYEYA RSEDSRCNFL QAFFGSVNVT MDDSIFDDE AVEEGIRSSL NSFADFLVEN    120
FFLPLKASAS RTPPAPQPKF RADVLLWGLW KEWPRSDATA SSAIDIVA                168

SEQ ID NO: 272           moltype = AA  length = 253
FEATURE                  Location/Qualifiers
source                   1..253
                         mol_type = protein
                         organism = unidentified
SEQUENCE: 272
QDAPSPPAQV PSRRPAVGSV ERVASLRRDC LIRDRHRCVI SRNFDMKEAE RRLDDSGYDH    60
ASDDEGHLLK DQEHGSFAEL EVAHILPHSL MTTTANSELN KSKETALTIL NMFDSGIVHL   120
IDGPDIDRPR NALTLSIDLH RQFGNFKVFF EPMPEPHTYR IDSTLRQPFR NPIFPVTRAL   180
YLTPERTIDP PSGRLLAVHR AICHILHLSA AGNYIDSILR DMDDGTVQAN GSTRLASIVR   240
LKLGGWWDGT VVG                                                      253

SEQ ID NO: 273           moltype = AA  length = 106
FEATURE                  Location/Qualifiers
```

```
source                      1..106
                            mol_type = protein
                            organism = unidentified
SEQUENCE: 273
MVNIPKTRRT YCKGKECKKH TQHKVTQYKA GKASLFAQGK RRYDRKQSGY GGQTKPVFHK    60
KAKTTKKVVL RLECTSCKTK AQLALKRCKH FELGGDKKTK GAALVF                  106

SEQ ID NO: 274              moltype = AA   length = 84
FEATURE                     Location/Qualifiers
source                      1..84
                            mol_type = protein
                            organism = unidentified
SEQUENCE: 274
MILEGSESKL RFSYDRPTRK DMSRHIMACA QHSSRVHQRC PTLPLRCVGC DSSTTAFQYH    60
LFACRSEDDF TTVHITNRKC QQDQ                                          84

SEQ ID NO: 275              moltype = AA   length = 41
FEATURE                     Location/Qualifiers
source                      1..41
                            mol_type = protein
                            organism = unidentified
SEQUENCE: 275
MKLTFKDLKQ EKFVIEVEPS ETVREVKQKL LKKKANMRRN E                       41

SEQ ID NO: 276              moltype = AA   length = 369
FEATURE                     Location/Qualifiers
source                      1..369
                            mol_type = protein
                            organism = unidentified
SEQUENCE: 276
GPEAGEVRNR GRALRDCSRS QAKIAQEKGE YEAERMKVIY SGKILQDDKT VESYNIQEKD    60
FLVCLPSKGP KPAASSSASQ APATPAPRAP VATPAAPAPA APAPASSTPA VPATPSPAGA    120
QTGPSFGDPS ALTMGSAAEG AVTQMEAMGF ARSDIDRAMR AAFFNPDRAV DYLLNGIPAD    180
VQQEQQQRQQ EQQADRAAEQ APVPSAEDAA AAAALGGDEG FNMFEAAAQA GDPRGGGARS    240
GGSEALANLD FLRSNPHFQQ LRQLVQQQPH MLEPILQQVA AGNPQISQII GQNSEQFLQL    300
LSEEGDEEDA ALPPGTQAIS VTEEERDAIE RLCRLGFPRD SVIQAYFACD KNEELAANFL    360
FDQPDDDEE                                                           369

SEQ ID NO: 277              moltype = AA   length = 375
FEATURE                     Location/Qualifiers
source                      1..375
                            mol_type = protein
                            organism = unidentified
SEQUENCE: 277
MKLTFKDLKQ EKFVIEVEPS ETVREVKQKI AQEKGEYEAE RMKVIYSGKI LQDDKTVESY    60
NIQEKDFLVC LPSKGPKPAA SSSASQAPAT PAPRAPVATP AAPAPAAPAP ASSTPAVPAT    120
PSPAGAQTGP SFGDPSALTM GSAAEGAVTQ MEAMGFARSD IDRAMRAAFF NPDRAVDYLL    180
NGIPADVQQE QQQRQQEQQA DRAAEQAPVP SAEDAAAAAA LGGDEGFNMF EAAAQAGDGR    240
GGGARSGGSE ALANLDFLRS NPHFQQLRQL VQQQPHMLEP ILQQVAAGNP QISQIIGQNS    300
EQFLQLLSEE GDEEDAALPP GTQAISVTEE ERDAIERLCR LGFPRDSVIQ AYFACDKNEE    360
LAANFLFDQP DDDEE                                                    375

SEQ ID NO: 278              moltype = AA   length = 342
FEATURE                     Location/Qualifiers
source                      1..342
                            mol_type = protein
                            organism = unidentified
SEQUENCE: 278
APGDMETADA KNRAMRAAGF IVPDTFEDLP EVLKTTYTGL VQKGVIVPKA EIDPPNIPMD    60
YQWASKLGLI RKPAAFISTI SDERGQELMY AGMRISDVFK EEIGIGGVIS LLWFKRRLPP    120
FACKFIEMVL QLTADHGPAV SGAMNTIITA RAGKDLISSL AAGLLTIGDR FGGALDGAAA    180
EFSRGLNSGA TPREFVDSMR KANRLIPGIG HKIKSKTNPD LRVVLVVDYV KKHFPSHKTL    240
DPFALAVEDVT TQKSNTLILN VDGAIAASFC DLLSGCGAFT EDEAADYLKN GTLNGLFVLG    300
RSIGFIGHYL DQRLLKQPLY RHPADDIFIN MQERVVFQPG SN                      342

SEQ ID NO: 279              moltype = AA   length = 182
FEATURE                     Location/Qualifiers
source                      1..182
                            mol_type = protein
                            organism = unidentified
SEQUENCE: 279
GAYKEGKFTS ESIQKSKLRF QDILVELPLR VHNSHLLTSF LHQVPQAPPA KNPLDFPSSL    60
AELSRDSDVS SNPFAPNLDT LDLSIDPFQY WQRALGREQQ KITAWQQKRK AENAARAASK    120
QPPLDENEWQ KLFKLPTEPS RLEALLVGRQ VEQYARQVDG FSATVSAKMF GVRGNLLPNE    180
IE                                                                  182

SEQ ID NO: 280              moltype = AA   length = 171
FEATURE                     Location/Qualifiers
source                      1..171
```

```
                         mol_type = protein
                         organism = unidentified
SEQUENCE: 280
MSAPTPSHPT  LTPWTSASTP  SSTGSAPSAA  SSRRSPHGNR  SARLRMLHAP  RASSRPLTRM    60
SGRSCSSCPR  SPAGSRLCLS  AGRSSSTPAR  STDSPPPFPP  RCLASGATSS  LTRSSRGRIL   120
RRRDRRLCIA  RRSRLGGVEY  MRHGYKKKDD  VVPPSTSSGQ  RCIESQKKKG  F            171

SEQ ID NO: 281           moltype = AA  length = 217
FEATURE                  Location/Qualifiers
source                   1..217
                         mol_type = protein
                         organism = unidentified
SEQUENCE: 281
MRRSSKFKNV  KILSSFGILC  SVALNSSMAE  PHHPFFCSHA  ACTLPHPAEN  ASLCINAGPV    60
SVIFVLYSIS  LGRRLPLTPN  ILAETVAENP  STWRAYCSTC  LPTSRASSLL  GSVGSLNSFC   120
HSFSSRGGCL  LAARAAFSAL  RFCCHAVIFC  CSRPRARCQY  WKGSMLRSRV  SRLGAKGLEL   180
TSESRESSAR  DEGKSRGFFA  GGACGTWCRK  LVRRWEL                              217

SEQ ID NO: 282           moltype = AA  length = 150
FEATURE                  Location/Qualifiers
source                   1..150
                         mol_type = protein
                         organism = unidentified
SEQUENCE: 282
MYSTPPSRER  LAMHKRRSRL  RNIRPLLDLV  REEVAPDAKH  LGGNGGGESV  DLAGVLLDLP    60
ADKQSLEPAG  LRGQLEQLLP  LILVKGRLLA  RGACSILSLA  LLLPCGDLLL  LAAEGALPVL   120
EGVDAEVQGV  KVGCEGVGAD  IGVARKLCKG                                      150

SEQ ID NO: 283           moltype = AA  length = 269
FEATURE                  Location/Qualifiers
source                   1..269
                         mol_type = protein
                         organism = unidentified
SEQUENCE: 283
MSNSFIRHLP  STLRAFRSST  AFSLTRSFSS  TMASNGTSTN  GVQHDARKVF  FFDIDNCLYP    60
KSYQIHDKMA  VLIDNYFQNH  LSLSQEDATT  LHQRYYKDYG  LAIEGLVRHH  KVDPLEYNEK   120
VDDALPLDDI  IKPDPKLRKL  LQDIDTDKVK  LWLFTNAYVN  HAKRVTRLLG  VDDLFEGMTF   180
CDYAAERLLC  KPTTEMYNKA  MQEANATDID  QCYFVDDSAL  NAAAAMKYGW  KTAHLVEPTA   240
KPPPQPVSQH  QISNLEELRK  VFPEVFKTS                                       269

SEQ ID NO: 284           moltype = AA  length = 256
FEATURE                  Location/Qualifiers
source                   1..256
                         mol_type = protein
                         organism = unidentified
SEQUENCE: 284
MARIFITGST  DGLGLLSAKL  LSEQGHSVFL  HARNAERASQ  AKAAVPKAQG  VIIGDLSNVS    60
DVKQLAADAN  KAGPFDAVVH  NAGLGLTTNG  QKTAEGVAQI  FAVNSMAPYI  LTALMDKPKR   120
LLYVSSGLHF  GGDPSLEDVT  WATREFRPSD  AYNDTKMQNV  MLSKAVAKRW  PDVQSGSLDP   180
GWVKTKLGGS  AAPGTTDAPA  EMIAEYAAGK  SCAGDQTGAY  LTPRGVEEPH  DATKLAEKQD   240
RLMQIYKEVS  GVSFPQ                                                      256

SEQ ID NO: 285           moltype = AA  length = 201
FEATURE                  Location/Qualifiers
source                   1..201
                         mol_type = protein
                         organism = unidentified
SEQUENCE: 285
MKLCLLGERN  TRYLLVNLHQ  TILLLGQLSR  IMRLFHATRS  QVGTCLIACA  RFAGSVLSNH    60
LCWSVGGARR  GRPAELSLHP  AWVKRAALHI  RPAFGDCFRE  HDVLHLCIVV  CIRWSELPCG   120
PSDVLEAGVA  TEVQSGADVQ  EPLRLVHESG  QNVRCHAVNG  KNLGYALSSL  LAIGGESEAS   180
IVNNGVKRSS  LVGIGGELLH  V                                               201

SEQ ID NO: 286           moltype = AA  length = 192
FEATURE                  Location/Qualifiers
source                   1..192
                         mol_type = protein
                         organism = unidentified
SEQUENCE: 286
MAIGQSSQQQ  ADGQNVVTQG  NSDKAANPMR  ELRIQKLVLN  ISVGESGDRL  TRAAKVLEQL    60
SGQTPVYSKA  RYTVRTFGIR  RNEKISVHVT  VRGAKAEEIL  ERGLKVKEYE  LRKRNFSATG   120
NFGFGISEHI  DLGIKYDPAI  GIYGMDFYVV  MSRPGERVAR  RRRAKTRVGA  SHKVNAPEVI   180
KWYKNRFEGI  VR                                                          192

SEQ ID NO: 287           moltype = AA  length = 213
FEATURE                  Location/Qualifiers
source                   1..213
                         mol_type = protein
                         organism = unidentified
```

```
SEQUENCE: 287
GHTGDVLSVS FSADNRQIVS ASRDRTIKLW NTLGECKFNI VDDGHSEWVS CVRFSPNPVI    60
PVIVSAGWDK VVKVWELSKC KLKTNHHGHT GYINTLAVSP DGSLAASGGK DGITMLWDLN   120
DGKHLYSLEA GDIVNSLVFS PNRYWLCAAT ASSIKIFDLE SKSIVDDLKP DFSAEYSDKA   180
QKPQCTSLAW SADGQTLFAG FSDNLVRVWV VTA                                213

SEQ ID NO: 288          moltype = AA   length = 347
FEATURE                 Location/Qualifiers
source                  1..347
                        mol_type = protein
                        organism = unidentified
SEQUENCE: 288
MAPSTQKQWT VKNGEQDFDG LVYGDAPVPT AGDSEVVVKL HGASLNYRDL IIPKGKYPFP    60
LSFPVVPGSD GAGEVVEVGS KVKQFKKGDK VVTLFNQLHQ YGPVDAAAAS SGLGGAVDGT   120
LRQYGVFNEN GVVRAPTNLN FLESSTLTCA GLTSWNALYG LKPLLPGQTV LVQGTGGVSI   180
FALQFAKAAG ATVIATTSSE EKGKRLKDLG ADHVINYKTQ TNWGEIARGL TRDNIGVDHI   240
IEVGGAGTLE QSFKCIKFEG VISIIGFLGG MNPSTIPNVL QTLSNICTVR GVYVGSKALM   300
NDMINAIEAN NIHPVVDGTV FTLEKTREAY EYMWAQKHFG KLTIQIA                 347

SEQ ID NO: 289          moltype = AA   length = 518
FEATURE                 Location/Qualifiers
source                  1..518
                        mol_type = protein
                        organism = unidentified
SEQUENCE: 289
MLEQQYQMRK EQQVQFTPMA SPSSTPYHMH QDFTVPGDFF SPLTSPALHA QNQPQSRQQF    60
TAHQQGYYTN PSTAASSAAP SPIDANGDVE MGGDGVALPE SASQPKKPSR RKPATPRTFA   120
MNKVKQSPIQ KPQKRKSVAL AHKDADAVVQ DAQRSGHIAP KSAGLQMPPP FESSENDSVS   180
PEALNDLPMG PPPRPGSVSQ SPAIAPQNQS VSGPAATPKS LLSMKGAQDM NAPASTGISG   240
QMGQASLEDL ELPEAAENPG STATHSQVLN SQEPTPRLMP SRKTPKLGPL STPSSGKPTS   300
ASNSPAHALS PMTASTPAGL LKDKKDNKGG RATSKKRGSV STTNSAMVSP ALRPKVSPSI   360
KPLLPEGTSL NSPTHALLLA SKSNYQNLLE GNHLPGISYP DSLSTGLTSK RTSHKVAEQG   420
RRNRINDALK EMQALIPASS GARAEELMTA DAGDDDSQET KEKDRDAAVK SNSSKAATVE   480
SANRYIRVLK ESDAAQKDAI ARPNSPGSRS LDPPDLDN                           518

SEQ ID NO: 290          moltype = AA   length = 126
FEATURE                 Location/Qualifiers
source                  1..126
                        mol_type = protein
                        organism = unidentified
SEQUENCE: 290
MRNILLVLAS AALAVVAQKP DLDVKGTFGD ANPFSKVVNG QSNKLYLTLD NHSPESLVVK    60
SISGSWSEKT SASSGQEKFL KNSTTQEKLT VPIPPKSEGA FQPPTVLTYQ FWSEFKPREL   120
LLTVLG                                                              126

SEQ ID NO: 291          moltype = AA   length = 91
FEATURE                 Location/Qualifiers
source                  1..91
                        mol_type = protein
                        organism = unidentified
SEQUENCE: 291
MVLALVGGAG YLAYNIYFPP ARKPRRSANT APTDAPAAPA DPDEWIPVHH KRAKKTSGGG    60
ATSGEESEAT EGYASEKSAS GAKKRGKGGR K                                   91

SEQ ID NO: 292          moltype = AA   length = 252
FEATURE                 Location/Qualifiers
source                  1..252
                        mol_type = protein
                        organism = unidentified
SEQUENCE: 292
MSDNNDGNHG GGVGASYYYG GIAIALCLVI VLTLVSRILY RRRVRNRLLR ANRQERITLR    60
DRGEAPGLPT YRESRNQPSL PRYTAEADYA PPPGPPPSNS PDNEGHHFHF HFPSLHVPQA   120
LHLRPRQADD PADQIPTVPP PSYEPPKYEP PSGAPPEQQQ EPVASGSSEH HHQQSALGEH   180
TAATAAATT PAEHSGESTE LRSASPSQPQ SQSQPQAPAQ PQEQDYGYDD ADFIHPEERR   240
RIEAAQRNDP QT                                                       252

SEQ ID NO: 293          moltype = AA   length = 161
FEATURE                 Location/Qualifiers
source                  1..161
                        mol_type = protein
                        organism = unidentified
SEQUENCE: 293
MSRIGDPTNN PATQQLYSDR PLHLPGPGLK PSRQLTISSA VAFREDSGQT RFNLISSDHR    60
EVLHISIRAR DNVLVLNTKA PDGDWGKEER HDLKPLFDTP LLPYITVMAT KNSYILSVPG   120
KREIIFNKRK GFMEPAVRIE YDYDEMSAFS DPCYITVPSS S                       161

SEQ ID NO: 294          moltype = AA   length = 84
FEATURE                 Location/Qualifiers
source                  1..84
```

```
SEQUENCE: 294
MPQEIKDIKN LLEIARRKDA RSARIKKTKT VGAKGEPAQL TKFKIRCSRY LYTLVVSDGE    60
KAEKLKQSLP PTLNVEEIGK VSKK                                          84

SEQ ID NO: 295           moltype = AA  length = 173
FEATURE                  Location/Qualifiers
source                   1..173
                         mol_type = protein
                         organism = unidentified
SEQUENCE: 295
MSHTFYDGTI VVLQGILETF SHILHKAEES PNSSAFPAAR LHEDMYPLTD QIRLATQFSE    60
YILAKVTGRE PRKFEGNPLT FAEFYERIDT MLKSLKEADK DVVNANADKE ELTQVGPTAK   120
IELSNAIYAH RIALPNIYFH LNIAYGILRK EGVPLGKLDY FAGFFPPSMA QGK          173

SEQ ID NO: 296           moltype = AA  length = 162
FEATURE                  Location/Qualifiers
source                   1..162
                         mol_type = protein
                         organism = unidentified
SEQUENCE: 296
MSRIGDFANN NQATQQLFSD RPMQLPGPGL KPSRQLTVSS AMAFRWDSGQ TRFNLISSDR    60
REVLHISIRA KDDVLVLNTK APDGNWGKEE RHELKPLFDT PMLPYITVTA TKTSYILSVP   120
GNQEIIFNKR KGFMEPAVKI EYDYDENPAF SDPCYVTVPH LS                      162

SEQ ID NO: 297           moltype = AA  length = 313
FEATURE                  Location/Qualifiers
source                   1..313
                         mol_type = protein
                         organism = unidentified
SEQUENCE: 297
MSEQLHYKGS LAGHGNWVTA IATSAENPDM ILTASRDKSV IVWQLTRDDA QYGYPKRILK    60
GHNHFVSDVS ISYDGQFALS SSWDKTLRLW DLNTGLTTRR FVGHEADVLS VSFSADNRQI   120
VSGSRDRTIK LWNTLGECKF DIKDEGHSEW VSCVRFSPNP MNPVIVSAGW DKVVKVWELS   180
NCKLKTNHYG HTGYINTVSV SPDGSLAASG GKDGITMLWD LNEGKHLYSL EAGDIVNALV   240
FSPNRYWLCA ATASCIKIFD LESKSIVDEL KPDFVDVGKN SREPEAVSLS WSADGQTLFA   300
GFTDNAVRVW TVA                                                      313

SEQ ID NO: 298           moltype = AA  length = 107
FEATURE                  Location/Qualifiers
source                   1..107
                         mol_type = protein
                         organism = unidentified
SEQUENCE: 298
GEGGGIHGTT FNSIMKCDVD VRKDLYGNIV MSGGTTMYPG IADRMQKEIT ALAPSSMKVK    60
IIAPPERKYS VWIGGSILAS LSTFQQMWIS KQEYDESGPS IVHRKCF                 107

SEQ ID NO: 299           moltype = AA  length = 111
FEATURE                  Location/Qualifiers
source                   1..111
                         mol_type = protein
                         organism = unidentified
SEQUENCE: 299
MRLSLEALAV DDRRAALVVL LLRDPHLLEG GQRSQDGTTN PHRVFTLRRS NDLDLHRRRS    60
KSGDFLLHTV GNTRVHSSTT RHDNVAIEIL TDVNITLHDG VEGGSVDTTT F            111

SEQ ID NO: 300           moltype = AA  length = 213
FEATURE                  Location/Qualifiers
source                   1..213
                         mol_type = protein
                         organism = unidentified
SEQUENCE: 300
MAFFPHYTTN LSPLLYLLDD DYAVYRSTCP KSNYHHKQHH SRRQPSPVRY FSPNFDMREG    60
NDSYYLDGEL PGVNQNDVDI EFSDPQTLVI KGRVERNYNN LDGMNEENQQ DEEQFSETLS   120
SKSYQPTVED EDEANHSPPV ATPTYSEKSV TEKTQKPAYK YRNSERAIGE FHRAFNLPTR   180
VDQDAVRATL RNGILSLELP KEPAPKMKKI RIE                                213

SEQ ID NO: 301           moltype = AA  length = 161
FEATURE                  Location/Qualifiers
source                   1..161
                         mol_type = protein
                         organism = unidentified
SEQUENCE: 301
MSRIGDPTNN PATQQLYSDR PLHLPGPGLK PSRQLTISSA VAFREDSGQT RFNLISSDHR    60
EVLHISIRAR DNVLVLNTKA PDGDWGKEER HDLKPLFDTP LLPYITVMAT KNSYILSVPG   120
KREIIFNKRK GFMEPAVRIE YDYDEMSAFS DPCYITVPSS S                       161

SEQ ID NO: 302           moltype = AA  length = 178
```

```
FEATURE                 Location/Qualifiers
source                  1..178
                        mol_type = protein
                        organism = unidentified
SEQUENCE: 302
MKAYWYDNQP GDQRLPHDSG RPVTESYLES IGVFYRHCPT IDLVDSLAAE RGYKNRDEVC    60
VSPQTMGDVY EEKVKTFFSE HLHEDEEIRY IRDGEGYFDV RGQEDEWVRI RLSKDDLIIL   120
PAGIYHRFTT DDKNYVKAMR LFQEEPKWTP LNRGPEVDVN PHRKTYLETV PSPAVAAN     178

SEQ ID NO: 303          moltype = AA   length = 216
FEATURE                 Location/Qualifiers
source                  1..216
                        mol_type = protein
                        organism = unidentified
SEQUENCE: 303
VAAGYTPEAL EILSKKKGGK YLVLEMDETY NPPAEETRTL YGVQLTQARN DAVISPQKTF    60
NTIITPKNTE SLPESALRDL TVATLALKYT QSNSVCYALN GQVVGLGAGQ QSRIHCTRLA   120
GDKTDNWWMR FHERVLNIKW KQGTKRADKS NAIDLLCSGQ TPRNDAEKVE YERVFAEVPA   180
PFTQEERDAW LSQLTNVAIS SDAFVCLSPL LEHSKF                             216

SEQ ID NO: 304          moltype = AA   length = 51
FEATURE                 Location/Qualifiers
source                  1..51
                        mol_type = protein
                        organism = unidentified
SEQUENCE: 304
FPFIDNVFRA ARSGVKYIAA PSGSQNDGPV FETAEKLGIS FVEQGTRLFH H             51

SEQ ID NO: 305          moltype = AA   length = 255
FEATURE                 Location/Qualifiers
source                  1..255
                        mol_type = protein
                        organism = unidentified
SEQUENCE: 305
VAAGYTPEAL EILSKKKGGK YLVLEMDETY NPPAEETRTL YGVQLTQARN DAVISPQKTF    60
NTIITPKNTE SLPESALRDL TVATLALKYT QSNSVCYALN GQVVGLGAGQ QSRIHCTRLA   120
GDKTDNWWMR FHERVLNIKW KQGTKRADKS NAIDLLCSGQ TPRNDAEKVE YERVFAEVPA   180
PFTQEERDAW LSQLTNVAIS SDAFFPFIDN VFRAARSGVK YIAAPSGSQN DGPVFETAEK   240
LGISFVEQGT RLFHH                                                    255

SEQ ID NO: 306          moltype = AA   length = 316
FEATURE                 Location/Qualifiers
source                  1..316
                        mol_type = protein
                        organism = unidentified
SEQUENCE: 306
MCDRSRIGPK GWEAVVSTQA VVSTQAVVST QAVVSTQAVV STQAVVSTQS AQPGAISAPV    60
AAGKDVELQW TEWPESHHGP VITYLANCNG DCSEVDKSSL EFFKIDQKGL IDDSNVPGTW   120
ATDKLISNNN SYTVTIPSDI AAGNYVLRHE IIALHSAGNE DGAQNYPQCL NLKVTGGGNA   180
SPSGTLGTKL YNEDDSGILV SIYQQLDSYD IPGPALYSGA SSSSNSGSSS SVASATASAT   240
SAAASSPSSS QASGTPASQV KAQTASSTPS ASSGATSGSL SDYFSSLSAE EFLNVISETL   300
SWLVTDKIHA RDLSTA                                                   316

SEQ ID NO: 307          moltype = AA   length = 138
FEATURE                 Location/Qualifiers
source                  1..138
                        mol_type = protein
                        organism = unidentified
SEQUENCE: 307
MKSLLCTPLA TRMVPRTTPS VSTSRLLVVA TLLPQVLLVP SSTTRTTRVS LSVSTSSSLTP   60
TTSPALLCTL ALPRPPTLVL LPALLRPLLL PLLPLLPLPR PLRLPVPPLP RSRLRPLALL   120
LALRPVPLPA VCPTTSAL                                                 138

SEQ ID NO: 308          moltype = AA   length = 272
FEATURE                 Location/Qualifiers
source                  1..272
                        mol_type = protein
                        organism = unidentified
SEQUENCE: 308
VVSTQSAQPG AISAPVAAGK DVELQWTEWP ESHHGPVITY LANCNGDCSE VDKSSLEFFK    60
IDQKGLIDDS NVPGTWATDK LISNNNSYTV TIPSDIAAGN YVLRHEIIAL HSAGNEDGAQ   120
NYPQCLNLKV TGGGNASPSG TLGTKLYNED DSGILVSIYQ QLDSYDIPGP ALYSGASSSS   180
NSGSSSSVAS ATASATSAAA SSPSSSQASG TPASQVKAQT ASSTPSASSG ATSGSLSDYF   240
SSLSAEEFLN VISETLSWLV TDKIHARDLS TA                                 272

SEQ ID NO: 309          moltype = AA   length = 138
FEATURE                 Location/Qualifiers
source                  1..138
                        mol_type = protein
```

```
                        organism = unidentified
SEQUENCE: 309
MKSLLCTPLA TRMVPRTTPS VSTSRLLVVA TLLPQVLLVP SSTTRTTRVS LSVSTSSLTP      60
TTSPALLCTL ALPRPPTLVL LPALLRPLLL PLLPLLPLPR PLRLPVPPLP RSRLRPLALL     120
LALRPVPLPA VCPTTSAL                                                   138

SEQ ID NO: 310          moltype = AA   length = 305
FEATURE                 Location/Qualifiers
source                  1..305
                        mol_type = protein
                        organism = unidentified
SEQUENCE: 310
MLSMFTRVAR GQAKVFTRNA STASSKPTNQ SSNKAATIAA SISGVTAALY AHQYGLIDSV      60
FASGLEEGLH APHFPWSHNG WLDSFDHNSI RRGYQVYREV CSSCHSLDRI AWRNLVAVSH     120
TSDEARAMAE EQEYTDGPND QGESFQRPGK LADYMPAPYP NEEASRAANG GALPPDLSLI     180
VKARHGGADY IMALLTGYQD PPAGIQVQEG MNFNPYFPGG GIAMGRVLFD GLVEYDDGTP     240
ATTTQMAKDV ATFLSWASEP EHDDRKKMGF QAVIILSAMT AISLYVKRLK WSPIKTRKLT     300
YNPPK                                                                 305

SEQ ID NO: 311          moltype = AA   length = 165
FEATURE                 Location/Qualifiers
source                  1..165
                        mol_type = protein
                        organism = unidentified
SEQUENCE: 311
GGSPAKKSLI GAMEAQNLKT FPKQPIFQNS KTRGNKKVTK DRRWYKDVGL GFKTPQEAIT      60
GTYIDKKCPW TGEVSIRGRI LSGKVVSTKM TRTIVIRREY LHYVPKYNRY EKRHKNLPVH     120
ASPAFRIENG DQVVVGQCRP LSKTVRFNVL RVIKNKAAAK AFAKF                     165

SEQ ID NO: 312          moltype = AA   length = 72
FEATURE                 Location/Qualifiers
source                  1..72
                        mol_type = protein
                        organism = unidentified
SEQUENCE: 312
MPPRKPRCSF KECKEQAQRI VGDCSFCSGH FCSKHRMLEA HSCSGLEDCK KESHARNADK      60
LNSERTQVIK GV                                                          72

SEQ ID NO: 313          moltype = AA   length = 161
FEATURE                 Location/Qualifiers
source                  1..161
                        mol_type = protein
                        organism = unidentified
SEQUENCE: 313
MSRNFGDFST NQATQQLYSD RPLHLPGNGL KPARQLTISS AVAFRWDSDQ TRFNLISSDR      60
REVLHISIRA KDNVLVLNTK APDGDWGREE RHELKKLFDT PMLPYITVTA TKMTYNITVP     120
SGQEIIFNKR KGFMEPAVKI EYDYDEHSAF SDPCYITVPS S                         161

SEQ ID NO: 314          moltype = AA   length = 119
FEATURE                 Location/Qualifiers
source                  1..119
                        mol_type = protein
                        organism = unidentified
SEQUENCE: 314
LLASNSRSNE LSSPPSTHLH ISQSTMVSKI LFWSGFGIAV RLWQLGIEMR PILAKQGLWA      60
YPVFAGVGGS FGYWLQGVED RQLKILAQRR EAILDKRRRR DEREGLSNIE KEGTLAATP      119

SEQ ID NO: 315          moltype = AA   length = 91
FEATURE                 Location/Qualifiers
source                  1..91
                        mol_type = protein
                        organism = unidentified
SEQUENCE: 315
LNWSCNFADC WPRTPDRTNS PLLRQRTFTY RKAQWFPRFS SGVASASPSV SGNSVSKCVP      60
FLPSRVSGPT PSSQVSVEAS VTGSRVSRTV S                                     91

SEQ ID NO: 316          moltype = AA   length = 182
FEATURE                 Location/Qualifiers
source                  1..182
                        mol_type = protein
                        organism = unidentified
SEQUENCE: 316
MIHAQQCNCR SFSEGSENKQ QPTQQIMGSQ PKYPPSQCCS DPHARPVSGA CRGWLRGAAQ      60
ESSADGPRHP GASNRSFHRH LRRRGRPRDP AWQEWDAFRY RVARDGRRCR SHSRRESWKP     120
LCFAICEGAL TEERRVRSIG SSRPAISEIA GPIQTPATKA NTAGDNRESG ESTPANKKFS     180
AR                                                                    182

SEQ ID NO: 317          moltype = AA   length = 127
FEATURE                 Location/Qualifiers
```

```
source                  1..127
                        mol_type = protein
                        organism = unidentified
SEQUENCE: 317
MPSNAIAGLS PKAVKINNSQ RNKSWGRSQS TLLLNVAQTL TLVPSPALVE DGFAALRKNL    60
QLTVLDTLEP VTEASTDTCE DGVGPETLLG KNGTHFDTEL PETDGDAEAT PEENLGNHCA   120
LRYVKVR                                                             127

SEQ ID NO: 318          moltype = AA  length = 300
FEATURE                 Location/Qualifiers
source                  1..300
                        mol_type = protein
                        organism = unidentified
SEQUENCE: 318
MPFIKEAKSN SYFSRYQVKY RRRREGKTDF YARKRLVTQA KNKYNAPKYR LVVRFTNKDI    60
ICQIVSSKLQ GDVVLTHARA RELPRYGIKH GLTSWSSAYA VGLLVARRAL TKLGLADKYE   120
GDVEATGEYN LTEPLGDDEP RPFKVFLDVG LKRTSTGSRV FGALKGASDG GLYIPHSENR   180
FPGYDIESKE LDAEILNKYI LGGHIAEYME ALEEEDEERF KAQFSTYLED GIGSEDIEEI   240
FSGAHEAIRA DPTFKPSEAA KGTDWKSESK KHRAVRLTKQ QREDAIQQRI KYYQQAGDLE   300

SEQ ID NO: 319          moltype = AA  length = 212
FEATURE                 Location/Qualifiers
source                  1..212
                        mol_type = protein
                        organism = unidentified
SEQUENCE: 319
MAFMNLPWPT ECLHAALKNG SLPFWGFVIY RTTYTAQSDA AWPQIIELIA SYMKALLYHE    60
YNDKKKDGDE PTVYDEIWAR HQLTIMDDRQ FNGASVFDIQ LHFEKWVEAQ GKRDESTMYR   120
MCMVIDDESI QTLLEAPPGE NRKLGRRIGG PVRFVKVVEA FPELDSLDEF QGWMKCEINA   180
LWPLWKMMSD GDEMRMSYDE MKGNGKQVYG AI                                 212

SEQ ID NO: 320          moltype = AA  length = 192
FEATURE                 Location/Qualifiers
source                  1..192
                        mol_type = protein
                        organism = unidentified
SEQUENCE: 320
MTEKLYTEQV NAFGNELPPL SYKDLDKLPL HQNVIKETLR IHNSIHTLMR KVKNPLPVPG    60
TRFVIPTSHT LLASPGVTTR DDSHFRNAMT WDPHRWETRS EVEDDGETID YGYGVVSKGT   120
KSPYLPFGAG RHRCIGEKFA YLNLTVIVAT LVRNFRFSEP DDREGVPETD YSSLFSRPMR   180
PATARWERRG EY                                                       192

SEQ ID NO: 321          moltype = AA  length = 210
FEATURE                 Location/Qualifiers
source                  1..210
                        mol_type = protein
                        organism = unidentified
SEQUENCE: 321
MAHWREEYLT ALAVRDQREK ANLSIYDAYT RLADSTAKLP ATIDTSGSPS GDKGPSGTYE    60
SEKTAFSQSR TAKKQQTEVE PSVTELLNTT RAELAEAQRS RAELRDRLER ATNEAEKLRK   120
QIGKDGRRIH GLENEVAQQQ KRRKDVEEEL RGKAKLLNEF QDEIAALTLQ VNMAERKAKK   180
LGEENDDLVN RWMKRMGQEA DAMNDASKFS                                    210

SEQ ID NO: 322          moltype = DNA  length = 53
FEATURE                 Location/Qualifiers
misc_feature            1..53
                        note = poly-A mRNA primer
misc_feature            52..53
misc_feature            52
                        note = a,c or g
misc_feature            53
                        note = n is a, c, g, or t
source                  1..53
                        mol_type = other DNA
                        organism = synthetic construct
SEQUENCE: 322
attctagagc gatcgcacat gtttttttt ttttttttttt tttttttttt tvn           53

SEQ ID NO: 323          moltype = DNA  length = 34
FEATURE                 Location/Qualifiers
misc_feature            1..34
                        note = poly-A mRNA primer
misc_feature            32..33
                        note = Ribonucleotide Guanosine
source                  1..34
                        mol_type = other DNA
                        organism = synthetic construct
misc_RNA                34
                        note = Locked Nucleic Acid (LNA)
```

-continued

```
SEQUENCE: 323
aagcagtggt atcaacgcag agtggcgcgc cggg                              34

SEQ ID NO: 324          moltype = DNA  length = 34
FEATURE                 Location/Qualifiers
misc_feature            1..32
                        note = oligo-capping rapid amplification of cDNA ends
                         primers
misc_feature            1
                        note = 5' Inverted Dideoxy-T
misc_feature            2..32
                        note = Ribonucleotide
source                  1..34
                        mol_type = other DNA
                        organism = synthetic construct
SEQUENCE: 324
aagcagtggt atcaacgcag agtggcgcgc cggg                              34

SEQ ID NO: 325          moltype = DNA  length = 33
FEATURE                 Location/Qualifiers
misc_feature            1..33
                        note = primer for amplification of prokaryote cDNA library
misc_feature            1
                        note = 5' Inverted Dideoxy-T
misc_feature            2..33
                        note = Ribonucleotide
source                  1..33
                        mol_type = other DNA
                        organism = synthetic construct
SEQUENCE: 325
taagcagtgg tatcaacgca gagtggcgcg ccg                               33

SEQ ID NO: 326          moltype = DNA  length = 20
FEATURE                 Location/Qualifiers
misc_feature            1..20
                        note = primer for CaMV 35S promoter
source                  1..20
                        mol_type = other DNA
                        organism = synthetic construct
SEQUENCE: 326
ccactgacgt aagggatgac                                              20

SEQ ID NO: 327          moltype = DNA  length = 20
FEATURE                 Location/Qualifiers
misc_feature            1..20
                        note = primer for CBF3 promoter
source                  1..20
                        mol_type = other DNA
                        organism = synthetic construct
SEQUENCE: 327
cagcatgctc tcactccaac                                              20

SEQ ID NO: 328          moltype = DNA  length = 20
FEATURE                 Location/Qualifiers
misc_feature            1..20
                        note = primer for Erd10 promoter
source                  1..20
                        mol_type = other DNA
                        organism = synthetic construct
SEQUENCE: 328
cgtgagaatg acacaaccac                                              20

SEQ ID NO: 329          moltype = DNA  length = 18
FEATURE                 Location/Qualifiers
misc_feature            1..18
                        note = primer for Kin1 promoter
source                  1..18
                        mol_type = other DNA
                        organism = synthetic construct
SEQUENCE: 329
ctcgtggcac cacactcc                                                18

SEQ ID NO: 330          moltype = DNA  length = 19
FEATURE                 Location/Qualifiers
misc_feature            1..19
                        note = primer for NOS/HSP terminator
source                  1..19
                        mol_type = other DNA
                        organism = synthetic construct
```

-continued

```
SEQUENCE: 330
ggaaattcgc tcgagatc                                                        19

SEQ ID NO: 331          moltype = DNA  length = 1391
FEATURE                 Location/Qualifiers
source                  1..1391
                        mol_type = genomic DNA
                        organism = Arabidopsis thaliana
SEQUENCE: 331
ataccggagc tcagagaatc atatgactaa ggacgtggtg gttgaaggaa atgagagaat          60
acatgaagaa gagaaacttc tttgagtgag aaggaagtgc gctggctgga gagaaaagag        120
agaaagagt ttcgagtgag agagagggcg ttgagattgt gatcaactta atgtaatatg         180
ttcttttatt acattttctt tttgtcatat actcaaacct tttactattt tgtctcataa        240
atctaacaca ccccaccatt tgttaatgca tgatggtaga aaatattaaa tataattaac        300
tactttatg tgatcaaaat taggtttcag actcgtttcg cgatccgatc tacaattaca         360
actgcatgct tctaattgat ctaaattcta aattttttat acatattaaa aaaacaactt        420
tttgttaaat tctcaatcat cattttttgtg attaacaatt ttttataact ctaaaccaat       480
aatatttgat tatttatttt atatgtataa tgatgattga gaattttaat tagcagtcta        540
tttagggttt tcctaaagtt acaatatgtt gttaccttc tagttaaatt ttccaaaata         600
ccatatttca taacttttca aactgtttat taattcaacc gtaaaaagca ctaaaatgtt        660
acatttgatc attcacccaa attaaattca aaagtttttc cgccaaaact acttggtgac        720
ttacgtgctt atatacggac gactattatt atgttctata cttttttata ctttgttgca        780
caaatatcta ctctcccaat tcatattcta gaaggatgtg ctataagaat gggagaaatt        840
acacaagaag agcatctta aatatcctct cacaatcttt atgtctaata cacgggtgaa         900
caattaacga caatttcttt attcaggaat ataaatga ataacggtta ccctacacct          960
agtacactaa atccttaaca gccacacatt catacgcaaa gagtttataa aactcataaa       1020
ggtataataa taacgagtga ataagtcaaa aaaagtcttc tctggacaca tggcagatct       1080
taatgagtga atccttaaac tactcattt acaattgctt cgctgtgtat agtttacgtg        1140
gcattaccag agacacaaac tccgtcttcg ccttttcttt tgcctctaaa atatcttccg       1200
ccattataaa acagcatgct ctcactccaa cttttattta tctacaaaca ttaaatccac       1260
ctgaactaga acagaaagag agagaaaacta ttatttcagc aaaccatacc aacaaaaaag     1320
acagagatct tttagttacc ttatccagtt tcttgaaaca gagtactctt ctgatcaggc      1380
gcgccgccat a                                                            1391

SEQ ID NO: 332          moltype = DNA  length = 1215
FEATURE                 Location/Qualifiers
source                  1..1215
                        mol_type = genomic DNA
                        organism = Arabidopsis thaliana
SEQUENCE: 332
ataccggagc tcgactaggt ggacaaaata atttgttaat taaataaaaa ttagttcaat          60
atagaaatga aaacgattgc tttgtttggt atgtgtcggt acagtgacca tcctaatgcc        120
taatataaaa gattcgatcg gtatgttaca agttgcgtgt atatgaaaac gtcacatttt        180
attaagtggc acgtcgttgt gatgaatctt tcaaccgaac acgattcata atctataagc        240
aaaatccgaa aatggtgcct tctcaatgcc ccctatctgt tcaatctttt tttttttttt        300
ttttttttgta tatctgttca atcttattta aatgtaatga caaattaaat gaagtttacg       360
ttagtaatat aagctgacaa acaacaccac attacataca taaaattaaa ttcttttaag       420
tatttcaata acgtttcttt atcttaaaaa ttaaatttac ttcgagagct tcctacttcg       480
tcaaaaataa aattttacttt tgctgcatgt ttttacttt ttttgtaac gtcttaaaaa        540
ggtgattaac gtcaacttaa ttcaccgaaa gtctctgcaa ttgatatttt ctgccgacgt       600
ggcataagaa gtccgattgg cccacatgac cgacatccac gcttaaacca atcaaaaccg      660
gccattcagt tccatctgtg ggctcctgaa acgttctctt gacacgtgtt taccatatat       720
tggcttaatc catccatagt ctttctattt actgacaggt agtattttc ctatcaatta       780
tttattttca cgtggcatga tggctatggc tagttgaacc tgtgaataac ttggtcatat      840
ctactctcta tttatttaga tgattcattt tcttgaagga cttgcaattt tatccccta      900
cttttatttc tttgagagat aacctaaaat tctcaaaatg agttggaaac atcccttga      960
agttcctcta caggctttct atgtgcataa gaatctgctt aacattggaa ataatatatg    1020
cattcttctc caattctcct agttggatac atatatgaag tctataaatt acacatattt    1080
cccacaaaaa ttattgtaag agtttatatt tcaacatata gtatgcaaac ttaaatcgtg    1140
agaatgacac aaccactaat tcaaaccact acattatata ttctaatcca ttcaaattca    1200
tggcgcgccg ccata                                                     1215

SEQ ID NO: 333          moltype = DNA  length = 960
FEATURE                 Location/Qualifiers
source                  1..960
                        mol_type = genomic DNA
                        organism = Arabidopsis thaliana
SEQUENCE: 333
ataccggagc tcggtaactt gaattcaacc atgaactgtt tggattggca aacataaact         60
caaataaaat atctaggtat aattgtggtt catacaagaa ttacttcata ctgttgggcc       120
aaaggacgta tccttccccg cacctccaaa ccatgggctt actactgatc cgacatcaaa      180
accgtgttag ttgcaaccaa cgaatgataa gtcaataaga ttcaacttgt caacaaatat      240
acagcttata tgacatgtct ggctccaaac tgaatttag tagaaagtta ctaattcata       300
aaattaattt atatcaatt tttcaatttt tattttataa attaaagaaa aaaacatgaa       360
aaatacggga ggttcggcaa acacaacatt taacttgcca aacgtatcat ctaactttcc     420
caccttatac aaggaaccat ttttccaata ataaagttttt ttttttttttg tcttcgcaaa    480
taagagcacg aaatgtttgc caaacgcata tgcaacaaac ccacgttaca taattctgtt    540
tacagccata gagcaagcta tattgttaaa gacctaaaaa aaactttact ataacatata    600
gaggcttcga gatatttcga aagactcaac ttatatataa ataaactcaa aaagaaaaca    660
```

-continued

```
cggaggcgag aggatcatac tctcacacag aaagagtcac attattatat cctctaaaaa 720
accaaactaa aacgacacgt gaagtcttga tcagccgata aatagctacc gacataaggc 780
aaaactgatc gtaccatcaa atgtaatcca cgtggtttta gattactcgt ggcaccacac 840
tccctttagc ctataaatat aaaccattaa gcccacatct cttctcatca tcactaacca 900
aaacacactt caaaaacgat tttacaagaa ataaatatct gaaaaaggcg cgccgccata 960
```

METHODS FOR IMPROVING TRAITS IN PLANTS

RELATED APPLICATIONS

This application is a Continuation of U.S. patent application Ser. No. 17/388,310, filed on Jul. 29, 2021, which is a Continuation of U.S. patent application Ser. No. 16/496,445 filed on Sep. 22, 2019 (issued as U.S. Pat. No. 11,111,491), which is the U.S. National Stage of International Patent Application No. PCT/IL2018/050349, filed on Mar. 27, 2018, which claims the benefit of priority of U.S. Provisional Application Nos. 62/477,517 and 62/644,600, filed on Mar. 28, 2017 and Mar. 19, 2018, respectively. The contents of the above applications are all incorporated by reference as if fully set forth herein in their entirety.

SEQUENCE LISTING

The official copy of the sequence listing is submitted electronically in ST.26 XML format having the file name "11184_033US-CON3_Seq_List.xml" created on Mar. 27, 2018, and having a size of 452,840 bytes, and is filed concurrently with the specification. The Sequence Listing ST.26 XML file is part of the specification and is herein incorporated by reference in its entirety.

FIELD OF THE INVENTION

The present invention generally relates to the field of improving traits in plants. More particularly, the present invention relates to improving traits in plants by transformation of expression libraries from predefined sources into plants and screening for desirable traits.

BACKGROUND OF THE INVENTION

The world population is estimated to be 9.2 billion in 2050. To sufficiently feed this population, the total food production will have to increase by 60%-70%. Climate models predict that warmer temperatures and increases in the frequency and duration of drought during the present century will have negative impact on agricultural productivity. For example, maize production in Africa could be at risk of significant yield losses as researchers predict that each degree-day that the crop spends above 30° C. reduces yields by 1% if the plants receive sufficient water. These predictions are similar to those reported for maize yield in the United States. It has been further shown that maize yields in Africa decreased by 1.7% for each degree-day the crop spent at temperatures of over 30° C. under drought. Wheat production in Russia decreased by almost one-third in 2010, largely due to the summer heat wave. Similarly, wheat production declined significantly in China and India in 2010, largely due to drought and sudden rise in temperature respectively, thereby causing forced maturity. These new global challenges require a more complex integrated agriculture.

In addition global warming leads to the concurrence of a number of abiotic and biotic stresses, thus affecting agricultural productivity. Occurrence of abiotic stresses can alter plant-pest interactions by enhancing host plant susceptibility to pathogenic organisms, insects, and by reducing competitive ability with weeds. On the contrary, some pests may alter plant response to abiotic stress factors.

Biotic stress factors are caused by pathogens, insects, pests, weeds, or intraspecific competition for resources. The ability of biotic stress factors to cause yield or quality loss depends on the environment and thus may vary from region to region or from one agroecology to another. For example, in Australia, barley foliar diseases are some of the major biotic stress factors causing substantial yield and quality losses. Although it is known that some plant species have resistance to various diseases, they are hard or even impossible to breed in conventional methods.

The challenge is to create crops that are resistance to biotic stress factors and are flexible and adaptable to diverse environments and populations. There are currently two major acceptable ways to adapt crops to new environments: developing new crops through conventional breeding (long-term endeavor starting with domestication) and introducing target traits into existing crops through plant breeding, which includes genetic engineering. To maintain productivity in the face of increased climatic variability, both the population and the plant cultivars will need to be continually developed to withstand "new" climate extremes and other stresses such as diseases, pathogens, insects, pests etc. In addition there is a constant need to find new herbicide tolerance or resistant genes for new chemicals and new herbicides mode of action.

Genetic engineering has the potential to address some of the most challenging biotic and abiotic constraints faced by farmers, which are not easily addressed through conventional plant breeding alone.

Advantageous outcomes of these genetic modifications include increased food production, reliability, and yields; enhanced taste and nutritional value; and decreased losses due to various biotic and abiotic stresses, such as fungal and bacterial pathogens. These objectives continue to motivate modern breeders and food scientists, who are seeking for newer genetic modification methods for identifying, selecting, and analyzing individual organisms that possess genetically enhanced features.

The option to transform plants with foreign genes and/or genes from the same specie or genus, that are hard or impossible to breed, overcomes species barriers, making it possible to exploit powerful 'super-traits' that are not attainable through traditional methods. However, the molecular interactions and outcomes of introduced trans-genes and endogenous genes are not predictable.

When genes coding for certain traits are transferred, typically from one plant species to another, the desired traits are not always expressed unless the environment interacts with the genes in the anticipated way triggering the desired response, which depends on the regulating sequences inserted with the gene. This means that new transgenic cultivars, developed under laboratory conditions in a controlled climate, have to be tested under field conditions, as in more traditional breeding methods, so currently there is little difference in the speed with which either method will result in the release of new cultivars.

The knowledge gained from basic plant research will underpin future crop improvements, but effective mechanisms for the rapid and effective translation of research discoveries into public good agriculture remain to be developed.

U.S. Pat. Nos. 6,030,779 , 6,368,798 disclose a process for identifying clones having a specified enzyme activity by selectively isolating target nucleic acid from genomic DNA population, by use of polynucleotide probe identifying the nucleic acid sequence encoding an enzyme having the specified enzyme activity; and transforming a host with the isolated target nucleic acid to produce a library of clones which are screened for the specified enzyme activity.

U.S. Pat. No. 6,972,183 discloses a process for screening an expression library to identify clones expressing enzymes having a desired activity. The process involves generating from genomic DNA samples of one or more microorganisms an expression library comprising a plurality of recombinant cell clones, and then introducing into capillaries in a capillary array a substrate and a subset of the clones. Interaction of the substrate and a clone expressing an enzyme having the desired activity produces an optically detectable signal, which can then be spatially detected to identify capillaries containing clones producing such a signal. The signal-producing clones can then be recovered from the identified capillaries.

EP patent application 1025262 and U.S. patent application No. 20020150949 teach a process for identifying clones having a specified activity of interest, by (i) generating expression libraries derived from nucleic acid directly isolated from the environment; (ii) exposing said libraries to a particular substrate or substrates of interest; and (iii) screening said exposed libraries utilizing a fluorescence activated cell sorter to identify clones which react with the substrate or substrates.

U.S. patent application No. 20100152051 relates to a method for the identification and/or characterization of clones conferring a desired biological property from an expression library. The method comprises the step of screening for the expression of at least one (poly) peptide, such as a tag expressed as a fusion protein, together with a recombinant insert of a clone of said expression library. Said (poly) peptide may be fused N-terminally or C-terminally to said insert. The method further comprises the steps of contacting a ligand specifically interacting with the (poly) peptide expressed by the insert of a clone conferring said desired biological property.

All the above methods are based upon screening a DNA library (produced from microorganisms or environmental sample) for a specific sequence or biochemical activity via interaction with a predetermined probe. In addition, the screening and selection for a clone having the predetermined sequence or activity is performed prior to transformation into plant cells and could be expressed in plant cells (tissue cultures) but not in whole plants. Thus by the up-to-date used methods, only the preselected clone is expressed in plants and the expression and effect of the selected sequence in plants is unpredictable. In addition, in the methods described above, one can screen only for known activities based on prior knowledge. Thus, these methods are limited under the scope of known enzyme activities and enzyme families and prior known function.

In view of the above, there is a long felt need for efficient methods for screening and identifying unknown sequences conferring desirable plant improving traits.

SUMMARY OF THE INVENTION

It is therefore one object of the present invention to disclose a method for screening for and identifying a desirable plant improving trait, the method comprises steps of: (a) obtaining genetic material from a sampling of a predefined source; (b) constructing an expression library from said genetic material; wherein said method further comprises steps of: (c) producing plants transformed with said expression library at a transformation efficiency of at least 0.05%-30%, representing at least $10^2$-$10^{10}$ transgenes; (d) screening for transformed plants expressing said desirable trait; and (e) identifying said transgene of said transformed plants expressing said desirable trait.

It is a further object of the present invention to disclose the method as defined above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose the method as defined in any of the above, wherein said step (a) further comprises steps of enriching said genetic material by growth on rich media or on selective media.

It is a further object of the present invention to disclose the method as defined in any of the above, wherein said step (a) further comprises steps of enhancing expression of said desirable trait by culturing said genetic material on selective media for said desirable trait.

It is a further object of the present invention to disclose the method as defined in any of the above, wherein said step (b) comprises steps of producing prokaryotic cDNA library or eukaryotic cDNA library or both.

It is a further object of the present invention to disclose the method as defined in any of the above, wherein said step (b) further comprises steps of cloning said cDNA library into at least one binary vector.

It is a further object of the present invention to disclose the method as defined in any of the above, wherein said binary vector comprises a constitutive promoter or a stress induced promoter.

It is a further object of the present invention to disclose the method as defined in any of the above, wherein said binary vector comprises bacterial selection marker and plant transformation selection marker.

It is a further object of the present invention to disclose the method as defined in any of the above, further comprises steps of transforming said cloned binary vectors into host cells.

It is a further object of the present invention to disclose the method as defined in any of the above further comprises steps of transforming said cloned binary vectors into *Agrobacterium tumefaciens*.

It is a further object of the present invention to disclose the method as defined in any of the above further comprises steps of introducing said transformed *Agrobacterium tumefaciens* into at least one of: whole plant, plant tissue and plant cell.

It is a further object of the present invention to disclose the method as defined in any of the above, comprises steps of introducing said transformed *Agrobacterium tumefaciens* by spraying said plants with an inoculum comprising transformed *Agrobacterium*.

It is a further object of the present invention to disclose the method as defined in any of the above, wherein said step (d) comprises growing said transformed plants under conditions selective for said desirable trait.

It is a further object of the present invention to disclose the method as defined in any of the above, further comprises steps of: (f) collecting T1 seeds from said transformed plants of step (d); (g) determining seed library transformation efficiency of said T1 seeds; (h) sowing said T1 seeds of step (e) under selective conditions allowing screening and selection of transformed plants expressing said desirable trait; (i) testing said selected plants expressing said desirable trait of step (g) for presence of said transgene; and (j) isolating and sequencing said transgene of said selected transformed plants positively tested for said transgene of step (h).

It is a further object of the present invention to disclose the method as defined in any of the above, further comprises steps of (k) collecting T2 seeds from said plants of (h), which are found positive for presence of said transgene; (l) growing plants of said T2 seeds under selective conditions allowing screening and selection of transformed plants expressing said desirable trait as compared to control plants transformed with known genes conferring said desirable trait; and (m) optionally, isolating and sequencing said transgene of said selected plants of step (j).

It is a further object of the present invention to disclose the method as defined in any of the above, comprises steps of (a) recloning and sequencing said isolated transgene of step (i) and/or (l); (b) transforming said recloned transgene into plants; (c) screening said transformed plants of step (b) for selection of transformed plants expressing said desirable trait; (d) isolating said transgene from said selected plants of step (c); and (e) optionally, repeating steps (a) to (d).

It is a further object of the present invention to disclose the method as defined in any of the above, wherein said environmental niche comprises ecological niche, populations, habitats, gene pools, prokaryotic culture, eukaryotic culture and any combination thereof.

It is a further object of the present invention to disclose the method as defined in any of the above, wherein said environmental niche comprises microbiome, microbiota, microbial culture, plant, yeast, algae, nematode or any other organism or combinations thereof.

It is a further object of the present invention to disclose the method as defined in any of the above, wherein said environmental niche comprises predefined biotic factors, abiotic factors and a combination thereof.

It is a further object of the present invention to disclose the method as defined in any of the above, wherein said sampling comprises soil sample, water sample, organic matter sample and any combination thereof.

It is a further object of the present invention to disclose the method as defined in any of the above, wherein said desirable trait is selected from the group consisting of resistance or tolerance to at least one biotic stress, resistance or tolerance to at least one abiotic stress, improved yield, improved biomass, improved food qualities and values, improved grain yield, herbicide or chemical resistance or tolerance and any combination thereof.

It is a further object of the present invention to disclose the method as defined in any of the above, wherein said abiotic stress is selected from the group consisting of: drought, salinity, heat, cold, fertilizer uptake, fertilizer usage efficiency and any combination thereof.

It is a further object of the present invention to disclose the method as defined in any of the above, wherein said biotic stress is selected from the group consisting of: plant diseases, pathogens, bacteria, viruses, fungi, parasites, beneficial and harmful insects, weeds, and cultivated or native plants or any combination thereof.

It is a further object of the present invention to disclose the method as defined in any of the above, wherein said step (a) comprises steps of extracting RNA from said sampling of said predefined environmental niche.

It is a further object of the present invention to disclose the method as defined in any of the above, wherein said RNA extraction is performed according to standard commercial kits or according to any other protocol for extraction of RNA from environmental sampling.

It is a further object of the present invention to disclose the method as defined in any of the above, wherein said protocol for extraction of RNA from environmental sampling comprises steps of: (a) obtaining a soil sample; (b) mixing said soil sample with an extraction buffer comprising 500 mM phosphate buffer pH 8 and 5% w/v cetyltrimethylammonium bromide (CTAB) with phenol (pH 8)/chloroform/IAA ratio of 25:24:1; (c) subjecting said mixture of step (b) to 15 min shaking at 37° C. or to a bead beater for 1 min; (d) centrifuging said mixture of step (c) at 2,500 g for about 10 minutes at room temperature to obtain an aqueous phase; (e) transferring said aqueous phase into a new tube; (f) adding to said aqueous phase within said tube of step (e) an equal amount of iso-propanol supplemented with 20 mg/ml crystal violet solution to obtain violate stained solution; (g) mixing said solution by inverting said tube of step (f) and then incubating said tube for about 30 minutes at room temperature; (h) centrifuging said tube of step (g) at 2,500 g for about 30 minutes at room temperature to obtain a violet stained layer; (i) transferring said violate stained layer into a new tube and centrifuging said tube for about 5 min at maximal speed to obtain pellet and supernatant; (j) washing said pellet with 80% v/v ice cold ethanol and centrifuging for additional 5 min to obtain pellet and supernatant; (k) removing said supernatant of step (j) and allowing said pellet to dry; and (l) suspending said dried pellet in water in a ratio of 100 µl water to 2 gr of soil of step (a).

It is a further object of the present invention to disclose a plant comprising said transgene identified by the method as defined in any of the above.

It is a further object of the present invention to disclose the plant as defined above, wherein said plant has at least one plant improving trait as compared to a plant of the same genus lacking said transgene.

It is a further object of the present invention to disclose a polynucleotide sequence obtainable by the method as defined in any of the above.

It is a further object of the present invention to disclose the polynucleotide as defined in any of the above, wherein said polynucleotide comprises a nucleotide sequence corresponding to the sequence as set forth in a polynucleotide sequence selected from the group consisting of SEQ ID NOs: 1-148 and any combination thereof.

It is a further object of the present invention to disclose a polynucleotide sequence having at least 80% sequence similarity to the polynucleotide sequence as defined in any of the above.

It is a further object of the present invention to disclose a polypeptide sequence obtainable by the method as defined in any of the above.

It is a further object of the present invention to disclose the polypeptide sequence as defined in any of the above, wherein said polypeptide comprises an amino acid sequence corresponding to the sequence as set forth in a polypeptide sequence selected from the group consisting of SEQ ID NOs: 149-321 and any combination thereof.

It is a further object of the present invention to disclose a polypeptide sequence having at least 60% sequence similarity to the polypeptide sequence as defined in any of the above.

It is a further object of the present invention to disclose the use of the method as defined in any of the above for identifying genes conferring plant improving traits selected from the group consisting of resistance or tolerance to abiotic stress, resistance or tolerance to biotic stress, improved yield, improved biomass, improved food qualities and values, improved grain yield, herbicide or chemical resistance or tolerance and any combination thereof.

It is a further object of the present invention to disclose the use as defined in any of the above, wherein said abiotic stress is selected from the group consisting of: drought, salinity, heat, cold, fertilize utilization and any combination thereof.

It is a further object of the present invention to disclose the use as defined in any of the above, wherein said biotic stress is selected from the group consisting of: plant diseases, pathogens, bacteria, viruses, fungi, parasites, beneficial and harmful insects, weeds, and cultivated or native plants or any combination thereof.

It is a further object of the present invention to disclose a method for screening for and identifying a drought or salinity resistance or tolerance improving trait in plants, said method comprises steps of: (a) obtaining genetic material derived from a low moisture or a high salinity source sample; (b) constructing expression library from said genetic material; wherein said method further comprises steps of: (c) producing plants transformed with said expression library at a transformation efficiency of at least 0.5%-30% representing at least $10^2$-$10^{10}$ transgenes; (d) screening for transformed plants resistant or tolerant to predetermined drought or salinity conditions; and (e) identifying said transgene of said drought or salinity resistant or tolerant transformed plants of step (d).

It is a further object of the present invention to disclose the method as defined in any of the above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose the method as defined in any of the above, wherein said step (b) further comprises steps of cloning said expression library into at least one binary vector.

It is a further object of the present invention to disclose the method as defined in any of the above, further comprises steps of: (f) collecting T1 seeds from said transformed plants of step (c); (g) sowing said T1 seeds in soil selective for transformed plants, with water content of about 100% capacity; (h) growing plants of said T1 seeds in drought or salinity conditions and/or without irrigation until most of the plants die, to produce transformed plants surviving said drought or salinity conditions; (i) growing said drought or salinity surviving transformed plants to produce T2 seeds; (j) screening said drought or salinity surviving transformed plants of step (i) for presence of a transgene; and (k) isolating and sequencing said transgene from positively screened plants of step (j).

It is a further object of the present invention to disclose the method as defined in any of the above, further comprises steps of (1) collecting T2 seeds from each of said transgene-containing positively screened drought or salinity surviving transformed plants of step (j); (m) growing T2 plants from each of said transgene-containing T2 seeds of step (1) under predetermined drought or salinity conditions as compared to control plants of the same genus and lacking said transgene or transformed with known genes conferring drought or salinity tolerance or drought or salinity resistance; (n) performing drought tolerance or resistance screening measurements for each of said transgene-containing T2 plants as compared to said control plants, said measurements are selected from the group consisting of: turgor pressure measurements, plant death, leaf area, fresh weight, leaf number, branch fresh weight, main branch length, flowers and pods production, Chlorosis and damage to leaves, state or performance of plants and any combination thereof; (o) isolating the transgene from said screened dough or salinity resistance performing T2 plants of step (n); (p) optionally, recloning said transgene into a binary vector; (q) optionally, transforming said cloned binary vector into plants and growing said transformed plants under predetermined drought or salinity conditions; and (r) optionally, repeating steps (1) to (q).

It is a further object of the present invention to disclose the method as defined in any of the above, wherein said step of growing T2 plants comprises steps of: (a) sowing said T2 seeds in soil selective for transformed plants, with water content of about 100% capacity; and (b) irrigating said plants when water content in the soil reaches about 5-10%.

It is a further object of the present invention to disclose the method as defined in any of the above, wherein said predetermined drought or salinity conditions are selected from the group consisting of low moisture, high salinity, dry soil and heat.

It is a further object of the present invention to disclose a polynucleotide sequence obtainable by the method as defined in any of the above.

It is a further object of the present invention to disclose the polynucleotide as defined in any of the above, wherein said polynucleotide comprises a nucleotide sequence corresponding to the sequence as set forth in a polynucleotide sequence selected from the group consisting of SEQ ID NOs: 1 to SEQ ID NO:148 and any combination thereof.

It is a further object of the present invention to disclose a polynucleotide sequence having at least 80% sequence similarity to the polynucleotide sequence as defined in any of the above.

It is a further object of the present invention to disclose a polypeptide sequence obtainable by the method as defined in any of the above.

It is a further object of the present invention to disclose the polypeptide sequence as defined in any of the above comprises an amino acid sequence corresponding to the sequence as set forth as set forth in polypeptide sequence selected from the group consisting of SEQ. ID Nos: 149-321 and any combination thereof.

It is a further object of the present invention to disclose a polypeptide sequence having at least 60% sequence similarity with the polypeptide sequence as defined in any of the above.

It is a further object of the present invention to disclose a method for extracting RNA from a soil sample comprising steps of: (a) obtaining a soil sample; (b) mixing said soil sample with an extraction buffer comprising 500 mM phosphate buffer pH 8 and 5% w/v cetyltrimethylammonium bromide (CTAB) with phenol (pH 8)/chloroform/IAA ratio of 25:24:1; (c) subjecting said mixture of step (b) to 15 min shaking at 37° C. or to a bead beater for 1 min; (d) centrifuging said mixture of step (c) at 2,500 g for about 10 minutes at room temperature to obtain an aqueous phase; (e) transferring said aqueous phase into a new tube; (f) adding to said aqueous phase within said tube of step (e) an equal amount of iso-propanol supplemented with 20 mg/ml crystal violet solution to obtain violate stained solution; (g) mixing said solution by inverting said tube of step (f) and then incubating said tube for about 30 minutes at room temperature; (h) centrifuging said tube of step (g) at 2,500 g for about 30 minutes at room temperature to obtain a violet stained layer; (i) transferring said violate stained layer into a new tube and centrifuging said tube for about 5 min at maximal speed to obtain pellet and supernatant; (j) washing said pellet with 80% v/v ice cold ethanol and centrifuging for additional 5 min to obtain pellet and supernatant; (k) removing said supernatant of step (j) and allowing said pellet to dry; and (l) suspending said dried pellet in water in a ratio of 100 µl water to 2 gr of soil of step (a).

It is a further object of the present invention to disclose a method for screening for and identifying a desirable plant improving trait, said method comprises steps of: (a) obtaining a sampling of a predefined source; (b) extracting RNA from said sampling; (c) constructing an expression library from RNA of step (b); wherein said method further comprises steps of: (d) producing plants transformed with said expression library at an efficiency of at least 0.05%-30% representing at least $10^2$-$10^{10}$ transgenes; (e) screening for transformed plants expressing said desirable trait; and (f) identifying said transgene of said transformed plants expressing said desirable trait.

It is a further object of the present invention to disclose the method as defined in any of the above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose an isolated polynucleotide having at least 80% sequence similarity to a nucleotide sequence selected from the group consisting of SEQ ID NOs: 1 to SEQ ID NO:148 and any combination thereof.

It is a further object of the present invention to disclose an isolated polypeptide having at least 60% sequence similarity to an amino acid sequence selected from the group consisting of SEQ. ID Nos: 149-321 and any combination thereof.

BRIEF DESCRIPTION OF THE DRAWINGS

In order to understand the invention and to see how it may be implemented in practice, several embodiments will now be described, by way of non-limiting example only, with reference to the accompanying drawing, in which:

FIG. 1A illustrates the pPA-35H vector, which has a constitutive CaMV 35S promoter. FIGS. 1B-D present vectors containing stress induced promoters of *Arabidopsis thaliana*: pPA-CH with CBF3 promoter (FIG. 1B), pPA-EH with Erd10 promoter (FIG. 1C) and pPA-KH with Kin1 promoter (FIG. 1D);

DETAILED DESCRIPTION OF THE PREFERRED EMBODIMENTS

Figure 1A:
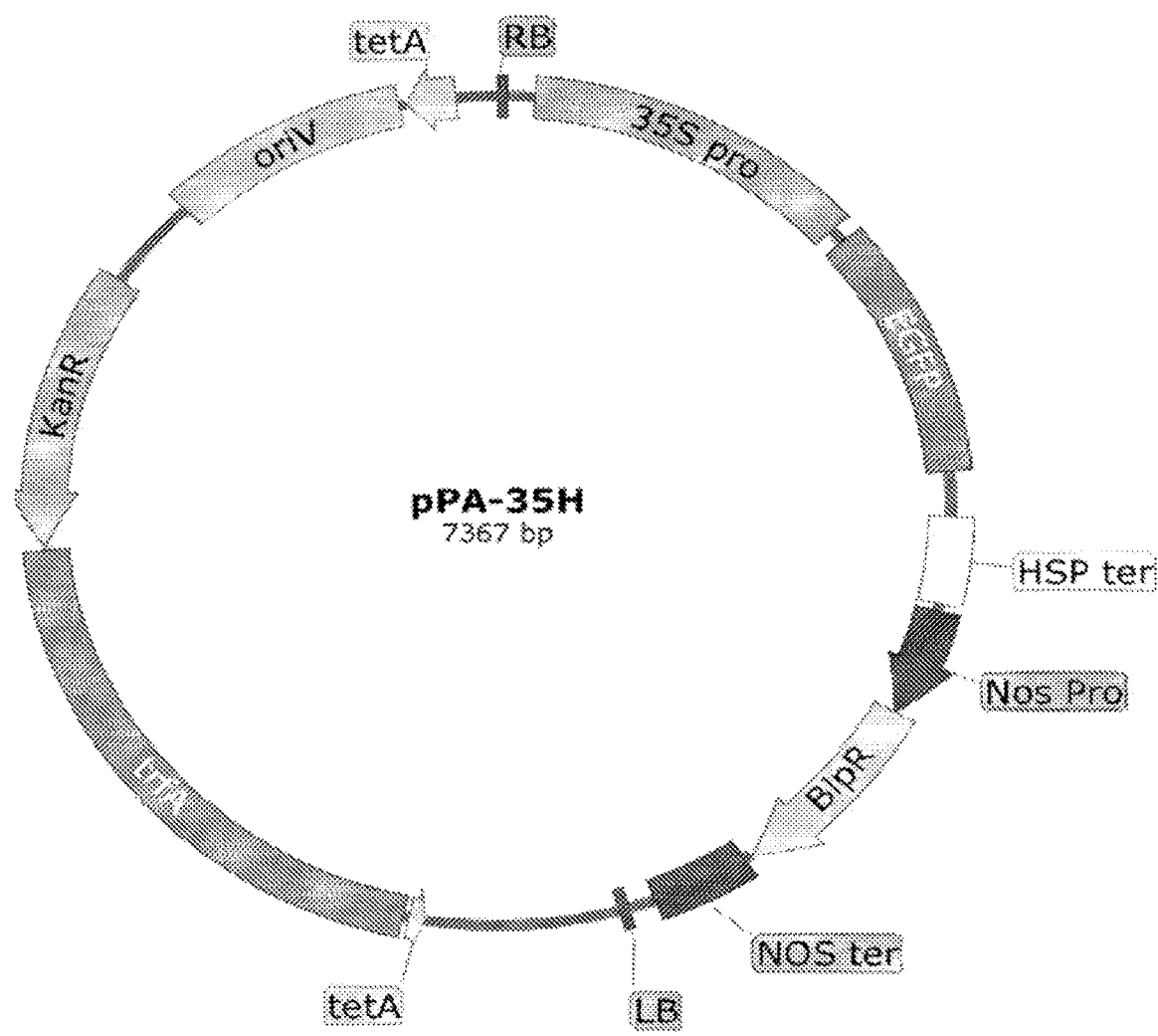
FIGS. 1A-D present schematic illustrations of binary vectors used for insertion of amplified cDNA clones between the promoter(s) (35S, CBF3, Erd10 and Kin1) and the HSP terminator.

The following description is provided, alongside all chapters of the present invention, so that to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for screening and identifying a desirable plant improving trait.

It is known that some plant species have resistance to various diseases. However, such species are usually hard or impossible to breed in conventional techniques and methods.

The present invention provides a method and platform to discover and identify genes from plants that have unique and valuable features, such as disease resistance, abiotic stress resistance or tolerance, food improving qualities (e.g. improved oils, protein content, amino acids, vitamins etc.) and then to insert or express them in desired crops through gene editing, or other transformation technique.

It is therefore within the scope of the present invention to introduce target traits into existing crops through plant breeding, which includes genetic engineering and gene (genome) editing.

The present invention provides a novel method for screening and identifying a desirable plant improving trait. The method comprises steps of: (a) obtaining genetic material from a sampling of a predefined environmental niche or genetic material extracted from other sources such as plants from the same or other genus; and (b) constructing an expression library from said genetic material. According to core aspects, the present invention further comprises steps of: (c) producing plants transformed with said expression library at an efficiency of at least 0.05%-30% representing at least $10^2$-$10^{10}$ transgenes; (d) screening for transformed plants expressing said desirable trait; and (e) identifying said transgene of said transformed plants expressing said desirable trait.

The present invention provides for the first time a method for screening for and selecting unknown sequences derived from predefined sources (e.g. ecological niches and/or plants) which confer improved traits in valuable crop plants. The current method is effective and advantageous upon common and conventional screening methods by the following aspects:

1. An expression library is prepared from genetic material or genetic pool (i.e. RNA) originating from predefined sources, such as extreme environment, plant material and other. In this way, only genes which are expressed in the preselected environmental conditions are used for the screening procedure in plants.
2. The entire expression library is transformed into plants at an efficiency of 0.05%-30% and representation of at least $10^2$-$10^{10}$ unique transgenes.
3. In the method of the present invention, the screening of the expressed library for the desirable phenotype is performed at the target organism, which is the plant. In this way there is no preselection and new and unique genes for the desired phenotype, which are expressible in plants, are revealed.

In the conventional methods, the first step is selecting genes for a predefined trait in a source genetic material, e.g. by probing a DNA library with known sequences in prokaryotic—or eukaryotic cells, and only then the preselected gene is expressed in plants. The outcome of such a conventional method is limited and has the following drawbacks:

1. The screening is performed in a host cell/organism which is not the target organism (usually in prokaryotic or unicellular organism).
2. The screening is limited since it is performed with known sequences or probes or activity. It was shown that functional screening methods require detectable levels of enzyme activity that cannot be always achieved, for example, only about 40% of the enzymatic activities are likely to be detected in *E. coli*-based expression systems (Gabor et al., 2004). In addition, it is herein pointed out that despite the advanced sequencing techniques available, ~35-60% of the total protein-coding genes display high similarities to "hypothetical proteins", "predicted proteins" or "protein of unknown function" (Culligan, et al., 2014; Venter, et al., 2004).
3. Only the preselected clone is transformed into plants.
4. The expression and effect of a preselected clone in the target plant is unpredictable.

For the aforementioned reasons the novel method of the present invention of screening plants transformed with an expression library for a desirable phenotype is advantageous.

It is herein acknowledged that drought and salinity are considered as two abiotic stresses that have major effects on plant growth and development.

With respect to drought, it is considered the most devastating environmental stress, which decreases crop growth and productivity. Drought severely affects plant growth and development with substantial reductions in growth rate and biomass accumulation. The main consequences of drought in plants are reduced rate of cell division and expansion, leaf size, stem elongation and root proliferation, and disturbed stomatal oscillations, and water use efficiency (WUE) (Farooq et al. 2009). This phenomenon involves genetic, physiological, and environmental events and their complex interactions. The rate and amount of plant growth depend on these events, which are affected by water deficit. Cell growth is one of the most drought-sensitive physiological processes due to the reduction in turgor pressure and water availability (Taiz and Zeiger, 2006). Under water deficiencies, cell elongation of higher plants can be inhibited by interruption of water flow from the xylem to the surrounding elongating cells. Impaired mitosis, reduced cell elongation and expansion result in reduced plant height, leaf area and crop growth (Nonami, 1998).

Salinity is also considered one of the major severe abiotic factors affecting crop growth and productivity. During salt stress, all major processes such as photosynthesis, protein synthesis and energy and lipid metabolism are affected (Parida & Das, 2005). During initial exposure to salinity, plants experience water stress, which in turn reduces leaf expansion. The osmotic effects of salinity stress can be observed immediately after salt application and are believed to continue for the duration of exposure, resulting in inhibited cell expansion and cell division, as well as stomatal closure. During long-term exposure to salinity, plants experience ionic stress, which can lead to premature senescence of adult leaves, and thus a reduction in the photosynthetic area available to support continued growth. In fact, excess sodium and more importantly chloride has the potential to negatively affect plant enzymes, resulting in reduced energy production and other physiological changes. It is further acknowledged that ionic stress results in premature senescence of older leaves and in toxicity symptoms (chlorosis, necrosis) in mature leaves. Without wishing to be bound by theory, the high sodium ions affect plants by disrupting protein synthesis and interfering with enzyme activity (Carillo et al., 2011).

The present invention provides a method for efficiently screening for novel genes conferring resistance or improved tolerance to drought and/or salinity in plants and especially in valuable crops.

The method of the present invention overcomes the above drawbacks by using expressed genetic material (such as RNA or mRNA) that represent the genes that are being expressed in selected organisms, e.g. as a result of environmental conditions (such as drought or high salt), and producing a cDNA library that represents the 'Meta-Expression' or metatranscriptome status of a certain biological niche or other genetic source. The entire cDNA library is then transformed into plants and expressed and screened for the desirable phenotype in the plants.

A core aspect of the present invention is that an expression library is produced from various sources (including plants) and environments. The expression library is transformed into plants, which is the target organism in order to improve its traits or functions. The plant expression library is then screened for the desirable trait, such as salt or drought resistance or tolerance, improved biomass and yield production, biotic stresses (diseases and pathogens) resistance or tolerance, improved nutritional value or improved fertilizers utilization.

It is herein acknowledged that the environments (such as soils) in which plants grow are inhabited by microbial communities, e.g. one gram of soil contains about 107-109 microbial cells (estimates of the number of species of bacteria per gram of soil vary between 2000 and 8.3 million, https://www.ncbi.nlm.nih.gov/pmc/articles/PMC2970868/) which comprise about one gigabase of sequence information, or more. The microbial communities which inhabit environments in which plants grow (such as soils) are complex and remain poorly understood despite their economic importance. Such microbial consortia provide the ecosystem necessary for plant growth, including fixing atmospheric nitrogen, nutrient cycling, disease suppression, and sequester iron and other metals.

It is within the scope of the present invention to use functional metagenomics and metatrascriptomics approaches to explore new genes which confer improved traits to plants.

Reference is now made to metagenomics approaches, employed by the present invention according to some aspects. Metagenomics is the study of genetic material derived from environmental samples. It generally refers to as environmental genomics, eco-genomics or community genomics. While traditional microbiology and microbial genome sequencing and genomics rely upon cultivated clonal cultures, environmental gene sequencing cloned specific genes to produce a profile of diversity in a natural sample. In some aspects, metagenomics uses the study of the genomes in a microbial community to constitute the first step to studying the microbiome. Its main purpose is to infer the taxonomic profile of a microbial community. The whole-metagenome sequencing (WMS) provides data on the functional profile of a microbial community. Such work revealed that the vast majority of microbial biodiversity had been missed by cultivation-based methods. In fact it is estimated that over 99% of all microorganisms in almost every environment on earth cannot be cultivated in the laboratory.

Metagenomics is herein also refers to metatranscriptomics, which studies and correlates the transcriptomes of a group of interacting organisms or species. Metatranscriptomics involves sequencing the complete (meta) transcriptome of the microbial community. In some aspects, metatranscriptomics informs the genes that are expressed by the community as a whole. With the use of functional annotations of expressed genes, it is possible to infer the functional profile of a community under specific conditions, which are usually dependent on the status of the host. While metagenomics provides data on the composition of a microbial community under different conditions, metatrascriptomics provides data on the genes that are collectively expressed under different conditions. Metatranscriptomics involves profiling of community-wide gene expression (RNA-seq). In specific aspects, metatranscriptomics describes the genes that are expressed in a specific microbial environment. Thus, metatranscriptomics is the study of the function and activity of the complete set of transcripts (RNA-seq) from environmental samples.

It is noted that gene expression is log-like distributed, for example, top 100 genes of highest expression can cover up to 30% of all transcripts. Even a single gene can cover up to 10%. Thus, a very high sequencing depth is required to see also lower expressed genes.

By using methods such as "shotgun" or PCR directed sequencing, largely unbiased samples of the genes from the members of sampled communities can be obtained. It is herein acknowledged that metagenomics approaches provide a powerful tool for utilizing microbial ecology to improve traits in plants, for example, biological mechanisms that can be harnessed for agriculture and improved plant traits.

As used herein, the term "about" denotes+25% of the defined amount or measure or value.

As used herein the term "similar" denotes a correspondence or resemblance range of about +20%, particularly #15%, more particularly about +10% and even more particularly about +5%.

As used herein the term "average" refers to the mean value as obtained by measuring a predetermined parameter in each plant of a certain plant population and calculating the mean value according to the number of plants in said population.

As used in this specification and the appended claims, the singular forms "a", "an", and "the" include plural referents unless the context clearly dictates otherwise. Thus, for example, reference to "a plant" includes one or more plants, reference to "a trait" includes one or more traits and reference to "a cell" includes mixtures of cells, tissues, and the like.

A "plant" as used herein refers to any plant at any stage of development, including a plant seed.

The term "plant" includes the whole plant or any parts or derivatives thereof, such as plant cells, plant protoplasts, plant cell tissue culture from which plants can be regenerated, plant callus or calli, meristematic cells, microspores, embryos, immature embryos, pollen, ovules, anthers, fruit, flowers, leaves, cotyledons, pistil, seeds, seed coat, roots, root tips and the like.

The term "plant cell" used herein refers to a structural and physiological unit of a plant, comprising a protoplast and a cell wall. The plant cell may be in a form of an isolated single cell or a cultured cell, or as a part of higher organized unit such as, for example, plant tissue, a plant organ, or a whole plant.

The term "plant cell culture" or "tissue culture" as used herein means cultures of plant units such as, for example, protoplasts, regenerable cells, cell culture, cells, cells in plant tissues, pollen, pollen tubes, ovules, embryo sacs, zygotes and embryos at various stages of development, leaves, roots, root tips, anthers, meristematic cells, microspores, flowers, cotyledons, pistil, fruit, seeds, seed coat or any combination thereof.

The term "plant material" or "plant part" used herein refers to leaves, stems, roots, root tips, flowers or flower parts, fruits, pollen, egg cells, zygotes, seeds, seed coat, cuttings, cell or tissue cultures, or any other part or product of a plant or any combination thereof.

A "plant organ" as used herein means a distinct and visibly structured and differentiated part of a plant such as a root, stem, leaf, flower, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture, protoplasts, meristematic cells, calli and any group of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "trait" refers to a characteristic or phenotype, particularly, to a plant improving characteristic or phenotype. A phenotypic trait may refer to the appearance or other detectable characteristic of an individual, resulting from the interaction of its genome, proteome and/or metabolome with the environment. For example, in the context of the present invention a plant improving trait or a desirable plant improving trait relates to resistance or tolerance to at least one biotic stress, resistance or tolerance to at least one abiotic stress, improved yield or biomass, improved grain yield, improved fertilizer uptake and usage efficiency and any combination thereof.

A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment. A dominant trait results in a complete phenotypic manifestation at heterozygous or homozygous state; conventionally, a recessive trait manifests itself only when present at homozygous state.

The term "phenotype" is understood within the scope of the present invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

It is within the scope of the current invention that "stress" may be defined as any external factor that has a negative influence on plant growth, function and/or reproduction The term "abiotic stress" is herein generally defined as the negative impact of non-living factors on the plant in a specific environment. The non-living variable must influence the environment beyond its normal range of variation to adversely affect the plant or plant population performance or physiology in a significant way. Non limiting examples of abiotic stress factors, or stressors, or environmental factors may encompass factors such as sunlight, wind, temperature (cold, heat), salinity, over watering (flooding), drought and factors such as fertilizer uptake and fertilizer usage efficiency and any combination thereof. Abiotic stress resistance or tolerance may enhance the growth and productivity of plants and specifically crops. It has been shown that abiotic stressors are most harmful and may result in synergistic effects when they occur together, in combinations of abiotic stress factors.

The term "drought" refers hereinafter to a physical phenomenon generally caused by an extended period of below average precipitation or irrigation. For example, not enough or low moisture (at the soil or at the air), water supply shortages, dry soil, moisture regimes, high salinity, heat and any combination thereof. Dry conditions may develop for different reasons. It can have a substantial impact on the ecosystem and agriculture, e.g. reduction in yield and crop damage.

Many organisms have drought tolerance physiological and genetic adaptations.

"Biotic stress" is herein defined as stress that occurs as a result of damage done to plants by other living organisms, such as bacteria, viruses, fungi, whitefly, *thrips*, spidermites, nematodes, parasites, beneficial and harmful insects, weeds, and cultivated or native plants. The types of biotic stresses imposed on a plant may be depended on both geography and climate and on the host plant and its ability to resist particular stresses.

As used herein, the phrase "resistance" refers to the ability of a plant to restrict the growth and development of a specified pathogen and/or the damage caused to the plant when compared to susceptible plants under similar environmental conditions. Resistant plants may exhibit some disease symptoms or damage under pathogen or pest pressure or under abiotic stress condition.

It is further within the scope of the present invention that resistance means that a plant completely immunizes itself from a particular stress, for example to a biotrophic pathogen infection. According to specific embodiments of the invention, by transformation of an expression library to a host plant, the transformed host acquires a resistance gene which prevents the proliferation of the pathogen and/or confers resistance to a particular abiotic stress (e.g. drought).

According to some aspects, resistance is an absolute term where the plant completely immunizes itself to a particular stress. It should be noted that this does not mean that tolerance cannot be obtained in case of biotic or abiotic stress.

The term "tolerance" refers hereinafter to the characteristic of a plant that allows a plant to avoid, tolerate or recover from biotic or abiotic stressors, under conditions that would typically cause a greater amount of injury to other plants of the same species. These inheritable characteristics influence the degree of damage caused to the plant. In terms of agricultural production tolerance means that the plant can be under stress (diseased/infected/or physiologically challenged) but the extent of loss does not exceed the economic threshold level (an extent of loss which do not hamper the economic potential of the produce). According to further aspects of the present invention, tolerance is a relative term. Examples of tolerance can be found in case of plant pathogens and all abiotic stresses, especially in the case of complex traits that are governed by multiple factors.

In general, 'resistance' and 'tolerance' are the terms used to denote the ability of the plant to manage the stress, be it biotic or abiotic.

The term "transformation" used herein refers to genetic alteration or modification induced by the introduction of exogenous DNA into a cell. This includes both integration of the exogenous DNA into the host genome, and/or introduction of plasmid DNA containing the exogenous DNA into the plant cell. Such a transformation process results in the uptake, incorporation and expression of exogenous genetic material (exogenous DNA, for examples expression library prepared from ecological niche sampling). Plant transformation may refer to the introduction of exogenous genes into plant cells, tissues or organs, employing direct or indirect means developed by molecular and cellular biology.

The term "environmental niche" or "ecological niche" generally refers to the behavior of a species living under specific environmental conditions. It includes the microbes, fungi, plants or other organisms that inhabit a given environmental location (extremophiles). The ecological niche describes how an organism or population responds to the distribution of resources and competitors and how it in turn alters those same factors. The type and number of variables comprising the dimensions of an environmental niche vary from one species to another and the relative importance of particular environmental variables for a species may vary according to the geographic abiotic and biotic contexts.

According to other aspects, the term "environmental niche" or "ecological niche" describes the relational position of a species or population in an ecosystem. More specifically, it describes how a population responds to the abundance of its resources and competitors and how it affects those same factors. The abiotic or physical environment is also part of the niche because it influences how populations affect, and are affected by, resources and competition. The description of a niche may include descriptions of the organism's life history, habitat, and place in the food chain. In context of the present invention "environmental niche" or "ecological niche" can be defined according to biotic factors or abiotic factors such as high salinity, drought conditions, elevated heat, cold conditions, pH or any other extreme environmental conditions.

It is within the scope of the current invention that the genetic material is derived from a sampling of a predefined environmental niche, including from soil, water, plant biomass, microorganisms, yeast, algae, nematode, etc.

The term "microbiome" or "microbiota" as used herein refers to an ecological community of commensal, symbiotic and pathogenic microorganisms found in and on all multicellular organisms from plants to animals. A microbiota includes bacteria, archaea, protists, fungi and viruses. Microbiota has been found to be crucial for immunologic, hormonal and metabolic homeostasis of their host. The synonymous term microbiome describes either the collective genomes of the microorganisms that reside in an environmental niche or the microorganisms themselves. The microbiome and host emerged during evolution as a synergistic unit from epigenetics and genomic characteristics, sometimes collectively referred to as a holobiont.

The term "genetic material" or "genetic pool" refers hereinafter to sum of a population's genetic material at a given time. It includes all genes and combinations of genes (sum of the alleles) in the population.

The term "isolated" as used hereinafter means that material is removed from its original environment (e.g., the natural environment if it is naturally occurring). For example, a naturally-occurring polynucleotide or polypeptide which is separated from some or all of the coexisting materials in the natural system is isolated.

The nucleic acid isolated or derived from microorganisms or any organism can preferably be inserted into a vector or a plasmid. Such vectors or plasmids are preferably those containing expression regulatory sequences, including promoters, enhancers and the like suitable for expression in plants. Particularly preferred plasmids and methods for introduction and transformation into them are described in detail in the protocol set forth herein.

The term "expression library" as used hereinafter refers to a collection of vectors or viruses (such as plant viruses used as virus-vectors) or plasmids or phages containing a representative sample of cDNA or genomic fragments that are constructed in such a way that they will be transcribed and or translated by the host organism (in the context of the present invention, plants). The technique uses expression vectors to generate a library of clones, with each clone transcribing one RNA and or expressing one protein. This expression library is then screened for the property of interest and clones of interest recovered for further analysis. One and non-limiting example would be using an expression library to isolate genes that could confer resistance or tolerance to drought.

It is within the scope of the present invention that the expression library (usually derived from microbial genetic material) can be constructed in a binary vector (or transfer DNA (T-DNA) binary system or a shuttle vector) able to replicate in multiple hosts (e.g. *E. coli* and *Agrobacterium tumefaciens*) to produce genetically modified plants. These are artificial vectors that have been created from the naturally occurring Ti plasmid found in *Agrobacterium tumefaciens*. In some aspects, the expression libraries are transferred from *Agrobacterium tumefaciens* to plants.

The term "editing" or "gene editing" or "genome editing" refers hereinafter to any conventional or known genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof. In the context of the present invention, the aforementioned gene editing techniques are used to edit a target gene in a desirable crop according to the information obtained from the transgene identified by the method of the present invention.

The term "corresponding to the sequence" refers hereinafter to sequence homology or sequence similarity. These terms relate to two or more nucleic acid or protein sequences, that are the same or have a specified percentage of amino acid residues or nucleotides that are the same, when compared and aligned for maximum correspondence, as measured using one of the available sequence comparison algorithms or by visual inspection.

According to further aspects of the invention, the term "corresponding to the nucleotide sequence" refers to variants, homologues and fragments of the indicated nucleotide sequence which possess or perform the same biological function or correlates with the same phenotypic characteristic of the indicated nucleotide sequence.

Another indication that two nucleic acid sequences are substantially similar or that a sequence is "corresponding to the nucleotide sequence" is that the two molecules hybridize to each other under stringent conditions. High stringency conditions, such as high hybridization temperature and low salt in hybridization buffers, permits only hybridization between nucleic acid sequences that are highly similar, whereas low stringency conditions, such as lower temperature and high salt, allows hybridization when the sequences are less similar.

The term "similarity" or "sequence similarity" refers hereinafter to the degree of resemblance between two sequences when they are compared. This is dependent on their identity and it shows the extent to which residues are aligned. Sequence similarity refers to an optimal matching problem (i.e. for sequence alignments). The optimal matching algorithm finds the minimal number of edit operations (inserts, deletes, and substitutions) in order to align one sequence to another sequence. Sequence similarity searches can identify "homologous" proteins or genes by detecting excess similarity, meaning, statistically significant similarity that reflects common ancestry.

It is within the scope of the current invention that similarity searching is an effective and reliable strategy or tool for identifying homologs (i.e. sequences that share a common evolutionary ancestor). Non limiting examples of similarity searching programs, include BLAST (e.g. Altschul et al. 1997); units 3.3 and 3.4), PSI-BLAST (e.g. Altschul et al., 1997), SSEARCH (e.g. Smith and Waterman, 1981); Pearson, 1991, unit 3.10), FASTA (e.g. Pearson and Lipman, 1988, unit 3.9) and the HMMER3 (e.g. Johnson et al., 2010). Such programs produce accurate statistical estimates, and can ensure that protein or nucleic acid sequences that share significant similarity also may have similar structures. Similarity searching is effective and reliable because sequences that share significant similarity can be inferred to be homologous; namely sharing a common ancestor.

Similarity is understood within the scope of the present invention to refer to a sequence similarity of at least 60%, particularly a similarity of at least 70%, preferably more than 80% and still more preferably more than 90%. The term "substantially similar" refers to a nucleic acid, which is at least 50% identical in sequence to the reference when the entire ORF (open reading frame) is compared, where the sequence similarity is preferably at least 70%, more preferably at least 80%, still more preferably at least 85%, especially more than about 90%, most preferably 95% or greater, particularly 98% or greater.

In some embodiments of the invention, such substantially similar sequences refer to polynucleotide or amino acid sequences that share at least about 60% similarity, preferably at least about 80% similarity, alternatively, about 90%, 95%, 96%, 97%, 98% or 99% similarity to the indicated polynucleotide or amino acid sequence/s.

The present invention encompasses nucleotide sequences having at least 60% similarity, preferably 70%, more preferably 80%, even more preferable 90% and especially more preferable 95% similarity to polynucleotide sequences identified by the method of the present invention or to a reference sequence.

The present invention further encompasses amino acid sequences having at least 60% similarity, preferably 70%, more preferably 80%, even more preferable 90% and especially more preferable 95% similarity to polypeptide sequences identified by the method of the present invention or to a reference sequence.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene or protein sequence.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

The term "identity" or "sequence identity" further refers hereinafter to the amount of characters which match exactly between two different sequences. Hereby, gaps are not counted and the measurement is relational to the shorter of the two sequences.

In other words, if two sequences, which are to be compared with each other, differ in length, sequence identity preferably relates to the percentage of the nucleotide residues of the shorter sequence, which are identical with the nucleotide residues of the longer sequence. As used herein, the percent of identity between two sequences is a function of the number of identical positions shared by the sequences, taking into account the number of gaps, and the length of each gap, which needs to be introduced for optimal alignment of the two sequences. The comparison of sequences and determination of identity percent between two sequences can be accomplished using a mathematical algorithm as known in the relevant art.

It is further within the scope that the terms "similarity" and "identity" additionally refer to local homology, identifying domains that are homologous or similar (in nucleotide and/or amino acid sequence). It is acknowledged that bioinformatics tools such as BLAST, SSEARCH, FASTA, and HMMER calculate local sequence alignments which identify the most similar region between two sequences. For domains that are found in different sequence contexts in different proteins, the alignment should be limited to the homologous domain, since the domain homology is providing the sequence similarity captured in the score. According to some aspects the term similarity or identity further includes a sequence motif, which is a nucleotide or amino-acid sequence pattern that is widespread and has, or is conjectured to have, a biological significance. Proteins may have a sequence motif and/or a structural motif, a motif formed by the three-dimensional arrangement of amino acids which may not be adjacent.

According to further embodiments, protein or polynucleotide sequences with specific location or domain sequence similarity are identified by the method of the present invention. When comparing residues with no conservation the low similarity is meaningless thus lower overall similarity sequences with high conservation in conserved region will be still considered as similar in a given range, for example of >60% (i.e. sequences showing low similarity of ~37% to the nearest homolog but possess all the conserved substrate binding residues of a specific protein family) that can be found in hmm-based search algorithms such as HMMER3.

The term "Conserved Domain Database (CDD)" refers to a collection of sequence alignments and profiles representing protein domains. It also includes alignments of the domains to known 3-dimensional protein structures in the database (i.e. Molecular Modeling Database (MMDB).

In some embodiments of the invention, such substantially identical sequences refer to polynucleotide or amino acid sequences that share at least about 60% identity, preferably at least about 80% identity, alternatively, about 90%, 95%, 96%, 97%, 98% or 99% identity to the indicated polynucleotide or amino acid sequence/s.

Polypeptides within the scope of the present invention are at least 50% identical to the protein identified by the method of the present invention; or at least 55% identical, or at least 60% identical, or at least 65% identical, or at least 70% identical, or at least 75% identical, or at least 80% identical, or at least 85% identical or at least 90% identical or at least 95% identical to the protein identified by the method of the present invention or to a reference sequence.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. J. Mol. Biol. 48:443).

The term "homolog" as used herein, refers to a DNA or amino acid sequence having a degree of sequence similarity in terms of shared amino acid or nucleotide sequences. There may be partial similarity or complete similarity (i.e., identity). For protein sequences, amino acid similarity matrices may be used as are known in different bioinformatics programs (e.g. BLAST, FASTA, Bestfit program-Wisconsin Sequence Analysis Package, Version 8 for Unix, Genetics Computer Group, University Research Park, 575 Science Drive Madison, WI 53711, Smith Waterman). Different results may be obtained when performing a particular search with a different matrix. Degrees of similarity for nucleotide sequences are based upon identity matches with penalties made for gaps or insertions required to optimize the alignment, as is well known in the art (e.g. Altschul S. F. et al., 1990, J Mol Biol 215 (3): 403-10; Altschul S. F. et al., 1997, Nucleic Acids Res. 25:3389-3402). Guidance in determining which amino acid residues may be substituted, inserted, or deleted without abolishing biological or activity may be found using computer programs well known in the art, for example, DNASTAR software.

The term "polymorphism" is understood within the scope of the invention to refer to the presence in a population of two or more different forms of a gene, genetic marker, or inherited trait or a gene product obtainable, for example, through alternative splicing, DNA methylation, etc.

The present invention encompasses "High-throughput screening" or "HTS" technique, which herein refers to a method to rapidly identify genes that modulate a particular biomolecular pathway or function. It includes metatranscriptomic and metagenomic gene expression.

The present invention outlines a procedure for producing expression libraries from genetic material isolated from ecological niches, which expression libraries can be transformed into the target plant for screening for a desirable trait such as tolerance or resistance to biotic or abiotic stress and improving yield or biomass production.

According to one embodiment, the present invention provides a method for screening for and identifying a desirable plant improving trait, the method comprises steps of: (a) obtaining genetic material from a sampling of a predefined environmental niche; and (b) constructing an expression library from the genetic material. According to core embodiments, the present invention further comprises steps of: (c) producing plants transformed with the expression library at an efficiency of at least 0.05%-30%, representing at least $10^2$-$10^{10}$ transgenes, thus creating the expressed library within the plants or seeds; (d) screening for transformed plants expressing the desirable trait; and (e) identifying the transgene of the transformed plants expressing the desirable trait.

It is further within the scope to disclose the method as defined in any of the above, wherein the step (a) further comprises steps of enriching the genetic material by growth on rich media or on selective media.

It is further within the scope to disclose the method as defined in any of the above, wherein the step (a) further comprises steps of enhancing expression of the desirable trait by culturing the genetic material on selective media for the desirable trait.

It is further within the scope to disclose the method as defined in any of the above, wherein the step (b) comprises steps of producing prokaryotic cDNA library or eukaryotic cDNA library or both.

It is further within the scope to disclose the method as defined in any of the above, wherein the step (b) further comprises steps of cloning the cDNA library into at least one binary vector.

It is further within the scope to disclose the method as defined in any of the above, wherein the binary vector comprises a constitutive promoter or a stress induced promoter.

It is further within the scope to disclose the method as defined in any of the above, wherein the binary vector comprises bacterial selection marker and plant transformation selection marker.

It is further within the scope to disclose the method as defined in any of the above, wherein the bacterial selection marker is Kanamycin resistance, or any other antibiotic resistance conferring gene, and the plant transformation selection marker is bar gene, conferring resistance to phosphinothricin containing herbicide (e.g. Basta herbicide).

Reference is now made to Glufosinate (also known as phosphinothricin and often an ammonium salt) is a naturally occurring broad-spectrum systemic herbicide produced by several species of *Streptomyces* soil bacteria. Glufosinate is a broad-spectrum herbicide that is used to control weeds. It is sold in formulations under brands including Basta, Rely, Finale, Challenge and Liberty. The bar gene confers resistance to the herbicide Basta (containing phosphinothricin).

It is further within the scope to disclose the method as defined in any of the above, further comprises steps of transforming the cloned binary vectors into host cells.

It is further within the scope to disclose the method as defined in any of the above, further comprises steps of transforming the cloned binary vectors into *Agrobacterium tumefaciens*.

It is further within the scope to disclose the method as defined in any of the above further comprises steps of introducing the transformed *Agrobacterium tumefaciens* into at least one of: whole plant, plant tissue and plant cell.

It is further within the scope to disclose the method as defined in any of the above, comprises steps of introducing the transformed *Agrobacterium tumefaciens* by spraying the plants with an inoculum comprising transformed *Agrobacterium*.

It is further within the scope to disclose the method as defined in any of the above, wherein the step (d) comprises growing the transformed plants under conditions selective for the desirable trait.

It is further within the scope to disclose the method as defined in any of the above, further comprises steps of:
  f. collecting T1 seeds from the transformed plants of step (d);
  g. determining seed library efficiency of the T1 seeds by calculating ratio of phosphinothricin resistant plants to total number of plants;
  h. sowing the T1 seeds of step (e) under selective conditions allowing screening and selection of transformed plants expressing the desirable trait;
  i. testing the selected plants expressing the desirable trait of step (g) for presence of the transgene; and
  j. isolating and sequencing the transgene of the selected transformed plants positively tested for the transgene of step (h).

It is further within the scope to disclose the method as defined in any of the above, further comprises steps of
  k. collecting T2 seeds from the plants of (h), which are found positive for presence of the transgene;
  l. growing plants of the T2 seeds under selective conditions allowing screening and selection of transformed plants expressing the desirable trait as compared to control plants transformed with known genes conferring the desirable trait; and
  m. optionally, isolating and sequencing the transgene of the selected plants of step (j).

It is further within the scope to disclose the method as defined in any of the above, comprises steps of
  a. recloning and sequencing the isolated transgene of step (i) and/or (1);
  b. transforming the recloned transgene into plants;
  c. screening the transformed plants of step (b) for selection of transformed plants expressing the desirable trait;
  d. isolating the transgene from the selected plants of step (c); and
  e. optionally, repeating steps (a) to (d).

It is further within the scope to disclose the method as defined in any of the above, wherein the environmental niche comprises samples derived from ecological niches, sources, populations, habitats, gene pools, prokaryotic culture, eukaryotic culture and any combination thereof.

It is further within the scope to disclose the method as defined in any of the above, wherein the environmental niche sampling comprises microbiome, microbiota or microbial culture, plant, yeast, algae, nematode or any other organism or combinations thereof.

It is further within the scope to disclose the method as defined in any of the above, wherein the environmental niche is defined according to biotic factors, abiotic factors and a combination thereof.

It is further within the scope to disclose the method as defined in any of the above, wherein the environmental niche sampling comprises soil sample, water sample, organic matter sample, any living organisms (such as plant, yeast, bacteria, microorganism, algae, nematode) and any combination thereof.

It is further within the scope to disclose the method as defined in any of the above, wherein the desirable trait is selected from the group consisting of resistance or tolerance to at least one biotic stress, resistance or tolerance to at least one abiotic stress, improved yield or biomass, improved grain yield, improved fertilizer uptake and improved usage efficiency and a combination thereof.

It is further within the scope to disclose the method as defined in any of the above, wherein the abiotic stress is selected from the group consisting of: drought, salinity, heat, cold, fertilizer uptake, fertilizer utilization efficiency and any combination thereof.

It is further within the scope to disclose the method as defined in any of the above, wherein the biotic stress is selected from the group consisting of: pathogens, bacteria, viruses, fungi, parasites, beneficial and harmful insects, weeds, and cultivated or native plants or any combination thereof.

It is further within the scope to disclose the method as defined in any of the above, wherein the method comprises steps of extracting RNA from the sampling of the predefined environmental niche.

It is further within the scope to disclose the method as defined in any of the above, wherein the RNA extraction is performed according to standard commercial kits or according to any other protocol for extraction of RNA from environmental sampling.

It is further within the scope to disclose the method as defined in any of the above, wherein the protocol for extraction of RNA from environmental sampling comprises steps of:
  a. obtaining a soil sample;
  b. mixing the soil sample with an extraction buffer comprising 500 mM phosphate buffer pH 8 and 5% w/v cetyltrimethylammonium bromide (CTAB) with phenol (pH 8)/chloroform/IAA ratio of 25:24:1;
  c. subjecting the mixture of step (b) to 15 min shaking at 37° C. or to a bead beater for 1 min;

d. centrifuging the mixture of step (c) at 2,500 g for about 10 minutes at room temperature to obtain an aqueous phase;
e. transferring the aqueous phase into a new tube;
f. adding to the aqueous phase within the tube of step (e) an equal amount of iso-propanol supplemented with 20 mg/ml crystal violet solution to obtain violate stained solution;
g. mixing the solution by inverting said tube of step (f) and then incubating the tube for about 30 minutes at room temperature;
h. centrifuging the tube of step (g) at 2,500 g for about 30 minutes at room temperature to obtain a violet stained layer;
i. transferring the violate stained layer into a new tube and centrifuging the tube for about 5 min at maximal speed to obtain pellet and supernatant;
j. washing the pellet with 80% v/v ice cold ethanol and centrifuging for additional 5 min to obtain pellet and supernatant;
k. removing the supernatant of step (j) and allowing the pellet to dry; and
l. suspending the dried pellet in water in a ratio of 100 µl water to 2 gr of soil of step (a).

It is further within the scope to disclose polynucleotide sequences obtainable by the method as defined above.

It is further within the scope to disclose the polynucleotide as defined above, wherein the polynucleotide comprises a nucleotide sequence corresponding to the sequence as set forth in a polynucleotide sequence selected from the group consisting of SEQ ID NOs: 1-148 and any combination thereof.

It is further within the scope to disclose a polynucleotide sequence having at least 80%, 85%, 90% or 95% sequence similarity to a polynucleotide sequence obtainable by the method as defined above.

It is further within the scope to disclose a polypeptide sequence obtainable by the method as defined above.

It is further within the scope to disclose the polypeptide sequence as defined above, wherein the polypeptide comprises an amino acid sequence corresponding to the sequence as set forth in a polypeptide sequence selected from the group consisting of SEQ ID NOs: 149-321 and any combination thereof.

It is further within the scope to disclose an amino acid sequence having at least 60%, 70%, 80% or 90% sequence similarity to an amino acid sequence obtainable by the method as defined above.

It is further within the scope to disclose the use of the method as defined above for identifying genes conferring resistance or tolerance to abiotic or biotic stress.

It is further within the scope to disclose the use of the method as defined above for identifying genes conferring improved yield and biomass, i.e. improved grain yield, in plants, for example by enhancing growth, with or without exposure to stress conditions.

It is further within the scope to disclose the use of the method as defined above for identifying genes conferring improved yield.

It is further within the scope to disclose the use as defined in any of the above, wherein the abiotic stress is selected from the group consisting of: drought, salinity, heat, cold, fertilizer utilization, fertilizer uptake and any combination thereof.

It is further within the scope to disclose the use as defined in any of the above, wherein the biotic stress is selected from the group consisting of: pathogens, bacteria, viruses, fungi, parasites, beneficial and harmful insects, weeds, and cultivated or native plants or any combination thereof.

It is further within the scope to disclose a method for screening for and identifying a drought resistance or tolerance improving trait in plants, the method comprises steps of: (a) obtaining genetic material derived from a low moisture or a high salinity environmental niche sample; and (b) constructing expression library from the genetic material. According to core embodiments, the method further comprises steps of: (c) producing plants transformed with the expression library at an efficiency of at least 0.05%-30%, representing at least $10^2$-$10^{10}$ transgenes; (d) screening for transformed plants surviving predetermined drought conditions; and (e) identifying the transgene of the drought surviving transformed plants of step (d).

It is further within the scope to disclose the method as defined above, wherein the step (b) further comprises steps of cloning the expression library into at least one binary vector.

It is further within the scope to disclose the method as defined in any of the above, further comprises steps of:
f. collecting T1 seeds from the transformed plants of step (c);
g. sowing the T1 seeds in soil selective for transformed plants, with water content of about 100% capacity;
h. growing plants of the T1 seeds in drought condition and/or without irrigation until most of the plants die, to produce transformed plants surviving the drought conditions;
i. growing the drought surviving transformed plants to produce T2 seeds;
j. screening the drought surviving transformed plants of step (i) for presence of a transgene;
k. isolating and sequencing the transgene from positively screened plants of step (j);

It is further within the scope to disclose the method as defined in any of the above, further comprises steps of
l. collecting T2 seeds from each of the transgene-containing positively screened drought surviving transformed plants of step (j);
m. growing T2 plants from each of the transgene-containing T2 seeds of step (1) under predetermined drought conditions as compared to control plants transformed with known genes conferring drought tolerance or drought resistance;
n. performing drought tolerance or resistance screen measurements for each of the transgene-containing T2 plants as compared to the control plants selected from the group consisting of: turgor measurements, number of plants death, state of plants and any combination thereof;
o. isolating the transgene from the screened drought resistance performing T2 plants of step (n);
p. optionally, recloning the transgene into a binary vector;
q. optionally, transforming the cloned binary vector into plants and growing the transformed plants under predetermined drought conditions; and
r. optionally, repeating steps (1) to (q).

It is further within the scope to disclose the method as defined in any of the above, wherein the step of growing T2 plants comprises steps of: (a) sowing the T2 seeds in soil selective for transformed plants, with water content of about 100% capacity; and (b) irrigating the plants when water content in the soil reaches about 5-10%.

It is further within the scope to disclose the method as defined in any of the above, wherein the predetermined drought conditions are selected from the group consisting of low moisture, high salinity, dry soil and heat.

It is further within the scope to disclose polynucleotide sequences obtainable by the method as defined in any of the above.

It is further within the scope to disclose the polynucleotide as defined above, wherein the polynucleotide comprises a nucleotide sequence corresponding to the sequence as set forth in a polynucleotide sequence selected from the group consisting of SEQ ID NOs: 1 to SEQ ID NO:148 and any combination thereof.

It is further within the scope to disclose polynucleotide sequences having at least 80%, 85%, 90% or 95% sequence similarity to polynucleotide sequences obtainable by the method as defined in any of the above.

It is further within the scope to disclose a polypeptide sequence obtainable by the method as defined in any of the above.

It is further within the scope to disclose the polypeptide sequence as defined above, wherein the polypeptide sequence comprises an amino acid sequence corresponding to the sequence as set forth as set forth in polypeptide sequence selected from the group consisting of SEQ. ID Nos: 149-321 and any combination thereof.

It is further within the scope to disclose polypeptide sequences having at least 60%, 70%, 80% or 90% sequence similarity to amino acid sequences obtainable by the method as defined in any of the above.

It is further within the scope of the present invention to disclose a method for extracting RNA from a soil sample comprising steps of:
  m. obtaining a soil sample;
  n. mixing said soil sample with an extraction buffer comprising 500 mM phosphate buffer pH 8 and 5% w/v cetyltrimethylammonium bromide (CTAB) with phenol (pH 8)/chloroform/IAA ratios of 25:24:1;
  o. subjecting said mixture of step (b) to about 15 min shake at 37° C. or to a bead beater for 1 min;
  p. centrifuging said mixture of step (c) at 2,500 g for about 10 minutes at room temperature to obtain an aqueous phase;
  q. transferring said aqueous phase into a new tube;
  r. adding to said aqueous phase within said tube of step (e) an equal amount of iso-propanol supplemented with 20 mg/ml crystal violet solution to obtain violate stained solution;
  s. mixing said solution by inverting said tube of step (f) and then incubating said tube for about 30 minutes at room temperature;
  t. centrifuging said tube of step (g) at 2,500 g for about 30 minutes at room temperature to obtain a violet stained layer;
  u. transferring said violate stained layer of step (h) into a new tube and centrifuging said tube for about 5 min at maximal speed to obtain pellet and supernatant;
  v. washing said pellet with 80% v/v ice cold ethanol and centrifuging for about additional 5 min to obtain pellet and supernatant;
  w. removing said supernatant of step (j) and the pellet is left to dry; and
  x. suspending said dried pellet in water in a ratio of 100 μl water to 2 gr of soil of step (a).

It is further within the scope of the present invention to disclose a method for screening for and identifying a desirable plant improving trait, said method comprises steps of:
  y. obtaining a sampling of a predefined environmental niche;
  z. extracting RNA from the sampling according to the method for extracting RNA from a soil sample as defined above;
  aa. constructing an expression library from the RNA of step (b);

The method further comprises steps of:
  bb. producing plants transformed with the expression library at an efficiency of at least 0.05%-30% representing at least $10^2$-$10^{10}$ transgenes;
  cc. screening for transformed plants expressing the desirable trait; and
  dd. identifying the transgene of the transformed plants expressing the desirable trait.

It is further within the scope of the present invention to disclose an isolated polynucleotide having a nucleotide sequence corresponding to the sequence as set forth in a polynucleotide sequence selected from the group consisting of SEQ ID NOs: 1 to SEQ ID NO: 148 and any combination thereof.

It is further within the scope of the present invention to disclose an isolated polypeptide having an amino acid sequence corresponding to the sequence as set forth in polypeptide sequence selected from the group consisting of SEQ. ID Nos: 149-321 and any combination thereof.

In order to understand the invention and to see how it may be implemented in practice, a plurality of preferred embodiments will now be described, by way of non-limiting example only, with reference to the following examples.

EXAMPLE 1

A Process for Improving Traits in Plants by Transformation of Expression Libraries from Ecological Niches into Plants and Screening for Desired Traits 1. Sample Collection and Processing In the first step, genetic pools of a varied environmental samples and sources such as soil, water or organic matter from different habitats have been isolated. The source is selected according to the specific desired target traits. For example, when screening for drought or salinity resistant gene, a dry land such as desert land or a high salinity land or other enforcement will be used, but not necessarily.

The microbiome found in each sample may optionally be enriched by growth on rich media or selectively grown with antibiotics. To enhance expression of potentially desired genes, the culture is grown in stress conditions or media resembling, associated with or affecting the target trait, such as salt or PEG rich media for drought or salinity resistance trait.

Sample enrichment is carried on rich growth media (e.g. YPD) for several days at 28° C.-37° C. in shaker incubator. If eukaryotic libraries are prepared, anti-bacterial antibiotics such as Penicillin-Streptomycin and Spectinomycin are added.

To induce stress resistant genes, the sample is grown under any desired environmental stress conditions. For example, to induce drought resistance genes, the sample is grown under high osmotic stress by adding PEG to the growth media (10%-30% w/v). High salt concentration media such as NaCl (5%-10% w/v) was used to induce high salinity stress. In addition, the samples are exposed to different nitrogen concentration (from 0-100 mM $KNO_3$ in water supplemented with 6 mM $KH_2PO_4$ and micro elements, see Table 1, http://www.gatfertilizers.com/properties-of-solid-and-liquid-fertilizers/as recommended by the manufacturer), extreme temperatures (50-60° C.) and any environmental stress desired.

TABLE 1

| Element | Percentage | gr/Lt |
|---|---|---|
| Iron | 1.09 | 12.20 |
| Manganese | 0.48 | 5.47 |
| Zinc | 0.15 | 1.75 |
| Copper | 0.05 | 0.55 |
| Molybdenum | 0.02 | 0.16 |
| Boron | 0.20 | 2.00 |

2. RNA Extraction

Total RNA extraction has been performed according to standard commercial kits such as RNeasy PowerSoil Total RNA Kit (Qiagen) and Quick-RNA (Zymo research). In addition, a unique protocol is used for extraction of RNA from soil samples, as follows:

In a 7 ml tube, 2 g of soil is disrupted with extraction buffer (500 mM Phosphate buffer pH 8 and 5% w/v CTAB with Phenol (pH 8), chloroform, IAA (25:24:1)). The tube is subjected to 15 min shaking at 37° C. or to a bead beater for 1 min. The tube is then centrifuged at 2,500 g for 10 minutes at room temperature. The aqueous phase is transferred into a new tube and an equal amount of iso-propanol supplemented with 5 µl of crystal violate solution (20 mg/ml) is added. The tubes are mixed by inverting and left to stand for 30 minutes at room temperature, then centrifuged at 2,500 g for 30 minutes at room temperature. The violate stained layer is transferred into a new 1.5 ml tube and centrifuged for 5 min at maximal speed. The pellet is washed with 500 µl of 80% v/v ice cold ethanol and centrifuged for additional 5 min. After centrifugation, the liquid is removed, and the pellet is left to dry. The dry pellet is suspended in 100 µl water.

3. Construction of cDNA Libraries 3.1. Eukaryotic cDNA Libraries

Figure 1B:
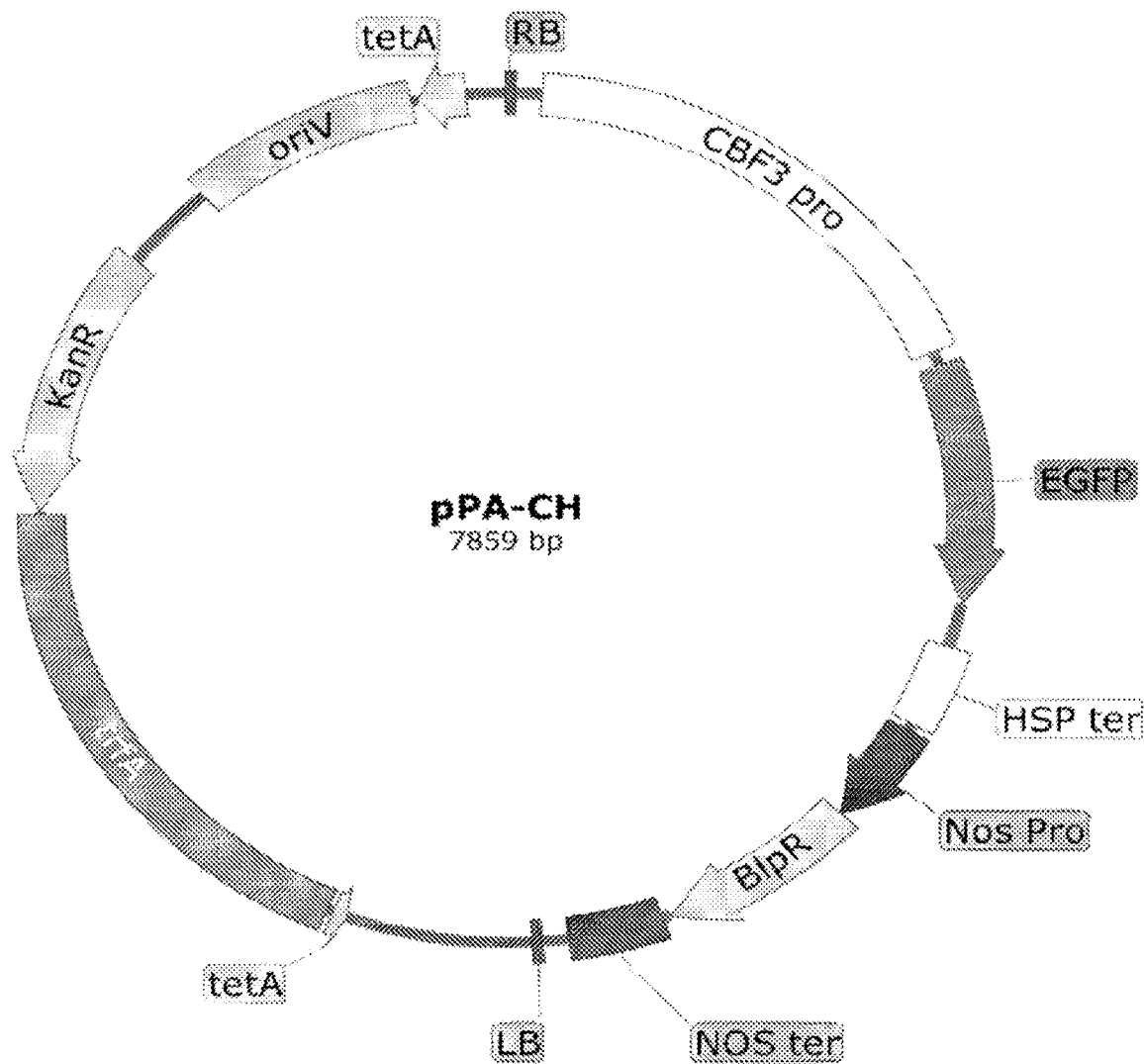
Figure 1C:
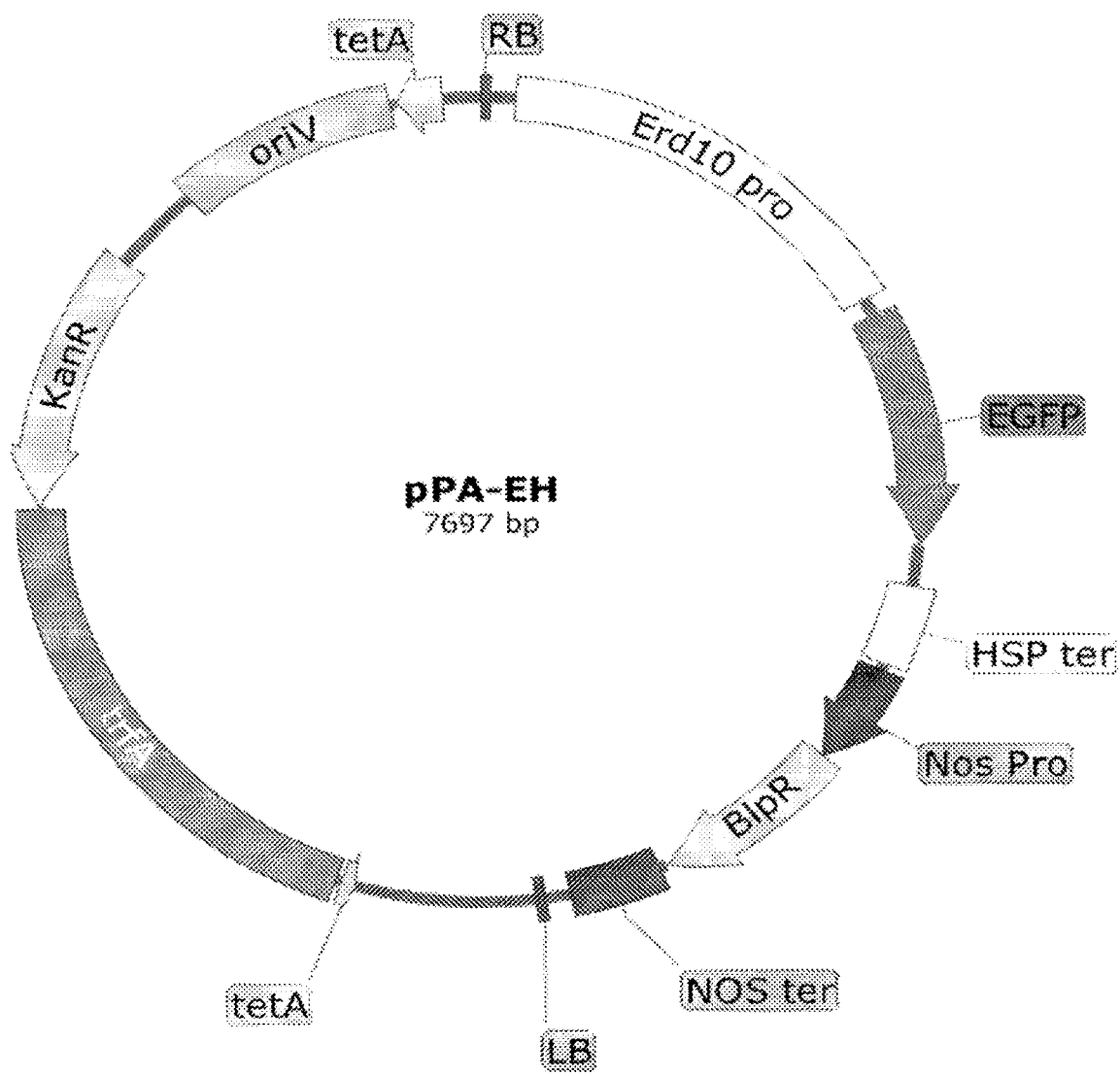
Figure 1D:
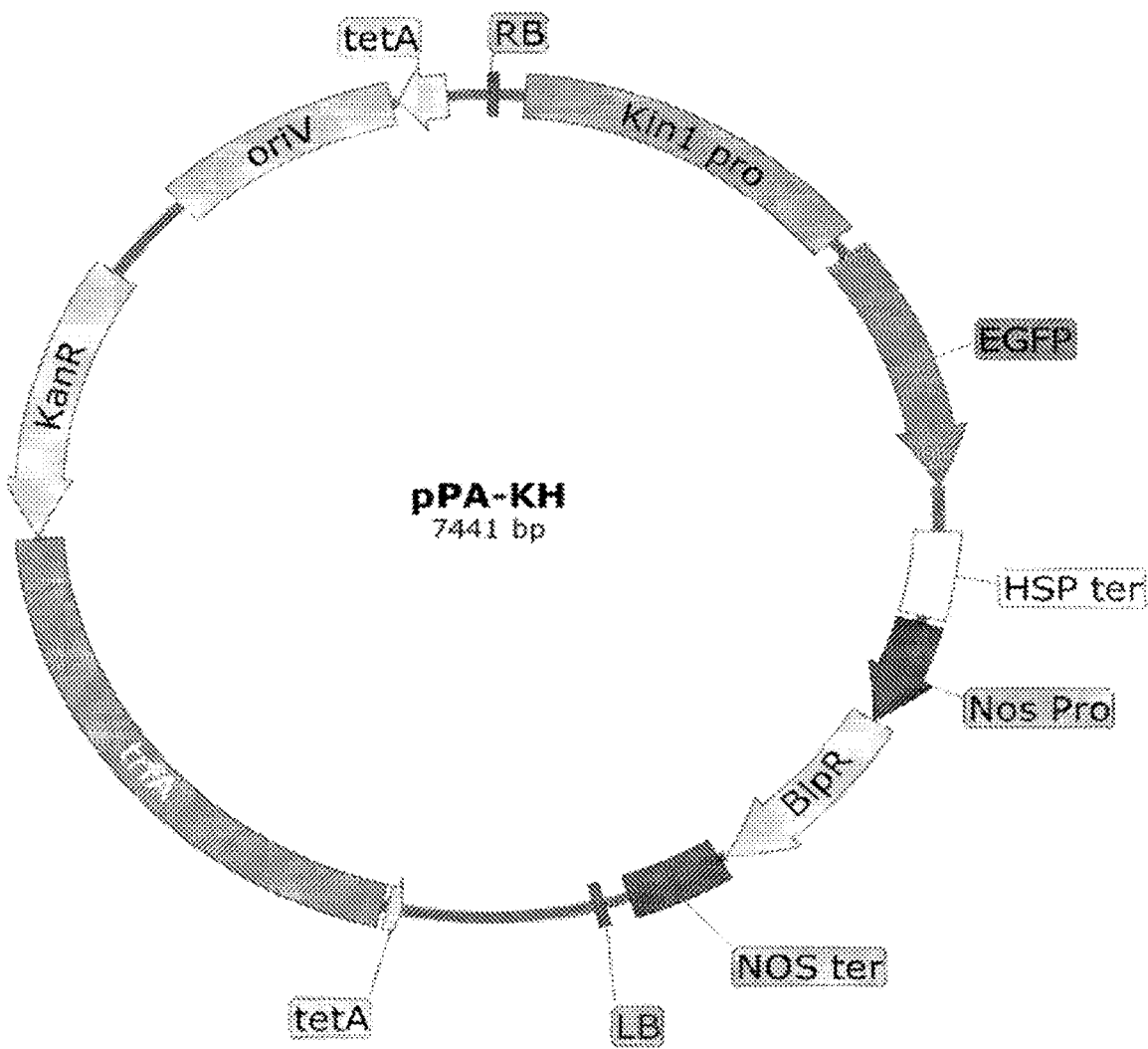
Figure 2:
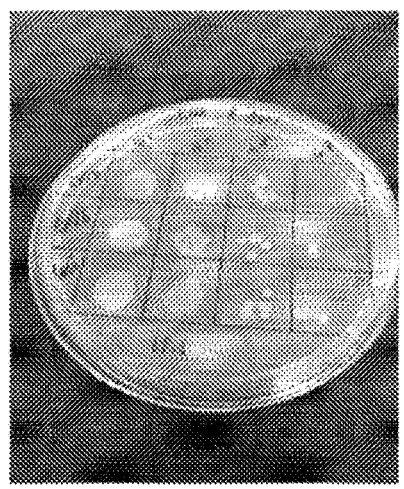
FIG. 2 presents a photographic illustration of *agrobacterium* library counting for 3 different libraries on LB petri dishes.

Eukaryotic cDNA libraries from total-RNA and mRNA are constructed based on template switching-reverse transcription of poly-A mRNA (SMART) or oligo-capping rapid amplification of cDNA ends (5'-RACE) methods. The reverse transcription of poly-A mRNA used are 5'-primers ATTCTAGAGCGATCGCA-CATGTTTTTTTTTTTTTTTTTTTTTTTTTTTTTTVN-3' (referred to ID as SEQ. NO: 321) and 5'-AAGCAGTGGTATCAACGCAGAGTGGCGCGCCr-GrGG-3' (referred to as SEQ. ID NO: 322). The oligo-capping rapid amplification of cDNA ends primers used are 5'-ATTCTAGAGCGATCGCA-CATGTTTTTTTTTTTTTTTTTTTTTTTTTTTTTTVN-3' (referred to as SEQ. ID NO: 321) and 5'-InvddT (5' Inverted Dideoxy-T)-r (AAGCAGUGGUAU-CAACGCAGAGUGGCGCGCCG)-3' (referred to as SEQ. ID NO: 323). The amplified cDNA is inserted into binary vectors (see FIGS. 1-4) between the promoter(s) (35S, KIN1, erd10 and/or CBF3) and the HSP or NOS terminator. FIG. 1A illustrates the pPA-35H vector, which has a constitutive CaMV 35S promoter with the GFP gene cloned between the promoter and terminator as an example. FIGS. 1B-D present vectors containing stress induced promoters from *Arabidopsis thaliana*: pPA-CH vector with CBF3 promoter having a nucleotide sequence as set forth in SEQ. ID NO: 330 (FIG. 1B), pPA-EH with Erd10 promoter having a nucleotide sequence as set forth in SEQ. ID NO: 331 (FIG. 1C) and pPA-KH with Kin1 promoter having a nucleotide sequence as set forth in SEQ. ID NO: 332 (FIG. 1D) with the GFP gene cloned between the promoter and terminator as an example (Plant Physiol. 1997 October; 115 (2): 327-334., Plant Journal (2004) 38, 982-993 incorporated herein by reference).

Figure 5:
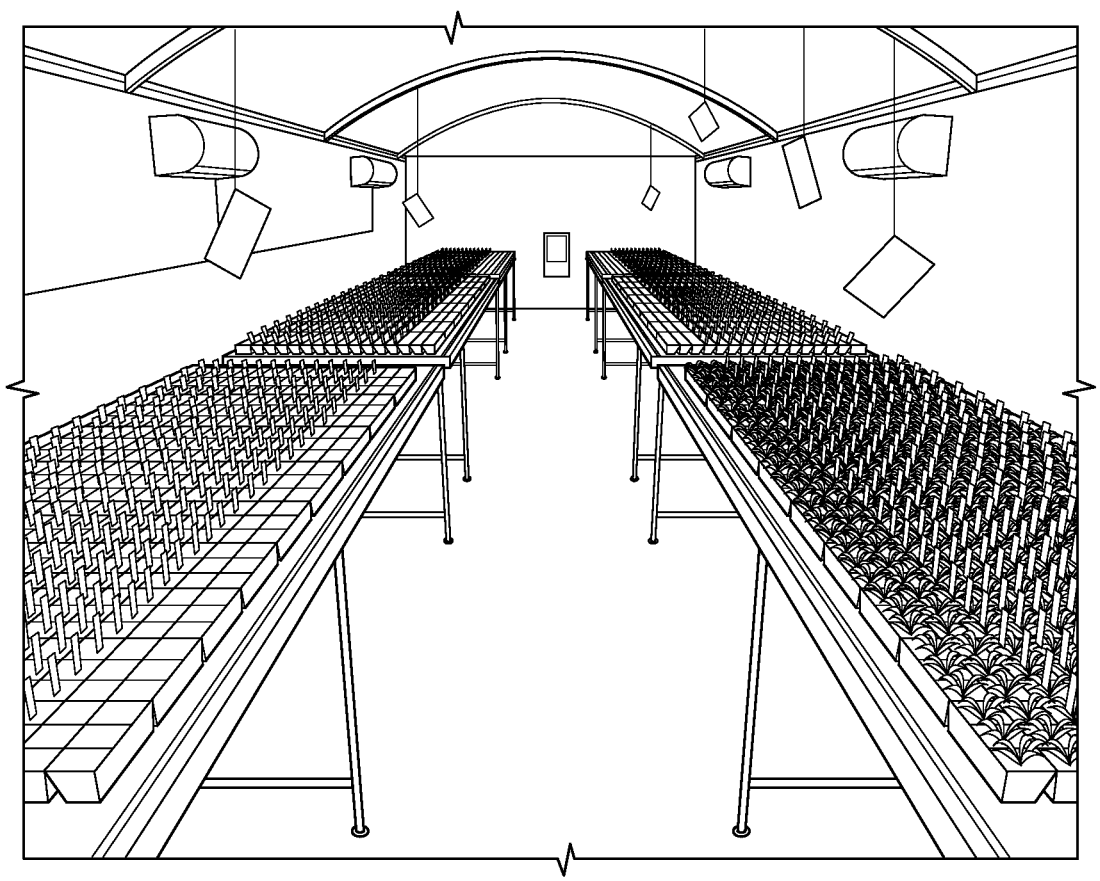
FIG. 5 presents a photographic illustration of T2 and T3 controlled experiments in the greenhouse.

These vectors contain Kanamycin as a bacterial selection and the bar gene as a transgenic plant selection conferring resistance to the phosphinothricin herbicide. At least one of the non-limiting examples of Gibson assembly, Restriction-ligation, Restriction free or In-Fusion methods is used and then ligation products are transformed to *E. coli* competent cells to grow under kanamycin selection. The library size is estimated by live count of transformed bacteria sown on LB petri dishes (usually 10^5-10^7) (FIG. 5). Vectors of the cDNA library are purified from *E. coli* bacteria with standard mini-prep kits and transformed to electrocompetent *Agrobacterium tumefaciens* GV3101 cells. The transformed *Agrobacterium* are grown on LB media under kanamycin and rifampicin selection (50 µg/ml each) over night at 28° C., (250 ml per 1 m² of target plant growth area). The growth arrested on ice for at list 30 min and then centrifuged for 10 min at 8000 rpm at 4° C. The pelleted *Agrobacterium* are suspended in suspension buffer (5% sucrose and 0.03% L-77 Silwet, Momentive, US).

3.2. Prokaryotes cDNA Libraries

Prokaryotes cDNA libraries from total RNA are constructed based on standard 5' and 3' RNA modifications with ScriptSeq™ Complete Kit (epicenter). Primers used are 5'-ATTCTAGAGCGATCGCA-CATGTTTTTTTTTTTTTTTTTTTTTTTTTTTTTTVN-3' (referred to as SEQ. ID NO: 321) and 5'-InvddT (5' Inverted Dideoxy-T)-r (AAGCAGUGGUAU-CAACGCAGAGUGGCGCGCCG)-3' (referred to as SEQ. ID NO: 324). The amplified cDNA inserted into carrier vectors barring Kanamycin and phosphinothricin resistance and then transformed to *E. coli* competent cells to grow under kanamycin selection (50 µg/ml). The library size is estimated by live count of transformed hosts (usually 10^5-10^7). Vectors of the cDNA library are purified from host cells with standard mini-prep kit (50 µl) and transformed to electrocompetent *Agrobacterium* GV3103 cells (100 µl). The transformed *Agrobacterium* are grown on LB media under kanamycin and rifampicin selection (50 µg/ml) over night at 28° C. (100 ml per 1 m² of target plant growth area). The growth is arrested on ice for at list 30 min and then centrifuged for 5 min at 8000 rpm at 4° C. The pelleted *Agrobacterium* are suspended in suspension buffer (5% sucrose and 0.03% L-77 Silwet).

4. Growing and Transformation of Plants 4.1. *Arabidopsis* Plants

Plants are grown in controlled greenhouses as a preparation for transformation. Plants are grown in soil composed of 75% peat, 25% perlite and are being irrigated routinely with water supplemented with fertilizer (e.g. Shefer 5.3.8, ICL Israel) according to manufacturer instructions, as needed. Plants start flowering after 3-4 weeks and then they are ready for transformation. Transformed *Agrobacterium* with expression libraries are grown as mentioned above and suspended in suspension buffer (5% sucrose and 0.03% L-77 Silwet) and are sprayed by 2 liter sprayers (e.g. Solo, Germany) on the flowers. After 5-6 weeks of continued growth when plants become dry, seeds are collected and kept in a cool dry place for 2 weeks or until used.

4.2. Tobacco Plants

Figure 3A:
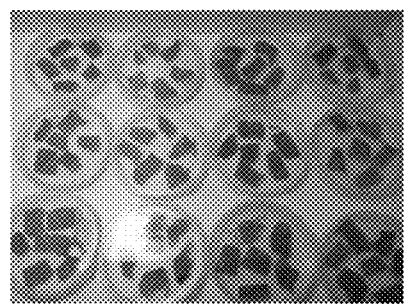
FIGS. 3A-3C presents a photographic illustration of tobacco tissue culture transformed with a library, 7 days after transformation (FIG. 3A), 40 days after transformation (FIG. 3B) and 6-8 weeks after transformation (FIG. 3C)
Figure 3B:
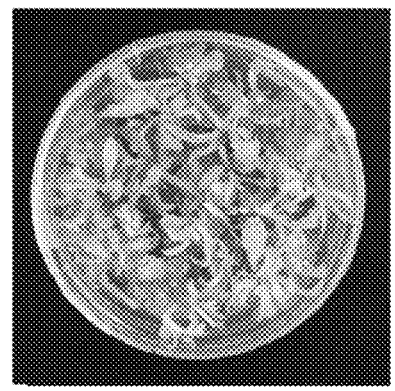
Figure 3C:

Tobacco leaves are cut into 1-2 cm² pieces and sterilized by 70% ethanol followed by 0.3% bleach treatments for 5 minutes. Leaf pieces are mixed with libraries transformed *Agrobacterium* (or with a any identified gene of SEQ ID 1-148 from Table 4), suspended in liquid Regeneration Medium (RM) supplemented with MS including Gamborg B5 vitamins, 3% sucrose, 2 mg/L BAP (6-Benzylaminopurine) and 0.2 mg/L NAA (Naphthalene acetic acid) (e.g. Duchefa, Netherland) for 30 minutes. Bacteria are than washed and leaf pieces are placed on RM plant-agar plates for one day in the dark. Leaf pieces are transferred to new selection RM plant-agar plates supplemented with 300 µg/ml of timentin antibiotic to kill the *Agrobacterium* and 1.5 µg/ml phosphoinotricin (e.g. Duchefa, Netherland) for selection of transgenic plants. FIG. 3A-B present a photographic illustration of tobacco tissue culture transformed with a library, 7 days after transformation (FIG. 3A) and 40 days after transformation (FIG. 3B). After 6-8 weeks, plantlets start to appear and are transferred to new vessels containing the same selection RM plant-agar, but BAP is excluded (see FIG. 3C). After rooting, plants are transferred to soil in the greenhouse.

EXAMPLE 2

A Process for Identifying Drought Resistance Traits in Plants

A. Screening for Drought and/or Salinity Resistant Plants/Genes

Figure 4:
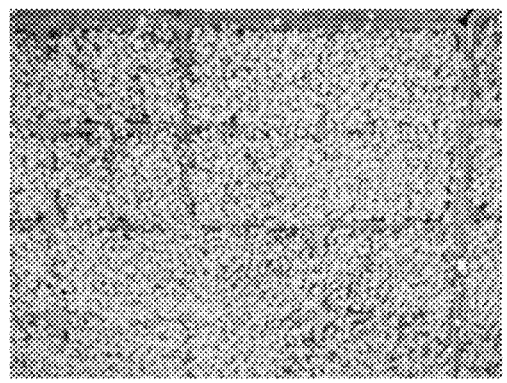
FIG. 4 presents a photographic illustration demonstrating selection for phosphinothricin resistance of 10 days old *Arabidopsis* expressing library seedlings. The green plants are resistant to phosphinothricin while small yellow plants are absent of the transgene and therefore susceptible.

*Arabidopsis* T1 seeds harboring the desired expression library are being used for the screen. At the first stage, the transformation efficiency is defined for a specific seed library. 1 ml of seeds (~50,000 seeds) is being sowed on soil irrigated with water supplemented with Basta (e.g. Bayer, Germany) according to manufacturer instructions. Seven days post sowing, the number of phosphinothricin resistant plants is counted and compared with phosphinothricin susceptible plants (FIG. 4). As demonstrated in FIG. 4, the bigger plants are resistant to phosphinothricin while small plants are absent of the transgene and therefore susceptible and will die. The seed library efficiency is represented by the ratio of the number of resistant plants to the number of total plants.

The library is then sowed according to the desired number of plants intended to be represented in the specific experiment and which represents best the library size. For example, if an expression library consists of 5×10⁴ genes, and the transformation efficiency is 1%, >5 million seeds should be sowed. In this case, in ~20 m² of soil, 50,000 Basta resistant plants will be grown for the experiment.

Soil is irrigated once, when seeds are sown, with water supplemented with phosphinothricin and fertilizer (e.g. Shefer 5.3.8, ICL Israel) according to manufacturer instructions, and soil water content reaches 100% capacity. Plants are grown in air-conditioned controlled greenhouses, and soil is not irrigated until most of the plants die from lack of water. Surviving plants, ~ 0.1% of initial phosphinothricin resistant plants, are being rescued by irrigation until they produce seeds which are being collected for T2 experiments. During their growth, the surviving plants are tested for their transgene, by gDNA extraction from one of their leaves and PCR using primers for the gene specific promoters (CaMV 35S, CBF3, Erd10 and Kin1) and terminators (NOS, HSP) (see Table 2). PCR products are being sequenced and the resulted sequence is blasted versus sequence databases such as NCBI, both for DNA comparisons (i.e. BLASTn) and for amino acid sequence comparisons (i.e. BLASTx).

Reference is now made to Table 2 presenting SEQ ID NOs of primer and promoter sequences used in the present invention:

TABLE 2

SEQ ID NOs of primer sequences

| SEQ ID NO. | Description |
| --- | --- |
| SEQ ID NO: 321 | Reverse primer for transcription of poly-A mRNA |
| SEQ ID NO: 322 | Forward primer for transcription of poly-A mRNA |
| SEQ ID NO: 323 | Forward primer for oligo-capping amplification of cDNA ends |
| SEQ ID NO: 324 | Forward primer for amplification of prokaryote cDNA library (e.g. derived from total RNA) |
| SEQ ID NO: 325 | Forward primer for CaMV 35S promoter |
| SEQ ID NO: 326 | Forward primer for CBF3 promoter |
| SEQ ID NO: 327 | Forward primer for Erd10 promoter |
| SEQ ID NO: 328 | Forward primer for Kin1 promoter |
| SEQ ID NO: 329 | Reverse primer for NOS/HSP terminator |
| SEQ ID NO: 330 | CBF3 promoter |
| SEQ ID NO: 331 | Erd10 promoter |
| SEQ ID NO: 332 | Kin1 promoter |

B. Subsequent Generations (T2, T3) Experiments

Seeds collected from drought surviving plants are being tested again in further experiments including repeats and controls to test their resistance/tolerance to drought (see FIG. 5).

Several genes were chosen to serve as controls in the drought experiments:

1) EGFP-jellyfish green fluorescent protein, cloned under the control of the various used promoters and HSP terminator (see vector maps of FIGS. 1A-D), is being served as a negative control for drought, since it was not been shown to be associated with improving plants resistance to drought (Yang T-T, et al., 1996).

2) mtlD-mannitol-1-phosphate dehydrogenase from *Escherichia coli*, cloned under the control of the various used promoters and HSP terminator (see vector maps of FIGS. 1A-D), is being served as a positive control since it was shown to be associated with improving plants resistance to drought and salt (Hema R. et al., 2014).

3) HRD—The HARDY gene from *Arabidopsis thaliana* cloned under the control of the various used promoters and HSP terminator (see vector maps of FIGS. 1A-D), is being served as a positive control since was shown to be associated with improving plants resistance to drought and salt (Karaba A, et al., 2007).

Plants identified as expressing unique genes in the screen experiments, including all controls, are sown in trays 38×28 cm with 16 plastic inserts in each tray (e.g. Desch Plantpak, Netherland), filled with soil supplemented with fertilizer and phosphinothricin as above. In each insert several seeds are sown and after 10 days a single phosphinothricin resistant plant is being kept for further experiments. Each experiment contains 20-40 repeats of each plant, representing the expressed unique genes, which are spread in random on the greenhouse tables. Irrigation of the soil is similar to the screen experiment; it is done when the seeds are sown, except when soil is completely dry and reaches weight lower then initial weight of soil before irrigation (~5%-10% of water content), then plants are irrigated again to check revival performance.

Figure 6:
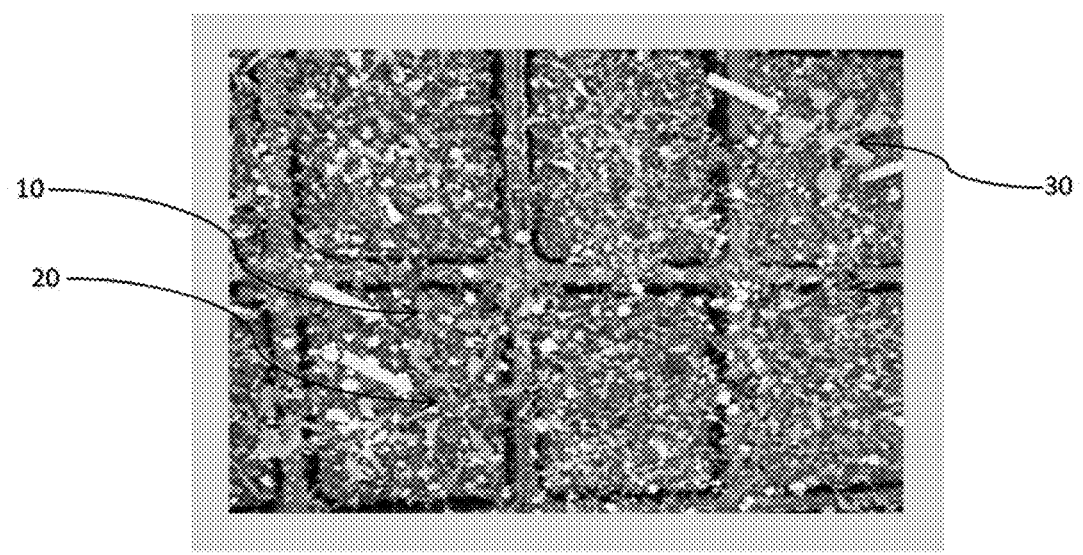
FIG. 6 presents photographic results of screening for transgenic plants resistance to drought.

Reference is now made to FIG. 6 showing photographic results of screening for transgenic plants resistance to drought grown under the conditions as described above. This figure shows that transgenic plants carrying drought resistance genes 10, 20 and 30 survive in severe drought conditions, while other transgenic plants that do not harbor drought resistant conferring genes do not survive the stress conditions. It is noted that within the small area shown in this figure (~15×25 cm), about 300 plants were screened while 3 survived the drought conditions.

When drought conditions start to develop, various measurements are taken, as shown in Table 3:
1) turgor observation, measured by scale of 1-10, when 1 is high turgor and 10 is total loss of turgor (see FIG. 7).
2) Weight of plant and pot, by scale in grams.
3) Death of plants observation, 10=dead and 1=alive (see FIG. 8)
4) State of plants observation in a scale of 1-10, when 1 is good state and 10 is poor.

TABLE 3

Measurements taken in drought experiments

| measurement | units | time of measurement |
| --- | --- | --- |
| Weight of pot | Grams | Start till end of experiment |
| Turgor | Observation units 1-10, where 1 is 0 turgor loss and 10 is 100% turgor loss | From beginning of turgor loss (~15-27 days from last irrigation) |
| Death | Observation units 1-10 | From first death observed |
| State of plants | Observation units 1-10 | During first 2 weeks and one day after revival |

Figure 7:
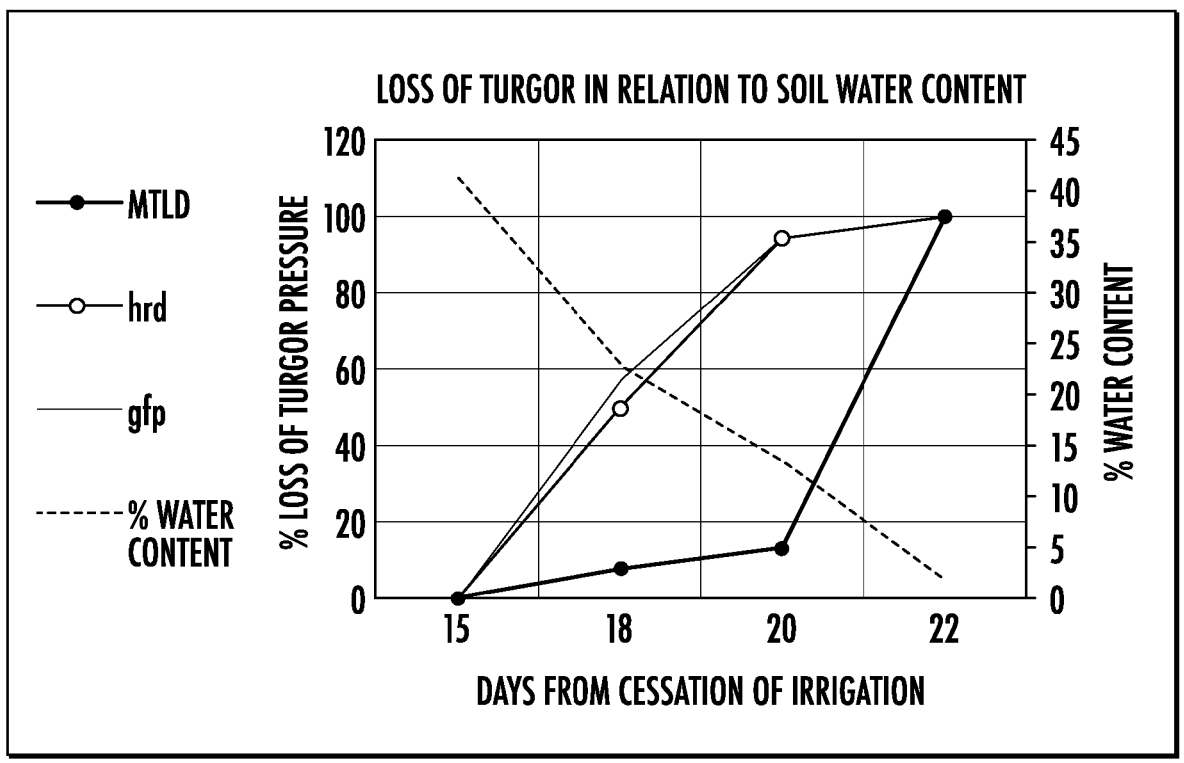
FIG. 7 presents a graphic illustration demonstrating loss of turgor pressure in plants expressing genes used as control relative to soil water content (dark gray), days after cessation of irrigation.

Reference is now made to FIG. 7, showing loss of turgor pressure in plants expressing genes used as control relative to soil water content (dark gray), days after cessation of irrigation. This figure shows curves of *Arabidopsis* plants, expressing different genes (indicated), as a response to growth under drought conditions. Dark line indicates soil water content from 40% in day 15 after water irrigation ceased, to close to 0% at day 22 after water irrigation ceased. The negative control GFP plant's loss of turgor pressure response is similar to that of HRD expressing plants, while mtlD expressing plants turgor pressure, seem to be less effected by drought until day 20 after water irrigation ceased.

It is demonstrated in this figure that plants expressing the positive control genes mtlD and HRD showed improved resistance to drought by showing significantly reduced loss of turgor pressure effects, while transgenic plants expressing the negative control GFP gene showed elevated loss of turgor pressure effect when exposed to the same water content loss.

Figure 8:
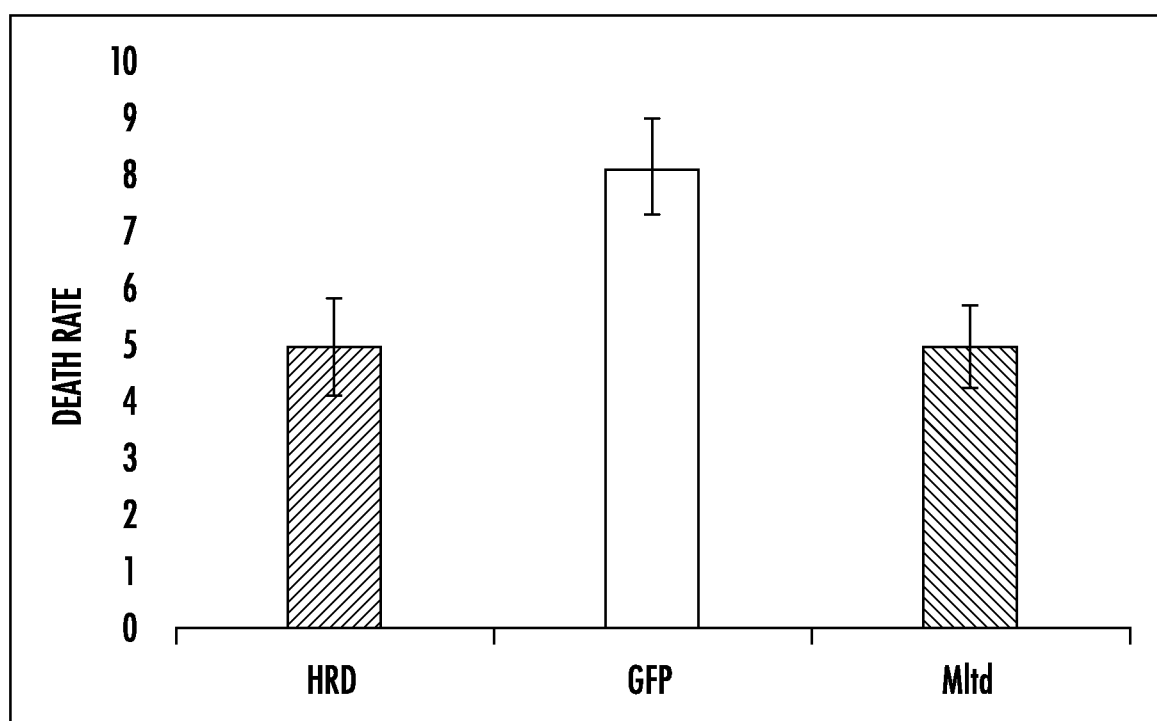
FIG. 8 presents a graphic illustration showing normalized death scale of positive control expressing transgenic plants as compared to GFP expressing plants.

Reference is now made to FIG. 8 showing normalized death scale of positive control expressing transgenic plants as compared to GFP expressing plants. As can be seen plants expressing the drought resistance positive control genes HRD and mtlD showed significantly reduced death rate as compared to the negative control GFP expressing plants.

Figure 9:
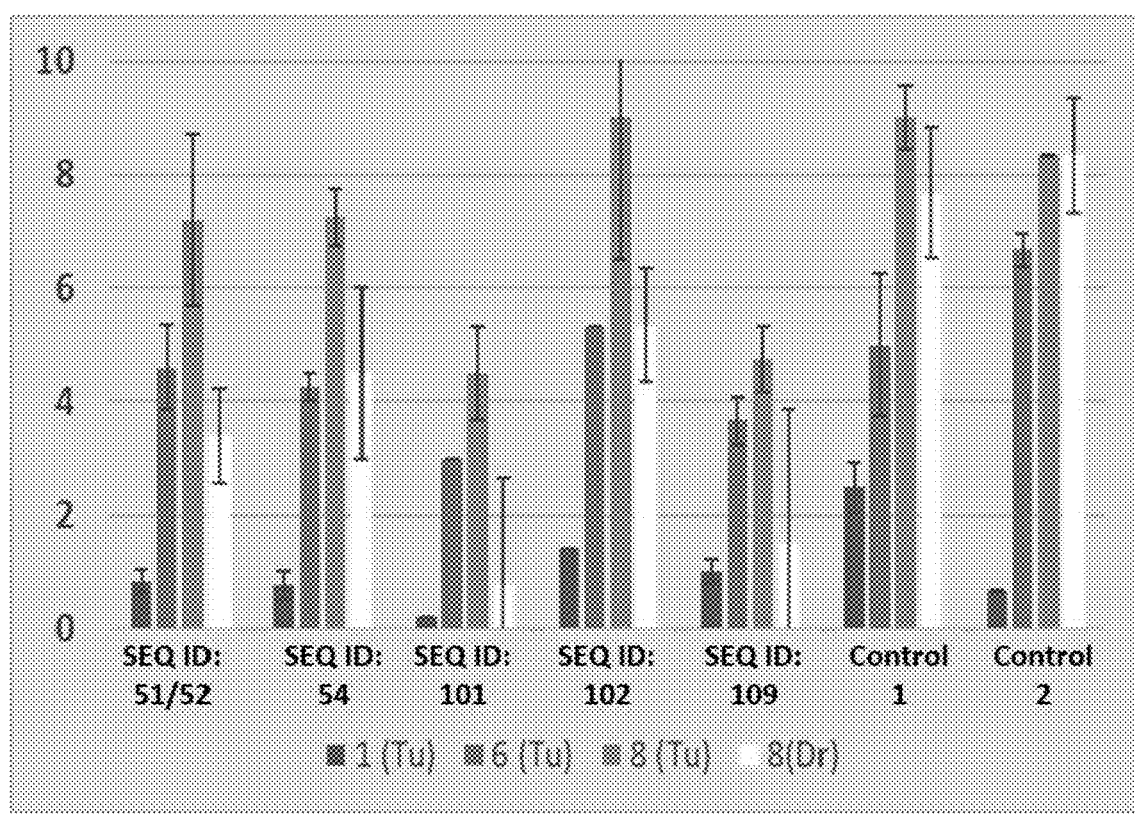
FIG. 9 graphically shows results of several drought resistance genes identified by the method of the present invention.

Reference is now made to FIG. 9 graphically showing phenotypic results of several drought resistance genes identified by the method of the present invention.

The graph shows average results of turgor pressure (Tu) and death rate (Dr) for several identified genes (see Table 4) under severe drought conditions. Scale for death and turgor loss is 1-10 when 10 is considered dry-brown and dead plants, or total loss of turgor, respectively. The results in the graph represent day 23 (1), day 28 (6) and day 30 (8) from sowing. Each column for each of the different expressed genes represents average of 5 repeats with 4 plants in each repeat. GFP expressing plants served as negative control and HRD as positive control. As can be seen, all tested genes identified by the method of the present invention showed significantly reduced turgor loss (by at least two fold after about 23 days from sowing) and reduced death rate (in the range of 9 to 2 fold after 30 days from sowing) as compared to plants expressing the negative control GFP gene. Moreover, plants expressing the newly discovered genes (see Table 4) demonstrated a significantly reduced death rated as compared to the positive control HRD expressing plants. These results indicate that by the method of the present invention, newly drought resistance genes are identified, which confer improved tolerance to drought in plants.

Another method used for evaluating plants performance in drought conditions is measuring their leaf area during the growth phase when drought conditions become prominent. About 10-14 days from sowing the plants, plant images were taken every 2-3 days together with a 50 mm² white surface. Image analysis was performed on pictures taken from the drought experiments and leaf area was calculated. The leaf area of several plant lines expressing novel genes identified as conferring drought resistance after re-cloning was compared to positive and negative controls (see Table 5 and FIG. 10).

Figure 10:
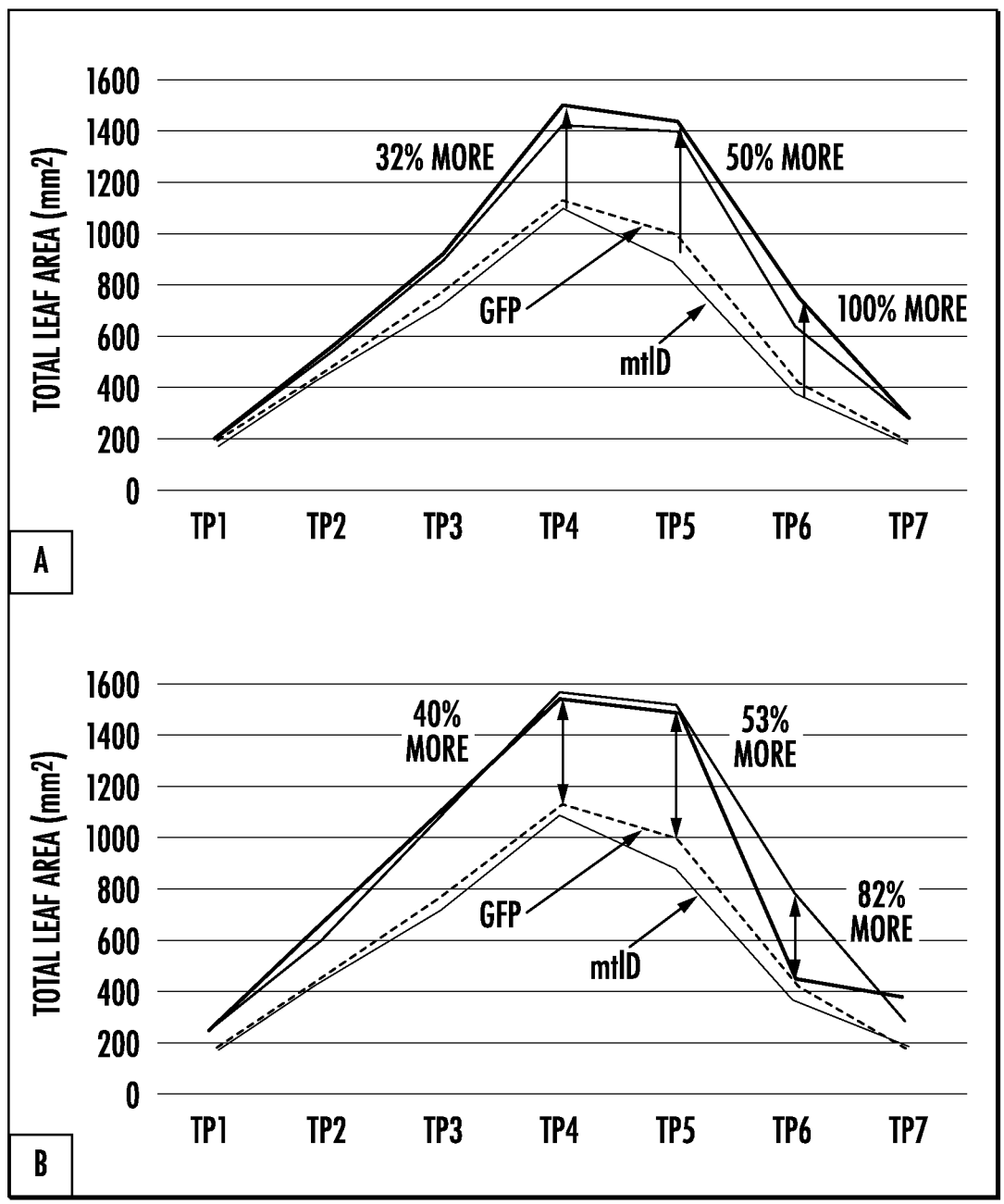
FIG. 10 graphically shows leaf area analysis of several transgenic plant lines expressing identified novel genes conferring drought resistance after re-cloning as compared to positive and negative controls.

The graph of FIG. 10 shows image analysis of leaf area of transformed plant lines. Two independent transformation events of the identified gene having SEQ ID NO: 16 (FIG. 10A) and two independent transformation events of the identified gene having SEQ ID NO: 25 (FIG. 10B) are shown in darker lines on top of each of the FIGS. 10A and 10B. These transgenic plants are compared to negative control plants expressing GFP, and positive control plants expressing mtlD, shown in lighter gray lines on the bottom of each of the FIGS. 10A and 10B. Improved performance under drought is shown as percentage from control plants at the indicated measured timepoint (TP) (arrows and percentages shown in the figure).

As can be seen in this figure, the total leaf area of plants expressing the newly identified tested genes was increased by between about 10% and about 82% (e.g. by about 45%) relative to plants expressing negative control genes.

To conclude, the present invention provides newly identified genes demonstrated to confer tolerance to drought conditions in plants.

C. Re-Cloning and Retransformation of Selected Genes into Plants

Selected genes from section B are re-cloned into the binary vectors as described above (i.e. FIG. 1A-D) and sequenced to confirm that it has the same sequence as the original gene from T1 and T2 experiments. Plants are transformed with the re-cloned gene and seeds are collected. Experiments are repeated as in B except for each gene 3-5 individual transgenic plants with different unrelated transformation events are tested. Each individual transgenic plant/event is subjected to 5-10 times of repeats in experiments, hence for each event for every gene 20-40 plants are tested, and for every different gene 60-200 plants are tested.

EXAMPLE 3

Polynucleotide Sequences Identified as Improving Drought and/or Salinity Resistance in Plants The process described above of screening of T1 transgenic seeds revealed about 1000 transgenes as candidate polynucleotide sequences for improving drought resistance in plants. Of these candidates, the screening of T2 seeds revealed about 140 best performing transgenes potentially improving drought resistance or tolerance in plants. These transgene sequences are subjected to further validation tests.

Reference is now made to Table 4, presenting examples of novel and unique polynucleotide sequences and polypeptides encoded by these sequences, found by the method of the present invention. These sequences are metatranscriptomes purified from environmentally challenged niches, SEQ ID NO:1 to SEQ ID NO:148 represent polynucleotide sequences found by the method of the present invention as candidates for improving drought resistance in plants (Table 4).

SEQ ID NO:149 to SEQ ID NO:321 represent polypeptide sequences encoded by the corresponding polynucleotide sequence found by the method of the present invention as candidates for improving drought resistance in plants (see Table 4).

Note that DNA sequences SEQ ID NO:9, SEQ ID NO:11, SEQ ID NO:20, SEQ ID NO: 21, SEQ ID NO:28, SEQ ID NO:36, SEQ ID NO:43, SEQ ID NO:47, SEQ ID NO: 51, SEQ ID NO:54, SEQ ID NO:55, SEQ ID NO:60, SEQ ID NO:75, SEQ ID NO:78, SEQ ID NO:80, SEQ ID NO:81, SEQ ID NO:85, SEQ ID NO:87, SEQ ID NO:97, SEQ ID NO: 98, SEQ ID NO: 105, SEQ ID NO:106, SEQ ID NO: 107, SEQ ID NO: 109, SEQ ID NO: 111, SEQ ID NO:112, SEQ ID NO:120, SEQ ID NO: 132, SEQ ID NO:134, SEQ ID NO: 135, SEQ ID NO:140, SEQ ID NO:141 encode more than one open reading frame (ORF) (referred to as SEQ. ID NO X. 1p and X.2p etc.) depending on different start codons.

TABLE 4

| SEQ ID Nos of polynucleotide and polypeptide sequences | |
|---|---|
| Polynucleotide SEQ ID NO. | Polynucleotide name |
| SEQ ID NO: 1 | A454 |
| SEQ ID NO: 2 | A456 |
| SEQ ID NO: 3 | A458.1 |
| SEQ ID NO: 4 | A458.2 |
| SEQ ID NO: 5 | A460 |
| SEQ ID NO: 6 | A462 |
| SEQ ID NO: 7 | A463 |
| SEQ ID NO: 8 | A466 |
| SEQ ID NO: 9 | A468 |
| SEQ ID NO: 10 | A470 |
| SEQ ID NO: 11 | A475 |
| SEQ ID NO: 12 | A477 |
| SEQ ID NO: 13 | A480 |
| SEQ ID NO: 14 | A481 |
| SEQ ID NO: 15 | A483 |
| SEQ ID NO: 16 | A484 |
| SEQ ID NO: 17 | A485a |
| SEQ ID NO: 18 | A485b |
| SEQ ID NO: 19 | A486 |
| SEQ ID NO: 20 | A498 |
| SEQ ID NO: 21 | A499 |
| SEQ ID NO: 22 | A501 |
| SEQ ID NO: 23 | A504.1 |
| SEQ ID NO: 24 | A504 |
| SEQ ID NO: 25 | A506 |
| SEQ ID NO: 26 | A507.1 |
| SEQ ID NO: 27 | A507.2 |
| SEQ ID NO: 28 | A510a |
| SEQ ID NO: 29 | A510b |
| SEQ ID NO: 30 | A512 |
| SEQ ID NO: 31 | A513a |
| SEQ ID NO: 32 | A513b |
| SEQ ID NO: 33 | A518 |
| SEQ ID NO: 34 | A520a |
| SEQ ID NO: 35 | AC2510 |
| SEQ ID NO: 36 | AD2607.1 |
| SEQ ID NO: 37 | AD2607.3 |
| SEQ ID NO: 38 | D860a |
| SEQ ID NO: 39 | D860b |
| SEQ ID NO: 40 | D862 |
| SEQ ID NO: 41 | D863 |
| SEQ ID NO: 42 | D881 |

TABLE 4-continued

| SEQ ID Nos of polynucleotide and polypeptide sequences | |
|---|---|
| Polynucleotide SEQ ID NO. | Polynucleotide name |
| SEQ ID NO: 43 | D890 |
| SEQ ID NO: 44 | De203 |
| SEQ ID NO: 45 | De214a |
| SEQ ID NO: 46 | De215a |
| SEQ ID NO: 47 | De215b.1 |
| SEQ ID NO: 48 | De215b.4 |
| SEQ ID NO: 49 | De215c |
| SEQ ID NO: 50 | De217 |
| SEQ ID NO: 51 | De223a |
| SEQ ID NO: 52 | De223b |
| SEQ ID NO: 53 | De227 |
| SEQ ID NO: 54 | De239a |
| SEQ ID NO: 55 | De245 |
| SEQ ID NO: 56 | De250.1 |
| SEQ ID NO: 57 | De250.2 |
| SEQ ID NO: 58 | De251 |
| SEQ ID NO: 59 | De313 |
| SEQ ID NO: 60 | F1022a |
| SEQ ID NO: 61 | F1022b |
| SEQ ID NO: 62 | G1085a |
| SEQ ID NO: 63 | G1181 |
| SEQ ID NO: 64 | G1190 |
| SEQ ID NO: 65 | H1301.1 |
| SEQ ID NO: 66 | H1301.2 |
| SEQ ID NO: 67 | K1464 |
| SEQ ID NO: 68 | K1475 |
| SEQ ID NO: 69 | M603 |
| SEQ ID NO: 70 | M606.1 |
| SEQ ID NO: 71 | M606.2 |
| SEQ ID NO: 72 | M607.1 |
| SEQ ID NO: 73 | M607.2 |
| SEQ ID NO: 74 | M609a.1 |
| SEQ ID NO: 75 | M609a.2 |
| SEQ ID NO: 76 | M609b |
| SEQ ID NO: 77 | M619a |
| SEQ ID NO: 78 | M619b |
| SEQ ID NO: 79 | M622a |
| SEQ ID NO: 80 | M622b |
| SEQ ID NO: 81 | M623a |
| SEQ ID NO: 82 | M623b.1 |
| SEQ ID NO: 83 | M623b.3 |
| SEQ ID NO: 84 | M623c |
| SEQ ID NO: 85 | M624 |
| SEQ ID NO: 86 | M625a.3 |
| SEQ ID NO: 87 | M625a |
| SEQ ID NO: 88 | M625b |
| SEQ ID NO: 89 | M631 |
| SEQ ID NO: 90 | M632a |
| SEQ ID NO: 91 | M635.1 |
| SEQ ID NO: 92 | M635.2 |
| SEQ ID NO: 93 | M638 |
| SEQ ID NO: 94 | M643 |
| SEQ ID NO: 95 | M649 |
| SEQ ID NO: 96 | M650a.3 |
| SEQ ID NO: 97 | M650a |
| SEQ ID NO: 98 | M650b |
| SEQ ID NO: 99 | M657 |
| SEQ ID NO: 100 | M659a |
| SEQ ID NO: 101 | M661 |
| SEQ ID NO: 102 | M663 |
| SEQ ID NO: 103 | M664.1 |
| SEQ ID NO: 104 | M664.2 |
| SEQ ID NO: 105 | M666 |
| SEQ ID NO: 106 | M671 |
| SEQ ID NO: 107 | M673 |
| SEQ ID NO: 108 | M676.3 |
| SEQ ID NO: 109 | M676 |
| SEQ ID NO: 110 | M677a |
| SEQ ID NO: 111 | M677b.1 |
| SEQ ID NO: 112 | M677b.3 |
| SEQ ID NO: 113 | M680 |
| SEQ ID NO: 114 | M691a.1 |
| SEQ ID NO: 115 | M691a.2 |
| SEQ ID NO: 116 | M691b |
| SEQ ID NO: 117 | M693 |
| SEQ ID NO: 118 | M697 |

TABLE 4-continued

SEQ ID Nos of polynucleotide and polypeptide sequences

| Polynucleotide SEQ ID NO. | Polynucleotide name |
|---|---|
| SEQ ID NO: 119 | M698 |
| SEQ ID NO: 120 | M705 |
| SEQ ID NO: 121 | M706 |
| SEQ ID NO: 122 | M715a |
| SEQ ID NO: 123 | M715b |
| SEQ ID NO: 124 | M719 |
| SEQ ID NO: 125 | M724 |
| SEQ ID NO: 126 | N1503a |
| SEQ ID NO: 127 | N1527.1 |
| SEQ ID NO: 128 | N1527.2 |
| SEQ ID NO: 129 | N1529 |
| SEQ ID NO: 130 | N1530 |
| SEQ ID NO: 131 | P1611 |
| SEQ ID NO: 132 | P1620.1 |
| SEQ ID NO: 133 | P1620.3 |
| SEQ ID NO: 134 | P1623a |
| SEQ ID NO: 135 | P1623b |
| SEQ ID NO: 136 | P1625a |
| SEQ ID NO: 137 | P1625b |
| SEQ ID NO: 138 | P1731 |
| SEQ ID NO: 139 | P1744 |
| SEQ ID NO: 140 | P1747.1 |
| SEQ ID NO: 141 | P1747.3 |
| SEQ ID NO: 142 | SN8 |
| SEQ ID NO: 143 | V1906b |
| SEQ ID NO: 144 | V1906c |
| SEQ ID NO: 145 | V1907a |
| SEQ ID NO: 146 | V1907b |
| SEQ ID NO: 147 | X2005 |
| SEQ ID NO: 148 | X2026 |
| SEQ ID NO: 149 | A454p |
| SEQ ID NO: 150 | A456p |
| SEQ ID NO: 151 | A458.1p |
| SEQ ID NO: 152 | A458.2p |
| SEQ ID NO: 153 | A460p |
| SEQ ID NO: 154 | A462p |
| SEQ ID NO: 155 | A463p |
| SEQ ID NO: 156 | A466p |
| SEQ ID NO: 157 | A468.1p |
| SEQ ID NO: 158 | A468.2p |
| SEQ ID NO: 159 | A470p |
| SEQ ID NO: 160 | A475.1p |
| SEQ ID NO: 161 | A475.2p |
| SEQ ID NO: 162 | A477p |
| SEQ ID NO: 163 | A480p |
| SEQ ID NO: 164 | A481p |
| SEQ ID NO: 165 | A483p |
| SEQ ID NO: 166 | A484p |
| SEQ ID NO: 167 | A485ap |
| SEQ ID NO: 168 | A485bp |
| SEQ ID NO: 169 | A486p |
| SEQ ID NO: 170 | A498.1p |
| SEQ ID NO: 171 | A498.2p |
| SEQ ID NO: 172 | A499.1p |
| SEQ ID NO: 173 | A499.2p |
| SEQ ID NO: 174 | A501p |
| SEQ ID NO: 175 | A504.1p |
| SEQ ID NO: 176 | A504.2p |
| SEQ ID NO: 177 | A506p |
| No ORF identified | No ORF identified |
| SEQ ID NO: 178 | A507.2p |
| SEQ ID NO: 179 | A510a.1p |
| SEQ ID NO: 180 | A510a.2p |
| No ORF identified | No ORF identified |
| SEQ ID NO: 181 | A512p |
| SEQ ID NO: 182 | A513ap |
| SEQ ID NO: 183 | A513bp |
| SEQ ID NO: 184 | A518p |
| SEQ ID NO: 185 | A520ap |
| SEQ ID NO: 186 | AC2510ap |
| SEQ ID NO: 187 | AD2607.1p |
| SEQ ID NO: 188 | AD2607.2p |
| SEQ ID NO: 189 | AD2607.3p |
| SEQ ID NO: 190 | D860ap |
| SEQ ID NO: 191 | D860bp |
| SEQ ID NO: 192 | D862p |
| SEQ ID NO: 193 | D863p |
| SEQ ID NO: 194 | D881p |
| SEQ ID NO: 195 | D890.1p |
| SEQ ID NO: 196 | D890.2p |
| SEQ ID NO: 197 | De203p |
| SEQ ID NO: 198 | De214ap |
| SEQ ID NO: 199 | De215ap |
| SEQ ID NO: 200 | De215b.1p |
| SEQ ID NO: 201 | De215b.2p |
| SEQ ID NO: 202 | De215b.3p |
| SEQ ID NO: 203 | De215b.4p |
| SEQ ID NO: 204 | De215cp |
| No ORF identified | No ORF identified |
| SEQ ID NO: 205 | De223a.1p |
| SEQ ID NO: 206 | De223a.2p |
| SEQ ID NO: 207 | De223bp |
| SEQ ID NO: 208 | De227p |
| SEQ ID NO: 209 | De239a.1p |
| SEQ ID NO: 210 | De239a.2p |
| SEQ ID NO: 211 | De245.1p |
| SEQ ID NO: 212 | De245.2p |
| SEQ ID NO: 213 | De250p |
| SEQ ID NO: 214 | De250.2p |
| SEQ ID NO: 215 | De251p |
| SEQ ID NO: 216 | De313p |
| SEQ ID NO: 217 | F1022a.1p |
| SEQ ID NO: 218 | F1022a.2p |
| SEQ ID NO: 219 | F1022bp |
| SEQ ID NO: 220 | G1085ap |
| SEQ ID NO: 221 | G1181p |
| SEQ ID NO: 222 | G1190p |
| SEQ ID NO: 223 | H1301.1p |
| SEQ ID NO: 224 | H1301.2p |
| No ORF identified | No ORF identified |
| SEQ ID NO: 225 | K1475p |
| SEQ ID NO: 226 | M603p |
| SEQ ID NO: 227 | M606.1p |
| SEQ ID NO: 228 | M606.2p |
| SEQ ID NO: 229 | M607. 1p |
| SEQ ID NO: 230 | M607.2p |
| SEQ ID NO: 231 | M609a.1p |
| SEQ ID NO: 233 | M609a.3p |
| SEQ ID NO: 232 | M609a.2p |
| SEQ ID NO: 234 | M609bp |
| SEQ ID NO: 235 | M619ap |
| SEQ ID NO: 236 | M619b.1p |
| SEQ ID NO: 237 | M619b.2p |
| SEQ ID NO: 238 | M622ap |
| SEQ ID NO: 239 | M622b.1p |
| SEQ ID NO: 240 | M622b.2p |
| SEQ ID NO: 241 | M623a.1p |
| SEQ ID NO: 242 | M623a.2p |
| No ORF identified | No ORF identified |
| SEQ ID NO: 243 | M623b.3p |
| SEQ ID NO: 244 | M623cp |
| SEQ ID NO: 245 | M624. 1p |
| SEQ ID NO: 246 | M624.2p |
| SEQ ID NO: 249 | M625a.3p |
| SEQ ID NO: 247 | M625a.1p |
| SEQ ID NO: 248 | M625a.2p |
| SEQ ID NO: 250 | M625bp |
| SEQ ID NO: 251 | M631p |
| SEQ ID NO: 252 | M632ap |
| SEQ ID NO: 253 | M635.1p |
| SEQ ID NO: 254 | M635.2p |
| SEQ ID NO: 255 | M638p |
| SEQ ID NO: 256 | M643p |
| SEQ ID NO: 257 | M649p |
| SEQ ID NO: 260 | M650a.3p |
| SEQ ID NO: 258 | M650a.1p |
| SEQ ID NO: 259 | M650a.2p |
| SEQ ID NO: 261 | M650b.1p |
| SEQ ID NO: 262 | M650b.2p |
| SEQ ID NO: 263 | M657p |
| SEQ ID NO: 264 | M659ap |
| SEQ ID NO: 265 | M661p |

TABLE 4-continued

SEQ ID Nos of polynucleotide and polypeptide sequences

| Polynucleotide SEQ ID NO. | Polynucleotide name |
|---|---|
| SEQ ID NO: 266 | M663p |
| SEQ ID NO: 267 | M664.1p |
| SEQ ID NO: 268 | M664.2p |
| SEQ ID NO: 269 | M666.1p |
| SEQ ID NO: 270 | M666.2p |
| SEQ ID NO: 271 | M671.1p |
| SEQ ID NO: 272 | M671.2p |
| SEQ ID NO: 273 | M673.1p |
| SEQ ID NO: 274 | M673.2p |
| SEQ ID NO: 277 | M676.3p |
| SEQ ID NO: 275 | M676.1p |
| SEQ ID NO: 276 | M676.2p |
| SEQ ID NO: 278 | M677ap |
| SEQ ID NO: 279 | M677b.1p |
| SEQ ID NO: 280 | M677b.2p |
| SEQ ID NO: 281 | M677b.3p |
| SEQ ID NO: 282 | M677b.4p |
| SEQ ID NO: 283 | M680p |
| SEQ ID NO: 284 | M691a.1p |
| SEQ ID NO: 285 | M691a.2p |
| SEQ ID NO: 286 | M691bp |
| SEQ ID NO: 287 | M693p |
| SEQ ID NO: 288 | M697p |
| SEQ ID NO: 289 | M698p |
| SEQ ID NO: 290 | M705.1p |
| SEQ ID NO: 291 | M705.2p |
| SEQ ID NO: 292 | M706p |
| SEQ ID NO: 293 | M715ap |
| SEQ ID NO: 294 | M715bp |
| SEQ ID NO: 295 | M719p |
| SEQ ID NO: 296 | M724p |
| SEQ ID NO: 297 | N1503ap |
| SEQ ID NO: 298 | N1527.1p |
| SEQ ID NO: 299 | N1527.2p |
| SEQ ID NO: 300 | N1529p |
| SEQ ID NO: 301 | N1530p |
| SEQ ID NO: 302 | P1611p |
| SEQ ID NO: 303 | P1620.1p |
| SEQ ID NO: 304 | P1620.2p |
| SEQ ID NO: 305 | P1620.3p |
| SEQ ID NO: 306 | P1623a.1p |
| SEQ ID NO: 307 | P1623a.2p |
| SEQ ID NO: 308 | P1623b.1p |
| SEQ ID NO: 309 | P1623b.2p |
| SEQ ID NO: 310 | P1625ap |
| SEQ ID NO: 311 | P1625bp |
| SEQ ID NO: 312 | P1731p |
| SEQ ID NO: 313 | P1744p |
| SEQ ID NO: 314 | P1747.1p |
| SEQ ID NO: 315 | P1747.2p |
| SEQ ID NO: 316 | P1747.3p |
| SEQ ID NO: 317 | P1747.4p |
| No ORF identified | No ORF identified |
| SEQ ID NO: 318 | V1906bp |
| No ORF identified | No ORF identified |
| SEQ ID NO: 319 | V1907ap |
| No ORF identified | No ORF identified |
| SEQ ID NO: 320 | X2005p |
| SEQ ID NO: 321 | X2026p |

Reference is now made to Table 5 presenting phenotypic results of several of the identified genes in the drought tolerance experiments. Plants were grown in soil in controlled greenhouses and tested for drought tolerance under the conditions mentioned above. During their growth, measurements and images were taken (see Table 3) and image analysis was applied converting the images to leaf area per plant. Results are shown as percentage of GFP expressing plants measurements that served as a negative control during the drought phase.

TABLE 5

Results of drought experiments conducted with T2 Arabidopsis plants

| Seq ID | DR | ±SD | Seq ID | DR | ±SD | Seq ID | DR | ±SD | Seq ID | DR | ±SD | Seq ID | DR | ±SD |
|---|---|---|---|---|---|---|---|---|---|---|---|---|---|---|
| SEQ ID NO: 1 | 116.00 | 3.13 | SEQ ID NO: 25 | 137.14 | 7.05 | SEQ ID NO: 55 | 144.00 | 5.56 | SEQ ID NO: 91/92 | 143.23 | 7.26 | SEQ ID NO: 122 | 120.00 | 10.25 |
| SEQ ID NO: 2 | 132.86 | 6.68 | SEQ ID NO: 26/27 | 135.00 | 7.64 | SEQ ID NO: | 134.00 | 3.28 | SEQ ID NO: 93 | 133.33 | 6.84 | SEQ ID NO: 124 | 130.73 | 5.93 |
| SEQ ID NO: 17/18 | 151.43 | 10.52 | SEQ ID NO: 28 | 187.64 | 11.00 | SEQ ID NO: 56/57 | 151.6 | 20.7 | SEQ ID NO: 94 | 102.50 | 7.08 | SEQ ID NO: 125 | 139.10 | 9.76 |
| SEQ ID NO: 5 | 146.9 | 20.6 | SEQ ID NO: 30 | 118.57 | 1.88 | SEQ ID NO: 58 | 134.08 | 4.45 | SEQ ID NO: 97 | 133.41 | 7.61 | SEQ ID NO: 127/128 | 119.09 | 4.03 |
| SEQ ID NO: 6 | 118.57 | 5.26 | SEQ ID NO: 31 | 112.56 | 4.97 | SEQ ID NO: 60 | 99.72 | 4.71 | SEQ ID NO: 99 | 137.50 | 8.80 | SEQ ID NO: 129 | 135.01 | 7.89 |
| SEQ ID NO: 7 | 156.7 | 23.4 | SEQ ID NO: 33 | 167.57 | 7.20 | SEQ ID NO: 62 | 277.71 | 16.80 | SEQ ID NO: 100 | 160.11 | 20.12 | SEQ ID NO: 129 | 196.80 | 9.06 |
| SEQ ID NO: 8 | 162.1 | 17.1 | SEQ ID NO: 34 | 118.92 | 5.31 | SEQ ID NO: 63 | 136.83 | 6.62 | SEQ ID NO: 101 | 182.50 | 10.00 | SEQ ID NO: 130 | 113.98 | 7.65 |
| SEQ ID NO: 9 | 138.24 | 20.36 | SEQ ID NO: 35 | 115.20 | 6.60 | SEQ ID NO: 64 | 107.77 | 10.82 | SEQ ID NO: 102 | 136.67 | 8.72 | SEQ ID NO: 131 | 110.33 | 6.64 |
| SEQ ID NO: 10 | 116.00 | 3.19 | SEQ ID NO: 36/37 | 109.71 | 7.79 | SEQ ID NO: 65/66 | 131.25 | 7.04 | SEQ ID NO: 103/104 | 121.79 | 7.45 | SEQ ID NO: 132/133 | 107.54 | 9.76 |
| SEQ ID NO: 11 | 107.14 | 2.93 | SEQ ID NO: 38 | 124.59 | 6.74 | SEQ ID NO: 67 | 186.67 | 9.85 | SEQ ID NO: 105 | 126.73 | 6.48 | SEQ ID NO: 134 | 114.17 | 5.84 |
| SEQ ID NO: 12 | 122.86 | 4.53 | SEQ ID NO: 40 | 154.29 | 10.83 | SEQ ID NO: 68 | 132.64 | 8.96 | SEQ ID NO: 106 | 125.00 | 5.94 | SEQ ID NO: 137 | 139.80 | 9.87 |
| SEQ ID NO: 13 | 160.00 | 12.32 | SEQ ID NO: 41 | 117.14 | 5.71 | SEQ ID NO: 69 | 145.00 | 7.07 | SEQ ID NO: 107 | 130.00 | 6.64 | SEQ ID NO: 138 | 115.04 | 6.38 |
| SEQ ID NO: 14 | 142.86 | 8.37 | SEQ ID NO: 42 | 118.27 | 3.56 | SEQ ID NO: 70/71 | 134.08 | 7.08 | SEQ ID NO: 109 | 175.00 | 7.38 | SEQ ID NO: 139 | 105.73 | 8.08 |
| SEQ ID NO: 15 | 145.71 | 7.24 | SEQ ID NO: 43 | 141.69 | 8.03 | SEQ ID NO: | | | SEQ ID NO: 110 | 118.92 | 5.89 | SEQ ID NO: 140/141 | | |
| SEQ ID | 136.13 | 8.55 | SEQ ID | 144.00 | 6.36 | SEQ ID NO: | | | | | | | | |

TABLE 5-continued

Results of drought experiments conducted with T2 *Arabidopsis* plants

| Seq ID | DR | ±SD | Seq ID | DR | ±SD | Seq ID | DR | ±SD | Seq ID | DR | ±SD | Seq ID | DR | ±SD |
|---|---|---|---|---|---|---|---|---|---|---|---|---|---|---|
| NO: 16 | | | NO: 44 | | | 72/73 | | | SEQ ID NO: 113 | 113.14 | 8.47 | SEQ ID NO: 142 | 141.43 | 3.65 |
| SEQ ID NO: 17 | 108.33 | 2.73 | SEQ ID NO: 45 | 142.70 | 9.33 | SEQ ID NO: 74/75/76 | 187.50 | 10.00 | SEQ ID NO: 114/115/116 | 108.04 | 5.44 | SEQ ID NO: 143 | 115.50 | 7.96 |
| SEQ ID NO: 19 | 121.67 | 5.66 | SEQ ID NO: 46 | 119.36 | 9.40 | SEQ ID NO: 77 | 125.00 | 8.29 | SEQ ID NO: 117 | 167.50 | 9.13 | SEQ ID NO: 145 | 112.59 | 7.32 |
| SEQ ID NO: 20 | 118.68 | 2.48 | SEQ ID NO: 50 | 110.51 | 7.81 | SEQ ID NO: 79 | 123.73 | 6.78 | SEQ ID NO: 118 | 131.68 | 8.77 | SEQ ID NO: 147 | 121.66 | 8.81 |
| SEQ ID NO: 21 | 116.67 | 4.01 | SEQ ID NO: 51 | 158.00 | 13.73 | SEQ ID NO: 81 | 159.79 | 8.45 | SEQ ID NO: 119 | 121.04 | 6.30 | SEQ ID NO: 148 | 121.07 | 5.86 |
| SEQ ID NO: 22 | 131.67 | 8.00 | SEQ ID NO: 53 | 119.42 | 8.70 | SEQ ID NO: 85 | 180.00 | 7.07 | SEQ ID NO: 120 | 104.85 | 7.51 | GFP | 100.00 | 6.55 |
| SEQ ID NO: 23/24 | 124.29 | 6.45 | SEQ ID NO: 54 | 145.00 | 11.92 | SEQ ID NO: 87 | 267.03 | 16.40 | SEQ ID NO: 121 | 113.85 | 6.36 | | | |
| | | | | | | SEQ ID NO: 89 | 173.33 | 4.58 | | | | | | |
| | | | | | | SEQ ID NO: 90 | 135.00 | 9.29 | | | | | | |

DR - performance (leaf area) under Drought shown in % of GFP expressing plants
SD - value shown ± standard deviation As shown in Table 5, all plants expressing the tested genes identified by the method of the present invention revealed increased leaf area by about 15% to about 90% under drought conditions as compared to plants expressing the negative control gene (GFP). These results demonstrate that the method of the present invention provides novel genes conferring improved drought tolerance in plants.

Reference is now made to Table 6 presenting results of drought experiments conducted with T2 *Arabidopsis* plants re-cloned with the relevant Seq. IDs. Different Seq. IDs were re-cloned and re-transformed into *Arabidopsis* plants generating several independent events (represented by E1-3 in Table 6). Plants were grown in soil in controlled greenhouses and tested for drought tolerance under the conditions mentioned above. During their growth, images were taken and image analysis was applied, converting the images into leaf area per plant. Results are shown in Table 6 as percentage of GFP expressing plants that served as a negative control during the drought phase.

TABLE 6

Results of drought experiments conducted with
T2 *Arabidopsis* plants re-cloned with the relevant Seq. IDs

| Seq ID | DR RC E1 | E1 ± SD | DR RC E2 | E2 ± SD | DR RC E3 | E3 ± SD |
|---|---|---|---|---|---|---|
| SEQ ID NO: 2 | 114.05 | 12.00 | 126.33 | 6.27 | 94.42 | 14.75 |
| SEQ ID NO: 7 | 125.74 | 7.50 | 118.43 | 12.40 | 82.39 | 17.20 |
| SEQ ID NO: 8 | 126.96 | 10.73 | 110.07 | 13.09 | 132.74 | 5.34 |
| SEQ ID NO: 9 | 159.34 | 19.75 | 151.99 | 27.05 | 113.97 | 18.65 |
| SEQ ID NO: 10 | 185.23 | 19.29 | 165.97 | 30.99 | 90.04 | 9.27 |
| SEQ ID NO: 11 | 116.91 | 9.54 | 106.90 | 10.41 | 106.32 | 10.87 |
| SEQ ID NO: 12 | 178.80 | 24.09 | 107.57 | 14.72 | 157.66 | 15.22 |
| SEQ ID NO: 14 | 162.78 | 14.10 | 151.93 | 9.90 | 123.68 | 10.10 |
| SEQ ID NO: 16 | 144.23 | 8.42 | 141.32 | 7.03 | 127.03 | 8.31 |
| SEQ ID NO: 18 | 176.30 | 26.57 | 126.24 | 11.63 | 138.53 | 23.03 |
| SEQ ID NO: 22 | 113.00 | 12.14 | 109.38 | 9.14 | 105.16 | 12.38 |
| SEQ ID NO: 25 | 150.56 | 7.57 | 153.02 | 9.91 | 120.25 | 13.63 |
| SEQ ID NO: 28 | 193.32 | 28.79 | | | | |
| SEQ ID NO: 30 | 123.33 | 11.83 | 113.97 | 8.18 | 112.53 | 16.34 |
| SEQ ID NO: 33 | 141.20 | 10.90 | 127.98 | 13.30 | 112.63 | 11.50 |
| SEQ ID NO: 34 | 167.25 | 12.60 | 150.19 | 13.30 | 138.48 | 10.20 |
| SEQ ID NO: 41 | 160.43 | 11.60 | 153.92 | 14.10 | 112.83 | 10.80 |
| SEQ ID NO: 43 | 229.50 | 18.12 | 136.33 | 32.37 | 106.83 | 26.53 |
| SEQ ID NO: 51 | 178.07 | 13.10 | 170.57 | 14.60 | 146.17 | 11.20 |
| SEQ ID NO: 54 | 169.39 | 15.50 | 131.72 | 11.30 | 120.10 | 16.70 |
| SEQ ID NO: 55 | 126.72 | 16.39 | 122.48 | 18.62 | 111.94 | 17.92 |
| SEQ ID NO: 56/57 | 138.08 | 8.64 | 134.76 | 9.21 | 127.74 | 10.65 |
| SEQ ID NO: 58 | 115.36 | 11.52 | 117.79 | 13.24 | 93.16 | 11.94 |
| SEQ ID NO: 60 | 151.90 | 12.80 | 137.24 | 11.90 | 93.80 | 5.60 |
| SEQ ID NO: 61 | 140.14 | 12.10 | 116.31 | 14.70 | 114.09 | 10.30 |
| SEQ ID NO: 74/75/76 | 175.07 | 13.50 | 160.92 | 12.30 | 105.95 | 11.30 |
| SEQ ID NO: 77 | 210.21 | 18.03 | 174.80 | 18.44 | 160.93 | 29.97 |
| SEQ ID NO: 78 | 182.00 | 15.30 | 175.52 | 16.80 | 115.61 | 11.10 |
| SEQ ID NO: 85 | 132.73 | 10.80 | 119.86 | 11.50 | 114.46 | 9.90 |
| SEQ ID NO: 89 | 167.95 | 21.26 | 154.64 | 21.46 | 142.21 | 29.65 |
| SEQ ID NO: 90 | 141.50 | 24.45 | 137.53 | 17.22 | 110.29 | 32.15 |
| SEQ ID NO: 91/92 | 219.30 | 29.16 | 192.51 | 22.47 | 92.77 | 20.90 |
| SEQ ID NO: 93 | 127.73 | 16.50 | 122.99 | 11.32 | 119.54 | 17.08 |

TABLE 6-continued

Results of drought experiments conducted with
T2 *Arabidopsis* plants re-cloned with the relevant Seq. IDs

| Seq ID | DR RC E1 | E1 ± SD | DR RC E2 | E2 ± SD | DR RC E3 | E3 ± SD |
|---|---|---|---|---|---|---|
| SEQ ID NO: 94 | 123.64 | 13.85 | 120.32 | 9.86 | 107.77 | 15.59 |
| SEQ ID NO: 95 | 129.53 | 9.05 | 108.36 | 9.42 | 98.43 | 14.09 |
| SEQ ID NO: 101 | 161.68 | 14.10 | 141.20 | 11.30 | 134.68 | 13.60 |
| SEQ ID NO: 105 | 204.51 | 27.93 | 188.14 | 5.31 | 156.19 | 17.89 |
| SEQ ID NO: 106 | 153.33 | 12.60 | 143.91 | 10.80 | 130.47 | 11.50 |
| SEQ ID NO: 109 | 141.18 | 14.20 | 134.15 | 11.60 | 124.80 | 10.30 |
| SEQ ID NO: 110 | 118.66 | 10.30 | 113.58 | 8.40 | 104.01 | 7.60 |
| SEQ ID NO: 111/112 | 228.16 | 35.62 | 202.43 | 18.73 | 132.98 | 18.32 |
| SEQ ID NO: 113 | 158.59 | 24.54 | 155.03 | 21.36 | 135.44 | 17.44 |
| SEQ ID NO: 126 | 185.07 | 13.40 | 147.37 | 16.20 | 131.05 | 10.80 |

DR - performance (leaf area) under drought shown as % of GFP expressing plants
RC E1-3 - performance with re-cloned relevant Seq. ID event 1-3
SD - value shown ± standard deviation As shown in Table 6, plants expressing the re-cloned genes identified by the method of the present invention presented enhanced leaf area as compared to plats expressing the negative control gene, in *Arabidopsis* plants subjected to drought conditions.

Reference is now made to Table 7 presenting results of drought experiments conducted with T2 tobacco plants. Different genes identified by the present invention were re-cloned and transformed into tobacco plants generating several independent events (represented by E1-3 in Table 7). Plants were grown in soil in controlled greenhouses and tested for drought tolerance under the conditions mentioned above. At the end of the experiment plant shoots fresh weight, leaves number, length of main branch and weight of main branch were evaluated. Results are shown in Table 7 as percentage of wild type (WT) plants that served as a negative control.

The results presented in Table 7 show that most of the genes identified by the present invention confer improved tolerance to drought conditions in Tobacco plants, as shown by the tested parameters (e.g. fresh weight, leaf number, branch fresh weight, branch length) as compared to negative control plants.

Reference is now made to Table 8 presenting results of salinity experiments of transgenic tobacco plants as compared to control WT plants. Different tobacco lines expressing various genes identified by the method of the present invention (see Table 4), were germinated in soil. Seven days post germination; plants were irrigated with fertilized water containing 400 mM NaCl. Leaf images were taken 14 days after irrigation with salt and analyzed for leaf area for the different independent events. Results are shown in Table 8 as percentage leaf area difference from WT plants.

TABLE 7

Results of drought experiments conducted with T2 Tobacco plants

| Seq ID | FW | FW ± SD | LN | LN ± SD | BFW | BFW ± SD | BL | BL ± SD |
|---|---|---|---|---|---|---|---|---|
| SEQ ID NO: 1 E1 | 104.71 | 11.18 | 73.58 | 11.63 | 106.78 | 14.75 | 122.73 | 9.25 |
| SEQ ID NO: 1 E2 | 97.28 | 2.18 | 67.92 | 4.76 | 86.18 | 5.10 | 97.27 | 8.86 |
| SEQ ID NO: 1 E3 | 99.22 | 11.21 | 64.15 | 7.70 | 116.72 | 6.30 | 118.18 | 8.90 |
| SEQ ID NO: 2 E1 | 122.23 | 2.70 | 116.76 | 4.84 | 115.42 | 3.47 | 97.33 | 4.87 |
| SEQ ID NO: 2 E2 | 119.11 | 5.62 | 101.62 | 3.97 | 122.99 | 2.70 | 114.84 | 2.98 |
| SEQ ID NO: 2 E3 | 116.69 | 9.00 | 111.35 | 4.58 | 117.50 | 14.45 | 102.67 | 9.91 |
| SEQ ID NO: 15 E1 | 111.60 | 4.18 | 98.38 | 7.58 | 113.65 | 4.39 | 102.08 | 4.89 |
| SEQ ID NO: 15 E2 | 121.87 | 2.88 | 118.92 | 2.53 | 122.25 | 3.70 | 100.59 | 3.71 |
| SEQ ID NO: 15 E3 | 113.93 | 5.39 | 116.76 | 6.42 | 103.32 | 7.79 | 95.25 | 9.41 |
| SEQ ID NO: 44 E1 | 124.04 | 4.23 | 118.92 | 6.69 | 130.31 | 5.23 | 94.66 | 6.12 |
| SEQ ID NO: 44 E2 | 121.17 | 8.34 | 108.11 | 3.54 | 128.45 | 14.00 | 112.02 | 8.14 |
| SEQ ID NO: 44 E3 | 113.80 | 10.36 | 117.84 | 7.28 | 118.83 | 9.15 | 90.80 | 8.89 |
| SEQ ID NO: 55 E1 | 120.52 | 3.43 | 123.24 | 5.53 | 122.56 | 5.65 | 102.08 | 5.33 |
| SEQ ID NO: 55 E2 | 117.85 | 8.35 | 113.51 | 3.42 | 121.35 | 11.26 | 95.55 | 7.40 |
| SEQ ID NO: 55 E3 | 123.13 | 5.02 | 111.35 | 9.31 | 127.92 | 8.75 | 110.09 | 7.81 |
| SEQ ID NO: 56/57 E1 | 101.58 | 5.17 | 75.47 | 8.92 | 80.26 | 23.40 | 109.55 | 6.45 |
| SEQ ID NO: 56/57 E2 | 106.93 | 9.10 | 79.25 | 8.50 | 101.30 | 10.14 | 103.64 | 7.22 |
| SEQ ID NO: 56/57 E3 | 98.16 | 10.90 | 75.47 | 8.92 | 81.97 | 10.54 | 100.91 | 15.84 |
| SEQ ID NO: 142 E1 | 110.50 | 5.07 | 94.34 | 15.46 | 109.37 | 7.31 | 116.82 | 16.89 |
| SEQ ID NO: 142 E2 | 119.83 | 5.07 | 94.34 | 1.98 | 105.75 | 5.15 | 118.64 | 19.00 |
| SEQ ID NO: 142 E3 | 114.89 | 2.74 | 98.11 | 6.86 | 101.90 | 5.94 | 95.45 | 19.44 |
| WT | 100.00 | 2.43 | 100.00 | 1.67 | 100.00 | 9.84 | 100.00 | 11.65 |

FW - fresh weight measured in grams
LN - leaf number
BFW - branch fresh weight measured in grams
BL - main branch length measured in cm
SD - value shown +/− standard deviation as % of measured trait
E1-3 - different independent events

TABLE 8

Results of salinity experiments on tobacco plants

| Seq ID | HST | ± SD |
|---|---|---|
| SEQ ID NO: 1 | 225.12 | 12.65 |
| SEQ ID NO: 2 | 240.63 | 28.91 |
| SEQ ID NO: 15 | 505.52 | 17.57 |
| SEQ ID NO: 44 | 767.46 | 7.48 |
| SEQ ID NO: 55 | 206.71 | 26.27 |
| SEQ ID NO: 56/57 | 286.19 | 4.86 |
| SEQ ID NO: 70/71 | 1366.07 | 4.70 |
| SEQ ID NO: 142 | 318.54 | 29.75 |
| WT | 100.00 | 13.22 |

HST - high salinity tolerance shown as % difference of leaf area as compared to WT
SD - value shown +/− standard deviation between 4 independent events The results of Table 8 clearly show that plants expressing the novel salinity tolerance genes identified by the present invention revealed significantly higher leaf area as compared to WT control plants.

Reference is now made to Table 9 presenting salinity experiments conducted on *Arabidopsis* plants expressing novel genes having Seq. IDs as indicated. Ten plants per event per pot were grown in soil in controlled greenhouse. After germination, all pots with plants were irrigated by submerging them with 100 mM NaCl. The results of Table 9 represent average data of 4 different events per Seq. ID and wild type plants (WT).

TABLE 9

Results of salinity experiments conducted on *Arabidopsis* plants expressing novel identified genes

| Seq ID | Flower & Pod production | FP ± SD | Chlorosis | Chlor ± SD |
|---|---|---|---|---|
| SEQ ID NO: 1 | 2.50 | 0.50 | 4.17 | 0.00 |
| SEQ ID NO: 2 | 3.75 | 0.48 | 4.58 | 0.00 |
| SEQ ID NO: 5 | 1.00 | 0.41 | 2.33 | 1.00 |
| SEQ ID NO: 6 | 3.25 | 0.25 | 4.42 | 0.00 |
| SEQ ID NO: 7 | 3.50 | 0.50 | 4.42 | 0.25 |
| SEQ ID NO: 8 | 4.00 | 0.41 | 4.67 | 0.00 |
| SEQ ID NO: 9 | 3.25 | 0.25 | 4.33 | 0.25 |
| SEQ ID NO: 10 | 2.25 | 0.48 | 3.42 | 0.41 |
| SEQ ID NO: 11 | 1.50 | 0.50 | 3.00 | 0.50 |
| SEQ ID NO: 12 | 2.75 | 0.63 | 3.83 | 0.63 |
| SEQ ID NO: 13 | 2.75 | 0.25 | 3.58 | 0.00 |
| SEQ ID NO: 16 | 2.75 | 0.63 | 4.08 | 0.00 |
| SEQ ID NO: 18 | 1.50 | 0.29 | 2.92 | 0.25 |
| SEQ ID NO: 22 | 2.50 | 0.87 | 3.33 | 0.41 |
| SEQ ID NO: 23/24 | 3.50 | 0.29 | 4.50 | 0.00 |
| SEQ ID NO: 25 | 2.25 | 0.75 | 3.08 | 0.29 |
| SEQ ID NO: 26/27 | 1.75 | 0.48 | 3.00 | 0.25 |
| SEQ ID NO: 29 | 2.50 | 0.29 | 3.83 | 0.25 |
| SEQ ID NO: 30 | 3.25 | 0.48 | 4.25 | 0.29 |
| SEQ ID NO: 30 | 3.00 | 0.71 | 4.33 | 0.00 |
| SEQ ID NO: 33 | 2.50 | 0.87 | 3.42 | 0.25 |
| SEQ ID NO: 94 | 2.50 | 0.29 | 3.67 | 0.29 |
| SEQ ID NO: 40 | 1.25 | 0.48 | 2.33 | 1.25 |
| SEQ ID NO: 43 | 2.00 | 0.41 | 3.75 | 0.25 |
| SEQ ID NO: 44 | 3.50 | 0.29 | 4.42 | 0.25 |
| SEQ ID NO: 55 | 2.00 | 0.41 | 3.67 | 0.00 |
| SEQ ID NO: 56/57 | 2.50 | 0.29 | 3.58 | 0.25 |
| SEQ ID NO: 58 | 1.75 | 0.85 | 2.67 | 1.04 |
| SEQ ID NO: 59 | 3.00 | 0.41 | 3.75 | 0.48 |
| SEQ ID NO: 70/71 | 1.75 | 0.63 | 2.67 | 1.00 |
| SEQ ID NO: 77 | 2.00 | 0.00 | 3.50 | 0.29 |
| SEQ ID NO: 89 | 1.75 | 0.63 | 2.50 | 1.11 |
| SEQ ID NO: 90 | 3.00 | 0.71 | 3.83 | 0.25 |
| SEQ ID NO: 91/92 | 1.00 | 0.00 | 3.17 | 0.58 |
| SEQ ID NO: 93 | 2.75 | 0.25 | 4.17 | 0.25 |
| SEQ ID NO: 95 | 3.75 | 0.25 | 4.50 | 0.25 |
| SEQ ID NO: 99 | 2.00 | 0.41 | 3.00 | 0.25 |
| SEQ ID NO: 103/104 | 2.00 | 0.00 | 3.67 | 0.29 |

TABLE 9-continued

Results of salinity experiments conducted on *Arabidopsis* plants expressing novel identified genes

| Seq ID | Flower & Pod production | FP ± SD | Chlorosis | Chlor ± SD |
|---|---|---|---|---|
| SEQ ID NO: 106 | 1.00 | 0.00 | 2.25 | 0.29 |
| SEQ ID NO: 107 | 1.75 | 0.25 | 3.00 | 0.25 |
| SEQ ID NO: 110 | 1.75 | 0.25 | 2.83 | 0.25 |
| SEQ ID NO: 111/112 | 1.00 | 0.00 | 3.08 | 0.25 |
| SEQ ID NO: 113 | 1.25 | 0.75 | 1.83 | 1.44 |
| SEQ ID NO: 118 | 2.50 | 0.29 | 3.25 | 0.50 |
| SEQ ID NO: 119 | 2.25 | 1.03 | 2.75 | 1.19 |
| SEQ ID NO: 120 | 2.00 | 0.41 | 3.08 | 0.29 |
| SEQ ID NO: 124 | 1.75 | 0.25 | 3.00 | 0.00 |
| HRD | 1.25 | 0.25 | 2.83 | 0.48 |
| WT | 1.00 | 0.00 | 1.83 | 0.55 |

FP - Flowers and pods production
1-No Flowers
2-Few flowers formation with short flowering stems
3-Some flower formation almost no pods
4-Flowers and pods forming
Chlorosis - Chlorosis and damage to leaves
1-Completely dry leaves
2-Dry leaf edges
3-Yellow
4-Some Yellow
5-Green
± SD-standard deviation As shown in Table 9, plants expressing genes identified by the method of the present invention as conferring salinity tolerance, demonstrated significantly higher flowers and pods yield and significantly reduced chlorosis and damage effects to the leaves as compared to WT control plants subjected to the same salinity stress conditions.

To conclude, the experimental results presented above clearly demonstrate that by the unique method of the present invention, highly valuable stress tolerance (e.g. drought, salinity) genes in plants can be identified. The newly identified genes confer improved tolerance or resistance to the preselected stress in plants in various important parameters such as leaf area, turgor pressure, aerial yield and quality, flowers and fruits yield etc. These results show that the present invention provides a novel screening method that identifies stress tolerance plant genes that can be expressed in desirable and important crops to enable their growth and enhance their yield under various abiotic and biotic stress conditions.

REFERENCES

Gabor, E. M., Alkema, W. B. & Janssen, D. B. (2004) Quantifying the accessibility of the metagenome by random expression cloning techniques. Environ Microbiol 6, 879-886.

Culligan, E. P., Sleator, R. D., Marchesi, J. R. & Hill, C. (2014) Metagenomics and novel gene discovery: promise and potential for novel therapeutics. Virulence 5, 399-412

Venter, J. C. et al. Environmental genome shotgun sequencing of the Sargasso Sea. Science 304, 66-74.

Farooq, M., Wahid, A., Kobayashi, N., Fujita, D. & Basra, S. M. A. (2009) Plant drought stress: effects, mechanisms and management. Agron. Sustain. Dev. 29, 185-212.

Taiz L. & Zeiger E. (2006) Plant Physiology, 4th Ed., Sinauer Associates Inc. Publishers, Massachusetts.

Nonami H. (1998) Plant water relations and control of cell elongation at low water potentials, J. Plant Res. 111, 373-382.

Parida, A. K. & Das, A. B. (2005) Salt tolerance and salinity effects on plants: A review. Ecotoxicology and Environmental Safety, 60 (3), 324-349.

Carillo P, Annunziata M G, Pontecorvo G, Fuggi A, & Woodrow P. 2011. Salinity stress and salt tolerance, abiotic stress in plants-mechanisms and adaptations. In: Arun Shanker, editor Tech, DOI: 10.5772/22331.

Yang T-T, Cheng L & Kain S R (1996) Optimized codon usage and chromophore mutations provide enhanced sensitivity with the green fluorescent protein. Nucleic Acids Res 24:4592-4593

Hema R. Vemanna R S, Sreeramulu S, Reddy C P, Senthil-Kumar M, & Udayakumar M (2014) Stable Expression of milD) Gene Imparts Multiple Stress Tolerance in Finger Millet. PLOS ONE 9 (6): e99110.

Karaba A, Dixit S, Greco R, Aharoni A, Trijatmiko K R, Marsch-Martinez N, Krishnan A, Nataraja K N, Udayakumar M, & Pereira A (2007) Improvement of water use efficiency in rice by expression of HARDY, an *Arabidopsis* drought and salt tolerance gene. Proc Natl Acad Sci USA 104:5270-15275.

What is claimed is:

1. A plant comprising a transgene encoding a polypeptide sequence having at least 95% identity to the polypeptide sequences set forth in SEQ ID NO: 165 and wherein the transgene confers to the plant one or more of the following improved/increased characteristics: improved drought resistance, increased biomass, increased salinity tolerance, increased yield, wherein said improved/increased characteristic is in comparison to a WT version of the plant or to a GFP expressing version of the plant devoid of the transgene.

2. The plant according to claim 1, wherein said one or more improved/increased characteristics includes improved drought resistance and/or increased salinity tolerance.

3. The plant according to claim 1, wherein the transgene has a polynucleotide sequence having at least 80% identity to the polynucleotide sequences set forth in SEQ ID NO: 15.

4. The plant according to claim 1, wherein said transgene is expressed under a constitutive promoter or a stress induced promoter.

5. The plant according to claim 1, wherein the plant is an agricultural crop.

* * * * *